US008129500B2

(12) United States Patent
Ross et al.

(10) Patent No.: US 8,129,500 B2
(45) Date of Patent: Mar. 6, 2012

(54) PORPHYROMONAS GINGIVALIS POLYPEPTIDES AND NUCLEOTIDES

(75) Inventors: Bruce C. Ross, Victoria (AU); Ian G. Barr, Victoria (AU); Michelle A. Patterson, Victoria (AU); Catherine T. Agius, Victoria (AU); Linda J. Rothel, Victoria (AU); Mai B. Margetts, Victoria (AU); Dianna M. Hocking, Victoria (AU); Elizabeth A. Webb, Victoria (AU)

(73) Assignees: CSL Limited, Parkville, Victoria (AU); The University of Melbourne, Parkville, Victoria (AU)

( * ) Notice: Subject to any disclaimer, the term of this patent is extended or adjusted under 35 U.S.C. 154(b) by 0 days.

(21) Appl. No.: 12/382,845

(22) Filed: Mar. 25, 2009

(65) Prior Publication Data
US 2010/0034908 A1  Feb. 11, 2010

Related U.S. Application Data

(63) Continuation of application No. 11/589,261, filed on Oct. 30, 2006, now Pat. No. 7,544,777, which is a continuation of application No. 09/581,286, filed as application No. PCT/AU98/01023 on Dec. 10, 1998, now abandoned.

(30) Foreign Application Priority Data

Dec. 10, 1997 (AU) .......................... PP0839

(51) Int. Cl.
A61K 38/16 (2006.01)
A61K 39/395 (2006.01)
C12N 15/31 (2006.01)

(52) U.S. Cl. ..................................... 530/350; 424/278.1
(58) Field of Classification Search .................... None
See application file for complete search history.

(56) References Cited

U.S. PATENT DOCUMENTS

| | | | |
|---|---|---|---|
| 4,603,112 A | 7/1986 | Paoletti et al. | |
| 4,735,801 A | 4/1988 | Stocker | |
| 4,837,151 A | 6/1989 | Stocker | |
| 5,210,035 A | 5/1993 | Stocker | |
| 5,475,097 A | 12/1995 | Travis et al. | |
| 5,523,390 A | 6/1996 | Travis et al. | |
| 5,707,620 A | 1/1998 | Travis et al. | |
| 5,711,937 A | 1/1998 | Nishida et al. | |
| 6,129,917 A | 10/2000 | Potempa et al. | |
| 6,274,718 B1 | 8/2001 | Travis et al. | |
| 6,444,799 B1 | 9/2002 | Ross | |
| 6,511,666 B1 | 1/2003 | Reynolds et al. | |
| 6,528,038 B1 | 3/2003 | Reynolds et al. | |
| 6,726,898 B2 | 4/2004 | Jernberg | |
| 6,962,706 B1 | 11/2005 | O'Brien-Simpson et al. | |
| 7,204,991 B2 | 4/2007 | Barr et al. | |
| 7,262,271 B2 | 8/2007 | Reynolds et al. | |
| 7,341,727 B1 | 3/2008 | Tucker et al. | |
| 7,419,671 B2 | 9/2008 | Reynolds et al. | |
| 7,544,777 B2 | 6/2009 | Ross et al. | |
| 7,749,502 B2 | 7/2010 | Reynolds et al. | |
| 2003/0083287 A1 | 5/2003 | Burgess et al. | |
| 2005/0288866 A1 | 12/2005 | Sachdeva et al. | |
| 2006/0078950 A1 | 4/2006 | Progulske-Fox et al. | |
| 2007/0036734 A1 | 2/2007 | Tahara et al. | |
| 2007/0098649 A1 | 5/2007 | Wu et al. | |
| 2007/0189982 A1 | 8/2007 | Reynolds et al. | |
| 2008/0175867 A1 | 7/2008 | Reynolds et al. | |
| 2009/0169568 A1 | 7/2009 | Reynolds et al. | |
| 2010/0034908 A1 | 2/2010 | Ross et al. | |
| 2010/0092471 A1 | 4/2010 | Dashper et al. | |
| 2010/0209362 A1 | 8/2010 | Dashper et al. | |
| 2010/0297179 A1 | 11/2010 | Dashper et al. | |

FOREIGN PATENT DOCUMENTS

| | | |
|---|---|---|
| WO | WO 95/07286 | 3/1995 |
| WO | WO 95/09181 A1 | 4/1995 |
| WO | WO 95/11298 | 4/1995 |
| WO | WO 95/26404 A1 | 10/1995 |
| WO | WO 97/34629 A1 | 9/1997 |
| WO | WO 00/67917 | 11/2000 |
| WO | WO 00/75346 A1 | 12/2000 |
| WO | WO 02/102370 | 12/2002 |
| WO | WO 03/055529 | 7/2003 |
| WO | WO 03/080113 | 10/2003 |
| WO | WO 2005/019249 A2 | 3/2005 |
| WO | WO 2008/016385 A2 | 2/2008 |
| WO | WO 2008/124646 A2 | 10/2008 |

OTHER PUBLICATIONS

Scolnick et al; Trends in Biotech; 18(1), pp. 34-39, 2000.
Database EMBL (online) Oct. 8, 1999; "Complete ORF22 sequence from *Neisseria meningitidis* strain A"; retrieved from EBI Database Accession No. AAZ12027 & WO99/24578 (D6).
Chen, H.A., et al; "Immunodominant Antigens of *Porphyromonas gingivalis* in Patients with Rapidly Progressive Periodontitis"; *Oral Microbial Immunol*; vol. 10; pp. 193-201 (1995).
Database Uniprot Online; "48 kDa Outer Membrane Protein"; Database Accession No. Q44130; XP-002302627.
Database Uniprot Online, "Na(+)-translocating NADH-quinone reductase subunit A (EC 1.6.5.-) (Na(+)-translocating NQR su (Na(+)-NQR subunit A) (NQR complex subunit A) (NQR-1 subunit A)"; Database Accession No. P43955; XP-002302628.
U.S. Appl. No. 13/060,653, filed Feb. 24, 2011, Reynolds et al.
McGraw et al., "Purification, Characterization, and Sequence Analysis of a Potential Virulence Factor from *Porphyromonas gingivalis*, Peptidylarginine Deiminase," Infection and Immunity, vol. 67, No. 7, pp. 3248-3256, Jul. 1999.

(Continued)

*Primary Examiner* — Michael Borin
(74) *Attorney, Agent, or Firm* — Foley & Lardner LLP

(57) ABSTRACT

The present invention relates to isolated *Porphyromonas gingivalis* polypeptides and nucleotides. The polypeptides include an amino acid sequence selected from the group consisting of: SEQ. ID. NO. 110; SEQ. ID. NO. 111; SEQ. ID. NO. 112; SEQ. ID. NO. 113; SEQ ID NO: 120; SEQ. ID. NO. 123; SEQ. ID. NO. 124; SEQ. ID. NO. 125; SEQ. ID. NO. 130; SEQ. ID. NO. 131; SEQ. ID. NO. 132; SEQ. ID. NO. 133; SEQ. ID. NO. 135; SEQ. ID. NO. 136; SEQ. ID. NO. 137; SEQ. ID. NO. 138; SEQ. ID. NO. 143; SEQ. ID. NO. 144; SEQ. ID. NO. 145; SEQ. ID. NO. 146; SEQ. ID. NO. 147; SEQ. ID. NO. 148; and amino acid sequences at least 95% identical thereto.

3 Claims, No Drawings

OTHER PUBLICATIONS

Rosenstein et al., "Hypothesis: The Humoral Immune Response to Oral Bacteria Provides a Stimulus for the Development of Rheumatoid Arthritis," Inflammation, vol. 28, No. 6, pp. 311-318, 2004.
International Search Report issued on Aug. 17, 2007 in application No. PCT/AU2007/000890 (corresponding to US 2010/0092471).
International Search Report issued on Oct. 13, 2009 in application No. PCT/AU2009/001112 (corresponding to U.S. Appl. No. 13/060,653).
International Search Report issued on Jan. 31, 1997 in application No. PCT/AU96/00673 (corresponding to US 6,511,666 and US 2007/0189982).
International Search Report issued on Jan. 28, 1999 in application No. PCT/AU98/01023 (corresponding to US 7,544,777 and US 2010/0034908).
International Search Report issued on Sep. 12, 2008 in application No. PCT/AU2008/001018 (corresponding to U.S. Appl. No. 12/668,407).
International Search Report issued on Sep. 12, 2008 in application No. PCT/AU2008/001017 (corresponding to US 2010/0297179).
Office Action issued on Dec. 27, 2010 in U.S. Appl. No. 12/306,495 (US 2010/0092471).
Office Action issued on Jun. 3, 2010 in U.S. Appl. No. 12/306,495 (US 2010/0092471).
Office Action issued on Mar. 23, 2010 in U.S. Appl. No. 12/306,495 (US 2010/0092471).
Notice of Allowance issued on Dec. 5, 2008 in U.S. Appl. No. 11/589,261 (US 7,544,777).
Office Action issued on May 19, 2008 in U.S. Appl. No. 11/589,261 (US 7,544,777).
Office Action issued on Oct. 30, 2007 in U.S. Appl. No. 11/589,261 (US 7,544,777).
Office Action issued on Apr. 28, 2006 in U.S. Appl. No. 09/581,286.
Office Action issued on Sep. 16, 2005 in U.S. Appl. No. 09/581,286.
Office Action issued on Mar. 24, 2005 in U.S. Appl. No. 09/581,286.
Office Action issued on Aug. 25, 2004 in U.S. Appl. No. 09/581,286.
Office Action issued on Jan. 27, 2004 in U.S. Appl. No. 09/581,286.
Office Action issued on Oct. 1, 2002 in U.S. Appl. No. 09/581,286.
Office Action issued on Nov. 2, 2010 in U.S. Appl. No. 12/382,845 (US 2010/0034908).
Office Action issued on Sep. 17, 2010 in U.S. Appl. No. 11/654,512 (US 2007/0189982).
Office Action issued on Aug. 12, 2009 in U.S. Appl. No. 11/654,512 (US 2007/0189982).
Office Action issued on Oct. 23, 2008 in U.S. Appl. No. 11/654,512 (US 2007/0189982).
Office Action issued on Feb. 7, 2008 in U.S. Appl. No. 11/654,512 (US 2007/0189982).
Office Action issued on Aug. 21, 2007 in U.S. Appl. No. 11/654,512 (US 2007/0189982).
Office Action issued on Oct. 29, 2009 in U.S. Appl. No. 11/729,218 (US 2008/0175867).
Office Action issued on Apr. 10, 2009 in U.S. Appl. No. 11/729,218 (US 2008/0175867).
Office Action issued on Aug. 28, 2008 in U.S. Appl. No. 11/729,218 (US 2008/0175867).
Kyte et al., "A simple method for displaying the hydropathic character of a protein," Journal of Molecular Biology, vol. 157, Issue 1, pp. 105-132, May 1982, Abstract.
Aduse Opoku et al., "Characterization, Genetic Analysis, and Expression of a Protease Antigen (PrpRI) of Porphyromonas gingivalis W50," Infection & Immunity, vol. 63, No. 12, pp. 4744-4754, Dec. 1995.
Barkocy-Gallagher et al., "Analysis of the prtP Gene Encoding Porphypain, a Cysteine Proteinase of Porphyromonas gingivalis," J. of Bacteriolgy, vol. 178, No. 10, May 1996.
Bedi, "Comparative Study of Four Proteases from Spent Culture Media of Porphyromonas gingivalis (FAY-19M-1)," Preparative Biochemistry, pp. 133-154, Aug. 1995.
Ciborowski, "Purification and Characterization of Two Forms of a High-Molecular-Weight Cysteine Proteinase (Porphypain) from Porphyromonas gingivalis," J. of Bacteriology, pp. 4549-4557, 1994.

Okamoto et al., "Structural Characterization of Argingipain, a Novel Arginine-Specific Cysteine Proteinase as a Major Periodontal Pathogenic Factor from Porphyromonas gingivalis," Archives of Biochemistry & Biophysics, vol. 316, No. 2, pp. 917-925, Feb. 1, 1995.
Pavloff et al., "Molecular Cloning and Structural Characterization of the Arg-gingipain Proteinase of Porphyromonas gingivalis," J. of Biol. Chem., vol. 270, No. 3, pp. 1007-1010, Jan. 20, 1995.
Pike et al., "Lysine- and Arginine-specific Proteinases from Porphyromonas gingivalis," J. of Biol. Chem., vol. 269, No. 1, pp. 406-411, Jan. 7, 1994.
Slakeski et al., "Characterization of a Porphyromnas gingivalis Gene prtR That Encodes an Arginine-Specific Thiol Porteinase and Multiple Adhesins," Biochem. & Biophys. Res. Comm., vol. 224, pp. 605-610, 1996.
Yoshimura, "Characterization of a Trypsin-Like Protease From the Bacterium Bacteroides gingivalis Isolated From Human Dental Plaque," Archs. Oral. Biol.,vol. 29, No. 7, pp. 559-564, 1984.
Albandar et al., Destructive periodontal disease in adults 30 years of age and older in the United States, 1988-1994, Journal of Periodontology, vol. 70, pp. 13-29, 1999.
Alm et al., The MicrobesOnline Web site for comparative genomics, Genome Research, vol. 15, pp. 1015-1022, 2005.
Bramanti et al. Roles of porphyrins and host iron transport proteins in regulation of growth of Porphyromonas gingivalis W50, Journal of Bacteriology, vol. 173, pp. 7330-7339, 1991.
Brochu et al., Acquisition of iron from human transferrin by Porphyromonas gingivalis: a role for Arg- and Lys-gingipain activities, Oral Microbiology and Immunology, vol. 16, pp. 79-87, 2001.
Capestany et al., Role of the Poiphyromonas gingivalis InIJ Protein in Homotypic and Heterotypic Biofilm Development, Infection and Immunity, vol. 74, pp. 3002-3005, 2006.
Carter et al., Humanization of an Anti-p185HER2 Antibody for Human Cancer Therapy, Proceedings of the National Academy of Science USA, vol. 89, pp. 4285-4289, 1989.
Chen et al., Porphyromonas gingivalis gingipains and adhesion to epithelial cells, Infection and Immunity, vol. 69, pp. 3048-3056, 2001.
Cossart et aL, Bacterial invasion: the paradigms of enteroinvasive pathogens, Science, vol. 304, pp. 242-248, 2004.
Curtiss et al., A virulent Salmonella typhimurium Acya Acrp oral vaccine strains expressing a streptococcal colonization and virulence antigen, Vaccine, vol. 6, pp. 155-160, 1988.
Dashper et al., Characterization of a novel outer membrane herninbinding protein of Porphyromonas gingivalis, Journal of Bacteriololgy., vol. 182, pp. 6456-6462, 2000.
Dashper et al., Sodium ion-driven serine/threonine transport in Porphyromonas gingivalis, Journal of Bacteriology, vol. 183, pp. 4142-4148, 2001.
Dashper et al., Hemoglobin hydrolysis and haem acquisition by Porphyromonas gingivalis, Oral Microbiology and Immunology, vol. 9, pp. 50-56, 2004.
Dashper et al., A novel Porphyromonas gingivalis FeoB plays a role in manganese accumulation, The Journal of Biological Chemistry, vol. 280, pp. 28095-28102, 2005.
Database Ref. Seq, Accession Nos. NC_002950.2 and N13_904903, Jan. 12, 2009.
Devereaux et al., A comprehensive set of sequence analysis programs for the VAX, Nucleic Acids Research, vol. 12, pp. 387-395, 1984.
Diaz et al., The effect of oxygen on the growth and physiology of Porphyromonas gingivalis, Oral Microbiology and Immunology, vol. 19, pp. 88-94, 2004.
Diaz et al., Role of oxyR in the oral anaerobe Porphyromonas gingivalis, Journal of Bacteriology, vol. 188, pp. 2454-2462, 2006.
Dramsi et al., Entry of Listeria monocytogenes into hepatoeytes requires expression of in inIB, a surface protein of the intemalin multigene family, Molecular Microbiology, vol. 16, pp. 251-261, 1995.
Duran-Pinedo et al., The RprY response regulator of Porphyromonas gingivalis, Molecular Microbiology, vol. 64, pp. 1416, 2007.
Eymann et al., A comprehensive proteome map of growing Bacillus subtilis cells, Proteomics, vol. 4, pp. 2849-2876, 2004.
Fletcher et al., Virulence of a Porphyramonas gingivalis W83 mutant defective in the prtH gene, Infection and Immunity, vol. 63, pp. 1521-1528, 1995.

Genco et al., Characterization of a Tn4351-generated hemin uptake mutant of *Porphyramonas gingivalis*: evidence for the coordinate regulation of virulence factors by hemin, Infection and Immunity, vol. 63, pp. 2459-2466, 1995.

Guina et al., Quantitative proteomic analysis indicates increased synthesis of a quinolone by *Pseudomonas aeruginosa* isolates from cystic fibrosis airways, Proceedings of the National Academy of Science USA, vol. 100, pp. 2771-2776, 2003.

Haffajee et al., Microbial etiological agents of destructive periodontal diseases, Periodontology 2000, vol. 5, pp. 78-111, 1994.

Huse et al., Generation of a large combinatorial library of the immunoglobulin repertoire in phage lambda, Science, vol. 246, pp. 1275-1281, 1989.

Jones et al., Replacing the complementarity-determining regions in a human antibody with those from a mouse, Nature, vol. 321, pp. 522-525, 1986.

Lamont et aL, Interaction of *Porphyromonas gingivalis* with gingival epithelial cells maintained in culture, Oral Microbiology and Immunology, vol. 7, pp. 364-367, 1992.

Lamont et al., *Porphyromonas gingivalis* invasion of gingival epithelial cells, Infection and Immunity, vol. 63, pp. 3878-3885, 1995.

Li et al., Protein profiling with cleavable isotope-coded affinity tag (cICAT) reagents: the yeast salinity stress response, Molecular and Cellular Proteomics, vol. 2, pp. 1198-1204, 2003.

Marino et al., A framework for interpreting the leucine-rich repeats of the *Listeria* internalins, Proceedings of the National Academy of Science USA, vol. 97, pp. 8784-8788, 2000.

McKee et al., Effect of hemin on the physiology and virulence of *Bacteroides gingivalis* W50, Infection and Immunity, vol. 52, pp. 349-355, 1986.

Moore et al., The bacteria of periodontal diseases, Periodontology 2000, vol. 5, pp. 66-77, 1994.

Needleman et al., A general method applicable to the search for similarities in the amino acid sequence of two proteins, Journal of Molecular Biology, vol. 48, pp. 443-453, 1970.

Nelson et al., Complete genome sequence of the oral pathogenic Bacterium *Potphyromonas gingivalis* strain W83, Journal of Bacteriology, vol. 185, pp. 5591-5601, 2003.

Okano et al., Proteomics-based analysis of a counter-oxidative stress system in *Porphyromonas gingivalis*, Proteomics, vol. 6, pp. 251-258, 2006.

Park et al., Identification of *Porphyromonas gingivalis* genes specifically expressed in human gingival epithelial cells by using differential display reverse transcription—PCR, Infection and Immunity, vol. 72, pp. 3752-3758, 2004.

Pathirana et al., Flow cytometric analysis of adherence of *Porphyromonas gingivalis* to oral epithelial cells, Infection and Immunity, vol. 75, pp. 2484-2492, 2007.

Peng et al., Evaluation of multidimensional chromatography coupled with tandem mass spectrometry (LC/LC-MS/MS) for large-scale protein analysis: the yeast Proteome, Journal of Proteome Research, vol. 2, pp. 43-50, 2003.

Price et al., A novel method for accurate operon predictions in all sequenced prokaryotes, Nucleic Acids Research, vol. 33. pp. 880-892, 2005.

Reichman et al., Reshaping human antibodies for therapy, Natu e, vol. 332, pp. 323-327, 1988.

Ross et al., Identification of vaccine candidate antigens from a genomic analysis of *Porphyromonas gingivalis*, Vaccine, vol. 19, pp. 4135-4142, 2001.

Sabet et al., LPXTG protein In1J, a newly identified internalin involved in *Listeria monocytogenes* virulence, Infection and Immunity, vol. 73, pp. 6912-6922, 2005.

Schifferle et al., Effect of protoporphyrin DC limitation on *Porphyromonas gingivalis*, Journal of Endodonics, vol. 22, pp. 352-355, 1996.

Schramm et al., Nucleotide sequence of the colicin B activity gene cba: consensus pentapeptide among TonB-dependent colicins and receptors, Journal of Bacteriology, vol. 169, pp. 3350-3357, 1987.

Schubert et al., Structure of internalin, a major invasion protein of *Listeria monocytogenes*, in complex with its human receptor E-cadherin, Cell, vol. 111, pp. 825-836, 2002.

Seers et aL, The RgpB C-terminal domain has a role in attachment of RgpB to the outer membrane and belongs to a novel C-terminal—domain family found in *Porphyromonas gingivalis*, Journal of Bacteriology, vol. 188, pp. 6376-6386, 2006.

Shah et al., The porphyrin pigmentation of subspecies of *Bacteroides melaninogenicus*, Biochemical Journal, vol. 180, pp. 45-50, 1979.

Sharp et al., The codon Adaptation Index—a measure of directional synonymous codon usage bias, and its potential applications, Nucleic Acids Research, vol. 15, pp. 1281-1295, 1987.

Shi et al., Genetic analyses of proteolysis, hemoglobin binding, and hemagglutination of *Porphyromonas gingivalis*. Construction of mutants with a combination of rgpA, rgpl3, kgp, and hagA, The Journal of Biological Chemistry, vol. 274, pp. 17955-17604, 1999.

Shizukuishi et al., Effect of concentration of compounds containing iron on the growth of *Porphyromonas gingivalis*, FEMS Microbiology Letters, vol. 131, pp. 313-317, 1995.

Simpson et al., Characterization and expression of HmuR, a Tonl3-dependent hemoglobin receptor of *Porphyromonas gingivalis*, Journal of Bacteriology, vol. 182, pp. 5737-5748, 2000.

Smalley et al. Hacinin-binding proteins of *Porphyromonas gingivalis* W50 grown in a chemostat under haemin-1 imitation. Journal of General Microbiology, 1993, vol. 139, pp. 2145-2150.

Smalley et al., The periodontopathogen *Porphyromonas gingivalis* binds iron protoporphyrin IX in the mu-oxo dimeric form: an oxidative buffer and possible pathogenic mechanism, Biochemical Journal, vol. 331 (Pt3), pp. 681-685, 1998.

Smalley et al., The periodontal pathogen *Porphyromonas gingivalis* harnesses the chemistry of the mu-oxo bishaem of iron protoporphyrin IX to protect against hydrogen peroxide, FEMS Microbiology Letters, vol. 183, pp. 159-164, 2000.

Supek et al., INCA: synonymous codon usage analysis and clustering by means of self-organizing map, Bioinformatics, vol. 20, pp. 2329-2330, 2004.

Thompson et al., Clustal W: improving the sensitivity of progressive multiple sequence alignment through sequence weighting, position-specific gap penalties and weight matrix choice, Nucleic Acids Research, vol. 22, pp. 4673-4680, 1994.

Tribble et al., A Porphyromonas gingivalis haloacid dehalogenase family phosphatase interacts with human phosphoproteins and is important for invasion, Proceedings of the National Academy of Science USA, vol. 103, pp. 11027-11032, 2006.

Veith et al., Identification of a novel heterodimeric outer membrane protein of *Porphyromonas gingivalis* by two-dimensional gel electrophoresis and peptide mass fingerprinting, European Journal of Biochemistry, vol. 268, pp. 4748-4757, 2001.

Wang et al., An analysis of the proteomic profile for *Thermoanaerobacter tengcongensis* under optimal culture conditions, Proteomics, vol. 4, pp. 136-150, 2004.

Washburn et al., Large-scale analysis of the yeast proteome by multidimensional protein identification technology, Nature Biotechnology, vol. 19, pp. 242-247, 2001.

Yu et al., Predicting subcellular localization of proteins for Gram-negative bacteria by support vector machines based on n-peptide compositions, Protein Science, vol. 13, pp. 1402-1406, 2004.

Zhang et al., Differential protein expression by *Porphyromonas gingivalis* in response to secreted epithelial cell components, Proteomics, vol. 5, pp. 198-211, 2005.

Houghten et al., "Relative Importance of Position and Individual Amino Acid Residues in Peptide Antigen-Antibody Interactions: Implications in the Mechanism of Antigenic Drift and Antigenic Shift Vaccines," 1986, Fred Brown, Ed.

Lederman et al., "A Single Amino Acid Substitution in a Common African Allele of the CD4 Molecule Ablates Binding of the Monoclonal Antibody, OKT4," Molecular Immunology, vol. 28, pp. 1171-1181, 1991.

Li et al., "β-Endorphin omission analogs: Disssociation of immunoreactivity from other biological activities," Proc. Natl. Acad. Sci. USA, vol. 77, pp. 3211-3214, 1980.

Campbell, "Assay Techniques," Monoclonal Antibody Technology, Chapter 2, 1986.

Bohgal et al., "A cell-associated protein complex of *Porphyromonas gingivalis* W50 composed of Arg- and Lys-specific cysteine proteinases and adhesins," Microbiology, vol. 143, pp. 2485-2495, 1997.

Davey et al., "Enhanced Biofilm Formation and Loss of Capsule Synthesis: Deletion of a Putative Glycosyltransferase in *Porphyromonas gingivalis*," J. Bacteriology, vol. 188, No. 15, pp. 5510-5523, 2006.

Chung et al., "Identification of a *Porphyromonas gingivalis* Receptor for the *Streptococcus gordonii* SspB Protein," Infection and Immunity, vol. 68, No. 12, pp. 6758-6762, 2000.

Xie et al., "*Porphyromonas gingivalis* Genes involved in fimA Regulation," Infection and Immunity, vol. 72, No. 2, pp. 651-658, 2004.

Daep et al., "Structural Characterization of Peptide-mediated inhibition of *Porphyromonas gingivalis* biofilm formation," Infection and Immunity, vol. 74, No. 10, pp. 5756-5762, 2006.

Mendz et al., "Fumarate Reductase: A Target for Therapeutic Intervention against *Helicobacter pylori*," Archives of Biochemistry and Biophysics, vol. 321, No. 1, pp. 153-159, 1995.

Takahashi et al., "Metabolic Pathways for Cytotoxic End Product Formation from Glutamate- and Aspartate-Containing Peptides by *Porphyromonas gingivalis*," J. Bacteriol., vol. 182, No. 17, pp. 4704-4710, 2000.

PORPHYROMONAS GINGIVALIS POLYPEPTIDES AND NUCLEOTIDES

CROSS-REFERENCE TO RELATED APPLICATIONS

This application is a continuation of application Ser. No. 11/589,261, filed Oct. 30, 2006, which is a continuation of application Ser. No. 09/581,286, filed Jun. 28, 2000, which is a 317 of PCT/AU98/01023 filed Dec. 10, 1998, the entire contents of each of these applications is incorporated herein by reference. In particular, the entire contents of application Ser. No. 11/589,261, pending, is incorporated herein by reference, including specifically the sequence ID numbers: SEQ. ID. NO. 1 to SEQ ID NO: 721.

FIELD OF THE INVENTION

The present invention relates to *Porphyromonas gingivalis* nucleotide sequences, *P. gingivalis* polypeptides and probes for detection of *P. gingivalis*. The *P. gingivalis* polypeptides and nucleotides can be used in compositions for use in raising an immune response in a subject against *P. gingivalis* and treating or preventing or reducing the severity of the condition known as periodontitis.

BACKGROUND OF THE INVENTION

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is *P. gingivalis* as the recovery of this microorganism from adult periodontitis lesions can be up to 50% of the subgingival anaerobically cultivable flora, whereas *P. gingivalis* is rarely recovered, and then in low numbers, from healthy sites. A proportional increase in the level of *P. gingivalis* in subgingival plaque has been associated with an increased severity of periodontitis and eradication of the microorganism from the cultivable subgingival microbial population is accompanied by resolution of the disease. The progression of periodontitis lesions in non-human primates has been demonstrated with the subgingival implantation of *P. gingivalis*. These findings in both animals and humans suggest a major role for *P. gingivalis* in the development of adult periodontitis.

*P. gingivalis* is a black-pigmented, anaerobic, asaccharolytic, proteolytic Gram-negative rod that obtains energy from the metabolism of specific amino acids. The microorganism has an absolute growth requirement for iron, preferentially in the form of haeme or its Fe(III) oxidation product haemin and when grown under conditions of excess haemin is highly virulent in experimental animals. A number of virulence factors have been implicated in the pathogenicity of *P. gingivalis* including the capsule, adhesins, cytotoxins and extracellular hydrolytic enzymes.

In order to develop an efficacious and safe vaccine to prevent, eliminate or reduce *P. gingivalis* colonisation it is necessary to identify and produce antigens that are involved in virulence that have utility as immunogens possibly through the generation of specific antibodies. Whilst it is possible to attempt to isolate antigens directly from cultures of *P. gingivalis* this is often difficult. For example as mentioned above, *P. gingivalis* is a strict anaerobe and can be difficult to isolate and grow. It is also known that, for a number of organisms, when cultured in vitro that many virulence genes are down regulated and the encoded proteins are no longer expressed. If conventional chemistry techniques were applied to purify vaccine candidates potentially important (protective) molecules may not be identified. With DNA sequencing, as the gene is present (but not transcribed) even when the organism is grown in vitro it can be identified, cloned and produced as a recombinant DNA protein. Similarly, a protective antigen or therapeutic target may be transiently expressed by the organism in vitro or produced in low levels making the identification of these molecules extremely difficult by conventional methods.

With serological identification of therapeutic targets one is limited to those responses which are detectable using standard methods such as Western Blotting or ELISA. The limitation here is the both the level of response that is generated by the animal or human and determining whether this response is protective, damaging or irrelevant. No such limitation is present with a sequencing approach to the identification of potential therapeutic or prophylactic targets.

It is also well known that *P. gingivalis* produces a range of broadly active proteases (University of Melbourne International Patent Application No PCT/AU 96/00673, U.S. Pat. Nos. 5,475,097 and 5,523,390), which make the identification of intact proteins difficult because of their degradation by these proteases.

SUMMARY OF THE INVENTION

The present inventors have attempted to isolate *P. gingivalis* nucleotide sequences which can be used for recombinant production of *P. gingivalis* polypeptides and to develop nucleotide probes specific for *P. gingivalis*. The DNA sequences listed below have been selected from a large number of *P. gingivalis* sequences according to their indicative potential as vaccine candidates. This intuitive step involved comparison of the deduced protein sequence from the *P. gingivalis* DNA sequences to the known protein sequence databases. Some of the characteristics used to select useful vaccine candidates include; the expected cellular location, such as outer membrane proteins or secreted proteins, particular functional activities of similar proteins such as those with an enzymatic or proteolytic activity, proteins involved in essential metabolic pathways that when inactivated or blocked may be deleterious or lethal to the organism, proteins that might be expected to play a role in the pathogenesis of the organism eg. red cell lysis, cell agglutination or cell receptors and proteins which are paralogues to proteins with proven vaccine efficacy.

In a first aspect the present invention consists of an isolated antigenic *Porphyromonas gingivalis* polypeptide or an antigenic fragment thereof, the polypeptide comprising an amino acid sequence selected from the group consisting of: SEQ. ID. NO. 110; SEQ. ID. NO. 111; SEQ. ID. NO. 112; SEQ. ID. NO. 113; SEQ ID NO: 120; SEQ. ID. NO. 123; SEQ. ID. NO. 124; SEQ. ID. NO. 125; SEQ. ID. NO. 130; SEQ. ID. NO. 131; SEQ. ID. NO. 132; SEQ. ID. NO. 133; SEQ. ID. NO. 135; SEQ. ID. NO. 136; SEQ. ID. NO. 137; SEQ. ID. NO. 138; SEQ. ID. NO. 143; SEQ. ID. NO. 144; SEQ. ID. NO. 145; SEQ. ID. NO. 146; SEQ. ID. NO. 147; and SEQ. ID. NO. 148;

or amino acid sequences at least 95% identical to an amino acid sequence selected from the group consisting of: SEQ. ID. NO. 110; SEQ. ID. NO. 111; SEQ. ID. NO. 112; SEQ. ID.

NO. 113; SEQ ID NO: 120; SEQ. ID. NO. 123; SEQ. ID. NO. 124; SEQ. ID. NO. 125; SEQ. ID. NO. 130; SEQ. ID. NO. 131; SEQ. ID. NO. 132; SEQ. ID. NO. 133; SEQ. ID. NO. 135; SEQ. ID. NO. 136; SEQ. ID. NO. 137; SEQ. ID. NO. 138; SEQ. ID. NO. 143; SEQ. ID. NO. 144; SEQ. ID. NO. 145; SEQ. ID. NO. 146; SEQ. ID. NO. 147; and SEQ. ID. NO. 148;

or an amino acid sequence of at least 40 amino acids having a contiguous sequence of at least 40 amino acids identical to a contiguous amino acid sequence selected from the group consisting of: SEQ. ID. NO. 110; SEQ. ID. NO. 111; SEQ. ID. NO. 112; SEQ. ID. NO. 113; SEQ ID NO: 120; SEQ. ID. NO. 123; SEQ. ID. NO. 124; SEQ. ID. NO. 125; SEQ. ID. NO. 130; SEQ. ID. NO. 131; SEQ. ID. NO. 132; SEQ. ID. NO. 133; SEQ. ID. NO. 135; SEQ. ID. NO. 136; SEQ. ID. NO. 137; SEQ. ID. NO. 138; SEQ. ID. NO. 143; SEQ. ID. NO. 144; SEQ. ID. NO. 145; SEQ. ID. NO. 146; SEQ. ID. NO. 147; and SEQ. ID. NO. 148.

As used herein % identity for polypeptides is to be calculated using the alignment algorithm of Needleman and Munsch (9) using a standard protein scoring matrix (Blosum 50).

In a preferred embodiment the present invention provides a polypeptide or fragment thereof, the polypeptide comprising an amino acid sequence selected from the group consisting of: SEQ. ID. NO. 110; SEQ. ID. NO. 111; SEQ. ID. NO. 112; SEQ. ID. NO. 113; SEQ ID NO: 120; SEQ. ID. NO. 123; SEQ. ID. NO. 124; SEQ. ID. NO. 125; SEQ. ID. NO. 130; SEQ. ID. NO. 131; SEQ. ID. NO. 132; SEQ. ID. NO. 133; SEQ. ID. NO. 135; SEQ. ID. NO. 136; SEQ. ID. NO. 137; SEQ. ID. NO. 138; SEQ. ID. NO. 143; SEQ. ID. NO. 144; SEQ. ID. NO. 145; SEQ. ID. NO. 146; SEQ. ID. NO. 147; and SEQ. ID. NO. 148.

In a second aspect the present invention consists in an isolated DNA molecule, the DNA molecule comprising a nucleotide sequence which encodes the polypeptide of the first aspect of the present invention or a sequence which hybridises thereto under stringent conditions.

It is preferred that the isolated DNA molecule comprises a nucleotide sequence selected from the group consisting of SEQ ID NO: 36 to SEQ ID NO: 39; SEQ ID NO: 46; SEQ ID NO: 49 to SEQ ID NO: 51; SEQ ID NO: 56 to SEQ ID NO: 59; SEQ ID NO: 61 to SEQ ID NO:64; SEQ ID NO: 69 to SEQ ID NO: 74; SEQ ID NO: 3 to SEQ ID NO: 5; SEQ ID NO: 11; SEQ ID NO: 14 to SEQ ID NO: 16; SEQ ID NO: 21; SEQ ID NO: 22; SEQ ID NO: 24 to SEQ ID NO: 26; SEQ ID NO: 28 to SEQ ID NO: 33.

In a third aspect the present invention consists in a recombinant expression vector comprising the DNA molecule of the second aspect of the present invention operably linked to a transcription regulatory element.

The present invention also provides a cell comprising this recombinant expression vector.

In a further aspect the present invention consists in a method for producing a *P. gingivalis* polypeptide comprising culturing the cell under conditions that permit expression of the polypeptide.

In yet a further aspect the present invention provides a composition for use in raising an immune response directed against *P. gingivalis* in a subject, the composition comprising an effective amount of at least one polypeptide of the first aspect of the present invention, or at least one DNA molecule of the second aspect of the present invention, or both, and a pharmaceutically acceptable carrier. It is preferred that the pharmaceutically acceptable carrier is an adjuvant. In other aspects the present invention provides methods of treating *P. gingivalis* infection in subject comprising the administration of the composition to the subject such that treatment of *P. gingivalis* infection occurs. The treatment may be prophylactic or therapeutic.

In yet another aspect the present invention provides an antibody raised against a polypeptide of the first aspect the invention. The antibody may be polyclonal or monoclonal. The present invention also provides compositions including these antibodies. It is preferred that these compositions are adapted for oral use and may be, for example, dentrifices, mouthwashes, etc.

In a still further aspect the present invention provides a nucleotide probe comprising at least 18 nucleotides and having a contiguous sequence of at least 18 nucleotides identical to a contiguous nucleotide sequence selected from the group consisting of SEQ ID NO: 3 to SEQ ID NO: 5; SEQ ID NO: 11; SEQ ID NO: 14 to SEQ ID NO: 16; SEQ ID NO: 21; SEQ ID NO: 22; SEQ ID NO: 24 to SEQ ID NO: 26; SEQ ID NO: 28 to SEQ ID NO: 33; and sequences complementary thereto. It is preferred that the probe further comprises a detectable label.

The present invention also provides a method for detecting the presence of *P. gingivalis* nucleic acid in a sample comprising:
(a) contacting a sample with the nucleotide probe under conditions in which a hybrid can form between the probe and a *P. gingivalis* nucleic acid in the sample; and
(b) detecting the hybrid formed in step (a), wherein detection of a hybrid indicates the presence of a *P. gingivalis* nucleic acid in the sample.

DETAILED DESCRIPTION

Definitions

A purified or isolated polypeptide or a substantially pure preparation of a polypeptide are used interchangeably herein and, as used herein, mean a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 mg of the polypeptide.

A purified preparation of cells refers to, in the case of plant or animal cells, an in vitro preparation of cells and not an entire intact plant or animal. In the case of cultured cells or microbial cells, it consists of a preparation of at least 10% and more preferably 50% of the subject cells.

A purified or isolated or a substantially pure nucleic acid, e.g., a substantially pure DNA, (are terms used interchangeably herein) is a nucleic acid which is one or both of the following: not immediately contiguous with both of the coding sequences with which it is immediately contiguous (i.e., one at the 5' end and one at the 3' end) in the naturally occurring genome of the organism from which the nucleic acid is derived; or which is substantially free of a nucleic acid with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional *P. gingivalis* DNA sequence.

A "contig" as used herein is a nucleic acid representing a continuous stretch of genomic sequence of an organism.

An "open reading frame", also referred to herein as ORF, is a region of nucleic acid which encodes a polypeptide. This region may represent a portion of a coding sequence or a total sequence and can be determined from a stop to stop codon or from a start to stop codon.

As used herein, a "coding sequence" is a nucleic acid which is transcribed into messenger RNA and/or translated into a polypeptide when placed under the control of appropriate regulatory sequences. The boundaries of the coding sequence are determined by a translation start codon at the five prime terminus and a translation stop code at the three prime terminus. A coding sequence can include but is not limited to messenger RNA synthetic DNA, and recombinant nucleic acid sequences.

A "complement" of a nucleic acid as used herein refers to an anti-parallel or antisense sequence that participates in Watson-Crick base-pairing with the original sequence.

A "gene product" is a protein or structural RNA which is specifically encoded by a gene.

As used herein, the term "probe" refers to a nucleic acid, peptide or other chemical entity which specifically binds to a molecule of interest. Probes are often associated with or capable of associating with a label. A label is a chemical moiety capable of detection. Typical labels comprise dyes, radioisotopes, luminescent and chemiluminescent moieties, fluorophores, enzymes, precipitating agents, amplification sequences, and the like. Similarly, a nucleic acid, peptide or other chemical entity which specifically binds to a molecule of interest and immobilizes such molecule is referred herein as a "capture ligand". Capture ligands are typically associated with or capable of associating with a support such as nitrocellulose, glass, nylon membranes, beads, particles and the like. The specificity of hybridization is dependent on conditions such as the base pair composition of the nucleotides, and the temperature and salt concentration of the reaction. These conditions are readily discernible to one of ordinary skill in the art using routine experimentation.

Homologous refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100.

The terms peptides, proteins, and polypeptides are used interchangeably herein.

An "immunogenic component" as used herein is a moiety, such as an *P. gingivalis* polypeptide, analog or fragment thereof, that is capable of eliciting a humoral and/or cellular immune response in a host animal.

An "antigenic component" as used herein is a moiety, such as *P. gingivalis* polypeptide, analog or fragment thereof, that is capable of binding to a specific antibody with sufficiently high affinity to form a detectable antigen-antibody complex.

As used herein, the term "cell-specific promoter" means a DNA sequence that serves as a promoter, i.e., regulates expression of a selected DNA sequence operably linked to the promoter, and which effects expression of the selected DNA sequence in specific cells of a tissue. The term also covers so-called "leaky" promoters, which regulate expression of a selected DNA primarily in one tissue, but cause expression in other tissues as well.

As used herein, the term "control sequence" refers to a nucleic acid having a base sequence which is recognized by the host organism to effect the expression of encoded sequences to which they are ligated. The nature of such control sequences differs depending upon the host organism; in prokaryotes, such control sequences generally include a promoter, ribosomal binding site, terminators, and in some cases operators; in eukaryotes, generally such control sequences include promoters, terminators and in some instances, enhancers. The term control sequence is intended to include at a minimum, all components whose presence is necessary for expression, and may also include additional components whose presence is advantageous, for example, leader sequences.

As used herein, the term "operably linked" refers to sequences joined or ligated to function in their intended manner. For example, a control sequence is operably linked to coding sequence by ligation in such a way that expression of the coding sequence is achieved under conditions compatible with the control sequence and host cell.

A "sample" as used herein refers to a biological sample, such as, for example, tissue or fluid isolated from an individual (including without limitation plasma, serum, cerebrospinal fluid, lymph, tears, saliva and tissue sections) or from in vitro cell culture constituents, as well as samples from the environment.

The practice of the invention will employ, unless otherwise indicated, conventional techniques of chemistry, molecular biology, microbiology, recombinant DNA, and immunology well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (Editors), Current Protocols in Molecular Biology, Greene Pub. Associates and Wiley-Interscience (1988, including all updates until present). The disclosure of these texts are incorporated herein by reference.

Pharmaceutically Acceptable Carriers

The antibodies, polypeptides and DNA of the present invention can be included in compositions which include a carrier or diluent. These compositions include pharmaceutical compositions where the carrier or diluent will be pharmaceutically acceptable. Pharmaceutically acceptable carriers or diluents include those used in compositions suitable for oral, rectal, nasal, topical (including buccal and sublingual), vaginal, parenteral (including subcutaneous, intramuscular, intravenous, intradermal, intrathecal and epidural) administration. They are non-toxic to recipients at the dosages and concentrations employed. Representative examples of pharmaceutically acceptable carriers or diluents include, but are not limited to; water, isotonic solutions which are preferably buffered at a physiological pH (such as phosphate-buffered saline or Tris-buffered saline) and can also contain one or more of, mannitol, lactose, trehalose, dextrose, glycerol, ethanol or polypeptides (such as human serum albumin). The compositions may conveniently be presented in unit dosage form and may be prepared by any of the methods well known in the art of pharmacy.

As will be well understood by those skilled in the art alterations may be made to the amino acid sequences set out in the Sequence Listings. These alterations may be deletions, insertions, or substitutions of amino acid residues. The altered polypeptides can be either naturally occurring (that is to say, purified or isolated from a natural source) or synthetic (for example, by performing site-directed metagenesis on the encoding DNA). It is intended that such altered polypeptides which have at least 85%, preferably at least 95% identity with the sequences set out in the Sequence Listing are within the scope of the present invention. Antibodies raised against these altered polypeptides will also bind to the polypeptides having one of the sequences set out in the Sequence Listings. The level of % identity is to be calculated as set out above.

Protein sequences are homologous if they are related by divergence from a common ancestor. Consequently, a species homologue of the protein will be the equivalent protein which occurs naturally in another species. Within any one species a homologue may exist as numerous allelic variants, and these will be considered homologues of the protein. Allelic variants and species homologues can be obtained by following standard techniques known to those skilled in the art.

An allelic variant will be a variant that is naturally occurring within an individual organism.

Mutants, Variants and Homology—Nucleic Acids

Mutant polynucleotides will possess one or more mutations which are deletions, insertions, or substitutions of nucleotide residues. Mutants can be either naturally occurring (that is to say, isolated from a natural source) or synthetic (for example, by performing site-directed metagenesis on the DNA). It is thus apparent that polynucleotides of the invention can be either naturally occurring or recombinant (that is to say prepared using recombinant DNA techniques).

An allelic variant will be a variant that is naturally occurring within an individual organism.

Nucleotide sequences are homologous if they are related by divergence from a common ancestor. Consequently, a species homologue of the polynucleotide will be the equivalent polynucleotide which occurs naturally in another species. Within any one species a homologue may exist as numerous allelic variants, and these will be considered homologues of the polynucleotide. Allelic variants and species homologues can be obtained by following standard techniques known to those skilled in the art.

Antibody Production

Antibodies, either polyclonal or monoclonal, which are specific for a polypeptide of the present invention can be produced by a person skilled in the art using standard techniques such as, but not limited to, those described by Harlow et al. Antibodies: A Laboratory Manual, Cold Springs Harbor Laboratory Press (1988), and D. Catty (editor), Antibodies: A Practical Approach, IRL Press (1988).

Various procedures known in the art may be used for the production of polyclonal antibodies to epitopes of a protein. For the production of polyclonal antibodies, a number of host animals are acceptable for the generation of antibodies by immunization with one or more injections of a polypeptide preparation, including but not limited to rabbits, mice, rats, etc. Various adjuvants may be used to increase the immunological response in the host animal, depending on the host species, including but not limited to Freund's (complete and incomplete), mineral gels such as aluminium hydroxide, surface active substances such as lysolecithin, pluronic polyols, polyanions, oil emulsions, keyhole lympet hemocyanins, dinitrophenol, and potentially useful human adjuvants such as BCG (bacille Calmette-Guerin) and *Corynebacterium parvum*.

A monoclonal antibody to an epitope of a protein may be prepared by using any technique which provides for the production of antibody molecules by continuous cell lines in culture. These include but are not limited to the hybridoma technique originally described by Kohler and Milstein (1975, Nature 256, 493-497), and the more recent human B-cell hybridoma technique (Kesber et al. 1983, Immunology Today 4:72) and EBV-hybridoma technique (Cole et al. 1985, Monoclonal Antibodies and Cancer Therapy, Alan R. Liss, Inc. pp. 77-96). In addition, techniques developed for the production of "chimeric antibodies" by splicing the genes from antibody molecule of appropriate antigen specificity together with genes from a human antibody molecule of appropriate biological activity may be used (Mornison et al. 1984, Proc. Natl. Acad. Sci., 81:6851-6855; Neuberger et al. 1984 Nature 312:604-608; Takeda et al. 1985 Nature 31:452-454). Alternatively, techniques described for the production of single chain antibodies (U.S. Pat. No. 4,946,778) can be adapted to produce 4-specific single chain antibodies.

Recombinant human or humanized versions of monoclonal antibodies are a preferred embodiment for human therapeutic applications. Humanized antibodies may be prepared according to procedures in the literature (e.g. Jones et al. 1986, Nature 321:522-25; Reichman et al. 1988 Nature 332:323-27; Verhoeyen et al. 1988, Science 239:1534-36). The recently described "gene conversion metagenesis" strategy for the production of humanized monoclonal antibody may also be employed in the production of humanized antibodies (Carter et al. 1992 Proc. Natl. Acad. Sci. U.S.A. 89:4285-89). Alternatively, techniques for generating the recombinant phase library of random combinations of heavy and light regions may be used to prepare recombinant antibodies (e.g. Huse et al. 1989 Science 246:1275-81).

Antibody fragments which contain the idiotype of the molecule such as Fu F(ab1) and F(ab2) may be generated by known techniques. For example, such fragments include but are not limited to: the F(ab) E2 fragment which can be produced by pepsin digestion of the intact antibody molecule; the Fab' fragments which can be generated by reducing the disulfide bridges of the F(ab')2 fragment, and the two Fab fragments which can be generated by treating the antibody molecule with papain and a reducing agent. Alternatively, Fab expression libraries may be constructed (Huse et al. 1989, Science 246:1275-1281) to allow rapid and easy identification of monoclonal Fab fragment with the desired specificity to a protein.

Adjuvants

"Adjuvant" means a composition comprised of one or more substances that enhances the immunogenicity and efficacy of a vaccine composition. Non-limiting examples of suitable adjuvants include squalane and squalene (or other oils of animal origin); block copolymers; detergents such as Tween®-80; Quil® A, mineral oils such as Drakeol or Marcol, vegetable oils such as peanut oil; *Corynebacterium*-derived adjuvants such as *Corynebacterium parvum; Propionibacterium*-derived adjuvants such as *Propionibacterium acne; Mycobacterium bovis* (*Bacillus Calmetic* and *Guerinn* or BCG); interleukins such as interleukin 2 and interleukin-12; monokines such as interleukin 1; tumour necrosis factor; interferons such as gamma interferon; combinations such as saponin-aluminium hydroxide or Quil-A aluminium hydroxide; liposomes; ISCOM adjuvant; mycobacterial cell wall extract; synthetic glycopeptides such as muramyl dipeptides or other derivatives; Avridine; Lipid A; dextran sulfate; DEAE-Dextran or DHAE-Dextran with aluminium phosphate; carboxypolymethylene such as Carbopol' EMA; acrylic copolymer emulsions such as Neocryl A640 (e.g. U.S.

Pat. No. 5,047,238); vaccinia or animal posvirus proteins; sub-viral particle adjuvants such as cholera toxin, or mixtures thereof.

As used herein, stringent conditions are those that (1) employ low ionic strength and high temperature for washing, for example, 0.015 M NaCl/0.0015 M sodium citrate/0.1% NaDodSO4 at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS and 10% dextran sulfate at 42° C. in 0.2×SSC and 0.1% SDS As will be understood the present invention includes within its scope DNA vaccination. Further information regarding DNA vaccination may be found in Donnelly et al, Journal of Immunological Methods 176(1994) 145-152, the disclosure of which is incorporated herein by reference.

Throughout this specification the word "comprise", or variations such as "comprises" or "comprising", will be understood to imply the inclusion of a stated element or integer or group of elements or integers but not the exclusion of any other element or integer, or group of elements or integers.

Preparation of the *P. Gingivalis* Library for Sequencing.

To determine the DNA sequence of *P. gingivalis* genomic DNA was isolated from *P. gingivalis* strain W50 (ATCC 53978) essentially by the method described by Mamur J. (J. Mol. Biol. 3, 208-218, 1961). Cloning of DNA fragments was performed essentially as described by Fleischmann et al., (Science; 269, 496-512, 1995)(2). Briefly, purified genomic DNA from *P. gingivalis* was nebulized to fragment the DNA and was treated with Bal31 nuclease to create blunt ends then run twice through preparative 1% agarose gels. DNA fragments of 1.6-2.0 kb were excised from the gel and the DNA recovered. This DNA was then ligated to the vector pUC18 (SmaI digested and dephosphorylated; Pharmacia) and electrophoresed through a 1% preparative agarose gel. The fragment comprising linear vector plus one insert was excised, purified and this process repeated to reduce any vector without insert contamination. The recovered vector plus insert DNA was blunt-ended with T4 DNA polymerase, then a final ligation to produce circular DNA was performed. Aliquots of Epicurian Coli Electroporation-Competent Cells (Stratagene) were transformed with the ligated DNA and plated out on SOB agar antibiotic diffusion plates containing X-gal and incubated at 37° C. overnight. Colonies with inserts appeared white and those without inserts (vector alone) appeared blue. Plates were stored at 4° C. until the white clones were picked and expanded for the extraction of plasmid DNA for sequencing.

DNA Sequencing

Plasmid DNA was prepared by picking bacterial colonies into 1.5 ml of LB, TB or SOB broth supplemented with 50-100 ug/ml Ampicillin in 96 deep well plates. Plasmid DNA was isolated using the QIAprep Spin or QIAprep 96 Turbo miniprep kits (QIAGEN GmbH, Germany). DNA was eluted into a 96 well gridded array and stored at −20 C.

Sequencing reactions were performed using ABI PRISM Dye Terminator and ABI PRISM BIGDye Terminator Cycle Sequencing Ready Reaction kits with AmpliTaq DNA polymerase FS (PE Applied Biosystems, Foster City, Calif.) using the M13 Universal forward and reverse sequencing primers. Sequence reactions were conducted on either a Perkin-Elmer GeneAmp 9700 (PE Applied Biosystems) or Hybaid PCR Express (Hybaid, UK) thermal cyclers. Sequencing reactions were analysed on ABI PRISM 377 DNA sequencers (PE Applied Biosystems).

The sequences obtained are set out below. The relationship between these sequences is set out in Table 1. The initiation codon was calculated using a combination of sequence homology alignment (FASTA), signal sequence prediction (PSORT, SignalP) or ORF prediction (GeneMark).

TABLE 1

Reference table indicating the relationships of each sequence ID to the selected proteins.

| Protein name | DNA sequence of complete ORF | Amino acid sequence of complete ORF | DNA sequence of protein | Amino acid sequence of protein |
|---|---|---|---|---|
| PG1 | 1 | 75 | 34 | 108 |
| PG10 | 2 | 76 | 35 | 109 |
| PG100 | 3 | 77 | 36 | 110 |
| PG102 | 4 | 78 | 37, 38 | 111, 112 |
| PG104 | 5 | 79 | 39 | 113 |
| PG11 | 6 | 80 | 40 | 114 |
| PG12 | 7 | 81 | 41 | 115 |
| PG13 | 8 | 82 | 42 | 116 |
| PG14 | 9 | 83 | 43 | 117 |
| PG2 | 10 | 84 | 44, 45 | 118, 119 |
| PG21 | 11 | 85 | 46 | 120 |
| PG22 | 12 | 86 | 47 | 121 |
| PG24 | 13 | 87 | 48 | 122 |
| PG25 | 14 | 88 | 49 | 123 |
| PG27 | 15 | 89 | 50 | 124 |
| PG28 | 16 | 90 | 51 | 125 |
| PG29 | 17 | 91 | 52 | 126 |
| PG3 | 18 | 92 | 53 | 127 |
| PG4 | 19 | 93 | 54 | 128 |
| PG5 | 20 | 94 | 55 | 129 |
| PG54 | 21 | 95 | 56 | 130 |
| PG57 | 22 | 96 | 57, 58, 59 | 131, 132, 133 |
| PG6 | 23 | 97 | 60 | 134 |
| PG68 | 24 | 98 | 61, 62 | 135, 136 |
| PG75 | 25 | 99 | 63 | 137 |
| PG76 | 26 | 100 | 64 | 138 |
| PG8 | 27 | 101 | 65, 66, 67, 68 | 139, 140, 141, 142 |
| PG91 | 28 | 102 | 69 | 143 |
| PG94 | 29 | 103 | 70 | 144 |
| PG96 | 30 | 104 | 71 | 145 |
| PG97 | 31 | 105 | 72 | 146 |
| PG98 | 32 | 106 | 73 | 147 |
| PG99 | 33 | 107 | 74 | 148 |

DNA Sequence Analysis

DNA files in FASTA format were converted to GCG format files and imported into a database. The DNA files were translated into amino acid files using the program Flip obtained from ANGIS(Australian Genomic Information Service, University of Sydney, Australia). A series of bioinformatic analyses were performed on the proteins in order to select potential vaccine candidates. The programs used were FASTA homology searching (1), PSORT (2,3), SignalP (4), TopPred (5), and GeneMark (6). The proteins and their bioinformatic results were stored in the custom written database for search and retrieval of proteins with the desired characteristics The FASTA homology results for these proteins were then examined for any alignment with a protein suggesting surface location or vaccine efficacy. All proteins were searched for homology against a non-redundant bacterial protein database compiled by ANGIS using the FASTA algorithm. The settings used for the FASTA searches were Ktup=2, gap creation penalty=−12, gap extension penalty=−2, width for deriving alignment in opt=16 and the Blosum 50 scoring matrix. Individual FASTA search results were examined for significant homology by statistical probability and amino acid alignments. The results are set out in Table 2.

Protein files were then trimmed to the first, second, third, fourth and fifth methionine residues using a protein trimming program (ANGIS). The trimmed proteins were then subjected to PSORT analysis for the detection of signal sequences and the prediction of cell location. Proteins exhibiting a PSORT probability of outer membrane>0.8 were considered to indicate surface localisation. A second signal sequence detection program SignalP was also performed and, in certain instances, this program detected signals not identified with PSORT. All proteins identified by other methods were also analysed by PSORT and SignalP. Previously, the C-terminal amino acid of bacterial outer membrane proteins has been shown to be important for the assembly of the protein on the outer membrane (7). A typical structure definition for outer membrane proteins has been determined as the presence of a signal sequence at the N-terminus and a tyrosine or phenylalanine at the C-terminus. A number of the selected proteins exhibit this characteristic structure. The program TopPred was used to determine the presence and number of membrane spanning domains (MSDs) and the presence of such sequences indicates a preference to be attached to membranes such as the outer membrane. The results of PSORT, SignalP and TopPred analyses with the C-terminal amino acids of the selected proteins are set out in Table 3.

The 70 amino acids from the C-terminus of a number of *P. gingivalis* outer membrane proteins share 50-100% protein sequence identity. These proteins included RGP1, RGP2, KGP, HagA, HagC, HagD, prtH and prtT. This conserved motif may be involved in the attachment or sorting of proteins to the outer membrane. The protein data set was searched using FASTA homology as described above and a number of novel proteins were identified which demonstrate similar motifs at their C-termini. The results are listed in Table 4

The TonBIII box is a 30 amino acid motif present within TonB outer membrane receptors in a wide variety of bacteria. The TonBIII box of *P. gingivalis* (8) was used to search the protein data set for homology by FASTA as described above. Those proteins demonstrating significant homology are listed in Table 5.

TABLE 2

FASTA protein homology results of complete ORFs against a non-redundant protein database.

| Protein name | Homology description | Genbank accession number | Length of homolog | Length of *P. gingivalis* protein | FASTA homology results Identity % | Overlap | E value |
|---|---|---|---|---|---|---|---|
| PG1 | 48 kD outer membrane protein, *Actinobacillus pleuropneumoniae* | U24492 | 449aa | 451aa | 32 | 454aa | 1.40E−42 |
| PG2 | Outer membrane protein (susC), *Bacteroides thetaiotaomicron* | L49338 | 1038aa | 1017aa, 1014aa | 28 | 1099aa | 4.60E−32 |
| PG3 | Outer membrane porin F adhesin, *Pseudomonas fluorescens* | U19743 | 317aa | 223aa | 35 | 187aa | 1.10E−10 |
| PG4 | Outer membrane protein A, *Escherichia fergusonii* | M63352 | 243aa | 672aa | 48 | 88aa | 4.10E−10 |
| PG5 | Adhesin protein (AdcA), *Streptococcus pneumoniae* | Z71552 | 423aa | 315aa | 25 | 279aa | 9.40E−15 |
| PG6 | Hemolysin A (phyA), *Prevotella melaninogenica* | U27587 | 332aa | 324aa | 60 | 306aa | 3.00E−74 |
| PG8 | Heme uptake protein A, *Bacteriodes fragilis* | X97122 | 431aa | 598aa, 550aa, 458aa, 426aa | 79 | 417aa | 6.70E−121 |
| PG10 | Macrophage infectivity potentiator (MIP), *Legionella oakridgensis*. | U92214 | 234aa | 195aa | 50 | 201aa | 4.70E−31 |
| PG11 | Haemagglutinin (phg), *Prevotella intermedia* | AF017417 | 309aa | 313aa | 44 | 309aa | 3.60E−44 |
| PG12 | Outer membrane lipoprotein, *Haemophilus influenzae* | M68502 | 274aa | 271aa | 36 | 254aa | 9.60E−27 |
| PG13 | Ferric receptor (cfrA), *Campylobacter coli* | U80812 | 696aa | 757aa | 24 | 625aa | 1.20E−18 |
| PG14 | 36 kD antigen, *Helicobacter pylori* | U86610 | 329aa | 331aa | 37 | 326aa | 1.10E−35 |
| PG22 | Alpha-hemolysin gene, *Aeromonas hydrophila* | L36462 | 85aa | 106aa | 57 | 67aa | 2.60E−14 |
| PG24 | Putative hemolysin, *Streptococcus mutans* | AF051356 | 445aa | 417aa | 29 | 432aa | 1.80E−29 |
| PG25 | Cysteine protease, *Porphyromonas gingivalis* | U54691 | 1723aa | 293aa | 42 | 142aa | 1.10E−12 |
| PG27 | TonB linked adhesin, *Porphyromonas gingivalis* | Y07618 | 1097aa | 312aa | 45 | 360aa | 3.20E−41 |
| PG28 | Cysteine protease/hemagglutinin, *Porphyromonas gingivalis* | S75942 | 886aa | 843aa | 35 | 838aa | 7.00E−90 |
| PG54 | Protease 1, *Achromobacter lyticus* | J5128 | 653aa | 940aa | 24 | 695aa | 1.50E−22 |
| PG57 | Cysteine protease, *Porphyromonas gingivalis* | U68468 | 1358aa | 924aa, 922aa, 921aa | 31 | 742aa | 1.40E−23 |
| PG75 | Class 3 outer membrane porin (porB), *Neisseria meningitidis* | U07191 | 332aa | 391aa | 23 | 239aa | 4.60E−01 |
| PG91 | Neuraminidase (nanH), *Bacteroides fragilis* | D28493 | 544aa | 540aa | 24 | 251aa | 1.60E+00 |
| PG94 | Arginyl endopeptidase, *Porphyromonas gingivalis* | D26470 | 991aa | 1157aa | 24 | 328aa | 7.60E−08 |
| PG21 | Surface antigen gene, *Methanosarcina mazei* | X84710 | 783aa | 821aa | 37 | 331aa | 6.20E−33 |

TABLE 3

Results of PSORT, SignalP and TopPred analysis of the proteins. The signal present column indicates the presence of a signal sequence detected with either PSORT or SignalP. The terms in parentheses indicates the type of signal sequence as determined by PSORT. The cell location & probability values are generated by PSORT and represent the probability of the protein being in the cell compartments outer membrane (OM), inner membrane (IM), periplasmic space (PC) or cytoplasm (C). The number of transmembrane domains (TMDs) was determined by TopPred and does not include uncleavable signal sequences.

| Protein name | Protein seqID number | Protein Length | Signal Present | Methionine in ORF | SignalP cleavage site | PSORT cleavage site | Cell Location & probability OM | IM | PS | C | C-terminal Amino Acid | Number of TMD's |
|---|---|---|---|---|---|---|---|---|---|---|---|---|
| PG1 | 386 | 451aa | Y | 1 | 24 | 34 | 0 | 0 | 0 | 0.22 | N | 0 |
| PG2 | 424 | 1017aa | Y | 1 | 20 | 20 | 0.94 | 0 | 0.33 | 0 | F | 3 |

TABLE 3-continued

Results of PSORT, SignalP and TopPred analysis of the proteins. The signal present column indicates the presence of a signal sequence detected with either PSORT or SignalP. The terms in parentheses indicates the type of signal sequence as determined by PSORT. The cell location & probability values are generated by PSORT and represent the probability of the protein being in the cell compartments outer membrane (OM), inner membrane (IM), periplasmic space (PC) or cytoplasm (C). The number of transmembrane domains (TMDs) was determined by TopPred and does not include uncleavable signal sequences.

| Protein name | Protein seqID number | Protein Length | Signal Present | Methionine in ORF | SignalP cleavage site | PSORT cleavage site | OM | IM | PS | C | C-terminal Amino Acid | Number of TMD's |
|---|---|---|---|---|---|---|---|---|---|---|---|---|
| PG2   | 425 | 1014aa | Y              | 2 | 17 | 17 | 0.94 | 0    | 0.29 | 0    | F | 3 |
| PG3   | 434 | 223aa  | Y (lipoprotein) | 1 | —  | 18 | 0.79 | 0.76 | 0    | 0    | K | 3 |
| PG4   | 447 | 672aa  | Y (lipoprotein) | 1 | 22 | 22 | 0.79 | 0.7  | 0    | 0    | R | 0 |
| PG5   | 458 | 315aa  | Y              | 1 | 40 | 35 | 0    | 0.25 | 0    | 0    | R | 0 |
| PG6   | 475 | 324aa  | N              | 1 | —  | —  | 0    | 0    | 0    | 0.2  | S | 1 |
| PG8   | 498 | 598aa  | N              | 1 | —  | —  | 0    | 0    | 0    | 0.22 | N | 0 |
| PG8   | 499 | 550aa  | N              | 2 | —  | —  | 0    | 0    | 0    | 0.25 | N | 0 |
| PG8   | 500 | 458aa  | N              | 3 | —  | —  | 0    | 0    | 0    | 0.34 | N | 0 |
| PG8   | 501 | 426aa  | N              | 4 | —  | —  | 0    | 0    | 0    | 0.24 | N | 0 |
| PG10  | 387 | 195aa  | N              | 1 | —  | —  | 0    | 0    | 0    | 0.11 | K | 0 |
| PG11  | 400 | 313aa  | Y              | 1 | 22 | 26 | 0.24 | 0    | 0.93 | 0    | R | 1 |
| PG12  | 411 | 271aa  | Y (lipoprotein) | 3 | 27 | 29 | 0.79 | 0.7  | 0    | 0    | R | 0 |
| PG13  | 419 | 757aa  | Y              | 1 | 23 | 25 | 0.94 | 0    | 0.29 | 0    | N | 0 |
| PG14  | 420 | 331aa  | Y (uncleavable) | 1 | 35 | 26 | 0    | 0.58 | 0    | 0    | K | 1 |
| PG21  | 426 | 821aa  | Y              | 2 | 24 | 27 | 0.34 | 0    | 0.37 | 0    | G | 1 |
| PG22  | 427 | 106aa  | Y (uncleavable) | 1 | 41 | 41 | 0    | 0.29 | 0    | 0    | P | 0 |
| PG24  | 429 | 417aa  | Y              | 1 | 19 | 19 | 0    | 0.44 | 0    | 0    | N | 3 |
| PG25  | 430 | 293aa  | Y              | 1 | 27 | 28 | 0.2  | 0    | 0.62 | 0    | R | 0 |
| PG27  | 431 | 312aa  | N              | 1 | —  | —  | 0    | 0    | 0    | 0.28 | Q | 1 |
| PG28  | 432 | 843aa  | Y              | 1 | 21 | 21 | 0.93 | 0    | 0.24 | 0    | H | 1 |
| PG29  | 433 | 290aa  | Y              | 1 | 18 | 16 | 0.28 | 0    | 0.94 | 0    | K | 1 |
| PG54  | 463 | 940aa  | Y              | 1 | 27 | 20 | 0.86 | 0    | 0.25 | 0    | Q | 5 |
| PG57  | 467 | 925aa  | Y              | 1 | 28 | 24 | 0.53 | 0    | 0.2  | 0    | P | 3 |
| PG57  | 468 | 922aa  | Y              | 2 | 25 | 21 | 0.53 | 0    | 0.2  | 0    | P | 3 |
| PG57  | 469 | 921aa  | Y              | 3 | 24 | 20 | 0.53 | 0    | 0.2  | 0    | P | 3 |
| PG68  | 484 | 1226aa | Y              | 1 | 25 | 25 | 0.91 | 0    | 0.31 | 0    | Y | 0 |
| PG68  | 485 | 1225aa | Y              | 2 | 24 | 24 | 0.91 | 0    | 0.31 | 0    | Y | 0 |
| PG75  | 493 | 391aa  | Y              | 1 | 26 | 26 | 0.94 | 0    | 0.3  | 0    | H | 1 |
| PG76  | 494 | 446aa  | Y              | 1 | 21 | 22 | 0.94 | 0    | 0.32 | 0    | V | 3 |
| PG91  | 520 | 540aa  | Y              | 1 | 25 | 25 | 0.85 | 0    | 0.30 | 0    | E | 0 |
| PG94  | 523 | 1157aa | Y              | 1 | 23 | 28 | 0.8  | 0    | 0.25 | 0    | Q | 5 |
| PG96  | 525 | 563aa  | Y              | 1 | 23 | 23 | 0.40 | 0    | 0.33 | 0    | K | 0 |
| PG97  | 526 | 437aa  | Y              | 1 | 23 | 23 | 0.32 | 0    | 0.65 | 0    | Q | 0 |
| PG98  | 527 | 318aa  | Y (lipoprotein) | 1 | 19 | 19 | 0.79 | 0.7  | 0    | 0    | L | 1 |
| PG99  | 528 | 461aa  | Y (uncleavable) | 1 | 22 | 20 | 0    | 0    | 0.3  | 0    | R | 0 |
| PG100 | 388 | 279aa  | Y              | 1 | 20 | 18 | 0.26 | 0    | 0.54 | 0    | I | 0 |
| PG102 | 389 | 562aa  | Y              | 1 | 29 | 29 | 0.19 | 0    | 0.4  | 0    | S | 3 |
| PG102 | 390 | 558aa  | Y              | 2 | 25 | 25 | 0.26 | 0    | 0.46 | 0    | S | 3 |
| PG104 | 391 | 391aa  | Y              | 1 | 17 | 17 | 0.62 | 0    | 0.22 | 0    | R | 0 |

TABLE 4

Percentage identity and percentage similarity of various proteins with the 70 amino acids from the C-terminal of the P. gingivalis arginine protease 1 (RGP1), arginine protease 2 (RGP2), and the cysteine protease/hemagglutinin (prtT).

| Protein name | Percent identity | | | Percent similarity | | |
|---|---|---|---|---|---|---|
| | RGP1 | RGP2 | prtT | RGP1 | RGP2 | prtT |
| PG21  | 17 | 29 | 21 | 40 | 57 | 49 |
| PG25  | 43 | 41 | 9  | 64 | 73 | 14 |
| PG27  | 41 | 33 | 7  | 73 | 74 | 11 |
| PG28  | 21 | 26 | 34 | 49 | 57 | 74 |
| PG54  | 19 | 13 | 16 | 40 | 43 | 33 |
| PG57  | 11 | 14 | 19 | 20 | 24 | 34 |
| PG91  | 31 | 21 | 39 | 57 | 53 | 74 |
| PG96  | 0  | 13 | 20 | 0  | 24 | 43 |
| PG97  | 10 | 26 | 33 | 14 | 47 | 61 |
| PG98  | 16 | 20 | 0  | 47 | 54 | 0  |
| PG99  | 19 | 0  | 26 | 41 | 0  | 54 |
| PG100 | 20 | 21 | 24 | 39 | 57 | 41 |
| PG102 | 27 | 20 | 31 | 50 | 61 | 61 |
| PG104 | 16 | 23 | 26 | 46 | 44 | 49 |

TABLE 5

Percentage identity and percentage similarity of various proteins with the TonBIII box of P. gingivalis.

| Protein name | Percent identity | Percent similarity |
|---|---|---|
| PG2  | 46 | 71 |
| PG13 | 57 | 93 |

Cloning, Expression and Purification of Recombinant P. Gingivalis Genes.

PG1

Oligonucleotides to the 5' and 3' regions of the deduced protein were used to amplify the gene of interest from a preparation of P. gingivalis W50 genomic DNA using the TaqPlus Precision PCR System (Stratagene) and a PTC-100 (MJ Research) thermal cycler or similar device. The 5' oligonucleotide primer sequence was GCGCCATATGCTGGC-CGAACCGGCC (SEQ ID NO: 149) the 3' oligonucleotide primer sequence was GCGCCTCGAGTCAATTCATTTC-CTTATAGAG (SEQ ID NO: 150). The PCR fragment was purified, digested with Nde I, Xho I restriction enzymes (Promega) and ligated into the corresponding sites of the plasmid pProEx-1 (Gibco-BRL) and transformed into *E. coli* ER1793 cells (a gift from Elizabeth Raleigh, New England Biolabs). A resulting clone expressing the correct insert was selected and induced with or without 0.1 mM IPTG (Promega) for expression of the recombinant protein. Expression of the recombinant protein was determined by SDS-PAGE analysis and Western Blot using the one of the rabbit antisera described above or an anti-hexahistidine antibody (Clontech) that detects the hexahistidine tag that was fused to the *P. gingivalis* recombinant protein. PG1 was purified by disruption of the *E. coli* cells by sonication in binding buffer (Novagen) and solubilisation by the addition of sarkosyl (N-Lauroyl sarcosine) to a 1% final concentration. There after the preparation was diluted to 0.1% sarkosyl in binding buffer, bound to a Nickel-nitrilotriacetic acid column (Ni-NTA; Qiagen), after washing bound proteins were eluted with 1M imidazole in elution buffer (Novagen) according to the Qiagen recommendations with 0.1% sarkosyl added to all buffers. Following purification samples were dialysed against 500 mM NaCl, 20 mM Tris, 0.1% sarkosyl at pH7.4 to remove the imidazole, concentrated as required and stored at 4° C. until used. Purity and antigenicity were assessed by SDS-PAGE and Western blot using selected antisera (from those described above) and the protein concentration was determined by the BCA assay (Pierce).

PG2

The methods used for PG2 were essentially the same as for PG1 with the following exceptions. The 5' oligonucleotide primer sequence was CGCGGTATACATGAAAAGAAT-GACGC (SEQ ID NO: 151), the 3' oligonucleotide primer sequence was CGCGAGATCTGAAAGACAACT-GAATACC (SEQ ID NO: 152) and the PCR product was cloned into pGex-stop RBS(IV) (Patent application WO9619496, J C Cox, S E Edwards, I Frazer and E A Webb. Variants of human papilloma virus antigens) using the BstZ 171 and Bgl II restriction sites. 2% sarkosyl was used to solubilise PG2 and 8M urea was added to the solubilisation buffer and to all other buffers. Urea was removed from the purified protein by sequential dialysis (4M then 2M then 1M then 0.5M then 0M urea all in 50 mM Tris, 500 mM NaCl, 0.1% sarkosyl, pH7.4). Purified protein was stored at 4° C. until required.

PG3

The methods used for PG3 were essentially the same as for PG1 with the following exceptions. The 5' oligonucleotide primer sequence was GCGCGTATACATGAAGAAAT-CAAGTGTAG (SEQ ID NO: 153), the 3' oligonucleotide primer sequence was GCGCAGATCTCTTCAGCGTACCT-TGCTGTG (SEQ ID NO: 154) and DNA was amplified with Pfu DNA polymerase (Stratagene). The PCR product was cloned directly into pCR-Blunt and transformed into *E. coli* Top10F'(InVitrogen) before subcloning into the expression plasmid pGex-stop RBS(IV) using the Bst Z171 and Bgl II restriction sites and transformed into *E. coli* BL21DE3 (Pharmacia Biotech). The following modifications were made to the purification of PG3 from the PG1 method. Cells expressing the recombinant protein were disrupted by sonication in binding buffer and the insoluble inclusion bodies concentrated by centrifugation. Inclusion bodies were then solubilised in 6M urea (Sigma) in binding buffer and eluted with 6M urea added to the elution buffer. In some instances 6M guanidine hydrochloride (Sigma) was used instead of urea for these steps. Urea (or guanidine hydrochloride when it was substituted) was removed from the purified protein by sequential dialysis against reducing levels of urea (3M then 1.5M then 0.5M then 0M urea all in 50 mM Tris, 500 mM NaCl, 8% glycerol, pH7.4). Purified protein was stored frozen at −80° C. until required. Protein concentration was determined by the Coomassie Plus protein assay (Pierce).

PG4

The methods used for PG4 were essentially the same as for PG3 with the following exceptions. The 5' oligonucleotide primer sequence was CTTCTGTATACTTACAGCGGA-CATCATAAAATC (SEQ ID NO: 155), the 3' oligonucleotide primer sequence was TTCCAGGAGGGTACCACG-CAACTCTTCTTCGAT (SEQ ID NO: 156) and DNA was amplified with the Tth XL PCR kit (Perkin Elmer). The PCR product was cloned into the expression plasmid pGex-stop RBS(IV) using the Bst Z171 and Kpn I restriction sites and transformed into *E. coli* ER1793.

PG5

The methods used for PG5 were essentially the same as for PG3 with the following exceptions. The 5' oligonucleotide primer sequence was TTGCAACATATGATCAGAAC-GATACTTTCA (SEQ ID NO: 157) the 3' oligonucleotide primer sequence was AGCAATCTCGAGCGGTTCAT-GAGCCAAAGC (SEQ ID NO: 158) and DNA was amplified with the Tth XL PCR kit. The PCR product was cloned into the expression plasmid pET24 (Novagen) using the Nde I and Xho I restriction sites and transformed into *E. coli* BL21 (Pharmacia Biotech). Removal of urea was not proceeded past 1M urea as the protein was insoluble at lower concentrations of urea. Purified protein was stored at 4° C. until required.

PG6

The methods used for PG6 were essentially the same as for PG3 with the following exceptions. The 5' oligonucleotide primer sequence was TAAACATATGTGCCTCGAAC-CCATAATTGCTCCG (SEQ ID NO: 159), the 3' oligonucleotide primer sequence was CGTCCGCG-GAAGCTTTGATCGGCCATTGCTACT (SEQ ID NO: 160) and DNA was amplified with the Tth XL PCR kit. The PCR product was cloned into the expression plasmid pET24a using the Nde I and Hind III restriction sites and transformed into *E. coli* BL21.

PG8

The methods used for PG8 were essentially the same as for PG3 with the following exceptions. The 5' oligonucleotide primer sequence was CGCGGTATACATGGAGTTCAA-GATTGTG (SEQ ID NO:161), the 3' oligonucleotide primer sequence was CGCGAGATCTGTTTTCTGAAAGCTTTTC (SEQ ID NO: 162) and DNA was amplified with the TaqPlus Precision PCR System. The PCR product was cloned into the expression plasmid pProEx-1 using the Nde I and Xho I restriction sites and transformed into *E. coli* ER1793.

PG8A

PG8A is a shortened version of PG8 and has the first 173 amino acids removed. The methods used for PG8A were essentially the same as for PG3 with the following exceptions. The 5' oligonucleotide primer sequence was CGCGGTATA-CATGGAAAACTTAAAGAAC (SEQ ID NO: 163), the 3' oligonucleotide primer sequence was CGCGAGATCT-GTTTTCTGAAAGCTTTTC (SEQ ID NO: 164) and DNA was amplified with the TaqPlus Precision PCR System. The PCR product was cloned into the expression plasmid pGex-stop RBS(IV) using the Bst Z171 and Bgl II restriction sites and transformed into *E. coli* ER1793. Prior to dialysis of the purified protein EDTA (Sigma) was added to a final concentration of 10 mM.

PG10

The methods used for PG10 were essentially the same as for PG3 with the following exceptions. The 5' oligonucleotide primer sequence was CGCGGATATCATGGATAAAGT-GAGCTATGC (SEQ ID NO:165), the 3' oligonucleotide primer sequence was CGCGAGATCTTTTGTTGATACT-CAATAATTC (SEQ ID NO: 166) and DNA was amplified with the TaqPlus Precision PCR System. The PCR product was digested with Eco RV and Bgl II and ligated into the expression plasmid pGex-stop RBS(IV) using the Bst Z171 and Bgl II restriction sites and transformed into *E. coli* ER1793.

PG11

The methods used for PG11 were essentially the same as for PG1 with the following exceptions. The 5' oligonucleotide primer sequence was GCGCGTATACATGAGAGCAAA-CATTTGGCAGATACTTTCCG (SEQ ID NO: 167), the 3' oligonucleotide primer sequence was GCGCAGATCTGCG-CAAGCGCAGTATATCGCC (SEQ ID NO: 168) and DNA was amplified with Tli DNA polymerase (Promega). The PCR product was cloned into pCR-Blunt and transformed into *E. coli* Top10F' before subcloning into the expression plasmid pGex-stop RBS(IV) using the Bst Z171 and Bgl II restriction sites and transformed into *E. coli* ER1793. PG11 was purified by solubilisation of *E. coli* cells with 2% sarkosyl in binding buffer (Qiagen) which was diluted to 0.1% sarkosyl in binding buffer, bound to a Nickel-nitrilotriacetic acid column (Ni—NTA; Qiagen), after washing bound proteins were eluted with 1M imidazole (0.7% CHAPS (Sigma) in elution buffer; Qiagen) according to the Qiagen recommendations. Following purification samples were dialysed against 500 mM NaCl, 20 mM Tris, 0.7% CHAPS, 20% glycerol (Sigma) at pH7.4 to remove the imidazole, concentrated as required and stored at 4° C. until used.

PG12

The methods used for PG12 were essentially the same as for PG1 with the following exceptions. The 5' oligonucleotide primer sequence was GCGCGTATACATGAATAGCAGA-CATCTGACAATCACAATCATTGCCGG (SEQ ID NO: 169), the 3' oligonucleotide primer sequence was GCGCA-GATCTGCTGTTCTGTGAGTGCAGTTGTTTAAGTG (SEQ ID NO: 170) and DNA was amplified with Tli DNA polymerase. The PCR product was cloned into pCR-Blunt and transformed into *E. coli* Top10F' cells before subcloning into the expression plasmid pGex-stop RBS(IV) using the Bst Z171 and Bgl II restriction sites and transformed into *E. coli* BL21. Purification of the recombinant protein was essentially the same as PG11 except 0.5% DHPC (1,2-Diheptanoyl-sn-glycero-3-phosphocholine; Avanti) in 50 mM Tris, 50 mM NaCl, pH8.0 was used to solubilise the inclusion bodies instead of sarkosyl and the DHPC was diluted to 0.1% before addition to the Ni—NTA and 0.1% DHPC was added to all buffers.

PG13

The methods used for PG13 were essentially the same as for PG3 with the following exceptions. The 5' oligonucleotide primer sequence was GCGCCATATGCGGACAAAAAC-TATCTTTTTTGCG (SEQ ID NO:171), the 3' oligonucleotide primer sequence was GCGCCTCGAGGTTGT-TGAATCGAATCGCTATTTGAGC (SEQ ID NO: 172) and DNA was amplified with Tli DNA polymerase. The PCR product was cloned the expression plasmid pET24b using the Nde I and Xho I restriction sites and transformed into *E. coli* BL21. Purification of the recombinant protein was essentially the same as PG3 using 6M urea and 1% NOG (n-octyl glucoside; Sigma) was added to the dialysis buffer. Removal of urea was not proceeded past 2M urea as the protein was insoluble at lower concentrations of urea. Purified protein was stored at 4° C. until required.

PG14

The methods used for PG12 were essentially the same as for PG1 with the following exceptions. The 5' oligonucleotide primer sequence was GCGCGGCGCCATGACGGACAA-CAAACAACGTAATATCG (SEQ ID NO: 173), the 3' oligonucleotide primer sequence was GCGCCTCGAGTTACT-TGCGTATGATCACGGACATACCC (SEQ ID NO: 174) and DNA was amplified with Tli DNA polymerase. The PCR product was cloned the expression plasmid pProEx-1 using the Ehe I and Xho I restriction sites and transformed into *E. coli* BL21. Purification of the recombinant protein was essentially the same as PG12.

PG22

The methods used for PG22 were essentially the same as for PG1 with the following exceptions. The 5' oligonucleotide primer sequence was CCCCGGATCCGATGCGACTGAT-CAAGGC (SEQ ID NO: 175), the 3' oligonucleotide primer sequence was CCCCCTCGAGCGGAACGGGGTCAT-AGCC (SEQ ID NO: 176) and DNA was amplified with the TaqPlus Precision PCR System. The PCR product was cloned into the expression plasmid pET24b using the Bam HI and Xho I restriction sites and transformed into *E. coli* BL21DE3. Once PG22 was purified dialysis was performed in the same manner as for PG1 but in the presence of 1M imidazole.

PG24

The methods used for PG24 were essentially the same as for PG3 with the following exceptions. The 5' oligonucleotide primer sequence was CGCGGTATACATGAATTACCTG-TACATAC (SEQ ID NO: 177), the 3' oligonucleotide primer sequence was CGCGGGATCCGTTCGATTGGTCGTC-GATGG (SEQ ID NO: 178) and DNA was amplified with the TaqPlus Precision PCR System. The PCR product was digested with Bst Z171 and Bam HI and ligated into the expression plasmid pGex-stop RBS(IV) using the Bst Z171 and Bgl II restriction sites and transformed into *E. coli* ER1793. Due to the low level of expression of PG24 purification was not proceeded with except on small scale.

PG24A

A modified version of PG24 was also cloned and expressed. PG24A is the same as PG24 with the predicted N-terminal sequence removed. The methods used for PG24A were essentially the same as for PG3 with the following exceptions. The 5' oligonucleotide primer sequence was CGCGCATATGGAGATTGCTTTCCTTTCTTCG (SEQ ID NO: 179), the 3' oligonucleotide primer sequence was CGCGCTCGAGTTAGTTCGATTGGTCGTCG (SEQ ID NO: 180) and DNA was amplified with the TaqPlus Precision PCR System. The PCR product was cloned into the expression plasmid pProEx-1 using the Nde I and Xho I restriction sites and transformed into *E. coli* ER1793. Purification of the recombinant protein was essentially the same as PG3 except 8M urea was used to solubilise the inclusion bodies and in the buffers used for the Ni—NTA column purification. Urea was removed by sequential dialysis (4M then 2M, then 1M then 0.5M then 0M urea all in 50 mM Tris, 500 mM NaCl, 8% glycerol, pH7.4). Purified protein was stored frozen at −80° C. until required.

PG29

The methods used for PG29 were essentially the same as for PG3 with the following exceptions. The 5' oligonucleotide primer sequence was GCGCGATATCGCTAGCAT-GAAAAAGCTATTTCTC (SEQ ID NO: 181), the 3' oligonucleotide primer sequence was GCGCAGATCTCTC-GAGTTTGCCATCGGATTGCGGATTG (SEQ ID NO: 182) and DNA was amplified with Pfu DNA polymerase was used. The PCR product was cloned into pCR-Blunt (InVitrogen) and transformed into *E. coli* Top10F' before subcloning into the expression plasmid pGex-stop RBS(IV) using the EcoR V and Bgl II restriction sites and transformed into *E. coli* BL21. 6M urea was used throughout the purification process.

PG54

The methods used for PG54 were essentially the same as for PG3 with the following exceptions. The predicted N-terminal signal sequence was removed from the recombinant protein. The 5' oligonucleotide primer sequence was CGCTGAATTCCAGATTTCGTTCGGAGGGGAACCC (SEQ ID NO: 183), the 3' oligonucleotide primer sequence was CTATGCGGCCGCCTGCTTCACGATCTTTTGGCTCA (SEQ ID NO: 184) and DNA was amplified with the Tth XL PCR kit. The PCR product was cloned into the expression plasmid pET24a using the Eco RI and Not I restriction sites and transformed into *E. coli* BL21DE3. Expression studies and immunoreactivity studies were carried out on whole *E. coli* lysates. Purification was not done for these studies.

PG57

The methods used for PG57 were essentially the same as for PG3 with the following exceptions. The predicted N-terminal signal sequence was removed from the recombinant protein. The 5' oligonucleotide primer sequence was TGCTGGATCCCAAGAGATCTCAGGCATGAATGCA (SEQ ID NO: 185), the 3' oligonucleotide primer sequence was GAGTGCGGCCGCTCGGCCTCTTTATCTCTACCTTTTC (SEQ ID NO: 186) and DNA was amplified with the Tth XL PCR kit. The PCR product was cloned into the expression plasmid pET24a using the Bam HI and Not I restriction sites and transformed into *E. coli* BL21DE3. Expression studies and immunoreactivity studies were carried out on whole *E. coli* lysates. Purification was not done for these studies.

PG68

The methods used for PG68 were essentially the same as for PG3 with the following exceptions. The predicted N-terminal signal sequence was removed from the recombinant protein. The 5' oligonucleotide primer sequence was GCTTGCGGCCGCCCTTATGAAAGATTTGCAGAT (SEQ ID NO: 187), the 3' oligonucleotide primer sequence was GGTGCTCGAGTATACTCAACAAGCACCTTATGCAC (SEQ ID NO: 188) and DNA was amplified with the Tth XL PCR kit. The PCR product was cloned into the expression plasmid pET24a using the Not I and Xho I restriction sites and transformed into *E. coli* BL21DE3. Expression studies and immunoreactivity studies were carried out on whole *E. coli* lysates. Purification was not done for these studies.

PG75

The methods used for PG75 were essentially the same as for PG3 with the following exceptions. The predicted N-terminal signal sequence was removed from the recombinant protein. The 5' oligonucleotide primer sequence was GGCGGGATCCGCTCAGGAGCAACTGAATGTGGTA (SEQ ID NO: 189), the 3' oligonucleotide primer sequence was GAGTGCGGCCGCTGTGGAACAAATTGCGCAATCCATC (SEQ ID NO: 190) and DNA was amplified with the Tth XL PCR kit. The PCR product was cloned into the expression plasmid pET24a using the Bam HI and Not I restriction sites and transformed into *E. coli* BL21DE3. Expression studies and immunoreactivity studies were carried out on whole *E. coli* lysates. Purification was not done for these studies.

PG76

The methods used for PG76 were essentially the same as for PG3 with the following exceptions. The predicted N-terminal signal sequence was removed from the recombinant protein. The 5' oligonucleotide primer sequence was AGCAGAATTCGGAAACGCACAGAGCTTTTGGGAA (SEQ ID NO: 191), the 3' oligonucleotide primer sequence was GAGTGCGGCCGCTTACCTGCACCTTATGACTGAATAC (SEQ ID NO: 192) and DNA was amplified with the Tth XL PCR kit. The PCR product was cloned into the expression plasmid pET24a using the Eco RI and Not I restriction sites and transformed into *E. coli* BL21DE3. Expression studies and immunoreactivity studies were carried out on whole *E. coli* lysates. Purification was not done for these studies.

PG91

The methods used for PG91 were essentially the same as for PG3 with the following exceptions. The predicted N-terminal signal sequence was removed from the recombinant protein. The 5' oligonucleotide primer sequence was TGCTGAATTCCAGACGATGGGAGGAGATGATGTC (SEQ ID NO: 193), the 3' oligonucleotide primer sequence was GAGTGCGGCCGCTTTCCACGATGAGCTTCTCTACGAA (SEQ ID NO: 194) and DNA was amplified with the Tth XL PCR kit. The PCR product was cloned into the expression plasmid pET24a using the Eco RI and Not I restriction sites and transformed into *E. coli* BL21DE3. Expression studies and immunoreactivity studies were carried out on whole *E. coli* lysates. Purification was not done for these studies.

PG94

The methods used for PG94 were essentially the same as for PG3 with the following exceptions. The predicted N-terminal signal sequence was removed from the recombinant protein. The 5' oligonucleotide primer sequence was GGCCGAGCTCCAAGAGGAAGGTATTTGGAATACC (SEQ ID NO: 195), the 3' oligonucleotide primer sequence was GAGTGCGGCCGCTTTGTCCTACCACGATCATTTTCTT (SEQ ID NO: 196) and DNA was amplified with the Tth XL PCR kit. The PCR product was cloned into the expression plasmid pET24a using the Eco RI and Not I restriction sites and transformed into *E. coli* BL21DE3. Expression studies and immunoreactivity studies were carried out on whole *E. coli* lysates. Purification was not done for these studies.

PG96

The methods used for PG96 were essentially the same as for PG3 with the following exceptions. The predicted N-terminal signal sequence was removed from the recombinant protein. The 5' oligonucleotide primer sequence was TGCTGAGCTCCAAACGCAAATGCAAGCAGACCGA (SEQ ID NO: 197), the 3' oligonucleotide primer sequence was GAGTGCGGCCGCTTTTGAGAATTTTCATTGTCTCACG (SEQ ID NO: 198) and DNA was amplified with the Tth XL PCR kit. The PCR product was cloned into the expression plasmid pET24a using the Sac I and Not I restriction sites and transformed into *E. coli* BL21DE3. Expression studies and immunoreactivity studies were carried out on whole *E. coli* lysates. Purification was not done for these studies.

PG97

The methods used for PG97 were essentially the same as for PG3 with the following exceptions. The predicted N-terminal signal sequence was removed from the recombinant protein. The 5' oligonucleotide primer sequence was GGCGGGATCCCAGTTTGTTCCGGCTCCCACCACA (SEQ ID NO: 199), the 3' oligonucleotide primer sequence was GAGTGCGGCCGCTCTGTTTGATGAGCTTAGTGGTATA (SEQ ID NO: 200) and DNA was amplified with the Tth XL PCR kit. The PCR product was cloned into the expression plasmid pET24a using the Bam HI and Not I restriction sites and transformed into *E. coli* BL21DE3.

Expression studies and immunoreactivity studies were carried out on whole *E. coli* lysates. Purification was not done for these studies.

PG98

The methods used for PG98 were essentially the same as for PG3 with the following exceptions. The predicted N-terminal signal sequence was removed from the recombinant protein. The 5' oligonucleotide primer sequence was AGCAGAATTCCAAGAAAGAGTCGATGAAAAAGTA (SEQ ID NO: 201), the 3' oligonucleotide primer sequence was GAGTGCGGCCGCTTAGCTGTGTAACAT-TAAGTTTTTTATTGAT (SEQ ID NO: 202) and DNA was amplified with the Tth XL PCR kit. The PCR product was cloned into the expression plasmid pET24a using the Eco RI and Not I restriction sites and transformed into *E. coli* BL21DE3. Expression studies and immunoreactivity studies were carried out on whole *E. coli* lysates. Purification was not done for these studies.

PG99

The methods used for PG99 were essentially the same as for PG3 with the following exceptions. The predicted N-terminal signal sequence was removed from the recombinant protein. The 5' oligonucleotide primer sequence was TGCTGAATTCAAGGACAATTCTTCTTACAAACCT (SEQ ID NO: 203), the 3' oligonucleotide primer sequence was GAGTGCGGCCGCTTCGAATCACGACTTTTCTCACAAA (SEQ ID NO: 204) and DNA was amplified with the Tth XL PCR kit. The PCR product was cloned into the expression plasmid pET24a using the Eco RI and Not I restriction sites and transformed into *E. coli* BL21DE3. Expression studies and immunoreactivity studies were carried out on whole *E. coli* lysates. Purification was not done for these studies.

PG100

The methods used for PG100 were essentially the same as for PG3 with the following exceptions. The predicted N-terminal signal sequence was removed from the recombinant protein. The 5' oligonucleotide primer sequence was GGCAGAATTCCAGTCTTTGAGCACAATCAAAGTA (SEQ ID NO: 205), the 3' oligonucleotide primer sequence was GAGTGCGGCCGCTGATAGCCAGCTTGATGCTCTTAGC (SEQ ID NO: 206) and DNA was amplified with the Tth XL PCR kit. The PCR product was cloned into the expression plasmid pET24a using the Eco RI and Not I restriction sites and transformed into *E. coli* BL21DE3. Expression studies and immunoreactivity studies were carried out on whole *E. coli* lysates. Purification was not done for these studies.

PG102

The methods used for PG102 were essentially the same as for PG3 with the following exceptions. The predicted N-terminal signal sequence was removed from the recombinant protein. The 5' oligonucleotide primer sequence was GGC-CGAATTCCAGATGGATATTGGTGGAGACGAT (SEQ ID NO: 207), the 3' oligonucleotide primer sequence was GAGTGCGGCCGCTCTCTACAAT-GATTTTTTCCACGAA (SEQ ID NO: 208) and DNA was amplified with the Tth XL PCR kit. The PCR product was cloned into the expression plasmid pET24a using the Eco RI and Not I restriction sites and transformed into *E. coli* BL21DE3. Expression studies and immunoreactivity studies were carried out on whole *E. coli* lysates. Purification was not done for these studies.

PG104

The methods used for PG104 were essentially the same as for PG3 with the following exceptions. The predicted N-terminal signal sequence was removed from the recombinant protein. The 5' oligonucleotide primer sequence was GAACGGATCCAACGTGTCTGCTCAGTCACCCCGA (SEQ ID NO: 209), the 3' oligonucleotide primer sequence was GAGTGCGGCCGCTTCTGAGC-GATACTTTTGCACGTAT (SEQ ID NO: 210) and DNA was amplified with the Tth XL PCR kit. The PCR product was cloned into the expression plasmid pET24a using the Bam HI and Not I restriction sites and transformed into *E. coli* BL21DE3. Expression studies and immunoreactivity studies were carried out on whole *E. coli* lysates. Purification was not done for these studies.

Animal Antisera and Human Patient Sera.

Various antisera were raised for detecting the expression and refolding of the recombinant *P. gingivalis* proteins. A whole cell antisera was raised by injecting New Zealand White rabbits with 3 doses of sonicated *P. gingivalis* (strain W50) containing approximately 2 mg of protein. The first dose was given in Freunds complete adjuvant (FCA) and the second and third doses were given in Freunds incomplete adjuvant (IFA) at 3 week intervals. Doses (1 ml) were given intramuscularly into the hind legs and rabbits bled 7 days after the last dose, the blood clotted and serum removed and stored at −20° C. until required. A second rabbit antisera was produced in a similar manner but using a sarkosyl insoluble fraction (each dose was 0.69 mg of protein) derived from *P. gingivalis* W50 according to the method of Doidg and Trust T. et al 1994 as the immunogen. A third rabbit antisera was produced in a similar manner to the first only the sarkosyl soluble fraction (1 mg of protein per dose) derived from *P. gingivalis* W50 cells according to the method of Doidg P. and Trust T J. (1994 Infect Immun 62:4526-33) was used as the immunogen.

A "protected rat serum" pool was also used in these studies and was obtained from rats immunised with formalin killed whole *P. gingivalis* cells in FIA (strain ATCC 33277; 2 doses of $2 \times 10^9$ cells, 3 weeks apart). Rats were then challenged 2 weeks after their last dose with live *P. gingivalis* cells (strain 33277) given orally as previously described (Klaussen B. et al. 1991, Oral Microbiol Immunol 6:193-201) and the serum obtained from these rats 6 weeks after the final challenge inoculation at the time of sacrifice.

Human sera were obtained from adult patients undergoing treatment or assessment for periodontitis at an outpatient clinic. These patients had at least 6 teeth with 6 mm attachment loss and had *P. gingivalis* present in their sub-gingival plaque as detected using a *P. gingivalis* specific DNA probe. Sera was pooled from these patients and compared to a pool of sera from periodontally healthy patients.

Immunization and Murine Lesion Model Protocols

The mouse abscess model was used to assess the efficacy of immunising mice with recombinant *P. gingivalis* proteins in protecting mice from formation of a subcutaneous abscess. This model has been used by others as a predictor of potential vaccines against periodontal disease (Bird P S, et al. 1995 J. Periodontol. 66:351-362. BALB/c mice 6-8 weeks old were immunised by subcutaneously injecting them with 0.1 ml containing either 10 or 20 μg of recombinant *P. gingivalis* protein, 20 μg of *E. coli* lysate protein, $2 \times 10^9$ formalin killed cells of *P. gingivalis* strain 33277 emulsified in incomplete Freund's adjuvant (IFA; Sigma) on day 0. At day 21 mice were re-injected with the same dose and then bled 1 week later and evaluated for antibody levels. At day 35 mice all mice were challenged with approximately $2 \times 10^9$ cells of live *P. gingivalis* (ATCC 33277) by subcutaneous injection in the abdomen. Following challenge mice were monitored daily for weight loss and the size of the lesion measured for the next 10 days. Lesion sizes were measured by length and width and expressed as mm². Groups were statistically analysed using a Kruskal-Wallis one-way ANOVA and were also individually examined using the unpaired t test or Mann-Whitney rank sum test using the Instat statistical package.

FIG. 1 shows the results of one experiment at day 4 after challenge (lesions were at maximum size at this time point). Control mice immunised with *E. coli* lysate showed large lesions while mice immunised with killed cells of *P. gingivalis* strain 33277 were fully protected. This indicates that whole cells provide protection against *P. gingivalis* while *E. coli* protein immunised mice were not protected. Mice given the various PG recombinant proteins showed significant levels of protection for PG2, PG22, PG24 and PG29 ($p<0.05$ unpaired t test) while PG8A was not quite significantly different ($p=0.07$) compared to the *E. coli* control group.

FIG. 2 shows the results of a separate experiment using combinations of recombinant proteins. Mice given PG1+PG2 showed a significant level of protection compared to control mice give *E. coli* lysate ($p<0.026$ unpaired t test).

Immunoscreening

Cloned candidates were cultured in 15 ml of Terrific broth, induced with IPTG and sampled at 4 h post-induction. One ml of culture was removed, pelleted and the cells resuspended in a volume of PBS determined by dividing the OD $A_{600nm}$ of the culture by 8. An aliquot of lysate (100 µl) was added to 100 µl of 2× sample reducing buffer (125 mM Tris pH 6.8, 20% glycerol, 4% SDS, 80 mM DTT, 0.03% bromophenol blue) and boiled for 10 min. SDS-PAGE was performed according to the method of Laemmli UK. 1970 (Nature 227:680-685) using 4-20% 1.0 mm Tris-Glycine gels (Novex) according to the manufacturers recommendations. Proteins were transferred onto Hybond-C Extra nitrocellulose membranes (Amersham) by transblotting and the membranes were then blocked for 2 h at room temperature (RT) in 5% skim milk in 20 mM Tris, 0.5M NaCl, 0.05% Tween-20, pH 7.5 (TTBS).

Immunoscreening was performed separately with the rabbit anti-*P. gingivalis* whole cell serum, the rat protective serum, a pool of human periodontal patients serum, and in many cases an anti-T7-Tag antibody HRP conjugate (Novagen). Prior to use, the rabbit, rat and human sera were diluted 1/5000, 1/1000 and 1/500 respectively in 5% skim milk in TTBS and absorbed with 100 µl (for the rabbit serum) or 250 µl (for the rat and human sera) *E. coli* extract (20 mg/ml; Promega) for 6 h at RT.

Membranes were incubated overnight at RT with the absorbed antisera, or for 1 hr at RT with 1/5000 diluted anti-T7-Tag conjugate. Following 3×10 min washes with TTBS, HRP-conjugated anti-rabbit (Silenus), anti-mouse (Silenus) or anti-human (KPL) antibody, diluted 1/5000 in 5% skim milk in TTBS, was added for 1 h at RT. Membranes were washed as before, prior to addition of TMB membrane peroxidase substrate (KPL) for detection of immunoreactive proteins. Results of reactivity for the recombinant *P. gingivalis* proteins is shown in Table 7.

In addition some of the sera (pooled sera diluted 1/1000) from the mice immunised with *P. gingivalis* recombinant proteins (prior to challenge) were analysed for their reactivity against Western blots of whole native W50 *P. gingivalis* proteins using similar techniques as those outlined above. PG2, PG8A, PG29 and PG3 all showed bands at a similar molecular weight to that of the recombinant PG protein in the native W50 blot. This indicates that PG proteins are expressed in the W50 strain and that the recombinant proteins have at least some identical immunogenicity to the native proteins.

m-RNA Analysis

Hot Phenol RNA Extraction

*P. gingivalis* W50 cells (150 ml culture) were grown anaerobically to mid log phase (OD $A_{600}$=0.18) mixed with 50% glycerol and stored at −70° C. until RNA extraction. Cells were pelleted by centrifugation at 6000 g, and resuspended in 8 ml ASE (20 mM NaOAc, 0.5% SDS, 1 mM EDTA). An equal volume of 20 mM NaOAc(pH 4.5)-saturated phenol was added and mixed by shaking for 30 seconds, incubated at 65° C. for 5 minutes, followed by a further 5 second shaking and repeated incubation. After cooling, 2 ml chloroform was added and mixed by shaking for 5 seconds, and the mixture spun at 10000 g for 10 minutes at 4° C. The top aqueous phase was transferred and re-extracted by repeating the phenol and chloroform steps. The aqueous phase was transferred again and 100 U RNase inhibitor (RNAsin; Promega) were added. RNA was precipitated with 3 volumes 100% ethanol at −20° C. overnight. The RNA precipitate was recovered by centrifugation at 10000 g at 4° C. for 15 minutes, then washed with 100% ethanol, dried and resuspended in 600 µl sterile, deionised, dH$_2$O with 1 µl of fresh RNase inhibitor. RNA was aliquoted and stored at −70° C. The RNA concentration was determined spectrophotometrically. A formaldehyde RNA gel confirmed RNA integrity (Sambrook J. et al. 1989, Molecular Cloning. A laboratory manual. Cold Spring Laboratory Press, New York. 2nd Edition).

RT-PCR

The isolated RNA was used as a template for Reverse Transcription (RT) to produce cDNA. Varying RNA concentrations were used for the RT as each RNA transcript was potentially present at different levels. Subsequent amplification of the cDNA was performed using Polymerase Chain Reaction (PCR). RT-PCR was performed using GeneAmp® RNA PCR Kit (Perkin Elmer) according to the manufacturer's protocol with the following exception to the PCR; 35 cycles were performed as follows: Melt phase 95° C. for 30 seconds, Anneal phase varied between 50-60° C. for 30 seconds, Extension phase 72° C. for 1 minute. Amplification was performed in a PTC-100 Programable Thermal Controller (MJ Research Inc.). As a control to demonstrate that the amplified product did not arise from contaminating DNA, Reverse Transcriptase (RTase) was omitted from a parallel tube. The PCR products were examined against DNA markers (GIBCO 1 kB ladder) on a 1% agarose gel stained with ethidium bromide.

RT-PCR results are shown in Table 6 using the oligonucleotide primers as used in "Cloning, expression and purification of recombinant *P. gingivalis* genes" section described above, except for the following changes. For PG1 the 3' reverse primer used was GCGCCTCGAGATTCATTTCCTTATA-GAG (SEQ ID NO: 211), for PG4 the 5' forward primer was CTTCTTGTCGACTACAGCGGACATCATAAAATC (SEQ ID NO: 212) and the 3' reverse primer was TTCCAC-CTCGAGTTAACGCAACTCTTCTTCGAT (SEQ ID NO: 213), for PG6 the 5' forward primer was TAAAGAATTCT-GCCTCGAACCCATAATTGCTCCG (SEQ ID NO: 214), for PG10 the 5' forward primer was CGCGCATATG-GATAAAGTGAGCTATGC (SEQ ID NO: 215) and the 3' reverse primer was CGCGCTCGAGTTTGTTGATACT-CAATAATTC (SEQ ID NO: 216), for PG13 the 5' forward primer was GCCCGGCGCCATGCGGACAAAAAC-TATCTTTTTTGCG (SEQ ID NO: 217) and the 3' reverse primer was GCCCGGCGCCTTAGTTGTTGAATC-GAATCGCTATTTGAGC (SEQ ID NO: 218). Amplification of *P. gingivalis* transcripts is a likely indication that RNA for a specific candidate is present and that the protein is produced. However, where there is no amplification achieved this does not indicate that this gene is never transcribed and may be the result of the culture conditions or the state of the cells when harvested.

TABLE 6

Expression of PG m-RNA with in vitro grown *P. gingivalis* W50. The symbols are + band visible on agarose gel, − no band present on agarose gel, ND not detected.

| PG # | RNA µg | Annealing temp. ° C. | RT-PCR | PCR (-RT) | Approx. fragment size bp | Expected fragment size bp |
|---|---|---|---|---|---|---|
| 1 | 0.15 | 55 | + | − | 1300 | 1362 |
| 2 | 1.0 | 50 | + | − | 3200 | 3051 |
| 3 | 0.15 | 60 | + | − | 720 | 690 |
| 4 | 2.9 | 55 | − | − | N.D. | 2000 |
| 5 | 0.02 | 50 | + | − | 1000 | 947 |
| 6 | 1.0 | 55 | + | − | 1000 | 972 |
| 8A | 0.15 | 50 | + | − | 1200 | 1278 |
| 10 | 0.15 | 55 | + | − | 590 | 585 |
| 11 | 0.10 | 60 | + | − | 960 | 942 |
| 12 | 0.02 | 60 | + | − | 880 | 831 |
| 13 | 1.0 | 50 | + | − | 2150 | 2274 |
| 14 | 0.15 | 60 | + | − | 1050 | 996 |
| 22 | 1.0 | 60 | − | − | N.D. | 228 |
| 24 | 1.0 | 55 | + | + | 1150 | 1194 |
| 29 | 0.15 | 60 | + | − | 880 | 885 |

TABLE 7

Immunoblot results of proteins expressed in *E. coli* against rabbit, rat and human antisera. Deduced MW was calculated from amino acid sequence of the *P. gingivalis* proteins, some of which had their N-terminal signal sequences removed. Apparent MW was determined from SDS-PAGE gels. The N- and C-terminal tags add approximately 2.5 KDa to the deduced MW of the recombinant proteins. The symbols are + positive, − negative, +/− weak positive, ND not done.

| Protein number | Deduced MW (KDa) | Apparent MW (KDa) | T7 | Rabbit | Rat | Human |
|---|---|---|---|---|---|---|
| PG1 | 47.5 | 63 | ND | − | − | − |
| PG2 | 112.4 | 125.7 | ND | + | − | − |
| PG3 | 22.6 | 18.3 | ND | −[a] | − | − |
| PG4 | 75 | 90.6 | ND | − | − | − |
| PG5 | 34.9 | 43.8 | ND | − | − | − |
| PG6 | 36.7 | 47.1 | ND | − | − | − |
| PG8 | 67.5 | 63.1 | ND | −[b] | − | − |
| PG8A | 47.7 | 90.6 | ND | − | − | − |
| PG10 | 21.3 | 25.5 | ND | + | − | + |
| PG11 | 36.2 | 42.4 | ND | − | − | − |
| PG12 | 30.7 | 30.6 | ND | − | − | − |
| PG13 | 84.5 | 101 | ND | − | − | − |
| PG14 | 36 | 42.4 | ND | − | + | + |
| PG22 | 8.6 | 11.1 | ND | − | − | − |
| PG24A | 47 | 63.1 | ND | − | − | − |
| PG29 | 31.1 | 40.9 | ND | + | + | + |
| PG54 | 101.4 | 46.7 | + | + | − | − |
| PG57 | 100 | 134.5 | + | + | + | + |
| PG68 | 133.3 | 30.7 | + | − | + | + |
| PG75 | 40.7 | 46.7 | + | − | − | − |
| PG76 | 48.1 | 55.6 | + | − | − | + |
| PG91 | 57.2 | 85.7 | + | + | + | + |
| PG96 | 59.3 | 70.3 | + | + | + | + |
| PG97 | 44.4 | 57.5 | + | − | + | + |
| PG98 | 33.3 | 36 | + | − | − | − |
| PG99 | 40.7 | 55.6 | + | − | + | + |
| PG100 | 29.6 | 10.8 | + | − | − | − |
| PG102 | 59.3 | 70.3 | + | − | − | + |
| PG104 | 40.7 | 57.5 | + | − | − | + |

[a]Positive reaction detected with the rabbit antiserum to sarkosyl insoluble *P. gingivalis* antigen.
[b]Purified protein demonstrated weak positive reaction with the rabbit antiserum to whole *P. gingivalis*.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Lipman D J, Pearson W R. 1985. Rapid and sensitive protein similarity searches. Science 277:1435-1441.
2. Horton, P. and Nakai, K. (1996). A probabilistic classification system for predicting the cellular localization sites of proteins. Intellig. Syst. Mol. Biol. 4: 109-115.
3. Nakai K, Kanehisa M. 1991. Expert systems for predicting protein localization sites in Gram-negative bacteria. Proteins: Structure, Function, and Genetics 11:95-110.
4. Nielsen H, Engelbrecht J, Brunak S and von Heijne G. 1997. Identification of prokaryotic and eukaryotic signal peptides and prediction of their cleavage sites. Protein Engineering 10, 1-6.
5. Claros M G and G von Heijne. (1994). TopPred II: an improved software for membrane protein structure predictions. Comput. Appl. Biosci. 10: 685-686.
6. Borodovsky M, Rudd K E, and E V Koonin. (1994). Intrinsic and extrinsic approaches for detecting genes in a bacterial genome. Nucleic Acids Res. 22:4756-4767.
7. Struvye M, Moons M, Tommassen J. 1991. Carboxy-terminal phenylalanine is essential for the correct assembly of a bacterial outer membrane protein J. Mol. Biol. 218:141-148.
8. Aduse-Opoku J, Slaney J M, Rangarajan M, Muir J, Young K A, Curtis M A. 1997. The T1a receptor protein of *Porphyromonas gingivalis* W50: a homolog of the RI precursor (PrpRI) is an outer membrane receptor required for growth on low levels of hemin. J. Bacteriol. 179:4778-4788.
9. Needleman S B, Munsch C D. 1970. Ageneral method applicable to the search of similarity in the amino acid sequence of two proteins. J. Molec. Biol. 48: 443-453.

The invention claimed is:

1. An isolated antigenic *Porphyromonas gingivalis* polypeptide comprising the amino acid sequence of SEQ ID NO:145.

2. An immunogenic composition directed against *P. gingivalis*, comprising (i) an amount of the antigenic polypeptide of claim 1 effective to induce an immune response against *P. gingivalis* and (ii) a pharmaceutically acceptable carrier.

3. The composition as claimed in claim 2, wherein the pharmaceutically acceptable carrier comprises an adjuvant.

* * * * *

SEQUENCE LISTING

<160> NUMBER OF SEQ ID NOS: 218

<210> SEQ ID NO 1
<211> LENGTH: 1362
<212> TYPE: DNA
<213> ORGANISM: Porphyromonas gingivalis

<400> SEQUENCE: 1

```
ttctgtgtca tggcaaaagt tataaaaaca aaaaaggcc ttgcacttaa tctgaaagga      60
aaaccgctgc ccgagatgct ggccgaaccg gcccaaagtc ctacttacgc ggtcgtgccc    120
gacgattttg aaggtgttat ccccaaggtg acggctcgtc cggggataa ggtgcgtgcc     180
ggctcagcac tgatgcacca caaggcatat ccggagatga agtttacaag tccggttagc    240
ggcgaagtga tcgcggtgaa tcgcggtgcc aagcgcaagg tgttgagcat cgaggtgaaa    300
ccggacggac tgaacgaata cgagtcattc cctgtcgggg atccgtctgc cctctctgcc    360
gaacagatca aggagctttt actgtcgagc ggtatgtggg gttttattaa gcaacgtcct    420
tacgacatag tggctacacc ggatatagct ccacgcgaca tttatattac tgccaacttt    480
actgcaccat tggctccgga cttcgatttc atcgttcgag gagaagaacg cgccctgcag    540
actgccatcg atgccttggc caaactcacg acaggaaagg tgtatgtggg cctgaagccg    600
ggttcatctc tgggcttgca caatgcagaa atcgtagaag tacacggacc tcatccggca    660
ggtaacgtgg gcgtgctgat caatcatacg aagccaatca atcggggcga acggtgtgg    720
acgctcaagg ctaccgacct gatcgtgatc ggacgtttcc tgcttacggg caaagccgat    780
tttaccagaa tgattgccat gaccggctca gacgctgcag ctcacggata cgtccgtatt    840
atgccgggtt gcaatgtctt tgcttccttc cccggccgac tgacaataaa ggaatctcac    900
gagcgtgtga tcgatggcaa tgtgctgacc ggtaagaagc tctgcgagaa ggagcctttc    960
ctgtcagccc ggtgtgacca gatcacggtg atccccgaag cgacgatgt ggacgaactc    1020
ttcgggtggg ctgcaccccg tctcgatcag tacagcatga gcagagctta tttctcttgg    1080
ttgcagggga aaaacaaaga gtacgtactc gatgcccgga tcaagggtgg cgaacgtgct    1140
atgatcatga gcaacgagta tgaccgcgtt ttcccgatgg acatctatcc ggagtatttg    1200
ctcaaggcta ttatagcatt cgacatcgac aagatggagg acttaggcat atatgaagtg    1260
gctccggagg actttgccac ttgcgaattt gtggatacat ccaagatcga gctgcagcgt    1320
atcgttcgcg agggcttgga tatgctctat aaggaaatga at                      1362
```

<210> SEQ ID NO 2
<211> LENGTH: 603
<212> TYPE: DNA
<213> ORGANISM: Porphyromonas gingivalis

<400> SEQUENCE: 2

```
gaactaagca agtgttacat ggataaagtg agctatgctc tgggattgag catcggtaat      60
aatttcaagt cttcgggcat cgacagcgtc gttatggatg atttcatgca aggtctgtct    120
gatgtactgg aagaaaaagc ccctcagctc tcgtatgacg aggccaagcg cgaaatagag    180
gcgtatttca tggatttgca gcagaaggct gtcaaactga acaaagaggc cggagaagaa    240
ttcctcaaga taaatgcaca caaggaaggt gtgacgacct taccgagcgg cttgcaatac    300
gaagtcatta agatgggaga gggcccgaaa cccacccttt cggacacggt aacctgtcat    360
tatcacggta cgctcatcaa cggtatcgtt ttcgatagct ctatggacag gggagaaccg    420
gccagtttcc ctctaagagg agttatagcc ggctggacgg agattcttca attaatgcct    480
gtaggatcca agtggaaagt aactataccg agcgatctgg cgtatggaga tcgtggtgcc    540
ggcgaacata tcaaaccggg tagtacgctc attttttataa tcgaattatt gagtatcaac    600
aaa                                                                  603
```

```
<210> SEQ ID NO 3
<211> LENGTH: 837
<212> TYPE: DNA
<213> ORGANISM: Porphyromonas gingivalis

<400> SEQUENCE: 3
caaaaaaaca aacgaaagat gaaaaaagca ttacttattg gtgctgctct tttgggagca      60
gtcagttttg caagtgctca gtctttgagc acaatcaaag tacagaacaa ttcagtacag     120
caacctcgtg aggaagccac tattcaggtt tgtggagaat ggcagagca agttgactgc      180 attgggacag gtaattctgc aatcatagcc gctgcagcga aatttgaaag cgatgatctc     240
gaaagctatg ttggctggga gatcatgagt gttgatttct tccctggata taaagcgtgc     300
aagtacacat ctgcagtctg gctgatgat atgaccattt gggccaatc agaagatagt      360 gatcccgaaa tgcagactat caacaatctt gctctcaaga ctagtgtcaa gattgaagcc     420
ggcaagaatt acatagttgg ttatattgct aataccgcag gtggacatcc tatcggatgt     480
gatcagggcc ctgccgttga tggttatgga gatttggttt ctatatcaga gatggtggt     540 gctactttcc ctccgttcga atctcttcat caagcagttc ctaccttaaa ttacaacatc     600
tatgtcgttg ttcatttgaa gaagggtgaa ggtgttgagg ctgttcttac caacgacaag     660
gctaatgctt atgttcagaa tggcgttatc tatgtagccg gagctaatgg tcgtcaggta     720
tctctgttcg acatgaacgg taaggttgtt tataccggcg ttagcgaaac gattgcagct     780
cctcagaagg gcatgtatat cctccgtgta ggtgctaaga gcatcaagct ggctatc        837

<210> SEQ ID NO 4
<211> LENGTH: 1686
<212> TYPE: DNA
<213> ORGANISM: Porphyromonas gingivalis

<400> SEQUENCE: 4
acaagaaatg tttcactcat aaaaatgcca agaattatga aattaaaaat tgcactcaga      60
ctgctgctgg cgacttttgc catagttta tttagccctc tggccaaggc ccagatggat     120
attggtggag acgatgtatt gatcgagacg atgtccaccc tatcaggata ttcagaggat     180
ttttattaca agatggctgt ggcagacaat ggatggatct atgtgatgtt ggatttctct     240
cgtatttatt ttgatgatgt caggctgtat cgttccaaag acggtggtgc tacttaccaa     300
aagttagggt ctttggggtc tttggtgcct tatgacttcg atgtctcgca ttgcgatttt     360
attgtaacgg gaaaggatga agatgatatc aatgtttgga cagtcatgac agcattcgaa     420
tatgtaggtg gtactattgg caatggcgtt ttgctgatgc atcgccatga tgcagatatc     480
aataatacag agtgtgtgta caagaaggat ttccctaata tagactgat gggtgtagcc     540 atcgcctcca actaccgtgc gccctctcct tacggtttgg ggggcgatcc ttttgctctc     600
gctgtcgccg ttagtggctc cggaagcgat cacagcttct tggactatat ttttttcgtta     660 gatggtggag tacactttga gcaaaagcgt atttacacaa gaccccaaaa actgactatc     720
aatagagtag acctttcatt aggcagtaca tctccttctc ttggatttaa tacttggcca     780
ctaatgggag tcgtattcga aatgaataag aaccttgatg gcttcgacat tggtttcatt     840
tccaactttg tggactatga tccccgctat gcgtggtctg aaccgataat aatagaagaa     900
gactgtggat ggactgattt taatcctttg ggagcactaa gtatagagat ccaaatgatg     960
ttggatgaca attcggataa taccgtgggt ggagaacgct cccataactt cctgatcact    1020
tacccgggcc attacgtata tccgaagcaa tctttcaatt attctcccgg acatacaccg    1080
acaaagaaag atctggtctt taaacactgt ataggtattc cggctttggc atacgataag    1140
```

```
gaaggcgatc gttatctgac tacttttcaa gatcacaatc taatgagata cagatggatc     1200
aaatacgatg acattaactc ttttatggt tggagttggc catatgtata tgcaaaagaa      1260
gctaaagata aaaagaggcg ccgtccgcaa gtagcactca atcctaccaa tggaaaggct     1320
tgttgggtat ggcatactcg caagagccca tatgatgaaa ccaaaccaca tcctactcct     1380
gtaattatta acatttcct atggtccgat acggagtggg tacatgctct ggacgtgggg     1440
gacgtattgc agaaggaggg tagcatgaag ctctaccca atcctgccaa agaatatgtt     1500
ctgatcaacc tacccaaaga aggggggcac gaggcagtcg tatacgacat gcagggccga    1560
atcgtggaga agtttcatt ttcagggaaa gaatataagc tgaatgtgca gtatctgtcc    1620
aaaggtacgt acatgctgaa agttgtagcg gatacggagt atttcgtgga aaaaatcatt     1680
gtagag                                                                1686

<210> SEQ ID NO 5
<211> LENGTH: 1173
<212> TYPE: DNA
<213> ORGANISM: Porphyromonas gingivalis

<400> SEQUENCE: 5
caaatgaaac gattactccc ctttctcctt ttagcaggac tcgtagccgt aggaaacgtg      60
tctgctcagt caccccgaat ccctcaagtg atgtacaca ctcgcatcgc aagaaatgcc     120
cgttatcgac tggacaagat cagtgtcccg gattctcgtc agatattcga ttacttctat    180
aaagaagaaa cgatacccac taaaatacaa acgaccacag gaggtgcaat tacaagcatc    240
gattcgcttt tctatgaaga cgacaggttg gttcaggtgc gctattttga caataacctt    300
gaattaaaac aagcggagaa gtatgtatac gacggttcta gctggtcct tcgagaaatt    360 cgcaagtcgc cgacagacga aacgccaata aagaaagtta gctatcacta tctctgtggc    420
agcgatatgc cttttgagat tacgacagag atgagcgatg gctattttga aagccatacg    480
cttaactatc tgaatggaaa gattgcccga atagatatca tgactcaaca gaacccatcg    540
gccgaattga tcgaaacggg tagaatggta tatgagtttg atgccaataa tgatgctgta    600
ctgcttcgtg acagtgtatt tcttcctctt caaaacaagt gggtagaaat gtttactcac    660
cgttatacat acgacaataa gcataattgt attcgttggg aacaagacga attcggcacc    720
ctcacccttg ccaacaactt cgaatacgac accactatcc ctctgtcgtc tgtattgttc    780
cccacgcatg aggagttctt ccgtcctctt cttcccaatt ttatgaagca tatgcgtacg    840
aagcaaacgt atttcaataa ctccggagaa ggcttgtcag aggtatgcga ttacaactac    900
ttctataccg atatgcaggg taatgcactg accgatgttg ccgtgaacga atcgatcaag    960
atttatcctc gtcctgccac ggattttctg cgtatagaag gttcgcaact gcttcgcctt    1020
tcgctattcg acatgaacgg gaagctcatc agagctaccg aattgacagg cgatttggcc    1080
attatcggag ttgcatctct tccgagaggc acttacatcg cagaaataac tgctgcaaac    1140
agcaaaacca tacgtgcaaa agtatcgctc aga                                 1173

<210> SEQ ID NO 6
<211> LENGTH: 972
<212> TYPE: DNA
<213> ORGANISM: Porphyromonas gingivalis

<400> SEQUENCE: 6
ctaacgttgt tttgttgcaa ctatttcaaa cagatgagag caaacatttg gcagatactt      60
tccgtttcgg ttctctttttt cttcgggaca gcgatcggac aggctcagag tcgaaaccgt     120
```

```
acatacgagg cttatgtgaa acagtacgcc gacgaagcta tccgacagat gagccgctac    180
aatataccgg caagcatcac catagcacag gctttggtgg agacaggagc cggagccagt    240
acactggcca gcgtacacaa caatcacttc gggatcaaat gccacaaatc gtggacgggc    300
aagcgcacct atcgtaccga cgatgcgccg aacgaatgct tccgcagcta ttcggccgct    360
cgcgaatcgt atgaagatca ttcccgattt ctgctccaac cacgctatcg tcccctgttc    420
aaactcgaca gagaagacta tcggggctgg gctacggggt tgcaacgctg tggctatgcc    480
accaatcggg gctatgccaa tctgctgatc aagatggtgg agctgtatga gctatatgct    540
ttggatcgcg agaagtaccc ctcatggttc cacaagtctt accccgggtc caacaaaaaa    600
tcccatcaaa cgaccaagca gaagcagagc ggactcaagc acgaagctta cttcagctac    660
ggactgctct acatcatagc caagcaaggc gataccttcg attctttggc cgaagagttc    720
gacatgagag cctccaaact ggccaaatac aacgatgctc ccgtggattt cccgatcgaa    780
aagggcgatg tgatctatct ggagaaaaag cacgcatgct ccatctccaa acacacacag    840
cacgtagtgc gtgtgggcga ttcgatgcac agtatctccc aacgctatgg catccggatg    900
aagaacctct acaagctcaa cgacaaggat ggcgaatata taccccaaga gggcgatata    960
ctgcgcttgc gc                                                        972

<210> SEQ ID NO 7
<211> LENGTH: 1119
<212> TYPE: DNA
<213> ORGANISM: Porphyromonas gingivalis

<400> SEQUENCE: 7
gggtcttgtg gaagtagccc agcaattggc cgatcagggt gttcgcgttg tgatcgccgg     60
attggacatg gactttcgac gtcagccttt cggacctatg ccgggcttgt gtgccatagc    120
cgactccgtg accaaagttc atgccgtgtg tgtggaatgc ggccgattgg ccagctattc    180
tttccgtcgt gtccaaggcg atcagcaagt gatgctgggc gaactgaacg aatacagtcc    240
cctctgcaga acctgctaca ggaaatgcag ttctccccca caaacagaag aaatccattc    300
gacaatatga atagcagaca tctgacaatc acaatcattg ccggcctctc cctctttgta    360
ctgacattgg gcggctgctc cgtagcccaa caagatacgc agtggactct cggcggaaag    420
ctctttactt cggcgtggat acaacgttcg gccgaatatc aagcgctttg cattcaggca    480
tacaacatcg ctacggaaag agtggacgct ctaccggcag aacgtaaaca aggagatagg    540
ccttatgcca tcgtaacgga catagacgaa accattttgg acaatacgcc taactccgtg    600
tatcaggctc tcaggggcaa ggattatgat gaagagactt gggggaaatg gtgtgcacag    660
gccgatgccg acacactggc aggagctttg tctttcttcc tccatgcagc gaacaagggg    720
atcgaggtct tttacgtcac caaccgcaga gacaatctgc gcgaagcaac tcttcagaac    780
cttcagcgtt acggattccc ctttgccgat gaagaacatt tgcttacgac ccatgggcca    840
tccgacaaag aaccccgtcg gctcaaaata caagaacagt atgaaatagt attgctcata    900
ggagacaact tgggcgactt ccaccacttc ttcaatacga agaagagtc cggacgcaaa    960 caggctctgg gcctgacagc cggggagttt ggccggcact tcatcatgct gcccaatccc   1020
aactacggat cttgggaacc ggcatggtac ggcgggaagt atccgccact gcccgaaaga   1080
gacaaagcac ttaaacaact gcactcacag aacagcaga                         1119

<210> SEQ ID NO 8
<211> LENGTH: 2289
```

<212> TYPE: DNA
<213> ORGANISM: Porphyromonas gingivalis

<400> SEQUENCE: 8

```
catttttag taacgattat gcggacaaaa actatctttt ttgcgattat ctctttatt      60
gctctattgt cgtcttctct gtcggctcag agcaaagccg ttttaaccgg tagtgtgtcg    120
gatgccgaaa ccggagagcc tcttgccggt gctcgaatcg aagtcaaaca caccaacata    180
gtagccggtg ccgatgccgg cggacatttc gagatcaaga acctgccggc agggcagcat    240
actattatat gttcgttggg ggggtatgga cagaaagagg aggtggttgc catcgaagcc    300
ggacagacca aaacgatctc ttttgcattg cgactgcgaa cgaacaactt ggaggaagtc    360
gtcgttaccg gtaccggtac acgttaccgc ttggtcgatg ctcctgtggc aacgaagtc     420
cttaccgcta aggacatagc ctctttctcg gctcctactt ccgaggcctt attgcagggg    480
ctgagtccgt cttttgactt cggccccaat ctgatgggct cttttcatgca gctgaacggc   540
cttagcagta agtatatcct catccttatc gatggtaagc gtgtgtacgg cgatgtaggc    600
ggtcaggccg atttgagtcg tatttctcct gatcagatcg aacggatcga actggtgaaa    660
ggtgcttcga gttcgctcta cggatccgat gccatcgccg gggtaatcaa tgtgatcaca    720
aaaagaata cgaatcgact gagtgcatat acgtcacatc gcatatcgaa gtacaacgat     780
cggcaaacca atacttcgct cgatataaac atcggtaagt tcagtagcaa taccaactat    840
ttcttctacc atacggatgg ctggcagaat agtccgttcg aaataaaaaa gaaaaaagga    900
tccggcgaac cggtcttgga ggaaacgtat aagaaaactt tcgtgcaca ggaaaatcag      960
ggtgtaagcc aatcgctttc ctattatgca actaacaatc ttagcttcag cggaaatgtg   1020
cagtacaata aacgtcagat cttcactccg acttttccg aaaagaaggc ctatgacatg    1080
gattatcgtg ctttgacggc ttcactcggt acgaactatc ttttcccaa tggtctgcat    1140
acgcttcttt tcgatgccgt ctacgatcgc ttccgtttcg gatatttgta tcatgacaag   1200
gacagcagtg agagcctgat caacaaccaa ggtcagaccg agcaacccac attctttccg    1260
ggtcagctac gcaataaaaa cgatcagatc cgatacacgg cagaggctcg cggtgtattt    1320
acactgcctt atgcgcagaa actgaccggc ggtttggagt atttccgtga ggaattgatc    1380
tctccctata atttgattac cgacaaggca gatgcttcca cgctctctgc ttatgtacaa    1440
gatgaatgga aaccgctcga ttggttcaat atgacagccg gtttccgtct ggtacaccat    1500
caggagttcg gtacacgaat gacgcctaag gtatccatac tcgccaagta tgggccgctg    1560
aacttccgcg ctacgtatgc taacggctat aagactccca cgctgaaaga gcttttttgca   1620
cggaacgaac tcaccactat gggttcgcac aatctctatc tcggcaatgc ggatcttaag    1680
ccacagatgt cggattatta tgctttgggc ttggagtaca atcaaggccc tatctcgttc    1740
agtgcaacgg tttatgacaa tgaacttcgc aatctgatct cctttatgga tataccgacc    1800
tcacccgagc acgaagctca gggaatcaag aaaaccaagc agtatgccaa cataggaaaa    1860
gctcgcagcc gcggccttga tgtcctatgt gatgcctcta tcggttgggg tatcaagtta    1920
ggagccggat acagcctcgt ggaagctaag aatctccaga cggatgagtg gctggaagga    1980
gctgcacgtc atcgtgccaa tgtgcacgcc gattgggttc actactgggg tcagtataga    2040
cttgcgtga gccttttcgg ccgtattcag agcgagcgtt actacaaaga cggcaatgct    2100
ccggactata ccttgtggcg actcgccaca tcgcatcgtt tcgctcattt ccgccacatc    2160
atcctggatg gaacgctcgg tatagacaac ctgtttgact acgtggatga tcgtcctatg    2220
ggtgtcaatt atgctaccgt aacgccggga cgtactttct ttgctcaaat agcgattcga    2280
``` ttcaacaac 2289

<210> SEQ ID NO 9
<211> LENGTH: 1095
<212> TYPE: DNA
<213> ORGANISM: Porphyromonas gingivalis

<400> SEQUENCE: 9

```
tgctgcgcaa ggcttcggga cacctctccc cggaagaagt cgtttcggaa tgataccgtt      60
tttccttatt tcgttattca tctgatcaaa catattatca ttatgacgga caacaaacaa     120
cgtaatatcg tattcccggc gtttctcctc ttgctgggag tcatcgcagt ggtgacgatc     180
gttggttttt tcatgctcag accggccgag gagattatcc aaggacagat agaagtgacc     240
gaataccgag tgtccagcaa agtgcccggg cgcatcaagg aacttagggt atccgaggga     300
cagcaggtgc aggccggcga taccctcgct gtcatcgaag cccccgacgt agcggctaag     360
atggagcagg caaaggctgc cgaagcagct gcacaggctc agaacgccaa ggctctcaaa     420
ggagcacgca gcgaacagat acaggcagcc tatgagatgt ggcagaaagc tcaggccggc     480
gtagccatag cgaccaagac acaccagcgc gtgcagaacc tctatgacca gggagtggta     540
ccggctcaga agttggacga agccactgcc cagcgcgatg cggccatcgc tacgcaaaaa     600
gcggccgaag cccagtacaa tatggctcgc aacggtgccg aacgcgaaga caagctggca     660
gcttctgccc tcgtcgatag agcgagagga gccgtcgccg aggtggagtc gtacatcaac     720
gaaacctacc tcatcgcccc acgggcaggc gaagtgtcgg agatattccc caagccggc      780
gaactcgtag gtaccggcgc acctatcatg aatatcgccg agatgggcga tatgtgggcc     840
agctttgccg ttcgtgagga tttcctcagc agcatgacca tggagccgt tctggagact      900
gtggtgccgg ctctgaatga agaaaagta cgcttcaaga tcacattcat caagaacatg     960
ggtacctatg ctgcctggaa agcgaccaag acaacagggc agtacgacct gaagaccttc    1020
gaggtaaagg ccacccttgc ggataaagac aaggcacaaa agctacgccc gggtatgtcc    1080
gtgatcatac gcaag                                                    1095
```

<210> SEQ ID NO 10
<211> LENGTH: 3138
<212> TYPE: DNA
<213> ORGANISM: Porphyromonas gingivalis

<400> SEQUENCE: 10

```
gacttcccctt gggttagggt aaaaccggag aagaaaagaa acaacataa cagtaataat       60
tttaagttta acgcaaaaga aaagtctatg aaaagaatga cgctattctt cctttgcttg     120
ctgacgagca ttgggtgggc tatggcccag aatagaaccg tgaagggtac agttatctcc     180
tccgaggata atgagcccct gatcggcgcg aatgtcgtgg ttgtcggaaa caccactatc     240
ggtgctgcaa ccgacttgga tggcaacttc acgcttagcg tgcctgccaa tgccaaaatg     300
ttgagagtgt cctattccgg tatgactacc aaagaggtcg ccatcgctaa tgtgatgaag     360
atcgtactgg atccggactc taaggttctg gagcaggtag ttgtattggg ttacggtacg     420
ggacagaaac tcagcactgt ttccggttct gtggccaaag tgtccagcga aaagctcgcg     480
gaaaagcccg ttgccaatat catggatgcc ctccaaggtc aggtagccgg tatgcaggtt     540
atgactacat ccggtgaccc tactgccgtc gcttctgtgg agatccatgg tacagggtcg     600
ttgggggcaa gctctgcacc attgtatatc gtggatggta tgcaaacttc tttggatgtt     660
gtggctacga tgaatccgaa tgattttgaa tctatgtccg ttttgaaaga tgcttctgca     720
```

```
acatctattt atggagctcg tgctgcaaac ggagtcgttt tcattcaaac gaagaaaggt     780
aaaatgagcg agagaggtcg tattaccttt aatgccagtt acgggatttc tcaaatcctg     840
aatactaagc cccttgataa tatgatgact ggagatgaat tgctggattt tcaggtgaag     900
gcaggttttt gggggaacaa tcaaaccgtt cagaaggtta agatatgat ccttgccgga      960 gctgaagatt tgtatggcaa ttatgattct ttgaaagatg agtatggtaa gacattgttc    1020
ccagtggatt ttaatcatga tgcagactgg ctcaaggctt tgtttaaaac agcacccacc    1080
agtcaaggtg atatttcttt ctccggaggg tctcagggaa cttcatatta tgcctctata    1140
ggctacttcg atcaggaagg tatggctcgt gaaccggcaa attttaagcg ctatagtggc    1200
cggctcaact tcgaaagtcg tatcaatgaa tggctgaaag ttggtgcaaa tttgtctggt    1260
gcgatagcga atagacgatc tgccgactat tttggaaagt attatatggg gtcaggtact    1320
ttcggtgtgt taacgatgcc tcgttattat aacccttttg atgtgaatgg ggatttagca    1380
gatgtctatt acatgtatgg agctaccaga ccttctatga cagaaccgta cttcgcaaaa    1440
atgagaccgt tcagttccga atcacatcag gccaatgtaa atggtttcgc ccagattact    1500
ccgatcaaag gccttacttt aaaggcacag gctggtgttg atattactaa tactcgcact    1560
tcttctaaga gaatgcccaa taatccgtat gattctactc ctcttgggga aagaagagaa    1620
agagcttatc gagatgttag caagtctttt acaaatacgg ctgaatataa gttttcaatt    1680
gatgaaaaac atgatcttac agcattgatg gggcatgaat atattgaata tgaaggggat    1740
gttattgggg catcttctaa aggatttgaa agtgataagt tgatgttact gagccaggga    1800
aaaaccggaa atagtttgtc tttgcctgaa cacagagtcg ctgaatatgc ctatttgtct    1860
ttctttagtc gttttaatta cggttttgac aaatggatgt atatagattt ctctgttcgt    1920
aatgaccaat cctctcgatt cggatccaat aatagaagcg cgtggttcta ttctgtcggt    1980
ggaatgtttg acatatataa taaattcatt caagaaagta attggctcag tgatcttcga    2040
ctgaaaatga gttatggtac aacgggtaac tcggagattg gtaattacaa ccaccaagca    2100
ctcgttactg tgaacaatta tactgaagat gctatggggc ttagcatttc tacagcaggc    2160
aatcccgacc tctcgtggga aaagcagtct cagttcaact tcggtttggc tgcaggggct    2220
ttcaataatc gcttatctgc agaggtagat ttctatgtcc gcactacgaa tgatatgttg    2280
attgatgtcc cgatgcctta tatcagtggt ttcttctcac agtatcagaa tgtaggctct    2340
atgaaaaata cgggtgtaga ccttcctctt aagggacga tctaccaaaa taaggactgg     2400
aatgtatatg cttctgcgaa tttcaactac aatagacagg aaataacaaa gcttttcttc    2460
ggtctcaata agtacatgtt gcctaatacc ggtactatat gggaaattgg gtaccccaat    2520
tcgttctata tggctgaata tgctggaatc gacaaaaaaa ccggtaagca gttgtggtat    2580
gttcctggtc aagtcgatgc ggatggtaat aaagttacaa caagccagta tcagctgac    2640 ttggagacac gaattgataa gtctgttact cctcctatta caggtggttt tcccttaggt    2700
gcttcttgga aaggactttc tttagatgct gattttgcct acatcgttgg taaatggatg    2760
atcaataatg accgttactt tacagagaat gcaggtggat tgatgcaatt aaataaagat    2820
aaaatgctat tgaatgcctg gacagaggat aataaagaaa cagatgttcc aaaattggga    2880
cagtctcctc agtttgatac gcatttgttg gagaatgctt ctttcctgcg tttgaagaat    2940
ctcaaactca cctatgtact ccccaatagt ctttttgctg gcagaatgt gattggtgga    3000 gctcgtgtct atttgatggc gcgcaatctg ttaactgtta cgaagtataa aggctttgac    3060
cctgaagcag gggggaatgt gggaaaaaat caatatccta attctaagca gtacgttgcg    3120
```

```
ggtattcagt tgtctttc                                            3138

<210> SEQ ID NO 11
<211> LENGTH: 2607
<212> TYPE: DNA
<213> ORGANISM: Porphyromonas gingivalis

<400> SEQUENCE: 11
tggcatagga atatttttat ctttgcgagt acatttagcc cgaaaaatat gctcccactg    60
ccataccgtt atgcaaaaac cgagcacctt tttctcgcaa aaggatactg caagaatcca   120
ataacaaaca taattatcct atttatgaag aaaaagaatt ttttgcttct tggcattttc   180
gttgctttgc tgactttcat cggcagcatg caggcacaac aggccaaaga ttatttcaac   240
tttgacgaac ggggcgaggc ctacttctca ttcaaagtgc ctgataggc cgttctacaa    300 gagctggctc tgatcatgtc catcgacgag tttgaccccg taaccaatga agccattgcc   360
tatgccagcg aagaggagtt cgaggcattc ctgcgctatg gctcaagcc tacattcttg   420 actcctccat ccatgcagcg cgctgtcgag atgttcgact accgctcagg agaaaaatac   480
gaatggaatg cttacccccac ctatgaagcc tatatcagca tgatggaaga gttccaaaca   540
aagtatccat cactttgtac tacttccgtc attggcaagt ccgtaaagga tcgtaaactg   600
atgatttgca agctgacgtc ctctgccaat acagggaaaa agcctcgcgt gctctatact   660
tctacgatgc acggagacga acgaccggga tatgtggtac tgctccgact catagaccat   720
ctgctgtcga actacgaatc cgatccgagg attaagaaca ttctggataa acggaagta    780 tggatctgcc ctttgaccaa tccggacgga gcatacagag ccggaaacca caccgtacaa   840
ggagctactc gctacaatgc caacaatgtc gatttgaacc gtaacttcaa ggatgatgta   900
gccggtgatc accccgatgg aaaaccttgg cagccggagg caactgcatt catggatttg   960
gaaggaaaca cctcttttcgt gctcggtgcc aatatacatg gaggaacaga ggtggtgaac  1020
tatccatggg ataataaaaa agaaagacat gcagacgatg agtggtacaa actgatcagt  1080
cgcaactacg cagccgcttg tcagagtatt tccgccagct acatgacctc cgaaaccaat  1140
tcgggaatca tcaacggttc agactggtat gtaattcgcg gaagtcgtca ggacaatgca  1200
aattatttcc atcgtctgcg agaaattacc cttgaaatca gcaacacgaa gttggtgccg  1260
gcctctcaac ttccaaagta ttggaatctg aacaaagaat ctctgcttgc tctgatcgaa  1320
gaatccttat acggcatcca tggtacagtg acttccgctg cgaacggaca gcctctcaaa  1380
tgccagatct tgatagaaaa ccatgacaag cgcaactccg atgtttactc cgatgctacc  1440
acaggctact acgtacgtcc tatcaaagcc ggcacttata cggtgaaata caaagccgag  1500
ggttatcctg aggcaactcg taccattacg atcaaggaca agaaaccgt catcatggac   1560 attgcattgg gcaactcggt tcctctgcct gtacccgatt tcacagcttc tcctatgacc  1620
atctcagtag gcgaaagcgt ccaattccaa gatcaaacga caataaccc cacgaattgg  1680 gagtggacgt tcgaaggcgg acagcctgcc atgagtacag agcagaatcc gctcgtatcc  1740
tatagtcatc ccggtcagta cgacgttacg ctcaaagtgt ggaatgcaag tggttccaac  1800
acgattacga aagaaaaatt catcactgtc aatgccgtta tgcctgtagc tgaattcgtc  1860
ggtaccccga cggaaataga gagggccag acggtatctt ccaaaaccaa tccaccaat   1920 gccaccaact acgtatggat attcgatggc ggcactcccg ctaccagtga agacgaaaac  1980
ccgactgtgc tttacagcaa agccggccaa tacgatgtca cgctcaaggc gatcagtgct  2040
tccggtgaaa cggtgaagac gaaagaaaaa tacatcactg tcaagaaagc tccggtccct  2100
```

```
gctccggtag ccgacttcga aggaacacct cgaaaagtaa agaaaggcga gacagttact    2160
ttcaaagact tgtctacgaa caatccgact tcatggcttt gggtgttcga aggcggctct    2220
cctgccacca gcacggagca aaacccggtg gtcacctaca atgaaacagg caagtacgat    2280
gtccagctga ctgccaccaa cgagggcgga agcaatgtga agaaagcaga agactacatt    2340
gaggttatcc tcgatgacag tgtcgaggac atagtggcac agacgggtat cgtcattcgt    2400
ccgcaaaacg gaacgaagca gatcctcata gaagccaacg ctgctatcaa agcgatcgtt    2460
ctctatgaca tcaatggacg ggtcgtactc aaaactactc cgaatcagct ccgctcgacc    2520
gtagatcttt ccatcctgcc cgaaggaatc tacaccatca atatcaaaac ggaaaaatcc    2580
gctcgcacgg aaaagatcca tatcggg                                        2607

<210> SEQ ID NO 12
<211> LENGTH: 318
<212> TYPE: DNA
<213> ORGANISM: Porphyromonas gingivalis

<400> SEQUENCE: 12
ctttcgtaca gtggagagag cgatgcaaaa gagtctgatc agaattgccg gaaatgtacc      60
ttcatcggct ttgaaaaacg agtaaatacg atgcgactga tcaaggcttt tctcgtgcaa    120
ctcttactgc tccccatttt cttctacaag cggtttatat cgccgcttac accgccttca    180
tgccggttta cccccctcatg ttcgtcctat gccatcgaag ccttacgtaa atatggcccg    240
ggcaaaggac tattgctgag catcaagcgt attctccgct gtcacccgtg gggtggaagt    300
ggctatgacc ccgttccg                                                  318

<210> SEQ ID NO 13
<211> LENGTH: 1368
<212> TYPE: DNA
<213> ORGANISM: Porphyromonas gingivalis

<400> SEQUENCE: 13
agaggaggac aaatccgccg acaccatacc gattcgtcaa ggggatcgga cagcaaagcc      60
tgccgcttct cctttcatgc cgagaccatc ggtttctcca accaccaaag agcaaaaatg    120
aattacctgt acatactgat tacacttttta ctctccggct ttttttccgg tgctgagatt    180
gctttccttt cttcggacaa actgcgtctt gagttggaca ggaatagagg cgatctcaca    240
ggcagagcgt taaacttgct gtatcgacat ccggaccaac tggtgactac tctccttgtg    300
ggtaataata tcgttttggt agtctatggt ctgctgatgg cgggattgct ggccgcacct    360
ttggcgcaat ggattgataa cgatgctatg atcgtcgttc tccaatctgt cttatccact    420
atcatcatac tgtttaccgg ggaatttcta cccaaagcca ttttcaagac caatgccaat    480
atgatgatga gggtattcgc cctccctatc gtagcgatct attatctgct ttatcctctg    540
tctaaactct tcaccggttt atctcgctct tttattcgtc tggtggacaa gaattatgtg    600
cctacaacag tagggttggg gcgcgtagat ctcgatcatt atttggcaga aaatatgtcc    660
ggagaaaacg aacagaacga cttgactacc gaagtgaaaa tcatccagaa tgcgctggat    720
ttttccggta ttcaggtgcg agactgcatg atcccacgca atgagatgat agcatgtgag    780
ttgcaaacgg atattgaagt actcaaaacg acttttatcg ataccggttt gtccaagatc    840
attatctaca gacagaacat agatgacgta gtaggatata tccattcgag cgaaatgttt    900
cgtgggcaag actggcaaaa acgtatcaat actactgtat tcgtacccga aagcatgtat    960
gccaataaac tgatgcgact actcatgcag cgcaagaaaa gcattgcgat cgtcatcgat    1020
```

```
gaacttggag gtacggccgg aatggtcaca ttagaggatt tggtagaaga gattttcggt    1080
gacattgagg acgaacacga cactcgcaag atcatagcca aacagctcgg ccctcatacc    1140
tatctggtca gtggtcgtat ggaaatagat gatgtgaacg aacgttttgg gttgtccttg    1200
cctgagtctg acgactacct taccgtggcc ggatttatcc tgaatagcca tcaaaatatc    1260
ccacaggcca atgaggtcgt ggagattgct ccttatactt ttaccattct cagatcttct    1320
tccaccaaga tcgaactggt gaaaatgtcc atcgacgacc aatcgaac                  1368
```

<210> SEQ ID NO 14
<211> LENGTH: 897
<212> TYPE: DNA
<213> ORGANISM: Porphyromonas gingivalis

<400> SEQUENCE: 14

```
ttaaaaaagg agataactat gaaacagaac tacttcaaaa gagtctgctc actgctttgg     60
ctggttttac ccatgcttat tatgccattg gaagtagcag ctcaagagat tattccgaac    120
gaagaggtgt tggaatcatt gactttcgtt gcaccggttg aggagacaga cgcaatagag    180
gcagaggtag aagctctgca ggagatagtc gctactgagg agattgcgga gcaggctgtt    240
cgttcttata cctacacggt ctatcgtgat ggcgtgaaga ttgcttcagg attgactgag    300 cccactttc tcgatgaaga tgttcctgcc ggcgaacata cctactgcgt agaagtacag     360
tatcagggag gcgtatccga caaagtatgc gtggacgtag aggtgaagga cttcaaaccg    420
gttaccaatc tcaccggaac tgcttccaat gacgaagttt ctttggactg ggacggtgtg    480
gaagagaaag ctgaagagcc ggcaagtgat aaagcagtca gctacaacgt ctacaagaat    540
ggaaccttga tcggtaatac agctgaaact cattatgtgg agaccggtgt agccaatggt    600
acatacatct acgaagtgga agtaaagtat cctgacggtg tatctccgaa ggtggctgta    660
accgtgaccg tgaccaacag ctcattgagc aatgtagatg gacaggctcc ttacacattg    720
cgagtagaag gcaagaagat tattgcggaa gcccatggta tgatcacgct ctacgacatc    780
aacggacgta ccgtggccgt agccccgaat cgattggaat acatggcgca aaccggtttc    840
tatgcagtgc gcttcgatgt ggggaataaa caccatgtat cgaaaataca agtaaga       897
```

<210> SEQ ID NO 15
<211> LENGTH: 1131
<212> TYPE: DNA
<213> ORGANISM: Porphyromonas gingivalis

<400> SEQUENCE: 15

```
ttgtttaatc ataaaaaatc atggtatgaa acatttcaat tttatctcgt tgttttccgc     60
tctggcttta ttcttttgtg tgaaaatacc cttgcacaac aaaaaacaga ggagtttgca    120
cctgtgtcgg atttacgtgc agaagcgtac ggctctaccg ttttcctcca ctggactccg    180
ccgtatgaca atccgatgat tcctctaagc gagagttttg aatcaggtat tccagctata    240
tggaagacca ttgacgcaga tggcgatggc tataattgga tgcatttgac caatttcacg    300
ggacagagtg gtctctgtgt ctcttcggct tcatacatag gcggcgtcgg agctttgact    360
ccggacaatt atctgataac acccgaatta aaactaccca cagacgcgtt ggtggaaata    420
atctattggg tatgtactca agatctcact gctccatcgg agcactatgc cgtttattcc    480
tcttctacag gcaataatgc tgctgacttt gttaatctct tatatgaaga gactttgact    540
gccaaacgga tacaatcccc cgagttgatc cgcggaaatc ggacacaagg tgtttggtat    600
caaagaaagg tggtactccc taacgatact aaatatgttg ctttccgcca ttttaattcc    660
```

```
acggataatt tctggctcaa tttggatgaa gtatctatcc tgtataccc  tcttccccga    720 agagctccgt gtccgcatcc gggtggttac acttattctg tattccgtga tggacaaaag    780
atagcgagtg gattgtcggc attggcatat atcgatacgg atgtaccgta tgggactcaa    840
gactattgtg tccaagtcaa ttatctgcaa ggagactcgt ataaagtctg caaaaatata    900
gtggtggcaa attctgcaaa catctatggg gcggataagc cttttgcgtt gaccgtggtt    960
ggcaagacca ttgtagcgag tgcttttcaa ggagagatca ctctttatga cattcgtggc   1020
cggctgatag cttccggctg cgatacgctt aggtacaaag cggaaaatgg ttttacctc    1080 attaaaatac aggtaaacgg aactgtctat actgagaaaa tccaaatcca a            1131

<210> SEQ ID NO 16
<211> LENGTH: 2547
<212> TYPE: DNA
<213> ORGANISM: Porphyromonas gingivalis

<400> SEQUENCE: 16
ttcggaatat caccttcaat gaaaaaaagt tttcttttag ccatagtaat gctctttggc     60
attgccatgc agggacattc tgctccggtt acgaaagagc gagctttgag tctggctcgg    120
ctggctttgc gacaggtatc cttgcgaatg ggacaaacag cagtatctga caagatttcc    180
atcgattacg tttatcggca aggagatgct gagaggggta tcacatcaca agaggaaggc    240
tctcctgcat atttttatgt agctaatcgt ggaaataatg agggctatgc tcttgtagca    300
gcagatgaca gaataccgac aattttagcc tattcaccca ttggccgttt cgacatggac    360
agtatgccgg acaatcttcg catgtggcta caaatttacg atcaggaaat aggcctgata    420
ctttccggaa aagctcagct caatgaagag atattacgta ccgagggcgt accggctgaa    480
gtacatgctc tgatggataa cggtcatttt gccaacgatc ccatgcgatg gaatcaaggt    540
tacccatgga caataagga  accactgctt cctaatggca atcatgccta taccggctgt    600
gttgctactg ctgcagcaca aatcatgcgc taccatagct ggccgcttca aggtgaaggc    660
tctttcgatt atcatgcagg ttcattagtt ggcaactggt ccggcacatt tggtgaaatg    720
tacgactgga tcaatatgcc cggaaatccc gaccttgata atctgactca atctcaagtg    780
gatgcctacg ccacactgat gcgtgatgtg agtgcatctg tttcgatgag tttttatgaa    840
aatggaagtg gtacgtacag cgtttatgta gtaggagcct tgcgaaacaa ctttcgctac    900
aagcgttcac tgcagctaca tgtacgcgcc ttatatacct cacaggagtg gcacgatatg    960
atccgcgggg aacttgcctc cggaaggccg gtctattatg cagggaataa ccagagcata   1020
ggacatgctt tcgtttgcga tggttatgct tcggatggta cttccatttt caactggggt   1080
tggggaggtg tttccaacgg cttctacaaa ctaacactcc tctcgccgac ttcgttgggt   1140
atcggaggtg agggaatagg ttttaccatt tatcaagaga tcatcaccgg tatcgaaccg   1200
gctaagactc ccgctgaagc cggtacagat gccttgccga tcttggcact gaaagacata   1260
gaagccgagt ataaaagtga atccggattg aacgtagggt attcgatata taatacaggt   1320
gaagagcaat caaatcttga cctcggatac agattgaaca aggctgacgg agaagtcata   1380
gaggtgaaaa cttcatctat caatatctct tggtacggat acggagagca tcccgagagt   1440
ttctcattgg cacctaatca gttgtcacaa ggaatcaaca ccatcaccct actttatcgt   1500
cgcacaggca ccgaacagtg ggagccggta cggcatgcac agggaggata tgtcaatagc   1560
attaaagtaa atacgacaga cccgaacaat gtcgtagtca cggtagataa taacgaaggc   1620
aagctcagta tcgtccccaa cagctttgtc gcagatctga attcttatga acatagtacg   1680
```

```
attacagtac agttcaatag cgacagccct gatgagatcc gtacaccegt agcctttgct   1740 ctatctacag gagctactgc ggacgatgta atatctttgg gctgggtaat ggctgaagtt   1800
ccgggcggta gcagcaacta tccggtggtt tggtctaaag acgttctcac tctctcggaa   1860
ggcgactata cattgtggta tagatttttcc atcaacaacc aaaaggatga atggaaaaag   1920
atcggaagcg tgtcagtaaa aacaccgaca gagtatacgc accccttatt cgaagtgggc   1980
cataatcaaa cttctaccta tacgctggat atggcacaca acagagtatt gcccgacttt   2040
acactcaaaa atctcggatt gcctttcaat ggtgagttgg ttgttgtttt ccgccaaaca   2100
caatcctcat cggggtcttt atgggcagct caagaaacag tacatatcaa gcaaggagaa   2160
actttcgtat ataaacctgt tgtcgaaggc cctatacctg atggatccta tcgtgcgacc   2220
ctccatgcat tcgtaaacgg acaacaacag ttgtacctca aggggaaaag gaactacacg   2280
gtgaagatcg tcaatggtac agcggtagaa gcaatagaat cgtcagaaga gatcagagta   2340
ttccctaatc cggcacgcga ttatgtgaaa atatcggcac cttgcattcc ccaagaaaca   2400
tctatcattc ttttcgatct gtcaggcaag attgtcatga agaatagttt atcagcgggg   2460
catggcagaa tggatgtcag ccgacttcct aatggggcct acatccttaa ggtggatgga   2520
tatacgacga aaataaatat agtgcac                                       2547

<210> SEQ ID NO 17
<211> LENGTH: 885
<212> TYPE: DNA
<213> ORGANISM: Porphyromonas gingivalis

<400> SEQUENCE: 17
acgaagaaaa cactgatgaa aaagctattt ctctcgctca cgagtcttgt aatggtcttc     60
gctgttgcaa gttgcgatat aatcgacaag gatcaaaccc tcttgccggc tccgaccaat    120
gtgacacccg ataatccgga tgacaatcct tcggagatcg acattacgca gacgcacaca    180
gaaaaatatg ttttggctga agaatttacc ggccaaaaat gtctcaactg tccgaaaggt    240
catcgcaaac tggcggctct caaggagcaa tacggtaaga gattgactgt tgtcggtata    300
catgccggcc ctggatctct cgtgccacct cttttccgta cagaagccgg agacgcatat    360
tatagcaagt tcgccaataa tacccctctc cctgcgctga tggtttcgcg caaaaagttc    420
ggctcttcct acgtttatga taagagctac aaaacgtggg acgtgcctat tgccgagcag    480
atggagcaaa aggcgaagat caatatcttt gccgtggccg aatacaccga tacccaaaag    540
atcaaggtga ctgtaaaggg taaaatactg gagggaata cactcccgaa gtccatggtt    600
caggtgtatc tgttggagga taagctgatc gctccgcagg tggatggcaa tacgacagtc    660
gagaattacg agcacaatca cgtgttgcgt ggagccgtta atggtatttg gggcgaagaa    720
tttgtgaatc tcaaagatta tttgtatact tacgccgttg aaccgctctc gggtatgtcc    780
ttcgtagccg agaattattc gattgtggct tttgtatacg atgtgcagac gttcgaagtg    840
tatgacgttg tgcatgtaaa gatcaatccg caatccgatg gcaaa                   885

<210> SEQ ID NO 18
<211> LENGTH: 690
<212> TYPE: DNA
<213> ORGANISM: Porphyromonas gingivalis

<400> SEQUENCE: 18
acgaataaaa aagaagagac aatgaagaaa tcaagtgtag tagcctcagt tttggccgtg     60
gctctcgtgt tcgccggttg cggactgaac aatatggcaa aaggcggcct tatcggcgcc    120
```

-continued

```
ggagtaggag gtgccattgg tgccggagta ggtaacgtag ccggaaatac ggctgtcggt      180
gccatcgtcg gtactgcagt cggtggagca gccggtgctc tcatcggaaa gaagatggac      240
aagcagaaaa aagaactgga ggccgcagta cccgatgcta cgattcagac agtaaatgac      300
ggagaggcta ttctggttac tttcgatagc ggtatcctct ttgcgacgaa ctccagcact      360
ctgagtccca actcacgcac tgcgctgacg aagtttgctg caaacatgaa caaaaacccc      420
gacacggata ttcgtatcgt aggccatacg acaataccg gctccgacaa gatcaacgat      480
cctctgtctg agacgtgc agccagcgta tattctttcc tgaattctca gggtgtgagt       540
atgtcgcgca tggcagccga agggcgtggg agccatgaac cggttgcaga caatagcaca      600
gttgccggac gttcggccaa ccgccgtgtg gaggtttata tcttgccgaa tgccaagatg      660
atcgaacaag cacagcaagg tacgctgaag                                       690
```

<210> SEQ ID NO 19
<211> LENGTH: 2037
<212> TYPE: DNA
<213> ORGANISM: Porphyromonas gingivalis

<400> SEQUENCE: 19

```
cctatccctt ttcttcttaa tatgtacagc ggacatcata aaatccatta tccttttctt      60
atcctgttgg tatgccttgc ttttgctgcc tgcaagagcg tgaagttgaa agatgcggag     120
aaggcacatg atcgccaaga gtataccaag gctgccgata tgtacaatac attatacagg      180
cgtacccgac gaaagcaggt ggagatgaaa gcttatacgg ctttccgatc cggtgaaaac      240
tatcgtgccg ccggcagaca agccaaagct ttgcgtggct atctgaatgc cagacgctac      300
gggtatccgg attctgtggt actgctccgt ttggcacaga cttatcagca aggaggtaac      360
tataaggaag ccgaggtact cttccgtgga tatctggaag cttatccgaa aagttatttt      420
gcagctatcg gtttggaggg gtgtctcttt gcccgccagc aaaaggaata tcctacacgt      480
taccggatac ggcgagctgc cgagtggaat tcggcacggg gcgacttcgg cccggcctat      540
gcacccgatg cttcggctct ctatttcaca tcgagcagaa gcaaagacga cggtttggat      600
aatagcagca taacgggact gaaacccaac gacatttata tcatcaaacg agatgcacaa      660
ggacgatggg gacgtcccga tagcgtgtcc ggaggaatca acactccatg ggatgaaggc      720
gtgccaacga tcacgcccga tggtagtacc atatattata cgttggcgca gcaaggagcc      780
gattacgacc gtacggtaca gatctattcc gccgctcgga gcggagaagg cggttggagc      840
aacggttcgc tcgtggacat tatgcgcgat tcgctccgta tggctgctca tccctctatg      900
tcggcatccg gcgattacct gtatttcgtc agcaatatag gcggtagcta tggcggcaag      960
gatatttatc gtgtcaaggt gtcggatcgt tcttatggtt caccggagaa tttggggcct     1020
gatatcaata cgccggggga cgaaatgttt cccttcatag atggggatag tacccttttc     1080
ttcgcttcgg acgacacgc cggtctggga ggactggata ttttcaaagc cacgctggac     1140
tctaccggcc aatggcatgt agtcaatatg ggacaaccgg tcaattcctc tgccgatgat     1200
ttcggcttgg ctgtggagcc taaaggcaaa acaaagaag aagctttgcc ggacaacgga     1260
gtcaaaggtg tatttttgttc caaccgaggc gatgcacgcg gatggccgca cctcttccat     1320
ttcgaactgc cggctatcta caccgagatt caaggttatg tgatggacag agaagaaaat     1380
cccatagccg gagccactgt caggatcgta ggcgaacgcg gccccgtagg acagggattc     1440
gtgactactc gtgacgatgg ctcctataag atgagcgtgc agggcgatac tcgctatgta     1500
atgcttgccg gagcatcggg ttatttgaat cagtacgtag aactcaagac cgataccgcc     1560
```

| | | | |
|---|---|---|---|
| aagcagagtg | agacctacta | tgtggacttt | ttccttgcat cgcgtgagaa agccgagggc | 1620 |
| ttgcaaaata | ttttctatga | tttcgataaa | gctactcttc gccccgaaag catgaagagc | 1680 |
| ttggacgaac | tgattcgtat | cctcacggac | aatccggata ttcggatcga attgggttcg | 1740 |
| catgccgaca | ggaaaggccc | cgatgcttac | aacctcggac tatctgaccg cagagccaaa | 1800 |
| tccgtggtgg | attacctcac | gagtcgtggc | atagcggccg acaggcttac gtggaaaggc | 1860 |
| tacggtaagt | ctgtccccaa | gacggtgaca | gccaaaattg ccgaacggca cgatttcctg | 1920 |
| aaggaaggcg | atgtgctcac | cgaggaattc | gtagcacctt tgaccgagga gcagcagtca | 1980 |
| gtctgcgacc | aactgaaccg | tcgtaccgag | ttccgtgtga tcgaagaaga gttgcgt | 2037 |

<210> SEQ ID NO 20
<211> LENGTH: 987
<212> TYPE: DNA
<213> ORGANISM: Porphyromonas gingivalis

<400> SEQUENCE: 20

| | | | |
|---|---|---|---|
| aaccttagga | cacagccttt | cttttggta | gatttgcaat ctatgatcag aacgatactt | 60 |
| tcacgatatg | tatcctcgaa | cttttggagt | cggggagcta cctttttttt cacgattttc | 120 |
| ccggccttca | tcctcgccgc | tactgctttg | ccggcttgtg gaggggtac tgcttcaggc | 180 |
| tccgatcgta | cgctggctgt | gaccatcgag | ccacagaaat acttcatcga gtccattgcg | 240 |
| gataagtcgg | tgcaggtggt | ggcattggta | ccggccggca gcaatccgga ggaatacgac | 300 |
| ccttcgccta | ccgtgatgaa | gcgtttgtcc | gaagcagatg cctacttcta tataggagga | 360 |
| ctggggttcg | agcaaagaaa | tctcgctgcc | attcgggaca ataaccctaa gctccctctt | 420 |
| ttcgaaatgg | gcaaagcctt | ggcggatgcc | ggaagtgcag atctccacgg ctcctgcaca | 480 |
| gatcattctc | atacagacct | gcatgcccat | gatccgcact attggagcag tgtggtaggg | 540 |
| gcaaaggcac | tcagtcgtgc | tgcatacgac | gcgcttgtgg agctttatcc gaacgagaaa | 600 |
| gacaaatggg | acaaagggca | cgaccgtctc | aacggacgta tcgacagcgt gaagagactc | 660 |
| gtcgatacca | tgtttgccaa | tggcaaagca | gacaaagcct tcgtcatata tcacccatcg | 720 |
| ctcagctttt | tcgcccaaga | gttcggcctg | cggcagatcg tcatagagga agatgggaaa | 780 |
| gagcctacgg | ctgcccacct | tcgtcgtgtg | atcgatcagg cacgtgccga tggtgtcaga | 840 |
| atcgtattta | tccaacccga | atttgaaacg | cgtcaggcgg aggacatcgc acgcgagatc | 900 |
| ggtgctcgtc | cggtaaggat | caatcctctg | cgcagctcgt gggaggagga aattttacat | 960 |
| attgctcgcg | ctttggctca | tgaacgg | | 987 |

<210> SEQ ID NO 21
<211> LENGTH: 2886
<212> TYPE: DNA
<213> ORGANISM: Porphyromonas gingivalis

<400> SEQUENCE: 21

| | | | |
|---|---|---|---|
| gccatttttg | tcgtatcatt | gcaaattgaa | aaaataacag agaataagta taattcagac | 60 |
| aagagcatga | acaaattta | caaatcactt | ttgcagtcag gactggctgc cttcgtgtcg | 120 |
| atggcaactg | cactgaccgc | ttctgcacag | atttcgttcg gaggggaacc cttgagtttc | 180 |
| tcttcaagat | ccgccggaac | gcattcattc | gacgatgcaa tgactatccg ccttactccg | 240 |
| gatttcaatc | cggaagacct | gatcgcacag | agccgttggc aatcgcaaag agatggccgg | 300 |
| cccgtccgga | taggacaagt | aataccggtg | gatgtggact ttgcatccaa ggcttcgcac | 360 |
| atctcttcca | tcggagacgt | agatgtatat | cgcctgcaat tcaagttgga aggagccaaa | 420 |

| | |
|---|---|
| gccattacgc tttattacga tgcattcaat attccggagg gcggacgcct ctatatctat | 480 |
| acccccgacc atgaaattgt gttgggagca tatacgaacg ccactcatcg ccgcaacgga | 540 |
| gcttttgcca cagagccggt accggggagt gagcttatta tggattatga agtgtctcgc | 600 |
| ggagggactt tgcctgacat caagatctcc ggtgcgggtt atatattcga caaagtcggc | 660 |
| ggacgcccg taacggataa ccattacggg atcggtgagg acgattccga ttcggattgc | 720 |
| gagatcaaca tcaattgtcc tgaaggtgca gactggcagg cagagaagaa cggtgtggtg | 780 |
| caaatgatca tggtaaaagg acagtatatc tcaatgtgct caggcaacct gctcaataat | 840 |
| acgaaaggag actttactcc gctgatcatt tctgccggac actgtgcttc cataacaacc | 900 |
| aatttcggtg taacgcaatc cgagttggat aagtggatct tcactttcca ctatgaaaaa | 960 |
| agaggatgca gcaatggtac attggccatc ttccgtggca acagtatcat cggagcttcc | 1020 |
| atgaaggctt tcctcccgat caaggtaaa tccgatggtc tcttgctgca actcaacgat | 1080 |
| gaagtccctc tgcgctatcg tgtctattac aatggatggg acagtacgcc cgatattccc | 1140 |
| tcgagcggtg ccggtattca tcatccggcc ggagatgcca tgaagatttc atcctaaag | 1200 |
| aagactccgg ctctgaatac atggatctcc tccagtggtt ccggagggac tgacgatcac | 1260 |
| ttctatttca atacgatca aggtggtacg aaggaggat cgtccggttc ttctctcttc | 1320 |
| aatcagaata gcacgtggt cggcacactg accgaggtg ccgcaattg tggcgggacg | 1380 |
| gagttctacg gcagactgaa cagtcattgg aacgagtatg catccgatgg caatacgagc | 1440 |
| cgcatggaca tctatctgga tccccaaaac aatggccaga cgaccatcct caacggaacg | 1500 |
| tatcgtgacg gttataagcc tttgccctct gtgccccggc tattgttgca gtctacaggc | 1560 |
| gatcaggtcg aattgaattg gacggctgtt cctgccgatc aatatccatc atcttatcag | 1620 |
| gtcgaatacc acatattccg aaatggaaag gaaatagcta cgacaaagga gttgtcctat | 1680 |
| tcggatgcca tcgacgaaag tattatcggt agcggtatca ttcgatacga agtaagcgca | 1740 |
| cgcttcattt atccctcgcc gttggatgga gtggaatctt ataaggatac ggacaagact | 1800 |
| tctgccgacc ttgccatagg agacattcag accaagctga agccggacgt aacacctctc | 1860 |
| cccggaggag gagtatcatt aagctggaaa gttcctttct taagccagtt ggtttcccga | 1920 |
| ttcggagaaa gccccaatcc tgtgttcaaa acctttgaag tgccctatgt ttctgccgca | 1980 |
| gccgcacaaa cccccaatcc tcccgttggc gtagtcattg cagacaagtt tatggccggt | 2040 |
| acatatcccg aaaaggctgc tatcgctgcc gtttatgtaa tgccatccgc tccggactct | 2100 |
| actttccacc tcttcctcaa gagcaacaca aacagaagat tgcagaaggt gacaactccc | 2160 |
| tccgattggc aggccggaac atggttgagg atcaatttgg ataagccgtt cccggtgaat | 2220 |
| aatgaccata tgcttttgc cggtatcaga atgcctaata agtacaagct caatcgtgct | 2280 |
| atccgttatg taagaaatcc ggataacctt ttctccatta ccgtaagaa gatttcatat | 2340 |
| aacaacggag tctcttcga aggctacgga ataccctcgc tcttgggcta tatggctatc | 2400 |
| aaatatctgg tggtaaatac cgatgctccg aagatcgata tgtcgcttgt acaggagcct | 2460 |
| tatgctaagg gaacgaatgt ggctccattc cccgaattgg tcggcatata tgtctataag | 2520 |
| aacggaacat ttatcggcac acaggatcca tccgtcacaa cttattcggt ttcagacgga | 2580 |
| acagagagcg atgaatacga aataaaactg gtatataagg gatcgggcat ttcgaatggc | 2640 |
| gttgctcaga ttgagaataa caatgctgtc gttgcatatc cgtctgttgt aacagatcgt | 2700 |
| ttcagcatta agaacgctca tatggttcac gctgccgccc tctactcatt ggatggcaag | 2760 |
| caggttcgtt cttggaacaa cctccgcaat ggcgtgacat tcagtgttca aggacttacg | 2820 |

```
gccggtactt atatgctcgt tatgcagacg gcaaacggcc ctgtgagcca aaagatcgtg   2880
aagcag                                                              2886

<210> SEQ ID NO 22
<211> LENGTH: 2814
<212> TYPE: DNA
<213> ORGANISM: Porphyromonas gingivalis

<400> SEQUENCE: 22
tcagaaaatt atagatacgg aaaaattacg aatcaaataa tggctatcat gatgaaaagt     60
attgttttta gagcatttct aacgattttg ctctcgtggg cagcgatcac gaatccgact    120
gctcaagaga tctcaggcat gaatgcatcc tgtctggctg ctccggctca accggatact    180
atcttatatg aaagttttga gaatggacct gttcccaatg ctggcttga  gatagatgct    240 gatgctgatg gtgccacttg gggaagccca tcaggctctt tctctgtacc ttacggacac    300
aatggccttt gcacctactc ccatatacgt tccggtatct caacagcggg caactatctg    360
attacaccca atatagaagg agccaaacgg gtcaagtact gggtatgcaa tcagtatagt    420
accaatccgg aacattacgc agtaatggta tcgacaacgg ggactgccat tgaagacttt    480
gttttgttgt ttgatgattc cataacaggg aaaccgactc ctcttgtatg gcgtagacga    540
atcgtggact taccggaagg gaccaaatat attgcatggc gacattacaa agtcaccgac    600
tcacacacag aattcttgaa attggatgat gtcactgtgt ataggtcgat cgaagggccc    660
gaacctgcta ccgacttcac agtaatcaat attggtcaga atgtgggacg attgacttgg    720
aactatccgg aggattatca accggaagga aaggggaatg aagagttgca gcttagcggc    780
tacaacatct atgcgaacgg tacactactg gcacaaataa aagatgtctc catactggag    840
tatgtggaca gcacttactc tttgcgagac aatcccttgc aagtggagta ctgcgttaca    900
gccgtttacg atgaaagcat agaatcttcg accgtatgtg gcacgctgca ttacgccacg    960
gatgccatcc tttatgaaaa ttttgagaat ggacctgttc ccaatggttg gcttgtgata   1020
gacgctgatg gagatggatt tagctgggga cactatttga atgcatacga cgcttttccc   1080
ggccataatg gaggccattg ctccttgtcg gcttcttatg ttccgggtat aggcccggtg   1140
actcccgaca actatctgat taccccccaag gttgaaggag ccaaacgtgt caagtactgg   1200
gtaagcacgc aggatgccaa ttgggcagcg gaacattacg cggtgatggc ttcgacaacg   1260
gggactgctg tcggagattt cgtcatattg ttcgaagaaa ccatgacagc gaagccgacc   1320
ggcgcatggt atgaaagaac catcaactta cctgaaggga ctaaatacat cgcatggcgg   1380
cattacaact gtaccgatat atatttcttg aagttggacg atatcactgt attcgggact   1440
cctgcatcag agcccgaacc tgttaccgat ttcgttgtct cgcttattga aaacaacaag   1500
ggacgattaa agtggaatta tcctaacggc tacgaacccg ataagactga tgataaagac   1560
ccattgcagc ttgccggcta caatatctat gcaaacggct cgctccttgt tcacatacaa   1620
gacccgactg ttttggagta tatcgatgag acttattctt cacgagacga tcaggtggaa   1680
gtggaatatt gtgtcactgc cgtttataac gacaatatcg agtcccaatc ggtttgcgat   1740
aagctgattt atgattctca atcggacatt atcttatatg aaggctttga ggccggaagt   1800
attcctgaag gctggttgtt gattgatgct gatggcgaca atgttaattg gactattat    1860 ccttggacta tgtatggaca tgacagtgag aagtgtattg catccccttc gtacttaccg   1920
atgattggcg ttttaactcc ggataactat ttggttacac ccagactcga aggagccaag   1980
cttgtcaagt attgggtaag tgcgcaagat gctgtttatt cggctgagca ttatgctgtg   2040
```

```
atggtttcta ctacgggaac tgctgttgaa gattttgtcc tcttgttcga agagacaatg    2100
accgctaagg ctaacggtgc atggtatgag cgaactatta cattgcctgc aggaacaaaa    2160
tatattgcct ggcggcatta tgattgcacc gatatgtttt tcttgctctt ggatgacatt    2220
acggtttatc gttctactga gactgttccc gagcctgtta ctgatttcgt tgtctcgctt    2280
attgagaata acaagggtcg cctgaaatgg aattatccta acggctacga acccgataag    2340
actgatgata aaaaccatt gcagcttacc ggctacaaca tctatgcaaa tggctcgctc    2400
cttgttcaca tacaagaccc gactgttttg gagtatatcg atgagactta ttcttcacga    2460
gacggtcagg tggaaatgga atattgtgtc actgccgttt ataacgacaa tatcgagtcc    2520
caatcggttt gcgataagct gaactatact atcacatcct tggataatat tcaatctgat    2580
acaagcttga aaatatatcc taatccggca tcgtatgtgg taaggataga gggattgagt    2640
cggagcaagt cgacaatcga gttgtataat gcgctgggaa tttgcatatt aagggaagag    2700
actcattcag agaaaacgga aatcgatgtt tcacgtctca atgacggagt ctacttgatt    2760
aaagtagtcg gtggaaataa acaacaacc gaaaaggtag agataaagag gccg    2814

<210> SEQ ID NO 23
<211> LENGTH: 1011
<212> TYPE: DNA
<213> ORGANISM: Porphyromonas gingivalis

<400> SEQUENCE: 23
cctcagcccg tcggccttaa agaaataacc attaaaccca tgtgcctcga acccataatt     60
gctccgattt catccgagtt gctcgagcag gagctgactg ccgatcgttt tctgcggatg    120
acaaacaaag ccggcaatga gatctatgtt tttacggccg aagaagctcc gcattgcatg    180
aaagaagtag gccgactgcg agaagaagcc tttcggcatt atggcggagg tactggcaag    240
gcgatcgata tagacgagtt cgacaccatg cccgggagtc acaaacagct gatcgtatgg    300
gatccgcaaa acaaggctat actcggaggc taccgcttta tctatgggcg ggacgttgct    360
ttcgataccg atggcaagcc tttgctggca acggcagaga tgtttcgctt cagtgatgct    420
tttttgcacg attatctccc ctacacagtc gaattgggac gttcgttcgt gtcgctccag    480
taccaatcga cacggatggg cacaaaggcc attttttgtg ctggacaatct ttgggacggt    540 atcggagcac tcactgtagt caatccagag gcactctatt tctatggcaa ggtgaccatg    600
tacaaagact atgatcggcg agctcgcaat ctgatcctgt attttcttcg caagcacttc    660
tccgatccgg aaggcttggt caagcctatt catccctac cgatagagat cagtgcggag    720
gacgaagcct tgttctcctc atccgacttt gacaccaatt acaagactct caatatagaa    780
gtgcgcaagc tgggtatcaa tatccctcct ctcgtgagtg catatatagc tttgtctccg    840
gagatgcgtg ttttcggcac tgcagtgaat gagtctttcg gagaggtgga ggaaaccggc    900
atattcattg ctgtgggtaa gatcctggaa gagaaaaaac aacggcacat agagagcttc    960
atcctcagcc ggaacgaaaa aaaggtctc gacagtagca atggccgatc a             1011

<210> SEQ ID NO 24
<211> LENGTH: 3753
<212> TYPE: DNA
<213> ORGANISM: Porphyromonas gingivalis
<220> FEATURE:
<221> NAME/KEY: misc_feature
<222> LOCATION: (3024)..(3024)
<223> OTHER INFORMATION: n is a, c, g, or t

<400> SEQUENCE: 24
```

```
aaatggaaat tggcatgcgc ttttgattgc gcgtgttgtt tcgatccatt tgtagtaact      60
aacgaggtaa taataatgat gaaacgatat acaataattc ttgcagtttt tcttttattc     120
tgcacggtat ttacctttca aataaaagct cgcccttatg aaagatttgc agatgtagag     180
aagccttgga ttcagaaaca ttcaatggat tctaaattgg tgcctgcaaa taagggtaac     240
ttaattcaag ctgaaattgt ataccaatct gtttctgaac atagtgactt agttatttca     300
cctgtgaacg aaataaggcc tgcaaatcgt ttcccttcgc ataggaagtc ttttttttgca    360 gaaaatctac gggcatctcc ccccgtagtt cccgttgccg tcgacaagta tgcggtaccg     420
gttgccaatc caatggatcc tgaaaatccc aatgcctggg atgtgacgct aaaaatcact     480
actaaagcgg taacagtacc tgtcgatgtg gtgatggtta tcgaccagtc ttcgtcaatg     540
ggagggcaaa acattgccag attaaagtct gccattgcat cgggacagcg ttttgtgaaa     600
aaaatgttgc ctaaggggac ggctacagaa ggggtgcgta tcgctcttgt gagttatgac     660
catgagcctc atcgcttatc tgattttacc aaagacactg ctttctctg tcaaaaaatc      720 cgggctttga ctcctatttg gggaacacat acccaggggg gcttaaaat ggcgagaaac      780 attatggcca cttctactgc tgtggataag catatcatat tgatgtctga cgggttagcg     840
acggagcagt atcctgttaa aaatgtaact actgcagact tcattggcaa aactggaaat     900
gcgaatgatc ccattgattt ggttatacaa ggagcaatta atttccctac aaattatgtt     960
tccaacaatc catctacacc tcttccccca aattatccaa ctcattcttc taaagttgga    1020
cggagaaatc tgccggaatc caaattcgat tatagtaatc tgagtgcaag gattactttt    1080
gatggtgttg ctggcgcatt ggtctatgaa ccgaggtttc ctcatcccta ttattattat    1140
ttcccttgta acgctgctat caatgaggct cagtttgcga aaactctgg ttatacaatc     1200 catactattg gctatgacct gggagatttt gccttggcca acaattcgtt gaaactaacc    1260
gctacagacg agaatcactt ctttacggcg acaccggcca atttagctgc agcgtttgat    1320
aatattgccc aaactattaa tataggtata cagagggggg aggtgacgga ctttgtagct    1380
cctggtttca tcgttaaaaa tctgacgcaa tcgggagatg ttactcattt gctaaatgtt    1440
tcaaatggaa cggtgcacta tgatgtctct actaaaaaac tgacatggac tactggtact    1500
atcctgagct catcagaagc taccataact tatcgtattt atgccgattt ggattatata    1560
cagaacaatg atattccggt aaatactact tctgctatcg gcccggatct tggtggattc    1620
gataccaata ccgaggcaaa attgacctat accaattcca atggcgaacc gaatcagcag    1680
ttaattttcc cacgtccgac ggttaagtta ggttatggtg ttattaagcg gcactatgta    1740
ttggtaaata aagacggtca acccatacag gcaaatggaa cagttgtcag ttccctaagc    1800
gaggctcatg ttctacagtc acaagatttc tttttgccct caggtggagg tcatattgtt    1860
cccaaatgga taaagttgga caaaacgacc gaagcattac agtactattc cgtaccgccg    1920
actaacacgg tcatcactac tgccgatggt aaacgttatc gttttgtcga agtcccaggc    1980
tccacgccga atccgggcca aatcggtatc agttggaaaa aaccggcagg aaacgcttac    2040
ttcgcttaca agctcctcaa ttattggatg ggaggaacaa cagaccaaca gagtgaatgg    2100
gatgtgacgt ccaattggac aggagcccaa gtaccgctca caggagaaga tgtagagttt    2160
gcaacgacag aaaatttcgg ttctccggcg gtagccgatt gcatgtccc gacaaccaac     2220 cccaaaatta tcggtaaccct tatcaataat tccgacaagg atttagttgt taccacaagc    2280
agtcaattga cgatcaacgg cgtggttgag gataacaatc cgaatgtcgg tacgatcgtc    2340
gtgaagtcgt cgaaagacaa tcctacgggg acattgcttt ttgccaatcc gggctataat    2400
```

```
caaaatgtag gggggaccgt cgagttttac aatcagggat atgattgtgc cgattgtggt    2460
atgtatcgca ggagctggca gtatttcggt atccctgtca atgaatcagg ttttccaatt    2520
aatgatgtgg gcgaaacga gaccgtcaac caatgggttg agcctttcaa tggcgataag    2580
tggcggccag caccttatgc acctgataca gagcttcaaa aattcaaggg ctaccagatc    2640
acgaatgacg tgcaggcaca gcctacggga gtttacagct tcaagggtat gatttgtgtg    2700
tgcgatgcct tcctgaatct gacacgcacg tccggtgtca actactcggg cgccaacttg    2760
atcggcaact catacactgg agccatcgac atcaagcagg gtattgtctt cccgccggaa    2820
gtcgagcaga cggtgtatct gttcaacacg ggaacacgcg accagtggcg taagcttaat    2880
ggaagcacgg tttcaggcta tcgagccggt cagtacctct ctgtacctaa gaatacagcg    2940
ggtcaggaca atcttccgga tcgtattcca tcgatgcatt ccttcttggt gaagatgcag    3000
aacggagcgt cttgtacgtt gcanatcttg tacgataagc tgctcaagaa cacgactgta    3060
aacaacggta atggtacgca gatcacatgg cgatccggca actccggatc ggcgaatatg    3120
ccgtcacttg tgatggatgt tcttggtaac gagtcggccg accgtttgtg gatctttacc    3180 gatggggtc tttcttttcgg attcgacaac ggctgggatg tcgcaagct gactgaaaaa    3240 ggtttgtcac aactttatgc gatgtctgac atcggtaatg ataaattcca ggttgcaggg    3300
gttccggagt tgaataacct gctgatcggc ttcgatgcgg ataaggatgg tcaatacacg    3360
ttggagtttg ctctttcgga tcattttgcg aaaggggctg tttacctgca cgatcttcag    3420
tcaggagcca acaccgtat tacgaattct acgtcgtatt cattcgatgc caagcgggga    3480
gattccgggg ctcgtttccg cttgtcatat ggatgtgatg agaacgtaga tgattcgcat    3540
gtcgtgagta caaatggccg tgaaattata attctgaatc aagatgctct tgactgcact    3600
gtaaccttat tcacaataga aggtaagctt cttcgccgct tgaaagtatt agctggtcat    3660
agagaagtca tgaaagtgca gaccggaggg gcctatattg tgcatcttca aaatgctttc    3720
actaatgatg tgcataaggt gcttgttgag tat                                 3753

<210> SEQ ID NO 25
<211> LENGTH: 1218
<212> TYPE: DNA
<213> ORGANISM: Porphyromonas gingivalis

<400> SEQUENCE: 25
atattcatag accccgataa gaatacaaaa caaaacgaac gaaatatgat tatcaagaaa      60
atgctgaaaa ataaattggc ccccttggcc atactgttcc tttttgctcc aaaggctatg     120
aaggctcagg agcaactgaa tgtggtacac acctctgtgc catcgctgaa tatcagtccg     180
gatgcacgtg cggccggtat ggggatata ggtgtggcaa cgacgccgga tgcgtattca     240
cagtattgga atccgagtaa atatgctttc atggatacga aagccggtat tagcttctca     300
tatacaccct ggctgtccaa gctggtcaat gatattgccc tgatgcagat gaccggtttc     360
tacaaattgg gaacagacga gaatcaggct attagtgctt ctctgcgtta tttcacatta     420
ggaaagttgg agactttcga cgaattgggc gaatccatgg gagaggccca tcccaatgaa     480
tttgctgtcg atttgggcta tagccgccag ttgtcggaga acttctccat ggctgttgca     540
ctgcgttaca tccgctcaga ccaaagcact cacaacaccg agagaatca ggccggaaat      600 gccttgcgg cggatatagc cggttatttg cagaagtatg tgctactggg taatgcggag     660
agcttgtggt cgttgggttt caacgtaaag aatatcggaa cgaagatctc ctatgacgga     720
ggtgtcacga gttttttcat ccctacttcg ttgaatctcg ggacggggct gttgtatccg     780
```

```
atcgatgact ataacagcat caatttcaac cttgaactta gcaagctgct tgtacccact    840
cctcctatca tggatcaaaa cgatcaggcc gggtatgagg ctgcactcaa gaaatatcag    900
gaaacttctt cgatcagcgg tatattctct tctttcggtg atgcgccggg aggactcaag    960
gaagaattcc gtgagattac atggggactt ggggctgaat atagctatga cgataaattt   1020
tttgttcgtg ccggatattc atacctgcac cccaccaaag gcaatttgca gtacttcacg   1080
gccggtgccg gcttcaaaat gaacatattc cgtatcgatg cttcctacct gttgtctacg   1140
atccagagta atccgttgga tcagactctg cggtttacgc ttgctttcga tatggatgga   1200
ttgcgcaatt tgttccac                                                 1218

<210> SEQ ID NO 26
<211> LENGTH: 1356
<212> TYPE: DNA
<213> ORGANISM: Porphyromonas gingivalis

<400> SEQUENCE: 26
ctaataatcg aaaaggaaat gaaaacaaca gttcaacaaa ttattctgtg cctggcttta     60
atgatgtcag gtgtattggg cggaaacgca cagagctttt gggaagaaat agctcctcct    120
tttatcagta atgagcctaa cgtcaagtat ataattccca atatggggat tgattcaaag    180
ggaacaatct atgtaaccgt gacaaaaagg attcagcagg gagcaaatta tacttctgag    240
caattgggta tgtactatcg accattaggt gataatgaac agtggtggaa acatgatccg    300
tattttgatg acaagatagt tgcggatatt cagacagatg catatggcag agtttatgta    360
tgtacgactt cttctcgaga tcaagagtat caactttata taaacgagca gaacgaatgg    420
aggtgtatat tcaaaacttc tgtgtctaca tatgagcatg gtatggctgt ttttcgctct    480
tcgacagggg tgacttatat aggtaccagg catcacatct tcgcatcagg tgtaaatgat    540
ttcgagttca acactatcta tgaagactct acacctatga gctgtcgctt tgcagaggct    600
acgaatagtg gcaccatcta tctggcattg atgcatgaaa ccacaatgtc tacgactatc    660
cttacttatc aaaacggtga gttcgtcgat atctcggaaa gtgaattgag taactcgatt    720
attgcatcca tgtgctctaa taaagaaggt gatataatag ctcttgttac ttcatataca    780
ggatttatga gtggaaccct tgcgatcaga aaagcagatg aaggcaaatg gcaacttgtt    840
ggcggagata tacagaatgc gatcgttcaa aatatatgca tgatggacga caacaagatt    900
gcttgtgaag tcttcgggac tcctaacgga gtagatggtc ggacaagggt tgtgtttct    960 gacgcatctg tctttgattt tgagtggtat gaagatgaaa tatacggagg cctgatattt   1020
gacactttct tctatagccc ttgggacaaa cttctttatg cgaaatttgg tgggattatg   1080
ctcaggagta aagagtcttt tataacctct ttcatttctc cgacagttgt acaaggagtg   1140
gatgtctata ctttggccgg gaagataagg atcgaaagtg aaactccggt gtctgaggtg   1200
ttgcttttcg acctggctgg caggatggta cttcggcaaa ccattgataa taaaatctat   1260
tcggacatag atactaacgg actaaagcga agcggtattt acgtagtctc ggtgcggctc   1320
tcttccggac aggtattcag tcataaggtg caggta                              1356

<210> SEQ ID NO 27
<211> LENGTH: 1842
<212> TYPE: DNA
<213> ORGANISM: Porphyromonas gingivalis

<400> SEQUENCE: 27
ccatataatg tccaatctat tagcaacaag acgattaaaa aacaaatgga aaacttaaag     60
```

```
aacattcagc ccagagagga tttcaactgg gaagagtttg aggccggtgg cgtccatgct    120
gccgtgagtc gtcaggagca ggaagctgct tatgacaaaa cgctcaatac catcaaggaa    180
aaggaagtgg taatgggtag ggtaactgct atcaacaagc gtgaagtggt tatcaatgta    240
gggtacaaat cggaaggtgt ggtacctgca acagaattcc gctacaatcc cgaactcaaa    300
gtgggagacg aagtggaagt ttatatcgag aatcaggaag ataagaaggg ccagctcgtc    360
ttgtctcacc gcaagggtcg tgccgctcgc tcttgggagc gcgtgaacga ggctctcgaa    420
aaagacgaaa tcgtaaaggg ctatgtgaag tgtcgtacca agggtggtat gatcgtcgat    480
gtattcggta tcgaggcttt cctcccggga tcacagatcg acgtgcgccc cattcgcgac    540
tacgatgcat tcgttgagaa gacgatggag ttcaagattg tgaaaatcaa tcaagaatat    600
aagaatgtag ttgtttccca aaggtgctc atcgaagcag agctcgaaca acagaagaaa    660
gaaatcatcg gcaagctcga aaagggcag gtactcgaag gtatcgtcaa gaatattact    720 tcttacgag tatttatcga cctcggtgga gtggatggtc ttatccatat cactgacctt    780
tcatggggtc gtgtggctca tccggaagaa atcgtacagc tggatcagaa gatcaatgtc    840
gttatcctcg acttgatga agatcgcaag cgtatcgctc tcggactcaa acagctgatg    900
cctcatcctt gggatgctct cgacagcgag cttaaggtag gcgataaggt gaagggtaaa    960
gttgtggtga tggcagatta cggtgctttc gttgagattg cacagggcgt tgagggtctt   1020
atccacgtaa gcgaaatgtc atggacacag cacttgcgtt ctgctcagga cttcctgcat   1080
gtaggcgacg aagtggaagc cgtgatcctg acgctcgacc gcgaagaacg caaaatgtcg   1140
ctcggtctga agcaactcaa gccggatcct tgggctgata tcgaaactcg tttccctgta   1200
ggctctcgtc accatgctcg tgttcgcaac ttcaccaatt tcggtgtatt cgttgagatc   1260
gaagagggcg tagatggcct tatccatatt tccgaccttt cttggacgaa gaagatcaaa   1320
caccccagcg agtttacgga agtaggtgct gatatcgaag ttcaggtaat cgagatcgac   1380
aaggaaaacc gtcgtctcag cttgggtcac aaacagttgg aagagaatcc ttgggatgta   1440 ttcgagacg tattcactgt aggatctatc cacgaaggaa cggtaatcga agtgatggac   1500
aagggtgctg tcgtttctct gccttacggt gtggaaggtt ttgccactcc gaagcacatg   1560
gtgaaggaag atggctcaca ggctgtactc gaagagaagt taccttcaa ggttattgag   1620 ttcaataagg atgccaagcg aatcattgta tctcatagcc gtgtattcga agatgagcag   1680
aaaatggctc agcgtgaagc caatgcgagg cgtaaggctg aagccaaagc ggctcagaaa   1740
gaagctgctg ccgaagctgc caatcctgca caggctgtag agaaagccac tctcggagac   1800
ctcggcgagc tggccgcttt gaagaaaag ctttcagaaa ac                       1842
```

<210> SEQ ID NO 28
<211> LENGTH: 1689
<212> TYPE: DNA
<213> ORGANISM: Porphyromonas gingivalis

<400> SEQUENCE: 28

```
tcgctaatca acaattcaag agactggagg gctcctgtcc gattgagtct caaaaaaaag    60
acaaaaacta tgaagacaaa agttttacgc aaattcgtgg tggcggcttt cgccgtcgca   120
accctctgtc ctctcgccca agcgcagacg atggaggag atgatgtcaa ggtggtccag   180
tacaatcagg aaaaactggt acaaacgagg atgagtgtgg cggacaacgg atggatctat   240
gtaatgaccc acagtggata cgacaccggc aatagcaatg tgaagatctt ccgctccaaa   300
gaccaaggtg ccacatacca aaagttgagg gattgggatc catcggatga ttatcagttt   360
```

```
caagacttcg atatcgtggt aacgggtaag aatgaatccg acatcaagat ttggtcggta        420
gagctcatga ataagcccgg aggatataag agtagagttg cggtcttcag tcgcgatgcc        480
aacgcgcaga atgcgaaact cgtgtataag gaagacttct ccaatgtgca gttgtacgat        540
gtggatatag cctccaacta tcgttcgcct tcttctctta acaatggtgg caacccttt         600 gctttggctt tcgcttacac cggcttcaac aatacgcaca aaataagttt tgtggactat        660
gtgttctctc tgaatggagg gcaaaatttc aataaaaact tactcttcag tcaagatgga       720
gagaagaaaa ttgacaaggt ggatctctca ttgggtagca cctctgaatc catgggtcac       780
aatgcctggc cgctaatggg tgtggtattc gaaatgaata acaaggggg aaaaagcgat        840 atcggtttct tgtcgaactt tgtcgacaat gatcccgaat ttcagtgtc aggccctata        900 aaagtgagtg aaagcgacat gtcgttcagc cccaaaatcc aaatgttgct ggacgaggat        960
aacaatacga tcaatgggga gagttgccac aacttcatga ttacgtacag cgattatgat       1020
tctgaatatt cggattggga cattcggtat gtatatccca agaaatcgtt caagtatgaa       1080
aaaggaaaaa ctccgactat ggatgatctg gtggaagctt tccttacagc ttcgtaccag       1140
agtgagacca actcggggct gggtatgac aagaacgcca atcactacct gattacatat       1200
gccaaaaaag aagagaacgg tacgaacacg ctgaaatacc gctgggccaa ttatgacaag       1260
attcataaca aagatttgtg gagcgacaca tttacgtata catcatctgc caatgctctc       1320
tacacacctc aagtagacat caatccgacc aagggtctcg tgtgctggtc atgggtggaa       1380
tatctgccgg gcaaacggat cgtttggtct gatacgcagt ggacccatgc caacggtgta       1440
gaagacatcg taatgcaaga aggcagcatg aagctctacc cgaatccggc tcaagaatat       1500
gctgtgatta gcctgccgac ggcagcaaac tgcaaggctt tgtttacga tatgcagggc       1560 agagtagtcg ctgaggcttc tttctccggc aacgaataca ggctgaacgt gcagcacttg       1620
gctaagggta cgtacatact caaggtcgta tccgatacgg agcgtttcgt agagaagctc       1680
atcgtggaa                                                              1689

<210> SEQ ID NO 29
<211> LENGTH: 3486
<212> TYPE: DNA
<213> ORGANISM: Porphyromonas gingivalis

<400> SEQUENCE: 29
gctatttctc agatgaaacg aatacttcca atagtcgcat tcctttctct cttccttgcc         60
cttgctttgc ctgcgaaagc gcaacgagct atggggaaga cggccgaccg ttcgctaatg        120
gcttcgggac attgggtcaa gatacgtgtc gatgcaagtg gagtgtatcg ccttacggac        180
gaacagctcc gtgccaatgg cttctccgat ccgtccaagg taggtgtgtt cggttatggt        240
ggaggggtgc ttcccgaaga tctgagccgg atcacgacag acgatttgcc tccggtaccg        300
gtactccgtc agggcaatgc gctgtatttc tatgccgtgg gcccggtgac atggttctac        360
aatccggcca aaaccaccat ggagcatacg gtgaatacat acagtacgca tggctactac        420
ttcctgtcgg atgctgccgg agcacccttg cagatgtccc aatatacggg tggaggtgcg        480
tcggccgagg ctttgatcga ctactacgat gagctgatgc tccatgaaca ggaattgtat        540
tcgcccaaag aatcgggacg agatctgtat ggcgagtctt tcagtgcagt caatacgcgt        600
acggtcaagt tcccttttgag gggcaacacc cgctcgtctg gcgaactcgg taccgtattc        660
tcatacatag ccaaggccag atcggccggt ggcggccgtg agatgtcgct ctcggcgaat       720
ggcattctga tcttcagcga tccttttttcc atgacatcga atgaagtctc caattcctat       780
```

```
ttggccggca agaagcgtcg tctctatcac agtacgccga tgaacagctt ggtcaatgag    840
ttgcgcttgg acgcgaacta tagcatgaca ggagatgcgg tcaatctgga tttcatagag    900
gtggctacac agaacgacct ccggtacgat ggcgcaccca tgcatatcag gcggttttcc    960
aatttgcccg ttttgggggg cgagtcctgc cggttcgtta tcagtgaggt gccggagtct   1020
ctggtggttt tgcaggccaa ttcttccctg acagcatcgc ttgttcccgt taagactgtc   1080
ggggataaga ccattgagtt cgtggctccg ccgaagggtc aggatcgtag gactatcaat   1140
acgttttatg ccgtggactt gtcacaggct tctgctccgg agatcctcgg agcggtaccc   1200
aatcaaaacc tgcatggaga ggaaatccct gatctgatca ttgtctctac tcaggcgctc   1260
ctccttgagg ctgatcgact ggccacctat cgtagagaga aaacgggct gaaggttttg    1320 gtcgtgttgc aggaacaggt gttcaacgag ttttcgggtg aactcccga tgctacagca    1380 taccgcctct tgccaaaat gttctacgac agatggaagg caaatgcacc tgtgggagag    1440
accttcccga tgcaaatgct tctcttcggt gatgggctc atgacaacag gaaggtctcc    1500
gtagcttggc agaaaccgta tctccaacaa acggagttct tgctgacatt ccaagccgtc   1560
aattcgacga acgtaaacag ttatgtgacg gatgattact tcggcttgct ggatgatcag   1620
ccggcctcgg tcaatatcgg ttggcgcaat tataatatgg ctgtagggcg attccccgta   1680
cgtactccgg ccgaagctcg catcgcagtg gacaagacca tccgatatga ggaggatcga   1740
gagagtggtg cctggcgtat tcgtgcctgt tttgcggcag acaacgggga caagcacgca   1800
accgagactt cccgtttgat cgataccgtc aagcgttatg ctcctgccat catgccggta   1860
cgcgcctttc aggacgtata tccgcatgtc atcgagaacg ggttgcacag cattccgggt   1920
gcaaagaaaa agatgctgga aacccttcag tcgggtatta tcctgcttaa ttatgctggt   1980
catggcggtc ctgccggatg gtcggacgag catttgctga cgctcaacga tatacacaaa   2040
ttcaattata agcatatgcc catttggatt actgccacgt gcgactttgc caactatgac   2100
agtcagacga cctcggcagg ggaggaggtt ttcctccatg agaagagtgg cactccgatc   2160
atgttctcga ctacgcgtgt cgtttacaat acgcagaatg agaagatcaa tggttttatg   2220
cttcggcgta tgttcgagaa agctaaggat gggcgttatc gtacgatggg cgagattatc   2280
cgatcggcca acaggggat gctcagtact gttttcccg attcgatcaa ccagttgagt     2340
ttctttctga tgggtgatcc gtccgtgcgt atgaatcttc ctacccacaa agtgcaattg   2400
accgcaatca acgggcagga tcccgaaggg cagtatggaa ctattatgct caagtctttg   2460
gaacgggtag ctctgaaggg taaggtaacc gatgaaaagg ggacattcga cgagacattc   2520
agtggcaagg ttttcctgac cgtcttcgat ggcagaaaga aaatgacagc tttggaagag   2580
gagggaaacg atctctctct tgtatattat gactatccta acgtgatgta tgccggtatt   2640
gccgaggtga agacggact cttcgaaact tcgtttatcg tacccaagga tgtgaactat   2700
tccgagcacg aaggccggat caatctttat gcttataacg agagcacaaa ggcggaagcc   2760 atggggtag acttctccat cagagtccaa ccgggtattc ctgatgaggt aacggaagat    2820
aatacaccgc ctgaaatcat aagctgcttc ctcaatgaca gtacattccg atcgggagat   2880
gaggttaatc ctactcctct gtttatggcc gaagtattcg acttgaatgg aatcaatatc   2940
acgggtagcg gagtagggca tgatattacg cttggtatcg atggccgtgc cgacctgacc   3000
tacaacctca atgcatattt cacaagttcg gctacggatg caggtgtggg cactattctc   3060
ttcatgatac cggctttggc cgaaggagat catactgccc gactgacggt ttgggacatt   3120
ttcaataatg ccgtccatca tgactttca ttcagagtgg tagatggcat tgctccggat    3180
```

```
gtggctgatg tgattctatt cccgaatccg gtacgcgaga gtgctacgtt ccgaatcttc    3240
cacaatcgcc ccggaagcga tttgaacgtg gccgtggaga tctatgactt caccggtcgt    3300
cttgtgaaca gtttgccagt caagacctat tcgtcttcct acggagaacc tatagagatc    3360
aagtgggatc tgacctccaa atacggagtg aagatcggaa acggattcta cctctatcgt    3420
tgtgtggtga actctcccgg aggacagacg gcctccatgg ccaagaaaat gatcgtggta    3480
ggacaa                                                               3486

<210> SEQ ID NO 30
<211> LENGTH: 1689
<212> TYPE: DNA
<213> ORGANISM: Porphyromonas gingivalis

<400> SEQUENCE: 30
catcataaaa catatcaaac aatgaaaaag cttttacagg ctaaagcctt gattctggca      60
ttgggactct ccaactgcc cgcaatcgcc caaacgcaaa tgcaagcaga ccgaacaaac     120
ggtcaatttg caacagaaga gatgcaacga gcattccagg aaacgaatcc ccctgcaggt     180
cctgtgcgtg ctatcgctga gtacgaacgc tctgcagccg ttttggtacg ctacccgttc     240
ggtatcccga tggaattgat caaagagctg gccaagaacg acaaggtgat taccattgtg     300
gcgagtgaaa gccaaaaaaa caccgttata acccagtaca cccaaagcgg tgtgaatctc     360
tctaattgcg atttcatcat tgcgaaaact gactcttact ggacacgcga ctataccggt     420
tggttcgcaa tgtacgatac gaacaaagta ggtctcgtgg actttatta taaccgccct     480 cgtcctaacg atgatgaatt ccccaaatac gaagcacaat atctgggcat cgagatgttc     540
gggatgaagc tcaagcagac cggtggcaac tacatgacgg acggatatgg atccgctgtg     600
cagtcacata tcgcatatac ggagaactcc tctctgtctc aagctcaagt aaatcaaaag     660
atgaaagact atctcggcat cacacatcat gatgtggtac aagatccgaa cggcgaatat     720
atcaaccatg tggactgttg gggcaagtat ttggcaccga acaaaatcct catcaggaaa     780
gtgcctgaca tcacccctca gcaccaagcc ctggaagata tggcagccta cttcgcagca     840
cagacctgcg catggggaac gaagtacgag gtatatcgcg ctttggccac caatgaacaa     900
ccgtacacga actctctgat tctgaacaac agggtatttg ttcctgtcaa tggccccgcc     960
tccgtggaca acgatgctct gaacgtctat aagacggcaa tgcccggtta cgaaattata    1020
ggtgtcaaag gggcttcagg aacaccttgg ttaggaacag atgccctgca ttgtcgtact    1080
cacgaggtag cggataaggg ctatctctat atcaagcact acccgatact gggcgaacag    1140
gcaggccctg attataagat cgaagcagat gtcgtctcat gcgccaatgc tactatctcg    1200
ccggtacaat gttactatcg tatcaatggt tccggtagct ttaaggctgc tgatatgacg    1260
atggaatcaa caggtcacta tacttatagc tttacaggtc ttaacaagaa tgataaggta    1320
gaatactata tctctgccgc tgacaatagt ggtcgcaaag agacttatcc ctttatcggc    1380
gaacctgatc ctttcaagtt tacgtgtatg aacgaaacca atacatgtac tgtgaccgga    1440
gctgccaaag ctcttcgtgc atggttcaac gccggtcgtt cagaactggc tgtttcggta    1500
agtttgaata ttgccggcac atatcggata aagctttata acaccgcagg agaagaagtc    1560
gctgcaatga ccaaggaatt agtagcaggg acgagtgtct tcagtatgga tgtgtattct    1620
caggctccgg gcacatatgt tctggttgtt gaaggaaatg gaatccgtga gacaatgaaa    1680
attctcaaa                                                           1689
```

<210> SEQ ID NO 31
<211> LENGTH: 1311
<212> TYPE: DNA
<213> ORGANISM: Porphyromonas gingivalis

<400> SEQUENCE: 31

| | | | | | |
|---|---|---|---|---|---|
| accacaaata | gaaaaccaaa | tactaatatg | aaactttcat | ctaagaaaat | cttagcaatc | 60 |
| attgcattgc | tgacgatggg | acatgctgtg | caggcacagt | tgttccggc | tcccaccaca | 120 |
| gggattcgca | tgtctgtcac | tacaaccaag | gccgtaggcg | aaaaaatcga | attgttggtt | 180 |
| cattccatag | agaagaaagg | catctggatc | gatctcaatg | gggatgccac | ttaccaacaa | 240 |
| ggagaggaaa | taaccgtatt | cgatgaggca | taccacgaat | acacgatcgg | gacgcaaacc | 300 |
| ctcactatct | atggtaatac | gacccgattg | ggctgtcgat | ctaccggtgc | aacggctgtc | 360 |
| gatgtaacga | aaaaccctaa | tctgacctat | ctcgcatgcc | cgaaaaataa | tctgaaatca | 420 |
| ttggacttga | cgcaaaaccc | aaagctgctg | cgagtttggt | gcgactctaa | cgaaatagaa | 480 |
| agtttggacc | tgagtggcaa | tccggctttg | atcatcctcg | gctgtgacag | gaataagctg | 540 |
| actgagctga | agaccgataa | caaccccaag | ttggcctctc | tttggtgttc | tgataataac | 600 |
| ctgacggagt | tggaactcag | tgccaatcct | cgtctcaatg | atctttggtg | cttcggtaat | 660 |
| cggatcacga | aactcgatct | gagtgccaat | cctctattgg | taacactttg | gtgcagtgac | 720 |
| aatgagcttt | cgaccttgga | tctttccaag | aattcggacg | ttgcttacct | ttggtgttca | 780 |
| tcgaacaaac | ttacatcctt | gaatctgtcg | ggggtgaagg | gactgagtgt | tttggtttgt | 840 |
| cattccaatc | agatcgcagg | tgaagaaatg | acgaaagtgg | tgaatgcttt | gcccacacta | 900 |
| tctcccggcg | caggcgctca | gagcaagttc | gtcgttgtag | acctcaagga | cactgatgag | 960 |
| aagaatatct | gtaccgtaaa | ggatgtggaa | aaagctaaaa | gtaagaactg | gcagtatttt | 1020 |
| gacttcaacg | gtgattctga | caatatgctt | ccatacgaag | gaagtccgac | atcgaacttg | 1080 |
| gcagtagatg | ctcccactgt | caggatatat | cccaatccgg | taggaagata | tgcgctcgtc | 1140 |
| gagatccccg | agtctctttt | agggcaggaa | gctgctttat | acgatatgaa | tggggtaaaa | 1200 |
| gtctatagtt | tcgcggtaga | gtctcttcgt | cagaacattg | acctgacaca | tcttcccgac | 1260 |
| ggcacttatt | tcttccgtct | cgataactat | accactaagc | tcatcaaaca | g | 1311 |

<210> SEQ ID NO 32
<211> LENGTH: 954
<212> TYPE: DNA
<213> ORGANISM: Porphyromonas gingivalis

<400> SEQUENCE: 32

| | | | | | |
|---|---|---|---|---|---|
| aatcatttga | agacaaatat | caagatgaga | aaaacaataa | ttttctgctt | gttgctcgcc | 60 |
| ctatttggct | gttcttgggc | acaagaaaga | gtcgatgaaa | agtattctc | cgcaggaaca | 120 |
| agtatttta | ggggcatcct | tgaaaaggtg | aaagcaccgc | ttatgtatgg | agatcgtgag | 180 |
| gtatggggta | tggctcgtgc | gagcgaggat | ttctttttta | cttcccgt | tacggatgac | 240 |
| ctcactcccg | tgcttttcta | taaccgtctt | acaaacgaac | cctgctttgt | gtcagaccaa | 300 |
| ggaataactg | agtatttcaa | attcgctcaa | gaaggtgatt | acattgaagt | cgaaggaagc | 360 |
| tctgtattca | tggcgaatct | tttgtactat | cgttttttcc | cgacaagaat | tacctcctat | 420 |
| aatgctccca | ttgaaggtgt | tgtgagcaag | acgggaaatc | ctgcttttac | aatcccgatg | 480 |
| ctcccgggg | tttctgattg | catagaaatc | tcaaacaacc | gcaaagtctt | tctgaccaat | 540 |
| caattagggg | ttgtaaacat | cactgacggg | atggaacctc | cgattattgc | cggagtctct | 600 |
| gcttcctatg | gatcttccgt | ccgggtgtat | ggtcatgtct | cacagcggtg | ggacatcata | 660 |

```
ggccattgct atttggatat ctacccaacc aattgctatc cgctcagcac gaaacccgtt       720
gcaggagacg atgaggtttt tgtcaaacaa caaggcaggc aaatagagat cgatagcaac       780
agccccatag tccaagtggt cgtatacgat cttgagggga aaagtgtttt tcgcaaaaga       840
atgaccgaaa acgcttatac cctatccttt agagcaccca tgctcggctt tatgaccatc       900
atgatcgaaa cacaaaattc gattatcaat aaaaaactta atgttacaca gcta             954

<210> SEQ ID NO 33
<211> LENGTH: 1383
<212> TYPE: DNA
<213> ORGANISM: Porphyromonas gingivalis

<400> SEQUENCE: 33
agacgggcag ttaaaatccg atcacctccc catatccact cattatttgt acgtaaatgt        60
cttttttcag actttaaata cttatattta tcccgaaaaa ttacccaaga gagattgggt       120
cgattgtcga tccgtcttaa gtcatacaat ccaataatca ttattgaaat gaaaaaaaca       180
accattattt ctttgattgt cttcggtgct ttctttgcag ccgtgggcca aaccaaggac       240
aattcttctt acaaaccttt ttcgaaagaa gatattgccg gaggagttta ctctctcccg       300
actcaaaatc gtgcgcagaa ggacaatgcc gagtggcttc ttacagcgac cgtctccaca       360
aaccagtctg cagatactca ctttatcttc gatgagaaca accgctatat cgctcgtgac       420
ataaaagcca atggggtaag aaaatccacg gactccattt actacgatgc caacgggcga       480
atatcgcatg tggatcttta tatctcgttc agtggcggag agcctgcact cgacacccga       540
ttcaagtaca cctatgatga cgagggaaag atgaccgtga gggaagtatt catgctggta       600
atggatccga atacacctat ctcacgcttg gaatatcatt atgatgcaca gggcagactg       660
acccactgga tttcttttgc tttcggggca gaatcccaaa agaatacgta tcactataat       720
gaaaaaggtc tgttggtcag cgaagtgctg agcaatgcaa tggggacaac ctattcagac       780
accggcaaaa cggaatacag ctatgacgat gcagataata tggtgaaggc cgagtacttc       840
gtcgtccagc aaggaaaggc atggcaagta ctcaaaagag aggaatacac ctatgaggac       900
aatatctgca tacaatattt ggctattaac ggtaccgaca caaaggtgta caagcgagac       960
atcgagagcg ataagtccat ctccgcaaat gtcattgaca ttccgtcaat gccggaacag      1020
acctggccta atatgtacgg attcaacgca aagcgactga agagactta ttcctcctac       1080 gaaggagatg tggctactcc tatattcgac tatatctata cgtacaaggc tcttacctca      1140
atggcaacac cttcgacaga agctcaggta gcagtctatc tcaatccgtc aacggaccgg      1200
ttagtgattc tggccaacgg catcacacat ctgagcatgt acgacttgca gggtaagctt      1260
atccgtgatt gtgccttgag cggcgataag gtggaaatgg gtgtcggatc tttgaccaaa      1320
gggacatacc tgcttaaagt gaatacggat cagggagcct ttgtgagaaa agtcgtgatt      1380
cga                                                                   1383

<210> SEQ ID NO 34
<211> LENGTH: 1353
<212> TYPE: DNA
<213> ORGANISM: Porphyromonas gingivalis

<400> SEQUENCE: 34
atggcaaaag ttataaaaac aaaaaaaggc cttgcactta atctgaaagg aaaaccgctg        60
cccgagatgc tggccgaacc ggcccaaagt cctacttacg cggtcgtgcc cgacgatttt      120
gaaggtgtta tccccaaggt gacggctcgt ccgggggata aggtgcgtgc cggctcagca      180
```

```
ctgatgcacc acaaggcata tccggagatg aagtttacaa gtccggttag cggcgaagtg    240
atcgcggtga atcgcggtgc caagcgcaag gtgttgagca tcgaggtgaa accggacgga    300
ctgaacgaat acgagtcatt ccctgtcggg gatccgtctg ccctctctgc cgaacagatc    360
aaggagcttt tactgtcgag cggtatgtgg ggttttatta agcaacgtcc ttacgacata    420
gtggctacac cggatatagc tccacgcgac atttatatta ctgccaactt tactgcacca    480
ttggctccgg acttcgattt catcgttcga ggagaagaac gcgccctgca gactgccatc    540
gatgccttgg ccaaactcac gacaggaaag gtgtatgtgg gcctgaagcc gggttcatct    600
ctgggcttgc acaatgcaga aatcgtagaa gtacacggac ctcatccggc aggtaacgtg    660
ggcgtgctga tcaatcatac gaagccaatc aatcggggcg aaacggtgtg gacgctcaag    720
gctaccgacc tgatcgtgat cggacgtttc ctgcttacgg gcaaagccga ttttaccaga    780
atgattgcca tgaccggctc agacgctgca gctcacggat acgtccgtat tatgccgggt    840
tgcaatgtct ttgcttcctt ccccggccga ctgacaataa ggaatctca cgagcgtgtg    900 atcgatggca atgtgctgac cggtaagaag ctctgcgaga aggagccttt cctgtcagcc    960
cggtgtgacc agatcacggt gatccccgaa ggcgacgatg tggacgaact cttcgggtgg   1020
gctgcacccc gtctcgatca gtacagcatg agcagagctt atttctcttg gttgcagggg   1080
aaaaacaaag agtacgtact cgatgcccgg atcaagggtg gcgaacgtgc tatgatcatg   1140
agcaacgagt atgaccgcgt tttcccgatg gacatctatc ggagtatttt gctcaaggct   1200
attatagcat tcgacatcga caagatggag gacttaggca tatatgaagt ggctccggag   1260
gactttgcca cttgcgaatt tgtggataca tccaagatcg agctgcagcg tatcgttcgc   1320
gagggcttgg atatgctcta taaggaaatg aat                                1353

<210> SEQ ID NO 35
<211> LENGTH: 585
<212> TYPE: DNA
<213> ORGANISM: Porphyromonas gingivalis

<400> SEQUENCE: 35
atggataaag tgagctatgc tctgggattg agcatcggta ataatttcaa gtcttcgggc     60
atcgacagcg tcgttatgga tgatttcatg caaggtctgt ctgatgtact ggaagaaaaa    120
gcccctcagc tctcgtatga cgaggccaag cgcgaaatag aggcgtattt catggatttg    180
cagcagaagg ctgtcaaact gaacaaagag gccggagaag aattcctcaa gataaatgca    240
cacaaggaag gtgtgacgac cttaccgagc ggcttgcaat acgaagtcat taagatggga    300
gagggcccga acccacccct ttcggacacg gtaacctgtc attatcacgg tacgctcatc    360
aacggtatcg ttttcgatag ctctatggac aggggagaac cggccagttt ccctctaaga    420
ggagttatag ccggctggac ggagattctt caattaatgc ctgtaggatc caagtggaaa    480
gtaactatac cgagcgatct ggcgtatgga gatcgtggtg ccggcgaaca tatcaaaccg    540
ggtagtacgc tcattttat aatcgaatta ttgagtatca acaaa                     585

<210> SEQ ID NO 36
<211> LENGTH: 819
<212> TYPE: DNA
<213> ORGANISM: Porphyromonas gingivalis

<400> SEQUENCE: 36
atgaaaaaag cattacttat tggtgctgct cttttgggag cagtcagttt tgcaagtgct     60
cagtctttga gcacaatcaa agtacagaac aattcagtac agcaacctcg tgaggaagcc    120
```

```
actattcagg tttgtggaga attggcagag caagttgact gcattgggac aggtaattct      180
gcaatcatag ccgctgcagc gaaatttgaa agcgatgatc tcgaaagcta tgttggctgg      240
gagatcatga gtgttgattt cttccctgga tataaagcgt gcaagtacac atctgcagtc      300
tgggctgatg atatgaccat tttgggccaa tcagaagata gtgatcccga aatgcagact      360
atcaacaatc ttgctctcaa gactagtgtc aagattgaag ccggcaagaa ttacatagtt      420
ggttatattg ctaataccgc aggtggacat cctatcggat gtgatcaggg ccctgccgtt      480
gatggttatg gagatttggt ttctatatca gaagatggtg gtgctacttt ccctccgttc      540
gaatctcttc atcaagcagt tcctaccttta aattacaaca tctatgtcgt tgttcatttg      600
aagaagggtg aaggtgttga ggctgttctt accaacgaca aggctaatgc ttatgttcag      660
aatggcgtta tctatgtagc cggagctaat ggtcgtcagg tatctctgtt cgacatgaac      720
ggtaaggttg tttataccgg cgttagcgaa acgattgcag ctcctcagaa gggcatgtat      780
atcctccgtg taggtgctaa gagcatcaag ctggctatc                             819

<210> SEQ ID NO 37
<211> LENGTH: 1662
<212> TYPE: DNA
<213> ORGANISM: Porphyromonas gingivalis

<400> SEQUENCE: 37
atgccaagaa ttatgaaatt aaaaattgca ctcagactgc tgctggcgac ttttgccata       60
gttttattta gccctctggc caaggcccag atggatattg gtggagacga tgtattgatc      120
gagacgatgt ccacccctatc aggatattca gaggattttt attacaagat ggctgtggca      180
gacaatggat ggatctatgt gatgttggat ttctctcgta tttattttga tgatgtcagg      240
ctgtatcgtt ccaaagacgg tggtgctact taccaaaagt tagggtcttt ggggtctttg      300
gtgccttatg acttcgatgt ctcgcattgc gattttattg taacgggaaa ggatgaagat      360
gatatcaatg tttggacagt catgacagca ttcgaatatg taggtggtac tattggcaat      420
ggcgttttgc tgatgcatcg ccatgatgca gatatcaata atacagagtg tgtgtacaag      480
aaggatttcc ctaataatag actgatgggt gtagccatcg cctccaacta ccgtgcgccc      540
tctccttacg gtttgggggg cgatcctttt gctctcgctg tcgccgttag tggctccgga      600
agcgatcaca gcttcttgga ctatattttt tcgttagatg gtggagtaca ctttgagcaa      660
aagcgtattt acacaagacc ccaaaaactg actatcaata gagtagacct ttcattaggc      720
agtacatctc cttctcttgg atttaatact tggccactaa tgggagtcgt attcgaaatg      780
aataagaacc ttgatggctt cgacattggt ttcatttcca actttgtgga ctatgatccc      840
cgctatgcgt ggtctgaacc gataataata gaagaagact gtggatggac tgattttaat      900
cctttgggag cactaagtat agagatccaa atgatgttgg atgacaattc ggataatacc      960
gtgggtggag aacgctccca taacttcctg atcacttacc cgggccatta cgtatatccg     1020
aagcaatctt tcaattattc tcccggacat acaccgacaa agaaagatct ggtctttaaa     1080
cactgtatag gtattccggc tttggcatac gataaggaag cgatcgtta tctgactact     1140 tttcaagatc acaatctaat gagatacaga tggatcaaat acgatgacat taactctttt     1200
tatggttgga gttggccata tgtatatgca aaagaagcta agataaaaa gaggcgccgt     1260 ccgcaagtag cactcaatcc taccaatgga aaggcttgtt gggtatggca tactcgcaag     1320
agcccatatg atgaaaccaa accacatcct actcctgtaa ttattaaaca tttcctatgg     1380
tccgatacgg agtgggtaca tgctctggac gtgggggacg tattgcagaa ggagggtagc     1440
```

```
atgaagctct accccaatcc tgccaaagaa tatgttctga tcaacctacc caaagaaggg    1500
gggcacgagg cagtcgtata cgacatgcag ggccgaatcg tggagaaagt ttcattttca    1560
gggaaagaat ataagctgaa tgtgcagtat ctgtccaaag gtacgtacat gctgaaagtt    1620
gtagcggata cggagtattt cgtggaaaaa atcattgtag ag                       1662
```

<210> SEQ ID NO 38
<211> LENGTH: 1650
<212> TYPE: DNA
<213> ORGANISM: Porphyromonas gingivalis

<400> SEQUENCE: 38

```
atgaaattaa aaattgcact cagactgctg ctggcgactt ttgccatagt tttatttagc      60
cctctggcca aggcccagat ggatattggt ggagacgatg tattgatcga gacgatgtcc     120
accctatcag atattcaga ggatttttat tacaagatgg ctgtggcaga caatggatgg      180
atctatgtga tgttggattt ctctcgtatt tattttgatg atgtcaggct gtatcgttcc     240
aaagacggtg gtgctactta ccaaaagtta gggtctttgg ggtctttggt gccttatgac    300
ttcgatgtct cgcattgcga ttttattgta acgggaaagg atgaagatga tatcaatgtt    360
tggacagtca tgacagcatt cgaatatgta ggtggtacta ttggcaatgg cgttttgctg    420
atgcatcgcc atgatgcaga tatcaataat acagagtgtg tgtacaagaa ggatttccct    480
aataatagac tgatgggtgt agccatcgcc tccaactacc gtgcgccctc tccttacggt    540 ttgggggcg atccttttgc tctcgctgtc gccgttagtg gctccggaag cgatcacagc     600
ttcttggact atatttttc gttagatggt ggagtacact ttgagcaaaa gcgtatttac     660
acaagacccc aaaaactgac tatcaataga gtagaccttt cattaggcag tacatctcct    720
tctcttggat ttaatacttg gccactaatg ggagtcgtat tcgaaatgaa taagaacctt    780
gatggcttcg acattggttt catttccaac tttgtggact atgatcccg ctatgcgtgg      840 tctgaaccga taataataga agaagactgt ggatggactg attttaatcc tttgggagca    900
ctaagtatag atatccaaat gatgttggat gacaattcgg ataataccgt gggtggagaa    960
cgctcccata acttcctgat cacttacccg ggccattacg tatatccgaa gcaatctttc    1020
aattattctc ccggacatac accgacaaag aaagatctgg tctttaaaca ctgtataggt    1080
attccggctt tggcatacga taaggaaggc gatcgttatc tgactacttt tcaagatcac    1140
aatctaatga gatacagatg gatcaaatac gatgacatta actctttta tggttggagt    1200 tggccatatg tatatgcaaa agaagctaaa gataaaaaga ggcgccgtcc gcaagtagca    1260
ctcaatccta ccaatggaaa ggcttgttgg gtatggcata ctcgcaagag cccatatgat    1320
gaaaccaaac cacatcctac tcctgtaatt attaaacatt tcctatggtc cgatacggag    1380
tgggtacatg ctctggacgt gggggacgta ttgcagaagg agggtagcat gaagctctac    1440
cccaatcctg ccaaagaata tgttctgatc aacctaccca agaagggggg gcacgaggca    1500
gtcgtatacg acatgcaggg ccgaatcgtg gagaaagttt catttcagg gaaagaatat    1560 aagctgaatg tgcagtatct gtccaaaggt acgtacatgc tgaaagttgt agcggatacg    1620
gagtatttcg tggaaaaaat cattgtagag                                     1650
```

<210> SEQ ID NO 39
<211> LENGTH: 1170
<212> TYPE: DNA
<213> ORGANISM: Porphyromonas gingivalis

<400> SEQUENCE: 39

```
atgaaacgat tactcccctt tctcctttta gcaggactcg tagccgtagg aaacgtgtct      60
gctcagtcac cccgaatccc tcaagtggat gtacacactc gcatcgcaag aaatgcccgt     120
tatcgactgg acaagatcag tgtcccggat tctcgtcaga tattcgatta cttctataaa     180
gaagaaacga tacccactaa aatacaaacg accacaggag gtgcaattac aagcatcgat     240
tcgcttttct atgaagacga caggttggtt caggtgcgct atttttgacaa taaccttgaa     300
ttaaaacaag cggagaagta tgtatacgac ggttctaagc tggtccttcg agaaattcgc     360
aagtcgccga cagacgaaac gccaataaag aaagttagct atcactatct ctgtggcagc     420
gatatgcctt ttgagattac gacagagatg agcgatggct atttttgaaag ccatacgctt     480
aactatctga tggaaagat tgcccgaata gatatcatga ctcaacagaa cccatcggcc     540
gaattgatcg aaacgggtag aatggtatat gagtttgatg ccaataatga tgctgtactg     600
cttcgtgaca gtgtatttct tcctcttcaa aacaagtggg tagaaatgtt tactcaccgt     660
tatacatacg acaataagca taattgtatt cgttgggaac aagacgaatt cggcaccctc     720
acccttgcca caacttcga atacgacacc actatccctc tgtcgtctgt attgttcccc     780
acgcatgagg agttcttccg tcctcttctt cccaatttta tgaagcatat gcgtacgaag     840
caaacgtatt tcaataactc cggagaaggc ttgtcagagg tatgcgatta caactacttc     900
tataccgata tgcagggtaa tgcactgacc gatgttgccg tgaacgaatc gatcaagatt     960
tatcctcgtc ctgccacgga ttttctgcgt atagaaggtt cgcaactgct tcgccttttcg    1020
ctattcgaca tgaacgggaa gctcatcaga gctaccgaat tgacaggcga tttggccatt    1080
atcggagttg catctcttcc gagaggcact tacatcgcag aaataactgc tgcaaacagc    1140
aaaaccatac gtgcaaaagt atcgctcaga                                      1170
```

<210> SEQ ID NO 40
<211> LENGTH: 939
<212> TYPE: DNA
<213> ORGANISM: Porphyromonas gingivalis

<400> SEQUENCE: 40

```
atgagagcaa acatttggca gatactttcc gtttcggttc tcttttttctt cgggacagcg      60
atcggacagg ctcagagtcg aaaccgtaca tacgaggctt atgtgaaaca gtacgccgac     120
gaagctatcc gacagatgag ccgctacaat ataccggcaa gcatcaccat agcacaggct     180
ttggtggaga caggagccgg agccagtaca ctggccagcg tacacaacaa tcacttcggg     240
atcaaatgcc acaaatcgtg gacgggcaag cgcacctatc gtaccgacga tgcgccgaac     300
gaatgcttcc gcagctattc ggccgctcgc gaatcgtatg aagatcattc ccgatttctg     360
ctccaaccac gctatcgtcc cctgttcaaa ctcgacagag aagactatcg gggctgggct     420
acggggttgc aacgctgtgg ctatgccacc aatcggggct atgccaatct gctgatcaag     480
atggtggagc tgtatgagct atatgctttg gatcgcgaga agtacccctc atggttccac     540
aagtcttacc ccgggtccaa caaaaaatcc catcaaacga ccaagcagaa gcagagcgga     600
ctcaagcacg aagcttactt cagctacgga ctgctctaca tcatagccaa gcaaggcgat     660
accttcgatt ctttggccga agagttcgac atgagagcct ccaaactggc caatacaaac     720
gatgctcccg tggatttccc gatcgaaaag ggcgatgtga tctatctgga gaaaaagcac     780
gcatgctcca tctccaaaca cacacagcac gtagtgcgtg tgggcgattc gatgcacagt     840
atctcccaac gctatggcat ccggatgaag aacctctaca agctcaacga caaggatggc     900
gaatatatac cccaagaggg cgatatactg cgcttgcgc                            939
```

<210> SEQ ID NO 41
<211> LENGTH: 813
<212> TYPE: DNA
<213> ORGANISM: Porphyromonas gingivalis

<400> SEQUENCE: 41

| | | | | | |
|---|---|---|---|---|---|
| atgaatagca | gacatctgac | aatcacaatc | attgccggcc | tctccctctt | tgtactgaca | 60 |
| ttgggcggct | gctccgtagc | ccaacaagat | acgcagtgga | ctctcggcgg | aaagctcttt | 120 |
| acttcggcgt | ggatacaacg | ttcggccgaa | tatcaagcgc | tttgcattca | ggcatacaac | 180 |
| atcgctacgg | aaagagtgga | cgctctaccg | gcagaacgta | acaaggaga | taggccttat | 240 |
| gccatcgtaa | cggacataga | cgaaaccatt | ttggacaata | cgcctaactc | cgtgtatcag | 300 |
| gctctcaggg | gcaaggatta | tgatgaagag | acttggggga | atggtgtgc | acaggccgat | 360 |
| gccgacacac | tggcaggagc | tttgtctttc | ttcctccatg | cagcgaacaa | ggggatcgag | 420 |
| gtcttttacg | tcaccaaccg | cagagacaat | ctgcgcgaag | caactcttca | gaaccttcag | 480 |
| cgttacggat | tccccttgc | cgatgaagaa | catttgctta | cgacccatgg | gccatccgac | 540 |
| aaagaaccc | gtcggctcaa | aatacaagaa | cagtatgaaa | tagtattgct | cataggagac | 600 |
| aacttgggcg | acttccacca | cttcttcaat | acgaaagaag | agtccggacg | caaacaggct | 660 |
| ctgggcctga | cagccgggga | gtttggccgg | cacttcatca | tgctgcccaa | tcccaactac | 720 |
| ggatcttggg | aaccggcatg | gtacggcggg | aagtatccgc | cactgcccga | aagagacaaa | 780 |
| gcacttaaac | aactgcactc | acagaacagc | aga | | | 813 |

<210> SEQ ID NO 42
<211> LENGTH: 2271
<212> TYPE: DNA
<213> ORGANISM: Porphyromonas gingivalis

<400> SEQUENCE: 42

| | | | | | |
|---|---|---|---|---|---|
| atgcggacaa | aaactatctt | ttttgcgatt | atctctttta | ttgctctatt | gtcgtcttct | 60 |
| ctgtcggctc | agagcaaagc | cgttttaacc | ggtagtgtgt | cggatgccga | aaccggagag | 120 |
| cctcttgccg | gtgctcgaat | cgaagtcaaa | cacaccaaca | tagtagccgg | tgccgatgcc | 180 |
| ggcggacatt | tcgagatcaa | gaacctgccg | gcagggcagc | atactattat | atgttcgttg | 240 |
| gggggtatg | gacagaaaga | ggaggtggtt | gccatcgaag | ccggacagac | caaaacgatc | 300 |
| tcttttgcat | tgcgactgcg | aacgaacaac | ttggaggaag | tcgtcgttac | cggtaccggt | 360 |
| acacgttacc | gcttggtcga | tgctcctgtg | gcaacggaag | tccttaccgc | taaggacata | 420 |
| gcctcttct | cggctcctac | ttccgaggcc | ttattgcagg | ggctgagtcc | gtcttttgac | 480 |
| ttcggcccca | atctgatggg | ctctttcatg | cagctgaacg | gccttagcag | taagtatatc | 540 |
| ctcatcctta | tcgatggtaa | gcgtgtgtac | ggcgatgtag | gcggtcaggc | cgatttgagt | 600 |
| cgtatttctc | ctgatcagat | cgaacggatc | gaactggtga | aggtgcttc | gagttcgctc | 660 |
| tacggatccg | atgccatcgc | cggggtaatc | aatgtgatca | caaaaaagaa | tacgaatcga | 720 |
| ctgagtgcat | atacgtcaca | tcgcatatcg | aagtacaacg | atcggcaaac | caatacttcg | 780 |
| ctcgatataa | acatcggtaa | gttcagtagc | aataccaact | atttcttcta | ccatacggat | 840 |
| ggctggcaga | atagtccgtt | cgaaataaaa | agaaaaaag | gatccggcga | accggtcttg | 900 |
| gaggaaacgt | ataagaaaac | ttttcgtgca | caggaaaatc | agggtgtaag | ccaatcgctt | 960 |
| tcctattatg | caactaacaa | tcttagcttc | agcggaaatg | tgcagtacaa | taaacgtcag | 1020 |
| atcttcactc | cgactttttc | cgaaaagaag | gcctatgaca | tggattatcg | tgctttgacg | 1080 |

```
gcttcactcg gtacgaacta tcttttcccc aatggtctgc atacgctttc tttcgatgcc    1140
gtctacgatc gcttccgttt cggatatttg tatcatgaca aggacagcag tgagagcctg    1200
atcaacaacc aaggtcagac cgagcaaccc acattctttc cgggtcagct acgcaataaa    1260
aacgatcaga tccgatacac ggcagaggct cgcggtgtat ttacactgcc ttatgcgcag    1320
aaactgaccg gcggtttgga gtatttccgt gaggaattga tctctcccta taatttgatt    1380
accgacaagg cagatgcttc cacgctctct gcttatgtac aagatgaatg gaaaccgctc    1440
gattggttca atatgacagc cggttttccg ctggtacacc atcaggagtt cggtacacga    1500
atgacgccta aggtatccat actcgccaag tatgggccgc tgaacttccg cgctacgtat    1560
gctaacggct ataagactcc cacgctgaaa gagcttttg cacgaacga actcaccact    1620 atgggttcgc acaatctcta tctcggcaat gcggatctta agccacagat gtcggattat    1680
tatgctttgg gcttggagta caatcaaggc cctatctcgt tcagtgcaac ggtttatgac    1740
aatgaacttc gcaatctgat ctcctttatg gatataccag cctcacccga gcacgaagct    1800
cagggaatca agaaaaccaa gcagtatgcc aacataggaa agctcgcag ccgcggcctt    1860 gatgtcctat gtgatgcctc tatcggttgg ggtatcaagt taggagccgg atacagcctc    1920
gtggaagcta agaatctcca gacggatgag tggctggaag gagctgcacg tcatcgtgcc    1980
aatgtgcacg ccgattgggt tcactactgg ggtcagtata gacttggcgt gagccttttc    2040
ggccgtattc agagcgagcg ttactacaaa gacggcaatg ctccggacta ccttgtgg    2100 cgactcgcca catcgcatcg tttcgctcat tccgccaca tcatcctgga tggaacgctc    2160
ggtatagaca acctgtttga ctacgtggat gatcgtccta tgggtgtcaa ttatgctacc    2220
gtaacgccgg gacgtacttt ctttgctcaa atagcgattc gattcaacaa c            2271
```

<210> SEQ ID NO 43
<211> LENGTH: 993
<212> TYPE: DNA
<213> ORGANISM: Porphyromonas gingivalis

<400> SEQUENCE: 43

```
atgacggaca acaaacaacg taatatcgta ttcccggcgt ttctcctctt gctgggagtc     60
atcgcagtgg tgacgatcgt tggttttttc atgctcagac cggccgagga gattatccaa    120
ggacagatag aagtgaccga ataccgagtg tccagcaaag tgcccgggcg catcaaggaa    180
cttagggtat ccagggggaca gcaggtgcag gccggcgata ccctcgctgt catcgaagcc    240
cccgacgtag cggctaagat ggagcaggca aaggctgccg aagcagctgc acaggctcag    300
aacgccaagg ctctcaaagg agcacgcagc gaacagatac aggcagccta tgagatgtgg    360
cagaaagctc aggccggcgt agccatagcg accaagacac cagcgcgt gcagaacctc    420 tatgaccagg gagtggtacc ggctcagaag ttggacgaag ccactgccca gcgcgatgcg    480
gccatcgcta cgcaaaaagc ggccgaagcc cagtacaata tggctcgcaa cggtgccgaa    540
cgcgaagaca gctggcagc ttctgccctc gtcgatagag cgagaggagc cgtcgccgag    600
gtggagtcgt acatcaacga aacctacctc atcgccccac gggcaggcga agtgtcggag    660
atattcccca agccggcga actcgtaggt accggcgcac ctatcatgaa atcgccgag    720 atgggcgata tgtgggccag cttttgccgtt cgtgaggatt tcctcagcag catgaccatg    780
ggagccgttc tggagactgt ggtgccggct ctgaatgaag aaaaagtacg cttcaagatc    840
acattcatca agaacatggg taccttatgct gcctggaaag cgaccaagac aacagggcag    900
tacgacctga agaccttcga ggtaaaggcc acccttgcgg ataaagacaa ggcacaaaag    960
```

```
ctacgcccgg gtatgtccgt gatcatacgc aag                              993

<210> SEQ ID NO 44
<211> LENGTH: 3051
<212> TYPE: DNA
<213> ORGANISM: Porphyromonas gingivalis

<400> SEQUENCE: 44
atgaaaagaa tgacgctatt cttcctttgc ttgctgacga gcattgggtg ggctatggcc    60
cagaatagaa ccgtgaaggg tacagttatc tcctccgagg ataatgagcc cctgatcggc   120
gcgaatgtcg tggttgtcgg aaacaccact atcggtgctg caaccgactt ggatggcaac   180
ttcacgctta gcgtgcctgc caatgccaaa atgttgagag tgtcctattc cggtatgact   240
accaaagagg tcgccatcgc taatgtgatg aagatcgtac tggatccgga ctctaaggtt   300
ctggagcagg tagttgtatt gggttacggt acgggacaga aactcagcac tgtttccggt   360
tctgtggcca aagtgtccag cgaaaagctc gcggaaaagc ccgttgccaa tatcatggat   420
gccctccaag gtcaggtagc cggtatgcag gttatgacta catccggtga ccctactgcc   480
gtcgcttctg tggagatcca tggtacaggg tcgttggggg caagctctgc accattgtat   540
atcgtggatg gtatgcaaac ttcttttgga ttgtggctac gatgaatcc gaatgatttt    600
gaatctatgt ccgttttgaa agatgcttct gcaacatcta tttatggagc tcgtgctgca   660
aacggagtcg tttcattca acgaagaaa ggtaaaatga gcgagagagg tcgtattacc     720
tttaatgcca gttacgggat ttctcaaatc ctgaatacta gccccttga taatatgatg    780
actggagatg aattgctgga ttttcaggtg aaggcaggtt ttgggggaa caatcaaacc    840
gttcagaagt taaagatat gatccttgcc ggagctgaag atttgtatgg caattatgat    900
tctttgaaag atgagtatgg taagacattg ttcccagtgg attttaatca tgatgcagac   960
tggctcaagc ctttgtttaa acagcacccc accagtcaag gtgatatttc tttctccgga  1020
gggtctcagg gaacttcata ttatgcctct ataggctact tcgatcagga aggtatggct  1080
cgtgaaccgg caaattttaa gcgctatagt ggccggctca acttcgaaag tcgtatcaat  1140
gaatggctga agttggtgc aaatttgtct ggtgcgatag cgaatagacg atctgccgac  1200
tattttggaa agtattatat ggggtcaggt actttcggtg tgttaacgat gcctcgttat  1260
tataaccctt ttgatgtgaa tggggattta gcagatgtct attacatgta tggagctacc  1320
agaccttcta tgacagaacc gtacttcgca aaaatgagac cgttcagttc cgaatcacat  1380
caggccaatg taaatggttt cgcccagatt actccgatca aaggccttac tttaaaggca  1440
caggctggtg ttgatattac taatactcgc acttcttcta agagaatgcc caataatccg  1500
tatgattcta ctcctcttgg ggaaagaaga gaaagagctt atcgagatgt tagcaagtct  1560
tttacaaata cggctgaata taagttttca attgatgaaa acatgatctt tacagcattg  1620
atggggcatg aatatattga atatgaaggg gatgttattg gggcatcttc taaaggattt  1680
gaaagtgata gttgatgtt actgagccag ggaaaaaccg gaaatagttt gtctttgcct  1740
gaacacagag tcgctgaata tgcctatttg tctttctttta gtcgttttaa ttacggtttt  1800
gacaaatgga tgtatataga tttctctgtt cgtaatgacc aatcctctcg attcggatcc  1860
aataatgaa gcgcgtggtt ctattctgtc ggtggaatgt ttgacatata ataaaattc    1920
attcaagaaa gtaattggct cagtgatctt cgactgaaaa tgagttatgg tacaacgggt  1980
aactcggaga ttggtaatta caaccaccaa gcactcgtta ctgtgaacaa ttatactgaa  2040
gatgctatgg ggcttagcat ttctacagca ggcaatcccg acctctcgtg ggaaaagcag  2100
```

```
tctcagttca acttcggttt ggctgcaggg gctttcaata atcgcttatc tgcagaggta    2160
gatttctatg tccgcactac gaatgatatg ttgattgatg tcccgatgcc ttatatcagt    2220
ggtttcttct cacagtatca gaatgtaggc tctatgaaaa atacgggtgt agacctttct    2280
cttaagggga cgatctacca aaataaggac tggaatgtat atgcttctgc gaatttcaac    2340
tacaatagac aggaaataac aaagcttttc ttcggtctca ataagtacat gttgcctaat    2400
accggtacta tatgggaaat tgggtacccc aattcgttct atatggctga atatgctgga    2460
atcgacaaaa aaaccggtaa gcagttgtgg tatgttcctg gtcaagtcga tgcggatggt    2520
aataaagtta caacaagcca gtactcagct gacttggaga cacgaattga taagtctgtt    2580
actcctccta ttacaggtgg tttctcctta ggtgcttctt ggaaaggact ttctttagat    2640
gctgattttg cctacatcgt tggtaaatgg atgatcaata atgaccgtta ctttacagag    2700
aatgcaggtg gattgatgca attaaataaa gataaaatgc tattgaatgc ctggacagag    2760
gataataaag aaacagatgt tccaaaattg ggacagtctc ctcagtttga tacgcatttg    2820
ttggagaatg cttctttcct gcgtttgaag aatctcaaac tcacctatgt actccccaat    2880 agtcttttg ctgggcagaa tgtgattggt ggagctcgtg tctatttgat ggcgcgcaat    2940
ctgttaactg ttacgaagta taaaggcttt gaccctgaag caggggggaa tgtgggaaaa    3000
aatcaatatc ctaattctaa gcagtacgtt gcgggtattc agttgtcttt c             3051
```

<210> SEQ ID NO 45
<211> LENGTH: 3042
<212> TYPE: DNA
<213> ORGANISM: Porphyromonas gingivalis

<400> SEQUENCE: 45

```
atgacgctat tcttcctttg cttgctgacg agcattgggt gggctatggc ccagaataga      60
accgtgaagg gtacagttat ctcctccgag gataatgagc ccctgatcgg cgcgaatgtc    120
gtggttgtcg gaaacaccac tatcggtgct gcaaccgact ggatggcaa cttcacgctt     180 agcgtgcctg ccaatgccaa atgttgaga gtgtcctatt ccggtatgac taccaaagag     240
gtcgccatcg ctaatgtgat gaagatcgta ctggatccgg actctaaggt tctggagcag    300
gtagttgtat tgggttacgg tacgggacag aaactcagca ctgtttccgg ttctgtggcc    360
aaagtgtcca gcgaaaagct cgcggaaaag cccgttgcca atatcattga tgccctccaa    420
ggtcaggtag ccgtatgca ggttatgact acatccggtg accctactgc cgtcgcttct     480
gtggagatcc atggtacagg gtcgttgggg gcaagctctg caccattgta tatcgtggat    540
ggtatgcaaa cttctttgga tgttgtggct acgatgaatc cgaatgattt tgaatctatg    600
tccgttttga agatgcttc tgcaacatct atttatggag ctcgtgctgc aaacggagtc     660
gttttcattc aaacgaagaa aggtaaatg agcgagagag gtcgtattac ctttaatgcc     720
agttacggga tttctcaaat cctgaatact aagcccttg ataatatgat gactggagat     780
gaattgctgg attttcaggt gaaggcaggt ttttggggga caatcaaac cgttcagaag     840 gttaaagata tgatccttgc cggagctgaa gatttgtatg caattatga ttctttgaaa     900 gatgagtatg gtaagacatt gttcccagtg gattttaatc atgatgcaga ctggctcaag    960
gctttgttta aaacagcacc caccagtcaa ggtgatattt cttcctccgg agggtctcag   1020
ggaacttcat attatgcctc tataggctac ttcgatcagg aaggtatggc tcgtgaaccg   1080 gcaaattta gcgctatag tggccggctc aacttcgaaa gtcgtatcaa tgaatggctg     1140
aaagttggtg caaatttgtc tggtgcgata gcgaatagac gatctgccga ctattttgga   1200
```

```
aagtattata tggggtcagg tactttcggt gtgttaacga tgcctcgtta ttataaccct    1260
tttgatgtga atggggattt agcagatgtc tattacatgt atggagctac cagaccttct    1320
atgacagaac cgtacttcgc aaaaatgaga ccgttcagtt ccgaatcaca tcaggccaat    1380
gtaaatggtt tcgcccagat tactccgatc aaaggcctta ctttaaaggc acaggctggt    1440
gttgatatta ctaatactcg cacttcttct aagagaatgc ccaataatcc gtatgattct    1500
actcctcttg gggaaagaag agaaagagct tatcgagatg ttagcaagtc ttttacaaat    1560
acggctgaat ataagttttc aattgatgaa aaacatgatc ttacagcatt gatgggcat     1620 gaatatattg aatatgaagg ggatgttatt ggggcatctt ctaaaggatt tgaaagtgat    1680
aagttgatgt tactgagcca gggaaaaacc ggaaatagtt tgtctttgcc tgaacacaga    1740
gtcgctgaat atgcctattt gtctttcttt agtcgtttta attacggttt tgacaaatgg    1800
atgtatatag atttctctgt tcgtaatgac caatcctctc gattcggatc caataataga    1860
agcgcgtggt tctattctgt cggtggaatg tttgacatat ataataaatt cattcaagaa    1920
agtaattggc tcagtgatct tcgactgaaa atgagttatg gtacaacggg taactcggag    1980
attggtaatt acaaccacca agcactcgtt actgtgaaca attatactga agatgctatg    2040
gggcttagca tttctacagc aggcaatccc gacctctcgt gggaaaagca gtctcagttc    2100
aacttcggtt tggctgcagg ggctttcaat aatcgcttat ctgcagaggt agatttctat    2160
gtccgcacta cgaatgatat gttgattgat gtcccgatgc cttatatcag tggtttcttc    2220
tcacagtatc agaatgtagg ctctatgaaa aatacgggtg tagacctttc tcttaagggg    2280
acgatctacc aaaataagga ctggaatgta tatgcttctg cgaatttcaa ctacaataga    2340
caggaaataa caaagctttt cttcggtctc aataagtaca tgttgcctaa taccggtact    2400
atatgggaaa ttgggtaccc caattcgttc tatatggctg aatatgctgg aatcgacaaa    2460
aaaaccggta agcagttgtg gtatgttcct ggtcaagtcg atgcggatgg taataaagtt    2520
acaacaagcc agtactcagc tgacttggag acacgaattg ataagtctgt tactcctcct    2580
attacaggtg gtttctcctt aggtgcttct tggaaaggac tttctttaga tgctgatttt    2640
gcctacatcg ttggtaaatg gatgatcaat aatgaccgtt actttacaga gaatgcaggt    2700
ggattgatgc aattaaataa agataaaatg ctattgaatg cctggacaga ggataataaa    2760
gaaacagatg ttccaaaatt gggacagtct cctcagtttg atacgcattt gttggagaat    2820
gcttctttcc tgcgttttga agatctcaaa ctcacctatg tactcccaa tagtcttttt     2880 gctgggcaga atgtgattgg tggagctcgt gtctatttga tggcgcgcaa tctgttaact    2940
gttacgaagt ataaaggctt tgaccctgaa gcaggggga atgtgggaaa aaatcaatat     3000
cctaattcta agcagtacgt tgcgggtatt cagttgtctt tc                       3042
```

<210> SEQ ID NO 46
<211> LENGTH: 2463
<212> TYPE: DNA
<213> ORGANISM: Porphyromonas gingivalis
<400> SEQUENCE: 46

```
atgaagaaaa agaatttttt gcttcttggc attttcgttg ctttgctgac tttcatcggc      60
agcatgcagg cacaacaggc caagattat tcaactttg acgaacgggg cgaggcctac        120
ttctcattca agtgcctga tagggccgtt ctacaagagc tggctctgat catgtccatc       180
gacgagtttg accccgtaac caatgaagcc attgcctatg ccagcgaaga ggagttcgag     240
gcattcctgc gctatgggct caagcctaca ttcttgactc ctccatccat gcagcgcgct     300
```

```
gtcgagatgt tcgactaccg ctcaggagaa aaatacgaat ggaatgctta ccccaccta       360
gaagcctata tcagcatgat ggaagagttc caaacaaagt atccatcact ttgtactact      420
tccgtcattg gcaagtccgt aaaggatcgt aaactgatga tttgcaagct gacgtcctct      480
gccaatacag ggaaaaagcc tcgcgtgctc tatacttcta cgatgcacgg agacgaaacg      540
accggatatg tggtactgct ccgactcata gaccatctgc tgtcgaacta cgaatccgat      600
ccgaggatta agaacattct ggataaaacg gaagtatgga tctgcccttt gaccaatccg      660
gacggagcat acagagccgg aaaccacacc gtacaaggag ctactcgcta caatgccaac      720
aatgtcgatt tgaaccgtaa cttcaaggat gatgtagccg gtgatcaccc cgatggaaaa      780
ccttggcagc cggaggcaac tgcattcatg gatttggaag gaaacacctc tttcgtgctc      840
ggtgccaata tacatggagg aacagaggtg gtgaactatc catgggataa taaaaaagaa      900
agacatgcag acgatgagtg gtacaaactg atcagtcgca actacgcagc cgcttgtcag      960
agtatttccg ccagctacat gacctccgaa accaattcgg gaatcatcaa cggttcagac     1020
tggtatgtaa ttcgcggaag tcgtcaggac aatgcaaatt atttccatcg tctgcgagaa     1080
attacccttg aaatcagcaa cacgaagttg gtgccggcct ctcaacttcc aaagtattgg     1140
aatctgaaca aagaatctct gcttgctctg atcgaagaat ccttatacgg catccatggt     1200
acagtgactt ccgctgcgaa cggacagcct ctcaaatgcc agatcttgat agaaaaccat     1260
gacaagcgca actccgatgt ttactccgat gctaccacag gctactacgt acgtcctatc     1320
aaagccggca cttatacggt gaaatacaaa gccgagggtt atcctgaggc aactcgtacc     1380
attacgatca aggacaaaga aaccgtcatc atggacattg cattgggcaa ctcggttcct     1440
ctgcctgtac ccgatttcac agcttctcct atgaccatct cagtaggcga aagcgtccaa     1500
ttccaagatc aaacgacaaa taaccccacg aattgggagt ggacgttcga aggcggacag     1560
cctgccatga gtacagagca gaatccgctc gtatcctata gtcatcccgg tcagtacgac     1620
gttacgctca aagtgtggaa tgcaagtggt tccaacacga ttacgaaaga aaaattcatc     1680
actgtcaatg ccgttatgcc tgtagctgaa ttcgtcggta ccccgacgga aatagaagag     1740
ggccagacgg tatcttttca aaaccaatcc accaatgcca ccaactacgt atggatattc     1800
gatggcggca ctcccgctac cagtgaagac gaaaacccga ctgtgcttta cagcaaagcc     1860
ggccaatacg atgtcacgct caaggcgatc agtgcttccg gtgaaacggt gaagacgaaa     1920
gaaaaataca tcactgtcaa gaaagctccg gtccctgctc cggtagccga cttcgaagga     1980
acacctcgaa aagtaaagaa aggcgagaca gttactttca aagacttgtc tacgaacaat     2040
ccgacttcat ggctttgggt gttcgaaggc ggctctcctg ccaccagcac ggagcaaaac     2100
ccggtggtca cctacaatga aacaggcaag tacgatgtcc agctgactgc caccaacgag     2160
ggcggaagca atgtgaagaa agcagaagac tacattgagg ttatcctcga tgacagtgtc     2220
gaggacatag tggcacagac gggtatcgtc attcgtccgc aaaacggaac gaagcagatc     2280
ctcatagaag ccaacgctgc tatcaaagcg atcgttctct atgacatcaa tggacgggtc     2340
gtactcaaaa ctactccgaa tcagctccgc tcgaccgtag atctttccat cctgcccgaa     2400
ggaatctaca ccatcaatat caaaacggaa aaatccgctc gcacggaaaa gatccatatc     2460
ggg                                                                   2463
```

<210> SEQ ID NO 47
<211> LENGTH: 228
<212> TYPE: DNA
<213> ORGANISM: Porphyromonas gingivalis

<400> SEQUENCE: 47

```
atgcgactga tcaaggcttt tctcgtgcaa ctcttactgc tccccatttt cttctacaag      60
cggtttatat cgccgcttac accgccttca tgccggttta cccctcatg ttcgtcctat     120
gccatcgaag ccttacgtaa atatggcccg ggcaaaggac tattgctgag catcaagcgt     180
attctccgct gtcacccgtg gggtggaagt ggctatgacc ccgttccg                228
```

<210> SEQ ID NO 48
<211> LENGTH: 1251
<212> TYPE: DNA
<213> ORGANISM: Porphyromonas gingivalis

<400> SEQUENCE: 48

```
atgaattacc tgtacatact gattacactt ttactctccg ctttttttc cggtgctgag      60
attgctttcc tttcttcgga caaactgcgt cttgagttgg acaggaatag aggcgatctc     120
acaggcagag cgttaaactt gctgtatcga catccggacc aactggtgac tactctcctt     180
gtgggtaata atatcgtttt ggtagtctat ggtctgctga tggcgggatt gctggccgca     240
cctttggcgc aatggattga taacgatgct atgatcgtcg ttctccaatc tgtcttatcc     300
actatcatca tactgtttac cggggaattt ctacccaaag ccattttcaa gaccaatgcc     360
aatatgatga tgagggtatt cgccctccct atcgtagcga tctattatct gctttatcct     420
ctgtctaaac tcttcaccgg tttatctcgc tcttttattc gtctggtgga caagaattat     480
gtgcctacaa cagtagggtt ggggcgcgta gatctcgatc attatttggc agaaaatatg     540
tccggagaaa acgaacagaa cgacttgact accgaagtga aaatcatcca gaatgcgctg     600
gattttccg gtattcaggt gcgagactgc atgatcccac gcaatgagat gatagcatgt     660
gagttgcaaa cggatattga agtactcaaa cgactttta tcgataccgg tttgtccaag     720
atcattatct acagacagaa catagatgac gtagtaggat atatccattc gagcgaaatg     780
tttcgtgggc aagactggca aaaacgtatc aatactactg tattcgtacc cgaaagcatg     840
tatgccaata actgatgcg actactcatg cagcgcaaga aaagcattgc gatcgtcatc     900
gatgaacttg gaggtacggc cggaatggtc acattagagg atttggtaga agagattttc     960
ggtgacattg aggacgaaca cgacactcgc aagatcatag ccaaacagct cggccctcat    1020
acctatctgg tcagtggtcg tatggaaata gatgatgtga cgaacgtttt ggggttgtcc    1080
ttgcctgagt ctgacgacta ccttaccgtg gccggattta tcctgaatag ccatcaaaat    1140
atcccacagg ccaatgaggt cgtggagatt gctccttata cttttaccat tctcagatct    1200
tcttccacca agatcgaact ggtgaaaatg tccatcgacg accaatcgaa c             1251
```

<210> SEQ ID NO 49
<211> LENGTH: 879
<212> TYPE: DNA
<213> ORGANISM: Porphyromonas gingivalis

<400> SEQUENCE: 49

```
atgaaacaga actacttcaa aagagtctgc tcactgcttt ggctggtttt acccatgctt      60
attatgccat tggaagtagc agctcaagag attattccga acgaagaggt gttggaatca     120
ttgactttcg ttgcaccggt tgaggagaca gacgcaatag aggcagaggt agaagctctg     180
caggagatag tcgctactga ggagattgcg gagcaggctg ttcgttctta tacctacacg     240
gtctatcgtg atggcgtgaa gattgcttca ggattgactg agcccacttt tctcgatgaa     300
gatgttcctg ccggcgaaca tacctactgc gtagaagtac agtatcaggg aggcgtatcc     360
```

```
gacaaagtat gcgtggacgt agaggtgaag gacttcaaac cggttaccaa tctcaccgga    420
actgcttcca atgacgaagt ttctttggac tgggacggtg tggaagagaa agctgaagag    480
ccggcaagtg ataaagcagt cagctacaac gtctacaaga atggaacctt gatcggtaat    540
acagctgaaa ctcattatgt ggagaccggt gtagccaatg gtacatacat ctacgaagtg    600
gaagtaaagt atcctgacgg tgtatctccg aaggtggctg taaccgtgac cgtgaccaac    660
agctcattga gcaatgtaga tggacaggct ccttacacat gcgagtaga aggcaagaag    720 attattgcgg aagcccatgg tatgatcacg ctctacgaca tcaacggacg taccgtggcc    780
gtagccccga atcgattgga atacatggcg caaaccggtt tctatgcagt gcgcttcgat    840
gtggggaata acaccatgt atcgaaaata caagtaaga                            879

<210> SEQ ID NO 50
<211> LENGTH: 936
<212> TYPE: DNA
<213> ORGANISM: Porphyromonas gingivalis

<400> SEQUENCE: 50
atgattcctc taagcgagag ttttgaatca ggtattccag ctatatggaa gaccattgac     60
gcagatggcg atggctataa ttggatgcat ttgaccaatt tcacgggaca gagtggtctc    120
tgtgtctctt cggcttcata cataggcggc gtcggagctt tgactccgga caattatctg    180
ataacacccg aattaaaact acccacagac gcgttggtgg aaataatcta ttgggtatgt    240
actcaagatc tcactgctcc atcggagcac tatgccgttt attcctcttc tacaggcaat    300
aatgctgctg actttgttaa tctcttatat gaagagactt tgactgccaa acggatacaa    360
tcccccgagt tgatccgcgg aaatcggaca caaggtgttt ggtatcaaag aaaggtggta    420
ctccctaacg atactaaata tgttgctttc cgccatttta attccacgga taatttctgg    480
ctcaatttgg atgaagtatc tatcctgtat accctcttc cccgaagagc tccgtgtccg    540
catccgggtg gttacactta ttctgtattc cgtgatggac aaaagatagc gagtggattg    600
tcggcattgg catatatcga tacgatgta ccgtatggga ctcaagacta ttgtgtccaa    660
gtcaattatc tgcaaggaga ctcgtataaa gtctgcaaaa atatagtggt ggcaaattct    720
gcaaacatct atggggcgga taagcctttt gcgttgaccg tggttggcaa gaccattgta    780
gcgagtgctt tcaaaggaga gatcactctt tatgacattc gtggccggct gatagcttcc    840
ggctgcgata cgcttaggta caaagcgaaa aatggttttt acctcattaa aatacaggta    900
aacggaactg tctatactga gaaaatccaa atccaa                              936

<210> SEQ ID NO 51
<211> LENGTH: 2529
<212> TYPE: DNA
<213> ORGANISM: Porphyromonas gingivalis

<400> SEQUENCE: 51
atgaaaaaaa gttttctttt agccatagta atgctctttg gcattgccat gcagggacat     60
tctgctccgg ttacgaaaga gcgagctttg agtctggctc ggctggcttt gcgacaggta    120
tccttgcgaa tgggacaaac agcagtatct gacaagattt ccatcgatta cgtttatcgg    180
caaggagatg ctgagagggg tatcacatca aagaggaag gctctcctgc atattttat     240 gtagctaatc gtggaaataa tgagggctat gctcttgtag cagcagatga cagaataccg    300
acaattttag cctattcacc cattggccgt ttcgacatgg acagtatgcc ggacaatctt    360
cgcatgtggc tacaaattta cgatcaggaa ataggcctga tactttccgg aaaagctcag    420
```

```
ctcaatgaag agatattacg taccgagggc gtaccggctg aagtacatgc tctgatggat      480
aacggtcatt ttgccaacga tcccatgcga tggaatcaag gttacccatg aacaataag      540 gaaccactgc ttcctaatgg caatcatgcc tataccggct gtgttgctac tgctgcagca      600
caaatcatgc gctaccatag ctggccgctt caaggtgaag gctctttcga ttatcatgca      660
ggttcattag ttggcaactg gtccggcaca tttggtgaaa tgtacgactg gatcaatatg      720
cccggaaatc ccgaccttga taatctgact caatctcaag tggatgccta cgccacactg      780
atgcgtgatg tgagtgcatc tgtttcgatg agtttttatg aaaatggaag tggtacgtac      840
agcgtttatg tagtaggagc cttgcgaaac aactttcgct acaagcgttc actgcagcta      900
catgtacgcg ccttatatac ctcacaggag tggcacgata tgatccgcgg ggaacttgcc      960
tccggaaggc cggtctatta tgcagggaat aaccagagca taggacatgc tttcgtttgc     1020
gatggttatg cttcggatgg tactttccat ttcaactggg gttggggagg tgtttccaac     1080
ggcttctaca aactaacact cctctcgccg acttcgttgg gtatcggagg tgagggaata     1140
ggttttacca tttatcaaga gatcatcacc ggtatcgaac cggctaagac tcccgctgaa     1200
gccggtacag atgccttgcc gatcttggca ctgaaagaca tagaagccga gtataaaagt     1260
gaatccggat tgaacgtagg gtattcgata tataatacag gtgaagagca atcaaatctt     1320
gacctcggat acagattgaa caaggctgac ggagaagtca tagaggtgaa aacttcatct     1380
atcaatatct cttggtacgg atacggagag catcccgaga gtttctcatt ggcacctaat     1440
cagttgtcac aaggaatcaa caccatcacc ctactttatc gtcgcacagg caccgaacag     1500
tgggagccgg tacggcatgc acagggagga tatgtcaata gcattaaagt aaatacgaca     1560
gacccgaaca atgtcgtagt cacggtagat aataacgaag gcaagctcag tatcgtcccc     1620
aacagctttg tcgcagatct gaattcttat gaacatagta cgattacagt acagttcaat     1680
agcgacagcc ctgatgagat ccgtacaccc gtagcctttg ctctatctac aggagctact     1740
gcggacgatg taatatcttt gggctgggta atggctgaag ttccgggcgg tagcagcaac     1800
tatccggtgg tttggtctaa agacgttctc actctctcgg aaggcgacta cattgtggg     1860 tatagatttt ccatcaacaa ccaaaaggat gaatggaaaa agatcggaag cgtgtcagta     1920
aaaacaccga cagagtatac gcacccctta ttcgaagtgg gccataatca aacttctacc     1980
tatacgctgg atatggcaca caacagagta ttgcccgact ttacactcaa aaatctcgga     2040
ttgcctttca atggtgagtt ggttgttgtt ttccgccaaa cacaatcctc atcggggtct     2100
ttatgggcag ctcaagaaac agtacatatc aagcaaggag aaactttcgt atataaacct     2160
gttgtcgaag gccctatacc tgatggatcc tatcgtgcga ccctccatgc attcgtaaac     2220
ggacaacaac agttgtacct caaggggaaa aggaactaca cggtgaagat cgtcaatggt     2280
acagcggtag aagcaataga atcgtcagaa gagatcagag tattccctaa tccggcacgc     2340
gattatgtgg aaatatcggc accttgcatt ccccaagaaa catctatcat tcttttcgat     2400
ctgtcaggca agattgtcat gaagaatagt ttatcagcgg ggcatggcag aatggatgtc     2460
agccgacttc ctaatggggc ctacatcctt aaggtggatg gatatacgac gaaaataaat     2520
atagtgcac                                                            2529
```

<210> SEQ ID NO 52
<211> LENGTH: 870
<212> TYPE: DNA
<213> ORGANISM: Porphyromonas gingivalis

<400> SEQUENCE: 52

```
atgaaaaagc tatttctctc gctcacgagt cttgtaatgg tcttcgctgt tgcaagttgc    60
gatataatcg acaaggatca aaccctcttg ccggctccga ccaatgtgac acccgataat   120
ccggatgaca atccttcgga gatcgacatt acgcagacgc acacagaaaa atatgttttg   180
gctgaagaat ttaccggcca aaaatgtctc aactgtccga aaggtcatcg caaactggcg   240
gctctcaagg agcaatacgg taagagattg actgttgtcg gtatacatgc cggccctgga   300
tctctcgtgc cacctctttt ccgtacagaa gccggagacg catattatag caagttcgcc   360 aataatacccc ctctccctgc gctgatggtt tcgcgcaaaa agttcggctc ttcctacgtt   420
tatgataaga gctacaaaac gtgggacgtg cctattgccg agcagatgga gcaaaaggcg   480
aagatcaata tctttgccgt ggccgaatac accgataccc aaaagatcaa ggtgactgta   540
aagggtaaaa tactggaggg gaatacactc ccgaagtcca tggttcaggt gtatctgttg   600
gaggataagc tgatcgctcc gcaggtggat ggcaatacga cagtcgagaa ttacgagcac   660
aatcacgtgt tgcgtggagc cgttaatggt atttggggcg aagaatttgt gaatctcaaa   720
gattatttgt atacttacgc cgttgaaccg ctctcgggta tgtccttcgt agccgagaat   780
tattcgattg tggcttttgt atacgatgtg cagacgttcg aagtgtatga cgttgtgcat   840
gtaaagatca atccgcaatc cgatggcaaa                                    870

<210> SEQ ID NO 53
<211> LENGTH: 669
<212> TYPE: DNA
<213> ORGANISM: Porphyromonas gingivalis

<400> SEQUENCE: 53
atgaagaaat caagtgtagt agcctcagtt ttggccgtgg ctctcgtgtt cgccggttgc    60
ggactgaaca atatggcaaa aggcggcctt atcggcgccg gagtaggagg tgccattggt   120
gccggagtag gtaacgtagc cggaaatacg gctgtcggtg ccatcgtcgg tactgcagtc   180
ggtggagcag ccggtgctct catcggaaag aagatggaca agcagaaaaa agaactggag   240
gccgcagtac ccgatgctac gattcagaca gtaaatgacg gagaggctat tctggttact   300
ttcgatagcg gtatcctctt tgcgacgaac tccagcactc tgagtcccaa ctcacgcact   360
gcgctgacga gttttgctgc aaacatgaac aaaaaccccg acacggatat tcgtatcgta   420
ggccatacgg acaataccgg ctccgacaag atcaacgatc tctgtctgag agacgtgca    480 gccagcgtat attctttcct gaattctcag ggtgtgagta tgtcgcgcat ggcagccgaa   540
gggcgtggga gccatgaacc ggttgcagac aatagcacag ttgccggacg ttcggccaac   600
cgccgtgtgg aggtttatat cttgccgaat gccaagatga tcgaacaagc acagcaaggt   660
acgctgaag                                                           669

<210> SEQ ID NO 54
<211> LENGTH: 2016
<212> TYPE: DNA
<213> ORGANISM: Porphyromonas gingivalis

<400> SEQUENCE: 54
atgtacagcg acatcataa aatccattat cctttctta tcctgttggt atgccttgct    60
tttgctgcct gcaagagcgt gaagttgaaa gatgcggaga aggcacatga tcgccaagag   120
tataccaagg ctgccgatat gtacaataca ttatacaggc gtacccgacg aaaagcaggtg   180 gagatgaaag cttatacggc tttccgatcc ggtgaaaact atcgtgccgc cggcagacaa   240
gccaaagctt tgcgtggcta tctgaatgcc agacgctacg ggtatccgga ttctgtggta   300
```

```
ctgctccgtt tggcacagac ttatcagcaa ggaggtaact ataaggaagc cgaggtactc    360
ttccgtggat atctggaagc ttatccgaaa agttattttg cagctatcgg tttggagggg    420
tgtctctttg cccgccagca aaaggaatat cctacacgtt accggatacg gcgagctgcc    480
gagtggaatt cggcacgggg cgacttcggc ccggcctatg cacccgatgc ttcggctctc    540
tatttcacat cgagcagaag caaagacgac ggtttggata atagcagcat aacgggactg    600
aaacccaacg acatttatat catcaaacga gatgcacaag gacgatgggg acgtcccgat    660
agcgtgtccg gaggaatcaa cactccatgg gatgaaggcg tgccaacgat cacgcccgat    720
ggtagtacca tatattatac gttggcgcag caaggagccg attacgaccg tacggtacag    780
atctattccg ccgctcggag cggagaaggc ggttggagca acggttcgct cgtggacatt    840
atgcgcgatt cgctccgtat ggctgctcat ccctctatgt cggcatccgg cgattacctg    900
tatttcgtca gcaatatagg cggtagctat ggcggcaagg atatttatcg tgtcaaggtg    960
tcggatcgtt cttatggttc accggagaat ttggggcctg atatcaatac gccggggac   1020 gaaatgtttc ccttcataga tggggatagt acccttttct tcgcttcgga cggacacgcc   1080
ggtctgggag gactggatat tttcaaagcc acgctggact ctaccggcca atggcatgta   1140
gtcaatatgg acaaccggt caattcctct gccgatgatt tcggcttggc tgtggagcct   1200
aaaggcaaaa acaagaaga agctttgccg gacaacggag tcaaaggtgt attttgttcc   1260
aaccgaggcg atgcacgcgg atggccgcac ctcttccatt tcgaactgcc ggctatctac   1320
accgagattc aaggttatgt gatggacaga aagaaaatc ccatagccgg agccactgtc   1380
aggatcgtag gcgaacgcgg ccccgtagga cagggattcg tgactactcg tgacgatggc   1440
tcctataaga tgagcgtgca gggcgatact cgctatgtaa tgcttgccgg agcatcgggt   1500
tatttgaatc agtacgtaga actcaagacc gataccgcca agcagagtga gacctactat   1560
gtggactttt tccttgcatc gcgtgagaaa gccgagggct tgcaaaatat tttctatgat   1620
ttcgataaag ctactcttcg ccccgaaagc atgaagagct tggacgaact gattcgtatc   1680
ctcacggaca atccggatat tcggatcgaa ttgggttcgc atgccgacag gaaaggcccc   1740
gatgcttaca acctcggact atctgaccgc agagccaaat ccgtggtgga ttacctcacg   1800
agtcgtggca tagcggccga caggcttacg tggaaaggct acggtaagtc tgtccccaag   1860
acggtgacag ccaaaattgc cgaacggcac gatttcctga aggaaggcga tgtgctcacc   1920
gaggaattcg tagcacctt gaccgaggag cagcagtcag tctgcgacca actgaaccgt   1980
cgtaccgagt tccgtgtgat cgaagaagag ttgcgt                             2016

<210> SEQ ID NO 55
<211> LENGTH: 945
<212> TYPE: DNA
<213> ORGANISM: Porphyromonas gingivalis

<400> SEQUENCE: 55
atgatcagaa cgatactttc acgatatgta tcctcgaact tttggagtcg gggagctacc     60
ttttttttca cgattttccc ggccttcatc ctcgccgcta ctgctttgcc ggcttgtgga    120
gggggtactg cttcaggctc cgatcgtacg ctggctgtga ccatcgagcc acagaaatac    180
ttcatcgagt ccattgcgga taagtcggtg caggtggtgg cattggtacc ggccggcagc    240
aatccggagg aatacgaccc ttcgcctacc gtgatgaagc gtttgtccga agcagatgcc    300
tacttctata taggaggact ggggttcgag caaagaaatc tcgctgccat tcgggacaat    360
aaccctaagc tccctctttt cgaaatgggc aaagccttgg cggatgccgg aagtgcagat    420
```

```
ctccacggct cctgcacaga tcattctcat acagacctgc atgcccatga tccgcactat    480
tggagcagtg tggtaggggc aaaggcactc agtcgtgctg catacgacgc gcttgtggag    540
ctttatccga acgagaaaga caaatgggac aaagggcacg accgtctcaa cggacgtatc    600
gacagcgtga agagactcgt cgataccatg tttgccaatg gcaaagcaga caaagccttc    660
gtcatatatc acccatcgct cagcttttc gcccaagagt tcggcctgcg gcagatcgtc    720
atagaggaag atgggaaaga gcctacggct gcccaccttc gtcgtgtgat cgatcaggca    780
cgtgccgatg tgtcagaat cgtatttatc aacccgaat ttgaaacgcg tcaggcggag    840
gacatcgcac gcgagatcgg tgctcgtccg gtaaggatca atcctctgcg cagctcgtgg    900
gaggaggaaa ttttacatat tgctcgcgct ttggctcatg aacgg                   945
```

```
<210> SEQ ID NO 56
<211> LENGTH: 2820
<212> TYPE: DNA
<213> ORGANISM: Porphyromonas gingivalis

<400> SEQUENCE: 56
atgaacaaat tttacaaatc acttttgcag tcaggactgg ctgccttcgt gtcgatggca     60
actgcactga ccgcttctgc acagatttcg ttcggagggg aacccttgag tttctcttca    120
agatccgccg gaacgcattc attcgacgat gcaatgacta ccgccttac tccgatttc    180 aatccggaag acctgatcgc acagagccgt tggcaatcgc aaagagatgg ccggcccgtc    240
cggataggac aagtaatacc ggtggatgtg gactttgcat ccaaggcttc gcacatctct    300
tccatcggag acgtagatgt atatcgcctg caattcaagt tggaaggagc caaagccatt    360
acgctttatt acgatgcatt caatattccg gagggcggac gcctctatat ctataccccc    420
gaccatgaaa ttgtgttggg agcatatacg aacgccactc atcgccgcaa cggagctttt    480
gccacagagc cggtaccggg gagtgagctt attatggatt atgaagtgtc tcgcggaggg    540
actttgcctg acatcaagat ctccggtgcg ggttatatat tcgacaaagt cggcggacgc    600
cccgtaacgg ataaccatta cgggatcggt gaggacgatt ccgattcgga ttgcgagatc    660
aacatcaatt gtcctgaagg tgcagactgg caggcagaga agaacggtgt ggtgcaaatg    720
atcatggtaa aaggacagta tatctcaatg tgctcaggca acctgctcaa taatacgaaa    780
ggagacttta ctccgctgat catttctgcc ggacactgtg cttccataac aaccaatttc    840
ggtgtaacgc aatccgagtt ggataagtgg atcttcactt tccactatga aaaagagga    900 tgcagcaatg gtacattggc catcttccgt ggcaacagta tcatcggagc ttccatgaag    960
gctttcctcc cgatcaaagg taaatccgat ggtctcttgc tgcaactcaa cgatgaagtc   1020
cctctgcgct atcgtgtcta ttacaatgga tgggacagta cgcccgatat tccctcgagc   1080
ggtgccggta ttcatcatcc ggccggagat gccatgaaga tttccatcct aaagaagact   1140
ccggctctga atacatggat ctcctccagt ggttccggag ggactgacga tcacttctat   1200
ttcaaatacg atcaaggtgg tacgaagga ggatcgtccg gttcttctct cttcaatcag   1260
aataagcacg tggtcggcac actgaccgga ggtgccggca attgtggcgg acggagttc   1320 tacggcagac tgaacagtca ttggaacgag tatgcatccg atggcaatac gagccgcatg   1380
gacatctatc tggatcccca aaacaatggc cagacgacca tcctcaacgg aacgtatcgt   1440
gacggttata agccttgcc ctctgtgccc cggctattgt tgcagtctac aggcgatcag   1500
gtcgaattga attggacggc tgttcctgcc gatcaatatc catcatctta tcaggtcgaa   1560
taccacatat tccgaaatgg aaaggaaata gctacgacaa aggagttgtc ctattcggat   1620
```

-continued

```
gccatcgacg aaagtattat cggtagcggt atcattcgat acgaagtaag cgcacgcttc   1680
atttatccct cgccgttgga tggagtggaa tcttataagg atacggacaa gacttctgcc   1740
gaccttgcca taggagacat tcagaccaag ctgaagccgg acgtaacacc tctcccggga   1800
ggaggagtat cattaagctg gaaagttcct ttcttaagcc agttggtttc ccgattcgga   1860
gaaagcccca atcctgtgtt caaaaccttt gaagtgccct atgtttctgc cgcagccgca   1920
caaaccccca atcctcccgt tggcgtagtc attgcagaca gtttatggc cggtacatat    1980 cccgaaaagg ctgctatcgc tgccgtttat gtaatgccat ccgctccgga ctctactttc   2040
cacctcttcc tcaagagcaa cacaaacaga agattgcaga aggtgacaac tccctccgat   2100
tggcaggccg aacatggtt gaggatcaat ttgataagc cgttcccggt gaataatgac     2160
catatgcttt ttgccggtat cagaatgcct aataagtaca agctcaatcg tgctatccgt   2220
tatgtaagaa atccggataa ccttttctcc attaccggta agaagatttc atataacaac   2280
ggagtctctt tcgaaggcta cggaataccc tcgctcttgg gctatatggc tatcaaatat   2340
ctggtggtaa ataccgatgc tccgaagatc gatatgtcgc ttgtacagga gccttatgct   2400
aagggaacga atgtggctcc attccccgaa ttggtcggca tatatgtcta taagaacgga   2460
acatttatcg gcacacagga tccatccgtc acaacttatt cggtttcaga cggaacagag   2520
agcgatgaat acgaaataaa actggtatat aagggatcgg gcatttcgaa tggcgttgct   2580
cagattgaga ataacaatgc tgtcgttgca tatccgtctg ttgtaacaga tcgtttcagc   2640
attaagaacg ctcatatggt tcacgctgcc gccctctact cattggatgg caagcaggtt   2700
cgttcttgga acaacctccg caatggcgtg acattcagtg ttcaaggact acggccggt    2760 acttatatgc tcgttatgca gacggcaaac ggccctgtga gccaaaagat cgtgaagcag   2820
```

<210> SEQ ID NO 57
<211> LENGTH: 2775
<212> TYPE: DNA
<213> ORGANISM: Porphyromonas gingivalis

<400> SEQUENCE: 57

```
atggctatca tgatgaaaag tattgttttt agagcatttc taacgatttt gctctcgtgg    60
gcagcgatca cgaatccgac tgctcaagag atctcaggca tgaatgcatc ctgtctggct   120
gctccggctc aaccggatac tatcttatat gaaagttttg agaatggacc tgttcccaat   180
ggctggcttg agatagatgc tgatgctgat ggtgccactt ggggaagccc atcaggctct   240
ttctctgtac cttacggaca caatggcctt tgcacctact cccatatacg ttccggtatc   300
tcaacagcgg gcaactatct gattacaccc aatatagaag gagccaaacg ggtcaagtac   360
tgggtatgca atcagtatag taccaatccg gaacattacg cagtaatggt atcgacaacg   420
gggactgcca ttgaagactt tgttttgttg tttgatgatt ccataacagg gaaaccgact   480
cctcttgtat ggcgtagacg aatcgtggac ttaccggaag ggaccaaata tattgcatgg   540
cgacattaca agtcaccga ctcacacaca gaattcttga aattggatga tgtcactgtg    600
tataggtcga tcgaagggcc cgaacctgct accgacttca cagtaatcaa tattggtcag   660
aatgtgggac gattgacttg gaactatccg gaggattatc aaccggaagg aaaggggaat   720 gaaagagttgc agcttagcgg ctacaacatc tatgcgaacg gtacactact ggcacaaata   780
aaagatgtct ccatactgga gtatgtggac agcacttact ctttgcgaga caatcccttg   840
caagtggagt actgcgttac agccgtttac gatgaaagca tagaatcttc gaccgtatgt   900
ggcacgctgc attacgccac ggatgccatc ctttatgaaa attttgagaa tggacctgtt   960
```

```
cccaatggtt ggcttgtgat agacgctgat ggagatggat ttagctgggg acactatttg    1020
aatgcatacg acgcttttcc cggccataat ggaggccatt gctccttgtc ggcttcttat    1080
gttccgggta taggcccggt gactcccgac aactatctga ttaccccaa ggttgaagga     1140 gccaaacgtg tcaagtactg ggtaagcacg caggatgcca attgggcagc ggaacattac    1200
gcggtgatgg cttcgacaac ggggactgct gtcggagatt tcgtcatatt gttcgaagaa    1260
accatgacag cgaagccgac cggcgcatgg tatgaaagaa ccatcaactt acctgaaggg    1320
actaaataca tcgcatggcg gcattacaac tgtaccgata tatttcttt gaagttggac     1380 gatatcactg tattcgggac tcctgcatca gagcccgaac ctgttaccga tttcgttgtc    1440
tcgcttattg aaaacaacaa gggacgatta aagtggaatt atcctaacgg ctacgaaccc    1500
gataagactg atgataaaga cccattgcag cttgccggct acaatatcta tgcaaacggc    1560
tcgctccttg ttcacataca agacccgact gttttggagt atatcgatga gacttattct    1620
tcacgagacg atcaggtgga agtggaatat tgtgtcactg ccgtttataa cgacaatatc    1680
gagtcccaat cggtttgcga taagctgatt tatgattctc aatcggacat tatcttatat    1740
gaaggctttg aggccggaag tattcctgaa ggctggttgt tgattgatgc tgatggcgac    1800
aatgttaatt gggactatta tccttggact atgtatggac atgacagtga aagtgtatt     1860 gcatcccctt cgtacttacc gatgattggc gttttaactc cggataacta tttggttaca    1920
cccagactcg aaggagccaa gcttgtcaag tattgggtaa gtgcgcaaga tgctgtttat    1980
tcggctgagc attatgctgt gatggtttct actacgggaa ctgctgttga agattttgtc    2040
ctcttgttcg aagagacaat gaccgctaag gctaacggtg catggtatga gcgaactatt    2100
acattgcctg caggaacaaa atatattgcc tggcggcatt atgattgcac cgatatgttt    2160
ttcttgctct tggatgacat tacggtttat cgttctactg agactgttcc cgagcctgtt    2220
actgatttcg ttgtctcgct tattgagaat aacaagggtc gcctgaaatg gaattatcct    2280
aacggctacg aacccgataa gactgatgat aaaaaaccat tgcagcttac cggctacaac    2340
atctatgcaa atggctcgct ccttgttcac atacaagacc cgactgtttt ggagtatatc    2400
gatgagactt attcttcacg agacggtcag gtggaaatgg aatattgtgt cactgccgtt    2460
tataacgaca atatcgagtc ccaatcggtt tgcgataagc tgaactatac tatcacatcc    2520
ttggataata ttcaatctga tacaagcttg aaaatatatc ctaatccggc atcgtatgtg    2580
gtaaggatag agggattgag tcggagcaag tcgacaatcg agttgtataa tgcgctggga    2640
atttgcatat aagggaaga gactcattca gagaaaacgg aaatcgatgt ttcacgtctc     2700
aatgacggag tctacttgat taaagtagtc ggtggaaata aacaacaac cgaaaaggta     2760 gagataaaga ggccg                                                     2775
```

<210> SEQ ID NO 58
<211> LENGTH: 2766
<212> TYPE: DNA
<213> ORGANISM: Porphyromonas gingivalis

<400> SEQUENCE: 58

```
atgatgaaaa gtattgtttt tagagcattt ctaacgattt tgctctcgtg ggcagcgatc     60
acgaatccga ctgctcaaga gatctcaggc atgaatgcat cctgtctggc tgctccggct    120
caaccggata ctatcttata tgaaagtttt gagaatggac ctgttcccaa tggctggctt    180
gagatagatg ctgatgctga tggtgccact tggggaagcc catcaggctc tttctctgta    240
ccttacggac acaatggcct ttgcacctac tcccatatac gttccggtat ctcaacagcg    300
```

```
ggcaactatc tgattacacc caatatagaa ggagccaaac gggtcaagta ctgggtatgc    360
aatcagtata gtaccaatcc ggaacattac gcagtaatgg tatcgacaac ggggactgcc    420
attgaagact ttgttttgtt gtttgatgat tccataacag ggaaaccgac tcctcttgta    480
tggcgtagac gaatcgtgga cttaccggaa gggaccaaat atattgcatg gcgacattac    540
aaagtcaccg actcacacac agaattcttg aaattggatg atgtcactgt gtataggtcg    600
atcgaagggc ccgaacctgc taccgacttc acagtaatca atattggtca gaatgtggga    660
cgattgactt ggaactatcc ggaggattat caaccgaagg aaagggggaa tgaagagttg    720
cagcttagcg gctacaacat ctatgcgaac ggtacactac tggcacaaat aaaagatgtc    780
tccatactgg agtatgtgga cagcacttac tctttgcgag acaatcccct gcaagtggag    840
tactgcgtta cagccgttta cgatgaaagc atagaatctt cgaccgtatg tggcacgctg    900
cattacgcca cggatgccat cctttatgaa aattttgaga atggacctgt tcccaatggt    960
tggcttgtga tagacgctga tggagatgga tttagctggg acactatttt gaatgcatac   1020
gacgcttttc ccggccataa tggaggccat tgctccttgt cggcttctta tgttccgggt   1080
ataggcccgg tgactcccga caactatctg attacccccca aggttgaagg agccaaacgt   1140
gtcaagtact gggtaagcac gcaggatgcc aattgggcag cggaacatta cgcggtgatg   1200
gcttcgacaa cggggactgc tgtcggagat ttcgtcatat tgttcgaaga aaccatgaca   1260
gcgaagccga ccggcgcatg gtatgaaaga accatcaact acctgaagg gactaaatac   1320 atcgcatggc ggcattacaa ctgtaccgat atatatttct tgaagttgga cgatatcact   1380
gtattcggga ctcctgcatc agagcccgaa cctgttaccg atttcgttgt ctcgcttatt   1440
gaaaacaaca agggacgatt aaagtggaat tatcctaacg gctacgaacc cgataagact   1500
gatgataaag acccattgca gcttgccggc tacaatatct atgcaaacgg ctcgctcctt   1560
gttcacatac aagacccgac tgttttggag tatatcgatg agacttattc ttcacgagac   1620
gatcaggtgg aagtggaata ttgtgtcact gccgtttata cgacaatat cgagtcccaa   1680 tcggtttgcg ataagctgat ttatgattct caatcggaca ttatcttata tgaaggcttt   1740
gaggccggaa gtattcctga aggctggttg ttgattgatg ctgatggcga caatgttaat   1800
tgggactatt atccttggac tatgtatgga catgacagtg agaagtgtat tgcatcccct   1860
tcgtacttac cgatgattgg cgtttttaact ccggataact atttggttac acccagactc   1920
gaaggagcca agcttgtcaa gtattgggta agtgcgcaag atgctgttta ttcggctgag   1980
cattatgctg tgatggtttc tactacggga actgctgttg aagatttttgt cctcttgttc   2040 gaagagacaa tgaccgctaa ggctaacggt gcatggtatg agcgaactat tacattgcct   2100
gcaggaacaa aatatattgc ctggcggcat tatgattgca ccgatatgtt tttcttgctc   2160
ttggatgaca ttacggttta tcgttctact gagactgttc ccgagcctgt tactgatttc   2220
gttgtctcgc ttattgagaa taacaagggt cgcctgaaat ggaattatcc taacggctac   2280
gaacccgata agactgatga taaaaaacca ttgcagctta ccggctacaa catctatgca   2340
aatggctcgc tccttgttca catacaagac ccgactgttt tggagtatat cgatgagact   2400
tattcttcac gagacggtca ggtggaaatg gaatattgtg tcactgccgt ttataacgac   2460
aatatcgagt cccaatcggt ttgcgataag ctgaactata ctatcacatc cttggataat   2520
attcaatctg atacaagctt gaaaatatat cctaatccgg catcgtatgt ggtaaggata   2580
gagggattga gtcggagcaa gtcgacaatc gagttgtata atgcgctggg aatttgcata   2640
ttaagggaag agactcattc agagaaaacg gaaatcgatg tttcacgtct caatgacgga   2700
```
gtctacttga ttaaagtagt cggtggaaat aaaacaacaa ccgaaaaggt agagataaag      2760
aggccg                                                                2766

<210> SEQ ID NO 59
<211> LENGTH: 2763
<212> TYPE: DNA
<213> ORGANISM: Porphyromonas gingivalis

<400> SEQUENCE: 59
atgaaaagta ttgttttag agcatttcta acgattttgc tctcgtgggc agcgatcacg        60
aatccgactg ctcaagagat ctcaggcatg aatgcatcct gtctggctgc tccggctcaa      120
ccggatacta tcttatatga aagttttgag aatggacctg ttcccaatgg ctggcttgag      180
atagatgctg atgctgatgg tgccacttgg ggaagcccat caggctcttt ctctgtacct      240
tacggacaca atggcctttg cacctactcc catatacgtt ccggtatctc aacagcgggc      300
aactatctga ttacacccaa tatagaagga gccaaacggg tcaagtactg gtatgcaat       360 cagtatagta ccaatccgga acattacgca gtaatggtat cgacaacggg gactgccatt      420
gaagactttg ttttgttgtt tgatgattcc ataacaggga aaccgactcc tcttgtatgg      480
cgtagacgaa tcgtggactt accggaaggg accaaatata ttgcatggcg acattacaaa      540
gtcaccgact cacacacaga attcttgaaa ttgatgatg tcactgtgta taggtcgatc       600
gaagggcccg aacctgctac cgacttcaca gtaatcaata ttggtcagaa tgtgggacga      660
ttgacttgga actatccgga ggattatcaa ccggaaggaa aggggaatga agagttgcag      720
cttagcggct acaacatcta tgcgaacggt acactactgg cacaaataaa agatgtctcc      780
atactggagt atgtggacag cacttactct ttgcgagaca atcccttgca agtggagtac      840
tgcgttacag ccgtttacga tgaaagcata gaatcttcga ccgtatgtgg cacgctgcat      900
tacgccacgg atgccatcct ttatgaaaat tttgagaatg gacctgttcc caatggttgg      960
cttgtgatag acgctgatgg agatggattt agctggggac actatttgaa tgcatacgac     1020
gcttttcccg gccataatgg aggccattgc tccttgtcgg cttcttatgt tccgggtata     1080
ggcccggtga ctcccgacaa ctatctgatt accccaagg ttgaaggagc caaacgtgtc      1140
aagtactggg taagcacgca ggatgccaat tgggcagcgg aacattacgc ggtgatggct     1200
tcgacaacgg ggactgctgt cggagatttc gtcatattgt tcgaagaaac catgacagcg     1260
aagccgaccg cgcatggta tgaaagaacc atcaacttac ctgaagggac taaatacatc      1320
gcatggcggc attacaactg taccgatata tatttcttga agttggacga tatcactgta     1380
ttcgggactc ctgcatcaga gcccgaacct gttaccgatt tcgttgtctc gcttattgaa     1440
aacaacaagg gacgattaaa gtggaattat cctaacggct acgaacccga taagactgat     1500
gataaagacc cattgcagct tgccggctac aatatctatg caaacggctc gctccttgtt     1560
cacatacaag acccgactgt tttggagtat atcgatgaga cttattcttc acgagacgat     1620
caggtggaag tggaatattg tgtcactgcc gtttataacg acaatatcga gtcccaatcg     1680
gtttgcgata agctgattta tgattctcaa tcggacatta tcttatatga aggctttgag     1740
gccggaagta ttcctgaagg ctggttgttg attgatgctg atggcgacaa tgttaattgg     1800
gactattatc cttggactat gtatggacat gacagtgaga agtgtattgc atcccttcg     1860 tacttaccga tgattggcgt tttaactccg gataactatt tggttacacc cagactcgaa     1920
ggagccaagc ttgtcaagta ttgggtaagt gcgcaagatg ctgtttattc ggctgagcat     1980
tatgctgtga tggtttctac tacgggaact gctgttgaag attttgtcct cttgttcgaa     2040

```
gagacaatga ccgctaaggc taacggtgca tggtatgagc gaactattac attgcctgca    2100
ggaacaaaat atattgcctg gcggcattat gattgcaccg atatgttttt cttgctcttg    2160
gatgacatta cggtttatcg ttctactgag actgttcccg agcctgttac tgatttcgtt    2220
gtctcgctta ttgagaataa caagggtcgc ctgaaatgga attatcctaa cggctacgaa    2280
cccgataaga ctgatgataa aaaccattg cagcttaccg gctacaacat ctatgcaaat     2340
ggctcgctcc ttgttcacat acaagacccg actgttttgg agtatatcga tgagacttat    2400
tcttcacgag acgtcaggt ggaaatgaa tattgtgtca ctgccgttta taacgacaat      2460
atcgagtccc aatcggtttg cgataagctg aactatacta tcacatcctt ggataatatt    2520
caatctgata caagcttgaa aatatatcct aatccggcat cgtatgtggt aaggatagag    2580
ggattgagtc ggagcaagtc gacaatcgag ttgtataatg cgctgggaat ttgcatatta    2640
agggaagaga ctcattcaga gaaaacggaa atcgatgttt cacgtctcaa tgacggagtc    2700
tacttgatta agtagtcgg tggaaataaa acaacaaccg aaaaggtaga gataaagagg     2760
ccg                                                                  2763

<210> SEQ ID NO 60
<211> LENGTH: 972
<212> TYPE: DNA
<213> ORGANISM: Porphyromonas gingivalis

<400> SEQUENCE: 60
atgtgcctcg aacccataat tgctccgatt tcatccgagt tgctcgagca ggagctgact      60
gccgatcgtt ttctgcggat gacaaacaaa gccggcaatg agatctatgt ttttacggcc    120
gaagaagctc cgcattgcat gaaagaagta ggccgactgc gagaagaagc ctttcggcat    180
tatggcggag gtactggcaa ggcgatcgat atagacgagt tcgacaccat gcccgggagc    240
tacaaacagc tgatcgtatg ggatccgcaa aacaaggcta tactcggagg ctaccgctt    300 atctatgggc gggacgttgc tttcgatacc gatggcaagc ctttgctggc aacggcagag    360
atgtttcgct tcagtgatgc tttttttgcac gattatctcc cctacacagt cgaattggga    420
cgttcgttcg tgtcgctcca gtaccaatcg acacggatgg gcacaaaggc cattttttgtg    480 ctggacaatc tttgggacgg tatcggagca ctcactgtag tcaatccaga ggcactctat    540
ttctatggca aggtgaccat gtacaaagac tatgatcggc gagctcgcaa tctgatcctg    600
tattttcttc gcaagcactt ctccgatccg gaaggcttgg tcaagcctat tcatccccta    660
ccgatagaga tcagtgcgga ggacgaagcc ttgttctcct catccgactt tgacaccaat    720
tacaagactc tcaatataga agtgcgcaag ctgggtatca atatccctcc tctcgtgagt    780
gcatatatag ctttgtctcc ggagatgcgt gttttcggca ctgcagtgaa tgagtctttc    840
ggagaggtgg aggaaaccgg catattcatt gctgtgggta agatcctgga agagaaaaaa    900
caacggcaca tagagagctt catcctcagc cggaacgaaa aaaaggtct cgacagtagc     960 aatggccgat ca                                                        972

<210> SEQ ID NO 61
<211> LENGTH: 3678
<212> TYPE: DNA
<213> ORGANISM: Porphyromonas gingivalis
<220> FEATURE:
<221> NAME/KEY: misc_feature
<222> LOCATION: (2949)..(2949)
<223> OTHER INFORMATION: n is a, c, g, or t

<400> SEQUENCE: 61
```

```
atgatgaaac gatatacaat aattcttgca gttttctttt tattctgcac ggtatttacc        60
tttcaaataa aagctcgccc ttatgaaaga tttgcagatg tagagaagcc ttggattcag       120
aaacattcaa tggattctaa attggtgcct gcaaataagg gtaacttaat tcaagctgaa       180
attgtatacc aatctgtttc tgaacatagt gacttagtta tttcacctgt gaacgaaata       240
aggcctgcaa atcgtttccc ttcgcatagg aagtcttttt ttgcagaaaa tctacgggca       300
tctcccccg tagttcccgt tgccgtcgac aagtatgcgg taccggttgc caatccaatg        360
gatcctgaaa atcccaatgc ctgggatgtg acgctaaaaa tcactactaa agcggtaaca       420
gtacctgtcg atgtggtgat ggttatcgac cagtcttcgt caatgggagg gcaaaacatt       480
gccagattaa agtctgccat tgcatcggga cagcgttttg tgaaaaaaat gttgcctaag       540
gggacggcta cagaagggt gcgtatcgct cttgtgagtt atgaccatga gcctcatcgc        600
ttatctgatt ttaccaaaga cactgctttt ctctgtcaaa aaatccgggc tttgactcct       660
atttggggaa cacatacccca ggggggctt aaaatggcga aaacattat ggccacttct        720
actgctgtgg ataagcatat catattgatg tctgacgggt tagcgacgga gcagtatcct      780
gttaaaaatg taactactgc agacttcatt ggcaaaactg gaaatgcgaa tgatcccatt       840
gatttggtta tacaaggagc aattaatttc cctacaaatt atgtttccaa caatccatct       900
acacctctta ccccaaatta tccaactcat tcttctaaag ttggacggag aaatctgccg       960
gaatccaaat tcgattatag taatctgagt gcaaggatta cttttgatgg tgttgctggc      1020
gcattggtct atgaaccgag gtttcctcat ccctattatt attatttccc ttgtaacgct      1080
gctatcaatg aggctcagtt tgcgaaaaac tctggttata caatccatac tattggctat      1140
gacctgggag atttttgcctt ggccaacaat tcgttgaaac taaccgctac agacgagaat     1200
cacttcttta cggcgacacc ggccaattta gctgcagcgt ttgataatat tgcccaaact      1260
attaatatag gtacagagag gggggaggtg acggactttg tagctcctgg tttcatcgtt      1320
aaaaatctga cgcaatcggg agatgttact catttgctaa atgtttcaaa tggaacggtg      1380
cactatgatg tctctactaa aaaactgaca tggactactg gtactatcct gagctcatca      1440
gaagctacca taacttatcg tatttatgcc gatttggatt atatacagaa caatgatatt      1500
ccggtaaata ctacttctgc tatcggcccg gatcttggtg gattcgatac caataccgag      1560
gcaaaattga cctataccaa ttccaatggc gaaccgaatc agcagttaat tttcccacgt      1620
ccgacggtta agttaggtta tggtgttatt aagcggcact atgtattggt aaataaagac      1680
ggtcaaccca tacaggcaaa tggaacagtt gtcagttccc taagcgaggc tcatgttcta      1740
cagtcacaag attttctttt gccctcaggt ggaggtcata ttgttcccaa atggataaag     1800
ttggacaaaa cgaccgaagc attacagtac tattccgtac cgccgactaa cacggtcatc      1860
actactgccg atggtaaacg ttatcgtttt gtcgaagtcc caggctccac gccgaatccg      1920
ggccaaatcg gtatcagttg aaaaaaccg gcaggaaacg cttacttcgc ttacaagctc       1980
ctcaattatt ggatgggagg aacaacagac caacagagtg aatgggatgt gacgtccaat      2040
tggacaggag cccaagtacc gctcacagga gaagatgtag agtttgcaac gacagaaaat     2100
ttcggttctc cggcggtagc cgatttgcat gtcccgacaa ccaacccaa aattatcggt       2160
aaccttatca ataattccga caaggattta gttgttacca caagcagtca attgacgatc      2220
aacggcgtgg ttgaggataa caatccgaat gtcggtacga tcgtcgtgaa gtcgtcgaaa     2280
gacaatccta cggggacatt gcttttgcc aatccgggct ataatcaaaa tgtagggggg       2340
accgtcgagt tttacaatca gggatatgat tgtgccgatt gtggtatgta tcgcaggagc     2400
```

```
tggcagtatt tcggtatccc tgtcaatgaa tcaggttttc caattaatga tgtgggcgga    2460
aacgagaccg tcaaccaatg ggttgagcct ttcaatggcg ataagtggcg gccagcacct    2520
tatgcacctg atacagagct tcaaaaattc aagggctacc agatcacgaa tgacgtgcag    2580
gcacagccta cgggagttta cagcttcaag ggtatgattt gtgtgtgcga tgccttcctg    2640
aatctgacac gcacgtccgg tgtcaactac tcgggcgcca acttgatcgg caactcatac    2700
actggagcca tcgacatcaa gcagggtatt gtcttcccgc cggaagtcga gcagacggtg    2760
tatctgttca acacgggaac acgcgaccag tggcgtaagc ttaatggaag cacggtttca    2820
ggctatcgag ccggtcagta cctctctgta cctaagaata cagcgggtca ggacaatctt    2880
ccggatcgta ttccatcgat gcattccttc ttggtgaaga tgcagaacgg agcgtcttgt    2940
acgttgcana tcttgtacga taagctgctc aagaacacga ctgtaaacaa cggtaatggt    3000
acgcagatca catggcgatc cggcaactcc ggatcggcga atatgccgtc acttgtgatg    3060
gatgttcttg gtaacgagtc ggccgaccgt tgtggatct ttaccgatgg gggtcttct    3120 ttcggattcg acaacggctg ggatggtcgc aagctgactg aaaaaggttt gtcacaactt    3180
tatgcgatgt ctgacatcgg taatgataaa ttccaggttg caggggttcc ggagttgaat    3240
aacctgctga tcggcttcga tgcggataag gatggtcaat acacgttgga gtttgctctt    3300
tcggatcatt ttgcgaaagg ggctgtttac ctgcacgatc ttcagtcagg agccaaacac    3360
cgtattacga attctacgtc gtattcattc gatgccaagc ggggagattc cggggctcgt    3420
ttccgcttgt catatggatg tgatgagaac gtagatgatt cgcatgtcgt gagtacaaat    3480
ggccgtgaaa ttataattct gaatcaagat gctcttgact gcactgtaac cttattcaca    3540
atagaaggta agcttcttcg ccgcttgaaa gtattagctg tcatagagaa agtcatgaaa    3600
gtgcagaccg aggggccta tattgtgcat cttcaaaatg ctttcactaa tgatgtgcat    3660
aaggtgcttg ttgagtat                                                3678
```

<210> SEQ ID NO 62
<211> LENGTH: 3675
<212> TYPE: DNA
<213> ORGANISM: Porphyromonas gingivalis
<220> FEATURE:
<221> NAME/KEY: misc_feature
<222> LOCATION: (2946)..(2946)
<223> OTHER INFORMATION: n is a, c, g, or t

<400> SEQUENCE: 62

```
atgaaacgat atacaataat tcttgcagtt tttcttttat tctgcacggt atttaccttt      60
caaataaaag ctcgcccctta tgaaagattt gcagatgtag agaagccttg gattcagaaa    120
cattcaatgg attctaaatt ggtgcctgca ataagggta acttaattca agctgaaatt      180
gtataccaat ctgtttctga acatagtgac ttagttattt cacctgtgaa cgaaataagg    240
cctgcaaatc gtttcccttc gcataggaag tctttttttg cagaaaatct acgggcatct    300
ccccccgtag ttcccgttgc cgtcgacaag tatgcggtac cggttgccaa tccaatggat    360
cctgaaaatc ccaatgcctg ggatgtgacg ctaaaaatca ctactaaagc ggtaacagta    420
cctgtcgatg tggtgatggt tatcgaccag tcttcgtcaa tgggagggca aaacattgcc    480
agattaaagt ctgccattgc atcgggacag cgttttgtga aaaaaatgtt gcctaagggg    540
acggctacag aaggggtgcg tatcgctctt gtgagttatg accatgagcc tcatcgctta    600
tctgatttta ccaagagacac tgcttttctc tgtcaaaaaa tccgggcttt gactcctatt    660
tggggaacac atacccaggg ggggcttaaa atggcgagaa acattatggc cacttctact    720
```

```
gctgtggata agcatatcat attgatgtct gacgggttag cgacggagca gtatcctgtt    780
aaaaatgtaa ctactgcaga cttcattggc aaaactggaa atgcgaatga tcccattgat    840
ttggttatac aaggagcaat taatttccct acaaattatg tttccaacaa tccatctaca    900
cctcttaccc caaattatcc aactcattct tctaaagttg gacggagaaa tctgccggaa    960
tccaaattcg attatagtaa tctgagtgca aggattactt ttgatggtgt tgctggcgca   1020
ttggtctatg aaccgaggtt tcctcatccc tattattatt atttcccttg taacgctgct   1080
atcaatgagg ctcagtttgc gaaaaactct ggttatacaa tccatactat ggctatgac    1140
ctgggagatt ttgccttggc caacaattcg ttgaaactaa ccgctacaga cgagaatcac   1200
ttctttacgg cgacaccggc caatttagct gcagcgtttg ataatattgc ccaaactatt   1260
aatataggta tacagagggg ggaggtgacg gactttgtag ctcctggttt catcgttaaa   1320
aatctgacgc aatcgggaga tgttactcat ttgctaaatg tttcaaatgg aacggtgcac   1380
tatgatgtct ctactaaaaa actgacatgg actactggta ctatcctgag ctcatcagaa   1440
gctaccataa cttatcgtat ttatgccgat ttggattata tacagaacaa tgatattccg   1500
gtaaatacta cttctgctat cggcccggat cttggtggat tcgataccaa taccgaggca   1560
aaattgacct ataccaattc caatggcgaa ccgaatcagc agttaatttt cccacgtccg   1620
acggttaagt taggttatgg tgttattaag cggcactatg tattggtaaa taagacggt    1680
caacccatac aggcaaatgg aacagttgtc agttccctaa gcgaggctca tgttctacag   1740
tcacaagatt tcttttttgcc ctcaggtgga ggtcatattg ttcccaaatg gataaagttg   1800
gacaaaacga ccgaagcatt acagtactat tccgtaccgc cgactaacac ggtcatcact   1860
actgccgatg gtaaacgtta tcgttttgtc gaagtcccag gctccacgcc gaatccgggc   1920
caaatcggta tcagttggaa aaaaccggca ggaaacgctt acttcgctta caagctcctc   1980
aattattgga tgggaggaac aacagaccaa cagagtgaat gggatgtgac gtccaattgg   2040
acaggagccc aagtaccgct cacaggagaa gatgtagagt ttgcaacgac agaaaatttc   2100
ggttctccgg cggtagccga tttgcatgtc ccgacaacca accccaaaat tatcggtaac   2160
cttatcaata attccgacaa ggatttagtt gttaccacaa gcagtcaatt gacgatcaac   2220
ggcgtggttg aggataacaa tccgaatgtc ggtacgatcg tcgtgaagtc gtcgaaagac   2280
aatcctacgg ggacattgct ttttgccaat ccgggctata atcaaaatgt agggggggacc   2340
gtcgagtttt acaatcaggg atatgattgt gccgattgtg gtatgtatcg caggagctgg   2400
cagtatttcg gtatccctgt caatgaatca ggttttccaa ttaatgatgt gggcggaaac   2460
gagaccgtca accaatgggt tgagccttc aatggcgata agtggcggcc agcaccttat   2520
gcacctgata cagagcttca aaaattcaag gctaccaga tcacgaatga cgtgcaggca   2580
cagcctacgg gagtttacag cttcaagggt atgatttgtg tgtgcgatgc cttcctgaat   2640
ctgacacgca cgtccggtgt caactactcg ggcgccaact tgatcggcaa ctcatacact   2700
ggagccatcg acatcaagca gggtattgtc ttcccgccgg aagtcgagca gacggtgtat   2760
ctgttcaaca cgggaacacg cgaccagtgg cgtaagctta atggaagcac ggtttcaggc   2820
tatcgagccg gtcagtacct ctctgtacct aagaatacag cgggtcagga caatcttccg   2880
gatcgtattc catcgatgca ttccttcttg gtgaagatgc agaacggagc gtcttgtacg   2940
ttgcanatct tgtacgataa gctgctcaag aacacgactg taaacaacgg taatggtacg   3000
cagatcacat ggcgatccgg caactccgga tcggcgaata tgccgtcact tgtgatggat   3060
gttcttggta acgagtcggc cgaccgtttg tggatcttta ccgatggggg tctttctttc   3120
```

```
ggattcgaca acggctggga tggtcgcaag ctgactgaaa aaggtttgtc acaactttat   3180
gcgatgtctg acatcggtaa tgataaattc caggttgcag gggttccgga gttgaataac   3240
ctgctgatcg gcttcgatgc ggataaggat ggtcaataca cgttggagtt tgctctttcg   3300
gatcattttg cgaaagggggc tgtttacctg cacgatcttc agtcaggagc caaacaccgt   3360
attacgaatt ctacgtcgta ttcattcgat gccaagcggg gagattccgg ggctcgtttc   3420
cgcttgtcat atggatgtga tgagaacgta gatgattcgc atgtcgtgag tacaaatggc   3480
cgtgaaatta taattctgaa tcaagatgct cttgactgca ctgtaacctt attcacaata   3540
gaaggtaagc ttcttcgccg cttgaaagta ttagctggtc atagagaagt catgaaagtg   3600
cagaccggag gggcctatat tgtgcatctt caaaatgctt tcactaatga tgtgcataag   3660
gtgcttgttg agtat                                                    3675

<210> SEQ ID NO 63
<211> LENGTH: 1173
<212> TYPE: DNA
<213> ORGANISM: Porphyromonas gingivalis

<400> SEQUENCE: 63
atgattatca agaaaatgct gaaaaataaa ttggccccct tggccatact gttcctttttt     60 gctccaaagg ctatgaaggc tcaggagcaa ctgaatgtgg tacacacctc tgtgccatcg    120
ctgaatatca gtccggatgc acgtgcggcc ggtatggggg atataggtgt ggcaacgacg    180
ccggatgcgt attcacagta ttggaatccg agtaaatatg ctttcatgga tacgaaagcc    240
ggtattagct tctcatatac accctggctg tccaagctgg tcaatgatat tgccctgatg    300
cagatgaccg gtttctacaa attgggaaca gacgagaatc aggctattag tgcttctctg    360
cgttatttca cattaggaaa gttggagact ttcgacgaat tgggcgaatc catggggagag   420 gcccatccca tgaatttgc tgtcgatttg ggctatagcc gccagttgtc ggagaacttc    480
tccatggctg ttgcactgcg ttacatccgc tcagaccaaa gcactcacaa caccggagag   540
aatcaggccg gaaatgcctt tgcggcggat atagccggtt atttgcagaa gtatgtgcta   600
ctgggtaatg cggagagctt gtggtcgttg ggtttcaacg taaagaatat cggaacgaag   660
atctcctatg acggaggtgt cacgagttttt ttcatcccta cttcgttgaa tctcgggacg   720
gggctgttgt atccgatcga tgactataac agcatcaatt tcaaccttga acttagcaag   780
ctgcttgtac ccactcctcc tatcatggat caaaacgatc aggccgggta tgaggctgca   840
ctcaagaaat atcaggaaac ttcttcgatc agcggtatat tctcttcttt cggtgatgcg   900 ccggaggac tcaaggaaga attccgtgag attacatggg gacttggggc tgaatatagc   960
tatgacgata aattttttgt tcgtgccgga tattcatacc tgcaccccac caaaggcaat  1020
ttgcagtact tcacggccgg tgccggcttc aaaatgaaca tattccgtat cgatgcttcc  1080
tacctgttgt ctacgatcca gagtaatccg ttggatcaga ctctgcggtt tacgcttgct  1140
ttcgatatgg atggattgcg caatttgttc cac                                1173

<210> SEQ ID NO 64
<211> LENGTH: 1338
<212> TYPE: DNA
<213> ORGANISM: Porphyromonas gingivalis

<400> SEQUENCE: 64
atgaaaacaa cagttcaaca aattattctg tgcctggctt taatgatgtc aggtgtattg    60 ggcggaaaacg cacagagctt tgggaagaa atagctcctc cttttatcag taatgagcct   120
```

```
aacgtcaagt atataattcc caatatgggg attgattcaa agggaacaat ctatgtaacc      180
gtgacaaaaa ggattcagca gggagcaaat tatacttctg agcaattggg tatgtactat      240
cgaccattag gtgataatga acagtggtgg aaacatgatc cgtattttga tgacaagata      300
gttgcggata ttcagacaga tgcatatggc agagtttatg tatgtacgac ttcttctcga      360
gatcaagagt atcaacttta tataaacgag cagaacgaat ggaggtgtat attcaaaact      420
tctgtgtcta catatgagca tggtatggct gtttttcgct cttcgacagg ggtgacttat      480
ataggtacca ggcatcacat cttcgcatca ggtgtaaatg atttcgagtt caacactatc      540
tatgaagact ctacacctat gagctgtcgc tttgcagagg ctacgaatag tggcaccatc      600
tatctggcat tgatgcatga aaccacaatg tctacgacta tccttactta tcaaaacggt      660
gagttcgtcg atatctcgga aagtgaattg agtaactcga ttattgcatc catgtgctct      720
aataaagaag gtgatataat agctcttgtt acttcatata caggatttat gagtggaacc      780
cttgcgatca gaaaagcaga tgaaggcaaa tggcaacttg ttggcggaga tatacagaat      840
gcgatcgttc aaaatatatg catgatggac gacaacaaga ttgcttgtga agtcttcggg      900
actcctaacg gagtagatgg tcggacaagg gttttgtgttt ctgacgcatc tgtctttgat      960
tttgagtggt atgaagatga aatatacgga ggcctgatat ttgacacttt cttctatagc     1020
ccttgggaca aacttcttta tgcgaaattt ggtgggatta tgctcaggag taaagagtct     1080
tttataacct ctttcatttc tccgacagtt gtacaaggag tggatgtcta tactttggcc     1140
gggaagataa ggatcgaaag tgaaactccg gtgtctgagg tgttgctttt cgacctggct     1200
ggcaggatgg tacttcggca aaccattgat aataaaatct attcggacat agatactaac     1260
ggactaaagc gaagcggtat ttacgtagtc tcggtgcggc tctcttccgg acaggtattc     1320
agtcataagg tgcaggta                                                   1338
```

<210> SEQ ID NO 65
<211> LENGTH: 1797
<212> TYPE: DNA
<213> ORGANISM: Porphyromonas gingivalis

<400> SEQUENCE: 65

```
atggaaaact taaagaacat tcagcccaga gaggatttca actgggaaga gtttgaggcc       60
ggtggcgtcc atgctgccgt gagtcgtcag gagcaggaag ctgcttatga caaaacgctc      120
aataccatca aggaaaagga agtggtaatg ggtagggtaa ctgctatcaa caagcgtgaa      180
gtggttatca atgtagggta caaatcggaa ggtgtggtac ctgcaacaga attccgctac      240
aatcccgaac tcaaagtggg agacgaagtg gaagtttata tcgagaatca ggaagataag      300
aagggccagc tcgtcttgtc tcaccgcaag ggtcgtgccg ctcgctcttg ggagcgcgtg      360
aacgaggctc tcgaaaaaga cgaaatcgta aagggctatg tgaagtgtcg taccaagggt      420
ggtatgatcg tcgatgtatt cggtatcgag gctttcctcc cgggatcaca gatcgacgtg      480
cgccccattc gcgactacga tgcattcgtt gagaagacga tggagttcaa gattgtgaaa      540
atcaatcaag aatataagaa tgtagttgtt tcccacaagg tgctcatcga agcagagctc      600
gaacaacaga gaaagaaat catcggcaag ctcgaaaaag ggcaggtact cgaaggtatc      660
gtcaagaata ttacttctta cggagtattt atcgacctcg gtgagtggga tggtcttatc      720
catatcactg acctttcatg gggtcgtgtg gctcatccgg aagaaatcgt acagctggat      780
cagaagatca atgtcgttat cctcgacttt gatgaagatc gcaagcgtat cgctctcgga      840
ctcaaacagc tgatgcctca tccttgggat gctctcgaca gcgagcttaa ggtaggcgat      900
```

```
aaggtgaagg gtaaagttgt ggtgatggca gattacggtg ctttcgttga gattgcacag      960
ggcgttgagg gtcttatcca cgtaagcgaa atgtcatgga cacagcactt gcgttctgct     1020
caggacttcc tgcatgtagg cgacgaagtg aagccgtga tcctgacgct cgaccgcgaa      1080
gaacgcaaaa tgtcgctcgg tctgaagcaa ctcaagccgg atccttgggc tgatatcgaa     1140
actcgtttcc ctgtaggctc tcgtcaccat gctcgtgttc gcaacttcac caatttcggt     1200
gtattcgttg agatcgaaga gggcgtagat ggccttatcc atatttccga cctttcttgg     1260
acgaagaaga tcaaacaccc cagcgagttt acggaagtag gtgctgatat cgaagttcag     1320
gtaatcgaga tcgacaagga aaaccgtcgt ctcagcttgg gtcacaaaca gttggaagag     1380
aatccttggg atgtattcga gacggtattc actgtaggat ctatccacga aggaacggta     1440
atcgaagtga tggacaaggg tgctgtcgtt tctctgcctt acggtgtgga aggttttgcc     1500
actccgaagc acatggtgaa ggaagatggc tcacaggctg tactcgaaga gaagttacct     1560
ttcaaggtta ttgagttcaa taaggatgcc aagcgaatca ttgtatctca tagccgtgta     1620
ttcgaagatg agcagaaaat ggctcagcgt gaagccaatg cagagcgtaa ggctgaagcc     1680
aaagcggctc agaagaagc tgctgccgaa gctgccaatc ctgcacaggc tgtagagaaa      1740
gccactctcg agacctcgg cgagctggcc gctttgaaag aaaagctttc agaaaac        1797

<210> SEQ ID NO 66
<211> LENGTH: 1650
<212> TYPE: DNA
<213> ORGANISM: Porphyromonas gingivalis

<400> SEQUENCE: 66
atgggtaggg taactgctat caacaagcgt gaagtggtta tcaatgtagg gtacaaatcg      60
gaaggtgtgg tacctgcaac agaattccgc tacaatcccg aactcaaagt gggagacgaa     120
gtggaagttt atatcgagaa tcaggaagat aagaagggcc agctcgtctt gtctcaccgc     180
aagggtcgtg ccgctcgctc ttgggagcgc gtgaacgagg ctctcgaaaa agacgaaatc     240
gtaaagggct atgtgaagtg tcgtaccaag ggtggtatga tcgtcgatgt attcggtatc     300
gaggctttcc tcccgggatc acagatcgac gtgcgcccca ttcgcgacta cgatgcattc     360
gttgagaaga cgatggagtt caagattgtg aaaatcaatc aagaatataa gaatgtagtt     420
gtttcccaca aggtgctcat cgaagcagag ctcgaacaac agaagaaaga atcatcggc     480 aagctcgaaa aagggcaggt actcgaaggt atcgtcaaga atattacttc ttacggagta     540
tttatcgacc tcggtggagt ggatggtctt atccatatca ctgaccttcc atgggtcgt    600 gtggctcatc cggaagaaat cgtacagctg atcagaaga tcaatgtcgt tatcctcgac    660
tttgatgaag atcgcaagcg tatcgctctc ggactcaaac agctgatgcc tcatccttgg    720
gatgctctcg acagcgagct taaggtaggc gataaggtga agggtaaagt tgtggtgatg    780
gcagattacg gtgctttcgt tgagattgca cagggcgttg agggtcttat ccacgtaagc    840
gaaatgtcat ggacacagca cttgcgttct gctcaggact tcctgcatgt aggcgacgaa    900
gtggaagccg tgatcctgac gctcgaccgc gaagaacgca aaatgtcgct cggtctgaag    960
caactcaagc cggatccttg ggctgatatc gaaactcgtt tccctgtagg ctctcgtcac   1020
catgctcgtg ttcgcaactt caccaatttc ggtgtattcg ttgagatcga agagggcgta   1080
gatggcctta tccatatttc cgaccttttct tggacgaaga agatcaaaca ccccagcgag   1140 tttacgaag taggtgctga tatcgaagtt caggtaatcg agatcgacaa ggaaaaccgt    1200
cgtctcagct tgggtcacaa acagttggaa gagaatcctt gggatgtatt cgagacggta    1260
```

| | |
|---|---|
| ttcactgtag gatctatcca cgaaggaacg gtaatcgaag tgatggacaa gggtgctgtc | 1320 |
| gtttctctgc cttacggtgt ggaaggtttt gccactccga agcacatggt gaaggaagat | 1380 |
| ggctcacagg ctgtactcga agagaagtta cctttcaagg ttattgagtt caataaggat | 1440 |
| gccaagcgaa tcattgtatc tcatagccgt gtattcgaag atgagcagaa aatggctcag | 1500 |
| cgtgaagcca atgcagagcg taaggctgaa gccaaagcgg ctcagaaaga agctgctgcc | 1560 |
| gaagctgcca atcctgcaca ggctgtagag aaagccactc tcggagacct cggcgagctg | 1620 |
| gccgctttga agaaaagct ttcagaaaac | 1650 |

<210> SEQ ID NO 67
<211> LENGTH: 1374
<212> TYPE: DNA
<213> ORGANISM: Porphyromonas gingivalis

<400> SEQUENCE: 67

| | |
|---|---|
| atgatcgtcg atgtattcgg tatcgaggct ttcctcccgg gatcacagat cgacgtgcgc | 60 |
| cccattcgcg actacgatgc attcgttgag aagacgatgg agttcaagat tgtgaaaatc | 120 |
| aatcaagaat ataagaatgt agttgtttcc cacaaggtgc tcatcgaagc agagctcgaa | 180 |
| caacagaaga agaaatcat cggcaagctc gaaaagggc aggtactcga aggtatcgtc | 240 |
| aagaatatta cttcttacgg agtatttatc gacctcggtg gagtggatgg tcttatccat | 300 |
| atcactgacc tttcatgggg tcgtgtggct catccggaag aaatcgtaca gctggatcag | 360 |
| aagatcaatg tcgttatcct cgactttgat gaagatcgca agcgtatcgc tctcggactc | 420 |
| aaacagctga tgcctcatcc ttgggatgct ctcgacagcg agcttaaggt aggcgataag | 480 |
| gtgaagggta aagttgtggt gatggcagat tacggtgctt tcgttgagat tgcacagggc | 540 |
| gttgagggtc ttatccacgt aagcgaaatg tcatggacac agcacttgcg ttctgctcag | 600 |
| gacttcctgc atgtaggcga cgaagtgaaa gccgtgatcc tgacgctcga ccgcgaagaa | 660 |
| cgcaaaatgt cgctcggtct gaagcaactc aagccggatc cttgggctga tatcgaaact | 720 |
| cgtttccctg taggctctcg tcaccatgct cgtgttcgca acttcaccaa tttcggtgta | 780 |
| ttcgttgaga tcgaagaggg cgtagatggc cttatccata tttccgacct tcttggacg | 840 |
| aagaagatca acaccccag cgagtttacg gaagtaggtg ctgatatcga agttcaggta | 900 |
| atcgagatcg acaaggaaaa ccgtcgtctc agcttgggtc acaaacagtt ggaagagaat | 960 |
| ccttgggatg tattcgagac ggtattcact gtaggatcta tccacgaagg aacggtaatc | 1020 |
| gaagtgatgg acaagggtgc tgtcgtttct ctgccttacg gtgtggaagg ttttgccact | 1080 |
| ccgaagcaca tggtgaagga agatggctca caggctgtac tcgaagagaa gttacctttc | 1140 |
| aaggttattg agttcaataa ggatgccaag cgaatcattg tatctcatag ccgtgtattc | 1200 |
| gaagatgagc agaaaatggc tcagcgtgaa gccaatgcag agcgtaaggc tgaagccaaa | 1260 |
| gcggctcaga agaagctgc tgccgaagct gccaatcctg cacaggctgt agagaaagcc | 1320 |
| actctcggag acctcggcga gctggccgct ttgaagaaa agctttcaga aaac | 1374 |

<210> SEQ ID NO 68
<211> LENGTH: 1278
<212> TYPE: DNA
<213> ORGANISM: Porphyromonas gingivalis

<400> SEQUENCE: 68

| | |
|---|---|
| atggagttca agattgtgaa aatcaatcaa gaatataaga atgtagttgt ttcccacaag | 60 |
| gtgctcatcg aagcagagct cgaacaacag aagaagaaa tcatcggcaa gctcgaaaaa | 120 |

```
gggcaggtac tcgaaggtat cgtcaagaat attacttctt acggagtatt tatcgacctc    180
ggtggagtgg atggtcttat ccatatcact gacctttcat ggggtcgtgt ggctcatccg    240
gaagaaatcg tacagctgga tcagaagatc aatgtcgtta tcctcgactt tgatgaagat    300
cgcaagcgta tcgctctcgg actcaaacag ctgatgcctc atccttggga tgctctcgac    360
agcgagctta aggtaggcga taaggtgaag ggtaaagttg tggtgatggc agattacggt    420
gctttcgttg agattgcaca gggcgttgag ggtcttatcc acgtaagcga aatgtcatgg    480
acacagcact tgcgttctgc tcaggacttc ctgcatgtag cgacgaagt ggaagccgtg    540 atcctgacgc tcgaccgcga agaacgcaaa atgtcgctcg gtctgaagca actcaagccg    600
gatccttggg ctgatatcga aactcgtttc cctgtaggct ctcgtcacca tgctcgtgtt    660
cgcaacttca ccaatttcgg tgtattcgtt gagatcgaag agggcgtaga tggccttatc    720
catatttccg acctttcttg gacgaagaag atcaaacacc ccagcgagtt tacgaagta    780 ggtgctgata tcgaagttca ggtaatcgag atcgacaagg aaaaccgtcg tctcagcttg    840
ggtcacaaac agttggaaga gaatccttgg gatgtattcg agacggtatt cactgtagga    900
tctatccacg aaggaacggt aatcgaagtg atggacaagg tgctgtcgt ttctctgcct    960 tacggtgtgg aaggttttgc cactccgaag cacatggtga aggaagatgg ctcacaggct   1020
gtactcgaag agaagttacc tttcaaggtt attgagttca ataaggatgc caagcgaatc   1080
attgtatctc atagccgtgt attcgaagat gagcagaaaa tggctcagcg tgaagccaat   1140
gcagagcgta aggctgaagc caaagcggct cagaaagaag ctgctgccga agctgccaat   1200
cctgcacagg ctgtagagaa agccactctc ggagacctcg gcgagctggc cgctttgaaa   1260
gaaaagcttt cagaaaac                                                 1278

<210> SEQ ID NO 69
<211> LENGTH: 1620
<212> TYPE: DNA
<213> ORGANISM: Porphyromonas gingivalis

<400> SEQUENCE: 69
atgaagacaa aagttttacg caaattcgtg gtggcggctt tcgccgtcgc aaccctctgt     60
cctctcgccc aagcgcagac gatgggagga gatgatgtca aggtggtcca gtacaatcag    120
gaaaaactgg tacaaacgag gatgagtgtg gcggacaacg gatggatcta tgtaatgacc    180
cacagtggat acgacaccgg caatagcaat gtgaagatct tccgctccaa agaccaaggt    240
gccacatacc aaaagttgag ggattgggat ccatcggatg attatcagtt tcaagacttc    300
gatatcgtgg taacgggtaa gaatgaatcc gacatcaaga tttggtcggt agagctcatg    360
aataagcccg gaggatataa gagtagagtt gcggtcttca gtcgcgatgc caacgcgcag    420
aatgcgaaac tcgtgtataa ggaagacttc tccaatgtgc agttgtacga tgtggatata    480
gcctccaact atcgttcgcc ttcttctctt aacaatggtg gcaacccttt tgctttggct    540
ttcgcttaca ccggcttcaa caatacgcac aaaataagtt ttgtggacta tgtgttctct    600
ctgaatggag ggcaaaattt caataaaaac ttactcttca gtcaagatgg agagaagaaa    660
attgacaagg tggatctctc attgggtagc acctctgaat ccatgggtca caatgcctgg    720
ccgctaatgg gtgtggtatt cgaaatgaat aaacaagggg gaaaagcga tatcggtttc    780 ttgtcgaact tgtcgacaa tgatcccgaa tttcagtggt caggccctat aaaagtgagt    840
gaaagcgaca tgtcgttcag ccccaaaatc caaatgttgc tggacgagga taacaatacg    900
atcaatgggg agagttgcca caacttcatg attacgtaca gcgattatga ttctgaatat    960
```

```
tcggattggg acattcggta tgtatatccc aagaaatcgt tcaagtatga aaaaggaaaa    1020
actccgacta tggatgatct ggtggaagct ttccttacag cttcgtacca gagtgagacc    1080
aactcggggc tggggtatga caagaacgcc aatcactacc tgattacata tgccaaaaaa    1140
gaagagaacg gtacgaacac gctgaaatac cgctgggcca attatgacaa gattcataac    1200
aaagatttgt ggagcgacac atttacgtat acatcatctg ccaatgctct ctacacacct    1260
caagtagaca tcaatccgac caagggtctc gtgtgctggt catgggtgga atatctgccg    1320
ggcaaacgga tcgtttggtc tgatacgcag tggacccatg ccaacggtgt agaagcatc     1380 gtaatgcaag aaggcagcat gaagctctac ccgaatccgg ctcaagaata tgctgtgatt    1440
agcctgccga cggcagcaaa ctgcaaggct gttgtttacg atatgcaggg cagagtagtc    1500
gctgaggctt ctttctccgg caacgaatac aggctgaacg tgcagcactt ggctaagggt    1560
acgtacatac tcaaggtcgt atccgatacg gagcgtttcg tagagaagct catcgtggaa    1620

<210> SEQ ID NO 70
<211> LENGTH: 3474
<212> TYPE: DNA
<213> ORGANISM: Porphyromonas gingivalis

<400> SEQUENCE: 70
atgaaacgaa tacttccaat agtcgcattc ctttctctct tccttgccct tgctttgcct      60
gcgaaagcgc aacgagctat ggggaagacg gccgaccgtt cgctaatggc ttcgggacat     120
tgggtcaaga tacgtgtcga tgcaagtgga gtgtatcgcc ttacggacga acagctccgt     180
gccaatggct tctccgatcc gtccaaggta ggtgtgttcg gttatggtgg agggggtgctt    240 cccgaagatc tgagccggat cacgacagac gatttgcctc cggtaccggt actccgtcag     300
ggcaatgcgc tgtatttcta tgccgtgggc ccggtgacat ggttctacaa tccggccaaa     360
accaccatgg agcatacggt gaatacatac agtacgcatg ctactactt cctgtcggat      420 gctgccggag cacctttgca gatgtcccaa tatacgggtg gaggtgcgtc ggccgaggct     480
ttgatcgact actacgatga gctgatgctc catgaacagg aattgtattc gcccaaagaa     540
tcgggacgag atctgtatgg cgagtctttc agtgcagtca atacgcgtac ggtcaagttc     600
cctttgaggg gcaacacccg ctcgtctggc gaactcggta ccgtattctc atacatagcc     660
aaggccagat cggccggtgg cggccgtgag atgtcgctct cggcgaatgg cattctgatc     720
ttcagcgatc ctttttccat gacatcgaat gaagtctcca attcctattt ggccggcaag     780
aagcgtcgtc tctatcacag tacgccgatg aacagcttgg tcaatgagtt gcgcttggac     840
gcgaactata gcatgacagg agatgcggtc aatctggatt tcatagaggt ggctacacag     900
aacgacctcc ggtacgatgg cgcacccatg catatcaggc ggttttccaa tttgcccgtt     960
ttggggggcg agtcctgccg gttcgttatc agtgaggtgc cggagtctct ggtggttttg    1020
caggccaatt cttccctgac agcatcgctt gttcccgtta agactgtcgg ggataagacc    1080
attgagttcg tggctccgcc gaagggtcag gatcgtagga ctatcaatac gttttatgcc    1140
gtggacttgt cacaggcttc tgctccggag atcctcggag cggtacccaa tcaaaacctg    1200
catggagagg aaatccctga tctgatcatt gtctctactc aggcgctcct ccttgaggct    1260
gatcgactgg ccacctatcg tagagagaaa acgggctga aggttttggt cgtgttgcag    1320
gaacaggtgt tcaacgagtt ttcgggtgga actcccgatg ctacagcata ccgcctcttt    1380
gccaaaatgt tctacgacag atggaaggca aatgcacctg tgggagagac cttcccgatg    1440
caaatgcttc tcttcggtga tgggggctcat gacaacagga aggtctccgt agcttggcag    1500
```

```
aaaccgtatc tccaacaaac ggagttcttg ctgacattcc aagccgtcaa ttcgacgaac    1560
gtaaacagtt atgtgacgga tgattacttc ggcttgctgg atgatcagcc ggcctcggtc    1620
aatatcggtt ggcgcaatta taatatggct gtagggcgat tccccgtacg tactccggcc    1680
gaagctcgca tcgcagtgga caagaccatc cgatatgagg aggatcgaga gagtggtgcc    1740
tggcgtattc gtgcctgttt tgcggcagac aacggggaca agcacgcaac cgagacttcc    1800
cgtttgatcg ataccgtcaa gcgttatgct cctgccatca tgccggtacg cgccttttcag   1860 gacgtatatc cgcatgtcat cgagaacggg ttgcacagca ttccgggtgc aaagaaaaag    1920
atgctggaaa cccttcagtc gggtattatc ctgcttaatt atgctggtca tggcggtcct    1980
gccggatggt cggacgagca tttgctgacg ctcaacgata tacacaaatt caattataag    2040
catatgccca tttggattac tgccacgtgc gactttgcca actatgacag tcagacgacc    2100
tcggcagggg aggaggtttt cctccatgag aagagtggca ctccgatcat gttctcgact    2160
acgcgtgtcg tttacaatac gcagaatgag aagatcaatg gttttatgct tcggcgtatg    2220
ttcgagaaag ctaaggatgg gcgttatcgt acgatgggcg agattatccg atcggccaaa    2280
caggggatgc tcagtactgt tttccccgat tcgatcaacc agttgagttt ctttctgatg    2340
ggtgatccgt ccgtgcgtat gaatcttcct acccacaaag tgcaattgac cgcaatcaac    2400
gggcaggatc ccgaagggca gtatggaact attatgctca gtctttgga acgggtagct    2460 ctgaagggta aggtaaccga tgaaaagggg acattcgacg agacattcag tggcaaggtt    2520
ttcctgaccg tcttcgatgg cagaaagaaa atgcagcctt ggaagagga gggaaacgat    2580 ctctctcttg tatattatga ctatcctaac gtgatgtatg ccggtattgc cgaggtgaaa    2640
gacggactct tcgaaacttc gtttatcgta cccaaggatg tgaactattc cgagcacgaa    2700
ggccggatca atctttatgc ttataacgag agcacaaagg cggaagccat gggggtagac    2760
ttctccatca gagtccaacc gggtattcct gatgaggtaa cggaagataa tacaccgcct    2820
gaaatcataa gctgcttcct caatgacagt acattccgat cgggagatga ggttaatcct    2880
actcctctgt ttatggccga agtattcgac ttgaatggaa tcaatatcac gggtagcgga    2940
gtagggcatg atattacgct ttgtatcgat ggccgtgccg acctgaccta caacctcaat    3000
gcatatttca caagttcggc tacggatgca ggtgtgggca ctattctctt catgataccg    3060
gctttggccg aaggagatca tactgcccga ctgacggttt gggacatttt caataatgcc    3120
gtccatcatg acttttcatt cagagtggta gatggcattg ctccggatgt ggctgatgtg    3180
attctattcc cgaatccggt acgcgagagt gctacgttcc gaatcttcca caatcgcccc    3240
ggaagcgatt tgaacgtggc cgtggagatc tatgacttca ccggtcgtct tgtgaacagt    3300
ttgccagtca agacctattc gtcttcctac ggagaaccta tagagatcaa gtgggatctg    3360
acctccaaat acggagtgaa gatcggaaac ggattctacc tctatcgttg tgtggtgaac    3420
tctcccggag acagacggc ctccatggcc aagaaaatga tcgtggtagg acaa           3474
```

<210> SEQ ID NO 71
<211> LENGTH: 1668
<212> TYPE: DNA
<213> ORGANISM: Porphyromonas gingivalis

<400> SEQUENCE: 71

```
atgaaaaagc ttttacaggc taaagccttg attctggcat gggactctt ccaactgccc      60 gcaatcgccc aaacgcaaat gcaagcagac cgaacaaacg gtcaatttgc aacagaagag    120
atgcaacgag cattccagga aacgaatccc cctgcaggtc ctgtgcgtgc tatcgctgag    180
```

```
tacgaacgct ctgcagccgt tttggtacgc tacccgttcg gtatcccgat ggaattgatc    240
aaagagctgg ccaagaacga caaggtgatt accattgtgg cgagtgaaag ccaaaaaaac    300
accgttataa cccagtacac ccaaagcggt gtgaatctct ctaattgcga tttcatcatt    360
gcgaaaactg actcttactg gacacgcgac tataccggtt ggttcgcaat gtacgatacg    420
aacaaagtag gtctcgtgga ctttatttat aaccgccctc gtcctaacga tgatgaattc    480
cccaaatacg aagcacaata tctgggcatc gagatgttcg ggatgaagct caagcagacc    540
ggtggcaact acatgacgga cggatatgga tccgctgtgc agtcacatat cgcatatacg    600
gagaactcct ctctgtctca agctcaagta aatcaaaaga tgaaagacta tctcggcatc    660
acacatcatg atgtggtaca agatccgaac ggcgaatata tcaaccatgt ggactgttgg    720
ggcaagtatt tggcaccgaa caaaatcctc atcaggaaag tgcctgacaa tcaccctcag    780
caccaagccc tggaagatat ggcagcctac ttcgcagcac agacctgcgc atggggaacg    840
aagtacgagg tatatcgcgc tttggccacc aatgaacaac cgtacacgaa ctctctgatt    900
ctgaacaaca gggtatttgt tcctgtcaat ggccccgcct ccgtggacaa cgatgctctg    960
aacgtctata agacggcaat gcccggttac gaaattatag gtgtcaaagg ggcttcagga   1020
acaccttggt taggaacaga tgccctgcat tgtcgtactc acgaggtagc ggataagggc   1080
tatctctata tcaagcacta cccgatactg ggcgaacagg caggccctga ttataagatc   1140
gaagcagatg tcgtctcatg cgccaatgct actatctcgc cggtacaatg ttactatcgt   1200
atcaatggtt ccggtagctt taaggctgct gatatgacga tggaatcaac aggtcactat   1260
acttatagct ttacaggtct taacaagaat gataaggtag aatactatat ctctgccgct   1320
gacaatagtg gtcgcaaaga gacttatccc tttatcggcg aacctgatcc tttcaagttt   1380
acgtgtatga acgaaaccaa tacatgtact gtgaccggag ctgccaaagc tcttcgtgca   1440
tggttcaacg ccggtcgttc agaactggct gttttcggtaa gtttgaatat tgccggcaca   1500
tatcggataa agctttataa caccgcagga gaagaagtcg ctgcaatgac caaggaatta   1560
gtagcaggga cgagtgtctt cagtatggat gtgtattctc aggctccggg cacatatgtt   1620
ctggttgttg aaggaaatgg aatccgtgag acaatgaaaa ttctcaaa              1668
```

<210> SEQ ID NO 72
<211> LENGTH: 1284
<212> TYPE: DNA
<213> ORGANISM: Porphyromonas gingivalis

<400> SEQUENCE: 72

```
atgaaacttt catctaagaa aatcttagca atcattgcat tgctgacgat gggacatgct     60
gtgcaggcac agtttgttcc ggctcccacc acagggattc gcatgtctgt cactacaacc    120
aaggccgtag gcgaaaaaat cgaattgttg gttcattcca tagagaagaa aggcatctgg    180
atcgatctca atgggatgc cacttaccaa caaggagagg aaataaccgt attcgatgag    240
gcataccacg aatacacgat cgggacgcaa accctcacta tctatggtaa tacgacccga    300
ttgggctgtc gatctaccgg tgcaacggct gtcgatgtaa cgaaaacccc taatctgacc    360
tatctcgcat gcccgaaaaa taatctgaaa tcattggact tgacgcaaaa cccaaagctg    420
ctgcgagttt ggtgcgactc taacgaaata gaaagtttgg acctgagtgg caatccggct    480
ttgatcatcc tcggctgtga caggaataag ctgactgagc tgaagaccga taacaacccc    540
aagttggcct ctctttggtg ttctgataat aacctgacgg agttggaact cagtgccaat    600
cctcgtctca atgatctttg gtgcttcggt aatcggatca cgaaactcga tctgagtgcc    660
```

```
aatcctctat tggtaacact ttggtgcagt gacaatgagc tttcgacctt ggatctttcc      720
aagaattcgg acgttgctta cctttggtgt tcatcgaaca aacttacatc cttgaatctg      780 tcggggtga  agggactgag tgttttggtt tgtcattcca atcagatcgc aggtgaagaa      840
atgacgaaag tggtgaatgc tttgcccaca ctatctcccg gcgcaggcgc tcagagcaag      900
ttcgtcgttg tagacctcaa ggacactgat gagaagaata tctgtaccgt aaaggatgtg      960
gaaaaagcta aaagtaagaa ctggcgagta tttgacttca acggtgattc tgacaatatg     1020
cttccatacg aaggaagtcc gacatcgaac ttggcagtag atgctcccac tgtcaggata     1080
tatcccaatc cggtaggaag atatgcgctc gtcgagatcc ccgagtctct tttagggcag     1140
gaagctgctt tatacgatat gaatggggta aaagtctata gtttcgcggt agagtctctt     1200
cgtcagaaca ttgacctgac acatcttccc gacggcactt atttcttccg tctcgataac     1260
tataccacta agctcatcaa acag                                            1284
```

<210> SEQ ID NO 73
<211> LENGTH: 930
<212> TYPE: DNA
<213> ORGANISM: Porphyromonas gingivalis

<400> SEQUENCE: 73

```
atgagaaaaa caataatttt ctgcttgttg ctcgccctat ttggctgttc ttgggcacaa       60
gaaagagtcg atgaaaaagt attctccgca ggaacaagta tttttagggg catccttgaa      120
aaggtgaaag caccgcttat gtatggagat cgtgaggtat ggggtatggc tcgtgcgagc      180
gaggatttct ttttatact  tcccgttacg gatgacctca ctcccgtgct tttctataac      240
cgtcttacaa acgaacctg  ctttgtgtca gaccaaggaa taactgagta tttcaaattc      300
gctcaagaag gtgattacat tgaagtcgaa ggaagctctg tattcatggc gaatcttttg      360
tactatcgtt ttttccccgac aagaattacc tcctataatg ctcccattga aggtgttgtg      420
agcaagacgg gaaatcctgc ttttacaatc ccgatgctcc cgggggtttc tgattgcata      480
gaaatctcaa acaaccgcaa agtctttctg accaatcaat tagggggttgt aaacatcact      540 gacgggatgg aacctccgat tattgccgga gtctctgctt cctatggatc ttccgtccgg      600
gtgtatggtc atgtctcaca gcggtgggac atcataggcc attgctattt ggatatctac      660
ccaaccaatt gctatccgct cagcacgaaa cccgttgcag gagacgatga ggttttttgtc      720 aaacaacaag gcaggcaaat agagatcgat agcaacagcc ccatagtcca agtggtcgta      780
tacgatcttg aggggaaaag tgttttttcgc aaaagaatga ccgaaaacgc ttatacccta      840
tcctttagag cacccatgct cggctttatg accatcatga tcgaaacaca aaattcgatt      900
atcaataaaa aacttaatgt tacacagcta                                       930
```

<210> SEQ ID NO 74
<211> LENGTH: 1215
<212> TYPE: DNA
<213> ORGANISM: Porphyromonas gingivalis

<400> SEQUENCE: 74

```
atgaaaaaaa caaccattat ttcttttgatt gtcttcggtg ctttctttgc agccgtgggc       60
caaaccaagg acaattcttc ttacaaacct ttttcgaaag aagatattgc cggaggagtt      120
tactctctcc cgactcaaaa tcgtgcgcag aaggacaatg ccgagtggct tcttacagcg      180
accgtctcca caaccagtc  tgcagatact cactttatct tcgatgagaa caaccgctat      240
atcgctcgtg acataaaagc caatgggggta agaaaatcca cggactccat ttactacgat      300
```

```
gccaacgggc gaatatcgca tgtggatctt tatatctcgt tcagtggcgg agagcctgca    360
ctcgacaccc gattcaagta cacctatgat gacgagggaa agatgaccgt gagggaagta    420
ttcatgctgg taatggatcc gaatacacct atctcacgct tggaatatca ttatgatgca    480
cagggcagac tgacccactg gatttctttt gctttcgggg cagaatccca aaagaatacg    540
tatcactata atgaaaaagg tctgttggtc agcgaagtgc tgagcaatgc aatggggaca    600
acctattcag acaccggcaa aacggaatac agctatgacg atgcagataa tatggtgaag    660
gccgagtact tcgtcgtcca gcaaggaaag gcatggcaag tactcaaaag agaggaatac    720
acctatgagg acaatatctg catacaatat ttggctatta acggtaccga cacaaaggtg    780
tacaagcgag acatcgagag cgataagtcc atctccgcaa atgtcattga cattccgtca    840
atgccggaac agacctggcc taatatgtac ggattcaacg caaagcgact gaaagagact    900
tattcctcct acgaaggaga gtggctact cctatattcg actatatcta tacgtacaag    960
gctcttacct caatggcaac accttcgaca gaagctcagg tagcagtcta tctcaatccg   1020
tcaacggacc ggttagtgat tctggccaac ggcatcacac atctgagcat gtacgacttg   1080
cagggtaagc ttatccgtga ttgtgccttg agcggcgata aggtggaaat gggtgtcgga   1140
tctttgacca aagggacata cctgcttaaa gtgaatacgg atcagggagc ctttgtgaga   1200
aaagtcgtga ttcga                                                    1215

<210> SEQ ID NO 75
<211> LENGTH: 454
<212> TYPE: PRT
<213> ORGANISM: Porphyromonas gingivalis

<400> SEQUENCE: 75

Phe Cys Val Met Ala Lys Val Ile Lys Thr Lys Lys Gly Leu Ala Leu
1               5                   10                  15

Asn Leu Lys Gly Lys Pro Leu Pro Glu Met Leu Ala Glu Pro Ala Gln
            20                  25                  30

Ser Pro Thr Tyr Ala Val Val Pro Asp Asp Phe Glu Gly Val Ile Pro
        35                  40                  45

Lys Val Thr Ala Arg Pro Gly Asp Lys Val Arg Ala Gly Ser Ala Leu
    50                  55                  60

Met His His Lys Ala Tyr Pro Glu Met Lys Phe Thr Ser Pro Val Ser
65                  70                  75                  80

Gly Glu Val Ile Ala Val Asn Arg Gly Ala Lys Arg Lys Val Leu Ser
                85                  90                  95

Ile Glu Val Lys Pro Asp Gly Leu Asn Glu Tyr Glu Ser Phe Pro Val
            100                 105                 110

Gly Asp Pro Ser Ala Leu Ser Ala Glu Gln Ile Lys Glu Leu Leu Leu
        115                 120                 125

Ser Ser Gly Met Trp Gly Phe Ile Lys Gln Arg Pro Tyr Asp Ile Val
    130                 135                 140

Ala Thr Pro Asp Ile Ala Pro Arg Asp Ile Tyr Ile Thr Ala Asn Phe
145                 150                 155                 160

Thr Ala Pro Leu Ala Pro Asp Phe Asp Phe Ile Val Arg Gly Glu Glu
                165                 170                 175

Arg Ala Leu Gln Thr Ala Ile Asp Ala Leu Ala Lys Leu Thr Thr Gly
            180                 185                 190

Lys Val Tyr Val Gly Leu Lys Pro Gly Ser Ser Leu Gly Leu His Asn
        195                 200                 205
```

```
Ala Glu Ile Val Glu Val His Gly Pro His Pro Ala Gly Asn Val Gly
    210                 215                 220

Val Leu Ile Asn His Thr Lys Pro Ile Asn Arg Gly Glu Thr Val Trp
225                 230                 235                 240

Thr Leu Lys Ala Thr Asp Leu Ile Val Ile Gly Arg Phe Leu Leu Thr
                245                 250                 255

Gly Lys Ala Asp Phe Thr Arg Met Ile Ala Met Thr Gly Ser Asp Ala
                260                 265                 270

Ala Ala His Gly Tyr Val Arg Ile Met Pro Gly Cys Asn Val Phe Ala
                275                 280                 285

Ser Phe Pro Gly Arg Leu Thr Ile Lys Glu Ser His Glu Arg Val Ile
    290                 295                 300

Asp Gly Asn Val Leu Thr Gly Lys Lys Leu Cys Glu Lys Glu Pro Phe
305                 310                 315                 320

Leu Ser Ala Arg Cys Asp Gln Ile Thr Val Ile Pro Glu Gly Asp Asp
                325                 330                 335

Val Asp Glu Leu Phe Gly Trp Ala Ala Pro Arg Leu Asp Gln Tyr Ser
                340                 345                 350

Met Ser Arg Ala Tyr Phe Ser Trp Leu Gln Gly Lys Asn Lys Glu Tyr
                355                 360                 365

Val Leu Asp Ala Arg Ile Lys Gly Gly Glu Arg Ala Met Ile Met Ser
370                 375                 380

Asn Glu Tyr Asp Arg Val Phe Pro Met Asp Ile Tyr Pro Glu Tyr Leu
385                 390                 395                 400

Leu Lys Ala Ile Ile Ala Phe Asp Ile Asp Lys Met Glu Asp Leu Gly
                405                 410                 415

Ile Tyr Glu Val Ala Pro Glu Asp Phe Ala Thr Cys Glu Phe Val Asp
                420                 425                 430

Thr Ser Lys Ile Glu Leu Gln Arg Ile Val Arg Glu Gly Leu Asp Met
                435                 440                 445

Leu Tyr Lys Glu Met Asn
    450

<210> SEQ ID NO 76
<211> LENGTH: 201
<212> TYPE: PRT
<213> ORGANISM: Porphyromonas gingivalis

<400> SEQUENCE: 76

Glu Leu Ser Lys Cys Tyr Met Asp Lys Val Ser Tyr Ala Leu Gly Leu
1               5                   10                  15

Ser Ile Gly Asn Asn Phe Lys Ser Ser Gly Ile Asp Ser Val Val Met
                20                  25                  30

Asp Asp Phe Met Gln Gly Leu Ser Asp Val Leu Glu Glu Lys Ala Pro
                35                  40                  45

Gln Leu Ser Tyr Asp Glu Ala Lys Arg Glu Ile Glu Ala Tyr Phe Met
    50                  55                  60

Asp Leu Gln Gln Lys Ala Val Lys Leu Asn Lys Glu Ala Gly Glu Glu
65                  70                  75                  80

Phe Leu Lys Ile Asn Ala His Lys Glu Gly Val Thr Thr Leu Pro Ser
                85                  90                  95

Gly Leu Gln Tyr Glu Val Ile Lys Met Gly Glu Gly Pro Lys Pro Thr
                100                 105                 110

Leu Ser Asp Thr Val Thr Cys His Tyr His Gly Thr Leu Ile Asn Gly
                115                 120                 125
```

```
Ile Val Phe Asp Ser Ser Met Asp Arg Gly Glu Pro Ala Ser Phe Pro
    130                 135                 140

Leu Arg Gly Val Ile Ala Gly Trp Thr Glu Ile Leu Gln Leu Met Pro
145                 150                 155                 160

Val Gly Ser Lys Trp Lys Val Thr Ile Pro Ser Asp Leu Ala Tyr Gly
                165                 170                 175

Asp Arg Gly Ala Gly Glu His Ile Lys Pro Gly Ser Thr Leu Ile Phe
            180                 185                 190

Ile Ile Glu Leu Leu Ser Ile Asn Lys
        195                 200
```

<210> SEQ ID NO 77
<211> LENGTH: 279
<212> TYPE: PRT
<213> ORGANISM: Porphyromonas gingivalis

<400> SEQUENCE: 77

```
Gln Lys Asn Lys Arg Lys Met Lys Lys Ala Leu Leu Ile Gly Ala Ala
1               5                   10                  15

Leu Leu Gly Ala Val Ser Phe Ala Ser Ala Gln Ser Leu Ser Thr Ile
                20                  25                  30

Lys Val Gln Asn Asn Ser Val Gln Gln Pro Arg Glu Glu Ala Thr Ile
            35                  40                  45

Gln Val Cys Gly Glu Leu Ala Glu Gln Val Asp Cys Ile Gly Thr Gly
        50                  55                  60

Asn Ser Ala Ile Ile Ala Ala Ala Lys Phe Glu Ser Asp Asp Leu
65                  70                  75                  80

Glu Ser Tyr Val Gly Trp Glu Ile Met Ser Val Asp Phe Phe Pro Gly
                85                  90                  95

Tyr Lys Ala Cys Lys Tyr Thr Ser Ala Val Trp Ala Asp Asp Met Thr
            100                 105                 110

Ile Leu Gly Gln Ser Glu Asp Ser Asp Pro Glu Met Gln Thr Ile Asn
        115                 120                 125

Asn Leu Ala Leu Lys Thr Ser Val Lys Ile Glu Ala Gly Lys Asn Tyr
130                 135                 140

Ile Val Gly Tyr Ile Ala Asn Thr Ala Gly Gly His Pro Ile Gly Cys
145                 150                 155                 160

Asp Gln Gly Pro Ala Val Asp Gly Tyr Gly Asp Leu Val Ser Ile Ser
                165                 170                 175

Glu Asp Gly Gly Ala Thr Phe Pro Pro Phe Glu Ser Leu His Gln Ala
            180                 185                 190

Val Pro Thr Leu Asn Tyr Asn Ile Tyr Val Val His Leu Lys Lys
        195                 200                 205

Gly Glu Gly Val Glu Ala Val Leu Thr Asn Asp Lys Ala Asn Ala Tyr
210                 215                 220

Val Gln Asn Gly Val Ile Tyr Val Ala Gly Ala Asn Gly Arg Gln Val
225                 230                 235                 240

Ser Leu Phe Asp Met Asn Gly Lys Val Val Tyr Thr Gly Val Ser Glu
                245                 250                 255

Thr Ile Ala Ala Pro Gln Lys Gly Met Tyr Ile Leu Arg Val Gly Ala
            260                 265                 270

Lys Ser Ile Lys Leu Ala Ile
        275
```

<210> SEQ ID NO 78
<211> LENGTH: 562

<212> TYPE: PRT
<213> ORGANISM: Porphyromonas gingivalis

<400> SEQUENCE: 78

```
Thr Arg Asn Val Ser Leu Ile Lys Met Pro Arg Ile Met Lys Leu Lys
1               5                   10                  15

Ile Ala Leu Arg Leu Leu Leu Ala Thr Phe Ala Ile Val Leu Phe Ser
            20                  25                  30

Pro Leu Ala Lys Ala Gln Met Asp Ile Gly Gly Asp Val Leu Ile
        35                  40                  45

Glu Thr Met Ser Thr Leu Ser Gly Tyr Ser Glu Asp Phe Tyr Tyr Lys
50                  55                  60

Met Ala Val Ala Asp Asn Gly Trp Ile Tyr Val Met Leu Asp Phe Ser
65                  70                  75                  80

Arg Ile Tyr Phe Asp Asp Val Arg Leu Tyr Arg Ser Lys Asp Gly Gly
                85                  90                  95

Ala Thr Tyr Gln Lys Leu Gly Ser Leu Gly Ser Leu Val Pro Tyr Asp
            100                 105                 110

Phe Asp Val Ser His Cys Asp Phe Ile Val Thr Gly Lys Asp Glu Asp
        115                 120                 125

Asp Ile Asn Val Trp Thr Val Met Thr Ala Phe Glu Tyr Val Gly Gly
130                 135                 140

Thr Ile Gly Asn Gly Val Leu Leu Met His Arg His Asp Ala Asp Ile
145                 150                 155                 160

Asn Asn Thr Glu Cys Val Tyr Lys Lys Asp Phe Pro Asn Asn Arg Leu
                165                 170                 175

Met Gly Val Ala Ile Ala Ser Asn Tyr Arg Ala Pro Ser Pro Tyr Gly
            180                 185                 190

Leu Gly Gly Asp Pro Phe Ala Leu Ala Val Ala Val Ser Gly Ser Gly
        195                 200                 205

Ser Asp His Ser Phe Leu Asp Tyr Ile Phe Ser Leu Asp Gly Gly Val
210                 215                 220

His Phe Glu Gln Lys Arg Ile Tyr Thr Arg Pro Gln Lys Leu Thr Ile
225                 230                 235                 240

Asn Arg Val Asp Leu Ser Leu Gly Ser Thr Ser Pro Ser Leu Gly Phe
                245                 250                 255

Asn Thr Trp Pro Leu Met Gly Val Val Phe Glu Met Asn Lys Asn Leu
            260                 265                 270

Asp Gly Phe Asp Ile Gly Phe Ile Ser Asn Phe Val Asp Tyr Asp Pro
        275                 280                 285

Arg Tyr Ala Trp Ser Glu Pro Ile Ile Glu Glu Asp Cys Gly Trp
290                 295                 300

Thr Asp Phe Asn Pro Leu Gly Ala Leu Ser Ile Glu Ile Gln Met Met
305                 310                 315                 320

Leu Asp Asp Asn Ser Asp Asn Thr Val Gly Gly Glu Arg Ser His Asn
                325                 330                 335

Phe Leu Ile Thr Tyr Pro Gly His Tyr Val Tyr Pro Lys Gln Ser Phe
            340                 345                 350

Asn Tyr Ser Pro Gly His Thr Pro Thr Lys Lys Asp Leu Val Phe Lys
        355                 360                 365

His Cys Ile Gly Ile Pro Ala Leu Ala Tyr Asp Lys Glu Gly Asp Arg
370                 375                 380

Tyr Leu Thr Thr Phe Gln Asp His Asn Leu Met Arg Tyr Arg Trp Ile
385                 390                 395                 400
```

-continued

```
Lys Tyr Asp Asp Ile Asn Ser Phe Tyr Gly Trp Ser Trp Pro Tyr Val
            405                 410                 415

Tyr Ala Lys Glu Ala Lys Asp Lys Lys Arg Arg Pro Gln Val Ala
        420                 425                 430

Leu Asn Pro Thr Asn Gly Lys Ala Cys Trp Val Trp His Thr Arg Lys
        435                 440                 445

Ser Pro Tyr Asp Glu Thr Lys Pro His Pro Thr Pro Val Ile Ile Lys
    450                 455                 460

His Phe Leu Trp Ser Asp Thr Glu Trp Val His Ala Leu Asp Val Gly
465                 470                 475                 480

Asp Val Leu Gln Lys Glu Gly Ser Met Lys Leu Tyr Pro Asn Pro Ala
                485                 490                 495

Lys Glu Tyr Val Leu Ile Asn Leu Pro Lys Glu Gly Gly His Glu Ala
            500                 505                 510

Val Val Tyr Asp Met Gln Gly Arg Ile Val Glu Lys Val Ser Phe Ser
        515                 520                 525

Gly Lys Glu Tyr Lys Leu Asn Val Gln Tyr Leu Ser Lys Gly Thr Tyr
    530                 535                 540

Met Leu Lys Val Val Ala Asp Thr Glu Tyr Phe Val Glu Lys Ile Ile
545                 550                 555                 560

Val Glu

<210> SEQ ID NO 79
<211> LENGTH: 391
<212> TYPE: PRT
<213> ORGANISM: Porphyromonas gingivalis

<400> SEQUENCE: 79

Gln Met Lys Arg Leu Leu Pro Phe Leu Leu Ala Gly Leu Val Ala
1               5                   10                  15

Val Gly Asn Val Ser Ala Gln Ser Pro Arg Ile Pro Gln Val Asp Val
            20                  25                  30

His Thr Arg Ile Ala Arg Asn Ala Arg Tyr Arg Leu Asp Lys Ile Ser
        35                  40                  45

Val Pro Asp Ser Arg Gln Ile Phe Asp Tyr Phe Tyr Lys Glu Glu Thr
    50                  55                  60

Ile Pro Thr Lys Ile Gln Thr Thr Thr Gly Gly Ala Ile Thr Ser Ile
65                  70                  75                  80

Asp Ser Leu Phe Tyr Glu Asp Asp Arg Leu Val Gln Val Arg Tyr Phe
                85                  90                  95

Asp Asn Asn Leu Glu Leu Lys Gln Ala Glu Lys Tyr Val Tyr Asp Gly
            100                 105                 110

Ser Lys Leu Val Leu Arg Glu Ile Arg Lys Ser Pro Thr Asp Glu Thr
        115                 120                 125

Pro Ile Lys Lys Val Ser Tyr His Tyr Leu Cys Gly Ser Asp Met Pro
    130                 135                 140

Phe Glu Ile Thr Thr Glu Met Ser Asp Gly Tyr Phe Glu Ser His Thr
145                 150                 155                 160

Leu Asn Tyr Leu Asn Gly Lys Ile Ala Arg Ile Asp Ile Met Thr Gln
                165                 170                 175

Gln Asn Pro Ser Ala Glu Leu Ile Glu Thr Gly Arg Met Val Tyr Glu
            180                 185                 190

Phe Asp Ala Asn Asn Asp Ala Val Leu Leu Arg Asp Ser Val Phe Leu
        195                 200                 205

Pro Leu Gln Asn Lys Trp Val Glu Met Phe Thr His Arg Tyr Thr Tyr
```

```
                210                 215                 220
Asp Asn Lys His Asn Cys Ile Arg Trp Glu Gln Asp Glu Phe Gly Thr
225                 230                 235                 240

Leu Thr Leu Ala Asn Asn Phe Glu Tyr Asp Thr Thr Ile Pro Leu Ser
                245                 250                 255

Ser Val Leu Phe Pro Thr His Glu Glu Phe Arg Pro Leu Leu Pro
                260                 265                 270

Asn Phe Met Lys His Met Arg Thr Lys Gln Thr Tyr Phe Asn Asn Ser
                275                 280                 285

Gly Glu Gly Leu Ser Glu Val Cys Asp Tyr Asn Tyr Phe Tyr Thr Asp
                290                 295                 300

Met Gln Gly Asn Ala Leu Thr Asp Val Ala Val Asn Glu Ser Ile Lys
305                 310                 315                 320

Ile Tyr Pro Arg Pro Ala Thr Asp Phe Leu Arg Ile Glu Gly Ser Gln
                325                 330                 335

Leu Leu Arg Leu Ser Leu Phe Asp Met Asn Gly Lys Leu Ile Arg Ala
                340                 345                 350

Thr Glu Leu Thr Gly Asp Leu Ala Ile Ile Gly Val Ala Ser Leu Pro
                355                 360                 365

Arg Gly Thr Tyr Ile Ala Glu Ile Thr Ala Ala Asn Ser Lys Thr Ile
                370                 375                 380

Arg Ala Lys Val Ser Leu Arg
385                 390

<210> SEQ ID NO 80
<211> LENGTH: 324
<212> TYPE: PRT
<213> ORGANISM: Porphyromonas gingivalis

<400> SEQUENCE: 80

Leu Thr Leu Phe Cys Cys Asn Tyr Phe Lys Gln Met Arg Ala Asn Ile
1               5                   10                  15

Trp Gln Ile Leu Ser Val Ser Val Leu Phe Phe Gly Thr Ala Ile
                20                  25                  30

Gly Gln Ala Gln Ser Arg Asn Arg Thr Tyr Glu Ala Tyr Val Lys Gln
                35                  40                  45

Tyr Ala Asp Glu Ala Ile Arg Gln Met Ser Arg Tyr Asn Ile Pro Ala
50                  55                  60

Ser Ile Thr Ile Ala Gln Ala Leu Val Glu Thr Gly Ala Gly Ala Ser
65                  70                  75                  80

Thr Leu Ala Ser Val His Asn Asn His Phe Gly Ile Lys Cys His Lys
                85                  90                  95

Ser Trp Thr Gly Lys Arg Thr Tyr Arg Thr Asp Asp Ala Pro Asn Glu
                100                 105                 110

Cys Phe Arg Ser Tyr Ser Ala Ala Arg Glu Ser Tyr Glu Asp His Ser
                115                 120                 125

Arg Phe Leu Leu Gln Pro Arg Tyr Arg Pro Leu Phe Lys Leu Asp Arg
                130                 135                 140

Glu Asp Tyr Arg Gly Trp Ala Thr Gly Leu Gln Arg Cys Gly Tyr Ala
145                 150                 155                 160

Thr Asn Arg Gly Tyr Ala Asn Leu Leu Ile Lys Met Val Glu Leu Tyr
                165                 170                 175

Glu Leu Tyr Ala Leu Asp Arg Glu Lys Tyr Pro Ser Trp Phe His Lys
                180                 185                 190

Ser Tyr Pro Gly Ser Asn Lys Lys Ser His Gln Thr Thr Lys Gln Lys
```

```
            195                 200                 205
Gln Ser Gly Leu Lys His Glu Ala Tyr Phe Ser Tyr Gly Leu Leu Tyr
        210                 215                 220

Ile Ile Ala Lys Gln Gly Asp Thr Phe Asp Ser Leu Ala Glu Glu Phe
225                 230                 235                 240

Asp Met Arg Ala Ser Lys Leu Ala Lys Tyr Asn Asp Ala Pro Val Asp
                245                 250                 255

Phe Pro Ile Glu Lys Gly Asp Val Ile Tyr Leu Glu Lys Lys His Ala
            260                 265                 270

Cys Ser Ile Ser Lys His Thr Gln His Val Val Arg Val Gly Asp Ser
        275                 280                 285

Met His Ser Ile Ser Gln Arg Tyr Gly Ile Arg Met Lys Asn Leu Tyr
    290                 295                 300

Lys Leu Asn Asp Lys Asp Gly Glu Tyr Ile Pro Gln Glu Gly Asp Ile
305                 310                 315                 320

Leu Arg Leu Arg

<210> SEQ ID NO 81
<211> LENGTH: 373
<212> TYPE: PRT
<213> ORGANISM: Porphyromonas gingivalis

<400> SEQUENCE: 81

Gly Ser Cys Gly Ser Ser Pro Ala Ile Gly Arg Ser Gly Cys Ser Arg
1               5                   10                  15

Cys Asp Arg Arg Ile Gly His Gly Leu Ser Thr Ser Ala Phe Arg Thr
            20                  25                  30

Tyr Ala Gly Leu Val Cys His Ser Arg Leu Arg Asp Gln Ser Ser Cys
        35                  40                  45

Arg Val Cys Gly Met Arg Pro Ile Gly Gln Leu Phe Phe Pro Ser Cys
    50                  55                  60

Pro Arg Arg Ser Ala Ser Asp Ala Gly Arg Thr Glu Arg Ile Gln Ser
65                  70                  75                  80

Pro Leu Gln Asn Leu Leu Gln Glu Met Gln Phe Ser Pro Thr Asn Arg
                85                  90                  95

Arg Asn Pro Phe Asp Asn Met Asn Ser Arg His Leu Thr Ile Thr Ile
            100                 105                 110

Ile Ala Gly Leu Ser Leu Phe Val Leu Thr Leu Gly Gly Cys Ser Val
        115                 120                 125

Ala Gln Gln Asp Thr Gln Trp Thr Leu Gly Gly Lys Leu Phe Thr Ser
    130                 135                 140

Ala Trp Ile Gln Arg Ser Ala Glu Tyr Gln Ala Leu Cys Ile Gln Ala
145                 150                 155                 160

Tyr Asn Ile Ala Thr Glu Arg Val Asp Ala Leu Pro Ala Glu Arg Lys
                165                 170                 175

Gln Gly Asp Arg Pro Tyr Ala Ile Val Thr Asp Ile Asp Glu Thr Ile
            180                 185                 190

Leu Asp Asn Thr Pro Asn Ser Val Tyr Gln Ala Leu Arg Gly Lys Asp
        195                 200                 205

Tyr Asp Glu Glu Thr Trp Gly Lys Trp Cys Ala Gln Ala Asp Ala Asp
    210                 215                 220

Thr Leu Ala Gly Ala Leu Ser Phe Phe Leu His Ala Ala Asn Lys Gly
225                 230                 235                 240

Ile Glu Val Phe Tyr Val Thr Asn Arg Arg Asp Asn Leu Arg Glu Ala
                245                 250                 255
```

```
Thr Leu Gln Asn Leu Gln Arg Tyr Gly Phe Pro Phe Ala Asp Glu Glu
            260                 265                 270

His Leu Leu Thr Thr His Gly Pro Ser Asp Lys Glu Pro Arg Arg Leu
            275                 280                 285

Lys Ile Gln Glu Gln Tyr Glu Ile Val Leu Leu Ile Gly Asp Asn Leu
            290                 295                 300

Gly Asp Phe His His Phe Phe Asn Thr Lys Glu Glu Ser Gly Arg Lys
305                 310                 315                 320

Gln Ala Leu Gly Leu Thr Ala Gly Glu Phe Gly Arg His Phe Ile Met
            325                 330                 335

Leu Pro Asn Pro Asn Tyr Gly Ser Trp Glu Pro Ala Trp Tyr Gly Gly
            340                 345                 350

Lys Tyr Pro Pro Leu Pro Glu Arg Asp Lys Ala Leu Lys Gln Leu His
            355                 360                 365

Ser Gln Asn Ser Arg
            370

<210> SEQ ID NO 82
<211> LENGTH: 763
<212> TYPE: PRT
<213> ORGANISM: Porphyromonas gingivalis

<400> SEQUENCE: 82

His Phe Leu Val Thr Ile Met Arg Thr Lys Thr Ile Phe Phe Ala Ile
1               5                   10                  15

Ile Ser Phe Ile Ala Leu Leu Ser Ser Leu Ser Ala Gln Ser Lys
            20                  25                  30

Ala Val Leu Thr Gly Ser Val Ser Asp Ala Glu Thr Gly Glu Pro Leu
            35                  40                  45

Ala Gly Ala Arg Ile Glu Val Lys His Thr Asn Ile Val Ala Gly Ala
            50                  55                  60

Asp Ala Gly Gly His Phe Glu Ile Lys Asn Leu Pro Ala Gly Gln His
65                  70                  75                  80

Thr Ile Ile Cys Ser Leu Gly Tyr Gly Gln Lys Glu Glu Val Val
            85                  90                  95

Ala Ile Glu Ala Gly Gln Thr Lys Thr Ile Ser Phe Ala Leu Arg Leu
            100                 105                 110

Arg Thr Asn Asn Leu Glu Glu Val Val Val Thr Gly Thr Gly Thr Arg
            115                 120                 125

Tyr Arg Leu Val Asp Ala Pro Val Ala Thr Glu Val Leu Thr Ala Lys
            130                 135                 140

Asp Ile Ala Ser Phe Ser Ala Pro Thr Ser Glu Ala Leu Leu Gln Gly
145                 150                 155                 160

Leu Ser Pro Ser Phe Asp Phe Gly Pro Asn Leu Met Gly Ser Phe Met
            165                 170                 175

Gln Leu Asn Gly Leu Ser Ser Lys Tyr Ile Leu Ile Leu Ile Asp Gly
            180                 185                 190

Lys Arg Val Tyr Gly Asp Val Gly Gly Gln Ala Asp Leu Ser Arg Ile
            195                 200                 205

Ser Pro Asp Gln Ile Glu Arg Ile Glu Leu Val Lys Gly Ala Ser Ser
            210                 215                 220

Ser Leu Tyr Gly Ser Asp Ala Ile Ala Gly Val Ile Asn Val Ile Thr
225                 230                 235                 240

Lys Lys Asn Thr Asn Arg Leu Ser Ala Tyr Thr Ser His Arg Ile Ser
            245                 250                 255
```

```
Lys Tyr Asn Asp Arg Gln Thr Asn Thr Ser Leu Asp Ile Asn Ile Gly
            260                 265                 270

Lys Phe Ser Ser Asn Thr Asn Tyr Phe Phe Tyr His Thr Asp Gly Trp
        275                 280                 285

Gln Asn Ser Pro Phe Glu Ile Lys Lys Lys Gly Ser Gly Glu Pro
    290                 295                 300

Val Leu Glu Glu Thr Tyr Lys Lys Thr Phe Arg Ala Gln Glu Asn Gln
305                 310                 315                 320

Gly Val Ser Gln Ser Leu Ser Tyr Tyr Ala Thr Asn Asn Leu Ser Phe
                325                 330                 335

Ser Gly Asn Val Gln Tyr Asn Lys Arg Gln Ile Phe Thr Pro Thr Phe
                340                 345                 350

Ser Glu Lys Lys Ala Tyr Asp Met Asp Tyr Arg Ala Leu Thr Ala Ser
            355                 360                 365

Leu Gly Thr Asn Tyr Leu Phe Pro Asn Gly Leu His Thr Leu Ser Phe
        370                 375                 380

Asp Ala Val Tyr Asp Arg Phe Arg Phe Gly Tyr Leu Tyr His Asp Lys
385                 390                 395                 400

Asp Ser Ser Glu Ser Leu Ile Asn Asn Gln Gly Gln Thr Glu Gln Pro
                405                 410                 415

Thr Phe Phe Pro Gly Gln Leu Arg Asn Lys Asn Asp Gln Ile Arg Tyr
            420                 425                 430

Thr Ala Glu Ala Arg Gly Val Phe Thr Leu Pro Tyr Ala Gln Lys Leu
        435                 440                 445

Thr Gly Gly Leu Glu Tyr Phe Arg Glu Glu Leu Ile Ser Pro Tyr Asn
    450                 455                 460

Leu Ile Thr Asp Lys Ala Asp Ala Ser Thr Leu Ser Ala Tyr Val Gln
465                 470                 475                 480

Asp Glu Trp Lys Pro Leu Asp Trp Phe Asn Met Thr Ala Gly Phe Arg
                485                 490                 495

Leu Val His His Gln Glu Phe Gly Thr Arg Met Thr Pro Lys Val Ser
            500                 505                 510

Ile Leu Ala Lys Tyr Gly Pro Leu Asn Phe Arg Ala Thr Tyr Ala Asn
        515                 520                 525

Gly Tyr Lys Thr Pro Thr Leu Lys Glu Leu Phe Ala Arg Asn Glu Leu
    530                 535                 540

Thr Thr Met Gly Ser His Asn Leu Tyr Leu Gly Asn Ala Asp Leu Lys
545                 550                 555                 560

Pro Gln Met Ser Asp Tyr Tyr Ala Leu Gly Leu Glu Tyr Asn Gln Gly
                565                 570                 575

Pro Ile Ser Phe Ser Ala Thr Val Tyr Asp Asn Glu Leu Arg Asn Leu
            580                 585                 590

Ile Ser Phe Met Asp Ile Pro Thr Ser Pro Glu His Glu Ala Gln Gly
        595                 600                 605

Ile Lys Lys Thr Lys Gln Tyr Ala Asn Ile Gly Lys Ala Arg Ser Arg
    610                 615                 620

Gly Leu Asp Val Leu Cys Asp Ala Ser Ile Gly Trp Gly Ile Lys Leu
625                 630                 635                 640

Gly Ala Gly Tyr Ser Leu Val Glu Ala Lys Asn Leu Gln Thr Asp Glu
                645                 650                 655

Trp Leu Glu Gly Ala Ala Arg His Arg Ala Asn Val His Ala Asp Trp
            660                 665                 670

Val His Tyr Trp Gly Gln Tyr Arg Leu Gly Val Ser Leu Phe Gly Arg
```

```
                675                 680                 685
Ile Gln Ser Glu Arg Tyr Tyr Lys Asp Gly Asn Ala Pro Asp Tyr Thr
            690                 695                 700
Leu Trp Arg Leu Ala Thr Ser His Arg Phe Ala His Phe Arg His Ile
705                 710                 715                 720
Ile Leu Asp Gly Thr Leu Gly Ile Asp Asn Leu Phe Asp Tyr Val Asp
                725                 730                 735
Asp Arg Pro Met Gly Val Asn Tyr Ala Thr Val Thr Pro Gly Arg Thr
            740                 745                 750
Phe Phe Ala Gln Ile Ala Ile Arg Phe Asn Asn
            755                 760

<210> SEQ ID NO 83
<211> LENGTH: 365
<212> TYPE: PRT
<213> ORGANISM: Porphyromonas gingivalis

<400> SEQUENCE: 83

Cys Cys Ala Arg Leu Arg Asp Thr Ser Pro Arg Lys Lys Ser Phe Arg
1               5                   10                  15
Asn Asp Thr Val Phe Pro Tyr Phe Val Ile His Leu Ile Lys His Ile
            20                  25                  30
Ile Ile Met Thr Asp Asn Lys Gln Arg Asn Ile Val Phe Pro Ala Phe
        35                  40                  45
Leu Leu Leu Leu Gly Val Ile Ala Val Thr Ile Val Gly Phe Phe
50                  55                  60
Met Leu Arg Pro Ala Glu Glu Ile Ile Gln Gly Gln Ile Glu Val Thr
65                  70                  75                  80
Glu Tyr Arg Val Ser Ser Lys Val Pro Gly Arg Ile Lys Glu Leu Arg
                85                  90                  95
Val Ser Glu Gly Gln Gln Val Gln Ala Gly Asp Thr Leu Ala Val Ile
            100                 105                 110
Glu Ala Pro Asp Val Ala Ala Lys Met Glu Gln Ala Lys Ala Ala Glu
        115                 120                 125
Ala Ala Ala Gln Ala Gln Asn Ala Lys Ala Leu Lys Gly Ala Arg Ser
130                 135                 140
Glu Gln Ile Gln Ala Ala Tyr Glu Met Trp Gln Lys Ala Gln Ala Gly
145                 150                 155                 160
Val Ala Ile Ala Thr Lys Thr His Gln Arg Val Gln Asn Leu Tyr Asp
                165                 170                 175
Gln Gly Val Val Pro Ala Gln Lys Leu Asp Glu Ala Thr Ala Gln Arg
            180                 185                 190
Asp Ala Ala Ile Ala Thr Gln Lys Ala Ala Glu Ala Gln Tyr Asn Met
        195                 200                 205
Ala Arg Asn Gly Ala Glu Arg Glu Asp Lys Leu Ala Ala Ser Ala Leu
210                 215                 220
Val Asp Arg Ala Arg Gly Ala Val Ala Glu Val Glu Ser Tyr Ile Asn
225                 230                 235                 240
Glu Thr Tyr Leu Ile Ala Pro Arg Ala Gly Glu Val Ser Glu Ile Phe
                245                 250                 255
Pro Lys Ala Gly Glu Leu Val Gly Thr Gly Ala Pro Ile Met Asn Ile
            260                 265                 270
Ala Glu Met Gly Asp Met Trp Ala Ser Phe Ala Val Arg Glu Asp Phe
        275                 280                 285
Leu Ser Ser Met Thr Met Gly Ala Val Leu Glu Thr Val Val Pro Ala
```

```
            290                 295                 300
Leu Asn Glu Glu Lys Val Arg Phe Lys Ile Thr Phe Ile Lys Asn Met
305                 310                 315                 320

Gly Thr Tyr Ala Ala Trp Lys Ala Thr Lys Thr Thr Gly Gln Tyr Asp
                325                 330                 335

Leu Lys Thr Phe Glu Val Lys Ala Thr Leu Ala Asp Lys Asp Lys Ala
                340                 345                 350

Gln Lys Leu Arg Pro Gly Met Ser Val Ile Ile Arg Lys
                355                 360                 365

<210> SEQ ID NO 84
<211> LENGTH: 1046
<212> TYPE: PRT
<213> ORGANISM: Porphyromonas gingivalis

<400> SEQUENCE: 84

Asp Phe Pro Trp Val Arg Val Lys Pro Glu Lys Arg Lys Gln His
1               5                   10                  15

Asn Ser Asn Asn Phe Lys Phe Asn Ala Lys Glu Lys Ser Met Lys Arg
                20                  25                  30

Met Thr Leu Phe Phe Leu Cys Leu Leu Thr Ser Ile Gly Trp Ala Met
            35                  40                  45

Ala Gln Asn Arg Thr Val Lys Gly Thr Val Ile Ser Ser Glu Asp Asn
50                  55                  60

Glu Pro Leu Ile Gly Ala Asn Val Val Val Gly Asn Thr Thr Ile
65                  70                  75                  80

Gly Ala Ala Thr Asp Leu Asp Gly Asn Phe Thr Leu Ser Val Pro Ala
                85                  90                  95

Asn Ala Lys Met Leu Arg Val Ser Tyr Ser Gly Met Thr Thr Lys Glu
            100                 105                 110

Val Ala Ile Ala Asn Val Met Lys Ile Val Leu Asp Pro Asp Ser Lys
        115                 120                 125

Val Leu Glu Gln Val Val Leu Gly Tyr Gly Thr Gly Gln Lys Leu
    130                 135                 140

Ser Thr Val Ser Gly Ser Val Ala Lys Val Ser Ser Glu Lys Leu Ala
145                 150                 155                 160

Glu Lys Pro Val Ala Asn Ile Met Asp Ala Leu Gln Gly Gln Val Ala
                165                 170                 175

Gly Met Gln Val Met Thr Thr Ser Gly Asp Pro Thr Ala Val Ala Ser
            180                 185                 190

Val Glu Ile His Gly Thr Gly Ser Leu Gly Ala Ser Ser Ala Pro Leu
        195                 200                 205

Tyr Ile Val Asp Gly Met Gln Thr Ser Leu Asp Val Val Ala Thr Met
    210                 215                 220

Asn Pro Asn Asp Phe Glu Ser Met Ser Val Leu Lys Asp Ala Ser Ala
225                 230                 235                 240

Thr Ser Ile Tyr Gly Ala Arg Ala Ala Asn Gly Val Val Phe Ile Gln
                245                 250                 255

Thr Lys Lys Gly Lys Met Ser Glu Arg Gly Arg Ile Thr Phe Asn Ala
            260                 265                 270

Ser Tyr Gly Ile Ser Gln Ile Leu Asn Thr Lys Pro Leu Asp Asn Met
        275                 280                 285

Met Thr Gly Asp Glu Leu Leu Asp Phe Gln Val Lys Ala Gly Phe Trp
    290                 295                 300

Gly Asn Asn Gln Thr Val Gln Lys Val Lys Asp Met Ile Leu Ala Gly
```

```
            305                 310                 315                 320
Ala Glu Asp Leu Tyr Gly Asn Tyr Asp Ser Leu Lys Asp Glu Tyr Gly
                325                 330                 335

Lys Thr Leu Phe Pro Val Asp Phe Asn His Asp Ala Asp Trp Leu Lys
                340                 345                 350

Ala Leu Phe Lys Thr Ala Pro Thr Ser Gln Gly Asp Ile Ser Phe Ser
                355                 360                 365

Gly Gly Ser Gln Gly Thr Ser Tyr Tyr Ala Ser Ile Gly Tyr Phe Asp
                370                 375                 380

Gln Glu Gly Met Ala Arg Glu Pro Ala Asn Phe Lys Arg Tyr Ser Gly
385                 390                 395                 400

Arg Leu Asn Phe Glu Ser Arg Ile Asn Glu Trp Leu Lys Val Gly Ala
                405                 410                 415

Asn Leu Ser Gly Ala Ile Ala Asn Arg Arg Ser Ala Asp Tyr Phe Gly
                420                 425                 430

Lys Tyr Tyr Met Gly Ser Gly Thr Phe Gly Val Leu Thr Met Pro Arg
                435                 440                 445

Tyr Tyr Asn Pro Phe Asp Val Asn Gly Asp Leu Ala Asp Val Tyr Tyr
                450                 455                 460

Met Tyr Gly Ala Thr Arg Pro Ser Met Thr Glu Pro Tyr Phe Ala Lys
465                 470                 475                 480

Met Arg Pro Phe Ser Ser Glu Ser His Gln Ala Asn Val Asn Gly Phe
                485                 490                 495

Ala Gln Ile Thr Pro Ile Lys Gly Leu Thr Leu Lys Ala Gln Ala Gly
                500                 505                 510

Val Asp Ile Thr Asn Thr Arg Thr Ser Ser Lys Arg Met Pro Asn Asn
                515                 520                 525

Pro Tyr Asp Ser Thr Pro Leu Gly Glu Arg Arg Glu Arg Ala Tyr Arg
                530                 535                 540

Asp Val Ser Lys Ser Phe Thr Asn Thr Ala Glu Tyr Lys Phe Ser Ile
545                 550                 555                 560

Asp Glu Lys His Asp Leu Thr Ala Leu Met Gly His Glu Tyr Ile Glu
                565                 570                 575

Tyr Glu Gly Asp Val Ile Gly Ala Ser Ser Lys Gly Phe Glu Ser Asp
                580                 585                 590

Lys Leu Met Leu Leu Ser Gln Gly Lys Thr Gly Asn Ser Leu Ser Leu
                595                 600                 605

Pro Glu His Arg Val Ala Glu Tyr Ala Tyr Leu Ser Phe Phe Ser Arg
                610                 615                 620

Phe Asn Tyr Gly Phe Asp Lys Trp Met Tyr Ile Asp Phe Ser Val Arg
625                 630                 635                 640

Asn Asp Gln Ser Ser Arg Phe Gly Ser Asn Asn Arg Ser Ala Trp Phe
                645                 650                 655

Tyr Ser Val Gly Gly Met Phe Asp Ile Tyr Asn Lys Phe Ile Gln Glu
                660                 665                 670

Ser Asn Trp Leu Ser Asp Leu Arg Leu Lys Met Ser Tyr Gly Thr Thr
                675                 680                 685

Gly Asn Ser Glu Ile Gly Asn Tyr Asn His Gln Ala Leu Val Thr Val
                690                 695                 700

Asn Asn Tyr Thr Glu Asp Ala Met Gly Leu Ser Ile Ser Thr Ala Gly
705                 710                 715                 720

Asn Pro Asp Leu Ser Trp Glu Lys Gln Ser Gln Phe Asn Phe Gly Leu
                725                 730                 735
```

-continued

Ala Ala Gly Ala Phe Asn Asn Arg Leu Ser Ala Glu Val Asp Phe Tyr
        740                 745                 750

Val Arg Thr Thr Asn Asp Met Leu Ile Asp Val Pro Met Pro Tyr Ile
        755                 760                 765

Ser Gly Phe Phe Ser Gln Tyr Gln Asn Val Gly Ser Met Lys Asn Thr
    770                 775                 780

Gly Val Asp Leu Ser Leu Lys Gly Thr Ile Tyr Gln Asn Lys Asp Trp
785                 790                 795                 800

Asn Val Tyr Ala Ser Ala Asn Phe Asn Tyr Asn Arg Gln Glu Ile Thr
                805                 810                 815

Lys Leu Phe Phe Gly Leu Asn Lys Tyr Met Leu Pro Asn Thr Gly Thr
                820                 825                 830

Ile Trp Glu Ile Gly Tyr Pro Asn Ser Phe Tyr Met Ala Glu Tyr Ala
            835                 840                 845

Gly Ile Asp Lys Lys Thr Gly Lys Gln Leu Trp Tyr Val Pro Gly Gln
        850                 855                 860

Val Asp Ala Asp Gly Asn Lys Val Thr Thr Ser Gln Tyr Ser Ala Asp
865                 870                 875                 880

Leu Glu Thr Arg Ile Asp Lys Ser Val Thr Pro Ile Thr Gly Gly
                885                 890                 895

Phe Ser Leu Gly Ala Ser Trp Lys Gly Leu Ser Leu Asp Ala Asp Phe
            900                 905                 910

Ala Tyr Ile Val Gly Lys Trp Met Ile Asn Asn Asp Arg Tyr Phe Thr
        915                 920                 925

Glu Asn Ala Gly Gly Leu Met Gln Leu Asn Lys Asp Lys Met Leu Leu
    930                 935                 940

Asn Ala Trp Thr Glu Asp Asn Lys Glu Thr Asp Val Pro Lys Leu Gly
945                 950                 955                 960

Gln Ser Pro Gln Phe Asp Thr His Leu Leu Glu Asn Ala Ser Phe Leu
                965                 970                 975

Arg Leu Lys Asn Leu Lys Leu Thr Tyr Val Leu Pro Asn Ser Leu Phe
                980                 985                 990

Ala Gly Gln Asn Val Ile Gly Gly Ala Arg Val Tyr Leu Met Ala Arg
            995                 1000                1005

Asn Leu Leu Thr Val Thr Lys Tyr Lys Gly Phe Asp Pro Glu Ala
    1010                1015                1020

Gly Gly Asn Val Gly Lys Asn Gln Tyr Pro Asn Ser Lys Gln Tyr
    1025                1030                1035

Val Ala Gly Ile Gln Leu Ser Phe
    1040                1045

<210> SEQ ID NO 85
<211> LENGTH: 869
<212> TYPE: PRT
<213> ORGANISM: Porphyromonas gingivalis

<400> SEQUENCE: 85

Trp His Arg Asn Ile Phe Ile Phe Ala Ser Thr Phe Ser Pro Lys Asn
1               5                   10                  15

Met Leu Pro Leu Pro Tyr Arg Tyr Ala Lys Thr Glu His Leu Phe Leu
            20                  25                  30

Ala Lys Gly Tyr Cys Lys Asn Pro Ile Thr Asn Ile Ile Leu Phe
        35                  40                  45

Met Lys Lys Lys Asn Phe Leu Leu Leu Gly Ile Phe Val Ala Leu Leu
    50                  55                  60

-continued

```
Thr Phe Ile Gly Ser Met Gln Ala Gln Gln Ala Lys Asp Tyr Phe Asn
 65                  70                  75                  80

Phe Asp Glu Arg Gly Glu Ala Tyr Phe Ser Phe Lys Val Pro Asp Arg
                 85                  90                  95

Ala Val Leu Gln Glu Leu Ala Leu Ile Met Ser Ile Asp Glu Phe Asp
            100                 105                 110

Pro Val Thr Asn Glu Ala Ile Ala Tyr Ala Ser Glu Glu Phe Glu
        115                 120                 125

Ala Phe Leu Arg Tyr Gly Leu Lys Pro Thr Phe Leu Thr Pro Pro Ser
130                 135                 140

Met Gln Arg Ala Val Glu Met Phe Asp Tyr Arg Ser Gly Glu Lys Tyr
145                 150                 155                 160

Glu Trp Asn Ala Tyr Pro Thr Tyr Glu Ala Tyr Ile Ser Met Met Glu
                165                 170                 175

Glu Phe Gln Thr Lys Tyr Pro Ser Leu Cys Thr Thr Ser Val Ile Gly
            180                 185                 190

Lys Ser Val Lys Asp Arg Lys Leu Met Ile Cys Lys Leu Thr Ser Ser
        195                 200                 205

Ala Asn Thr Gly Lys Lys Pro Arg Val Leu Tyr Thr Ser Thr Met His
210                 215                 220

Gly Asp Glu Thr Thr Gly Tyr Val Val Leu Leu Arg Leu Ile Asp His
225                 230                 235                 240

Leu Leu Ser Asn Tyr Glu Ser Asp Pro Arg Ile Lys Asn Ile Leu Asp
                245                 250                 255

Lys Thr Glu Val Trp Ile Cys Pro Leu Thr Asn Pro Asp Gly Ala Tyr
            260                 265                 270

Arg Ala Gly Asn His Thr Val Gln Gly Ala Thr Arg Tyr Asn Ala Asn
        275                 280                 285

Asn Val Asp Leu Asn Arg Asn Phe Lys Asp Val Ala Gly Asp His
290                 295                 300

Pro Asp Gly Lys Pro Trp Gln Pro Glu Ala Thr Ala Phe Met Asp Leu
305                 310                 315                 320

Glu Gly Asn Thr Ser Phe Val Leu Gly Ala Asn Ile His Gly Gly Thr
                325                 330                 335

Glu Val Val Asn Tyr Pro Trp Asp Asn Lys Lys Glu Arg His Ala Asp
            340                 345                 350

Asp Glu Trp Tyr Lys Leu Ile Ser Arg Asn Tyr Ala Ala Ala Cys Gln
        355                 360                 365

Ser Ile Ser Ala Ser Tyr Met Thr Ser Glu Thr Asn Ser Gly Ile Ile
370                 375                 380

Asn Gly Ser Asp Trp Tyr Val Ile Arg Gly Ser Arg Gln Asp Asn Ala
385                 390                 395                 400

Asn Tyr Phe His Arg Leu Arg Glu Ile Thr Leu Glu Ile Ser Asn Thr
                405                 410                 415

Lys Leu Val Pro Ala Ser Gln Leu Pro Lys Tyr Trp Asn Leu Asn Lys
            420                 425                 430

Glu Ser Leu Leu Ala Leu Ile Glu Glu Ser Leu Tyr Gly Ile His Gly
        435                 440                 445

Thr Val Thr Ser Ala Ala Asn Gly Gln Pro Leu Lys Cys Gln Ile Leu
450                 455                 460

Ile Glu Asn His Asp Lys Arg Asn Ser Asp Val Tyr Ser Asp Ala Thr
465                 470                 475                 480

Thr Gly Tyr Tyr Val Arg Pro Ile Lys Ala Gly Thr Tyr Thr Val Lys
                485                 490                 495
```

```
Tyr Lys Ala Glu Gly Tyr Pro Glu Ala Thr Arg Thr Ile Thr Ile Lys
            500                 505                 510

Asp Lys Glu Thr Val Ile Met Asp Ile Ala Leu Gly Asn Ser Val Pro
            515                 520                 525

Leu Pro Val Pro Asp Phe Thr Ala Ser Pro Met Thr Ile Ser Val Gly
        530                 535                 540

Glu Ser Val Gln Phe Gln Asp Gln Thr Thr Asn Asn Pro Thr Asn Trp
545                 550                 555                 560

Glu Trp Thr Phe Glu Gly Gly Gln Pro Ala Met Ser Thr Glu Gln Asn
                565                 570                 575

Pro Leu Val Ser Tyr Ser His Pro Gly Gln Tyr Asp Val Thr Leu Lys
            580                 585                 590

Val Trp Asn Ala Ser Gly Ser Asn Thr Ile Thr Lys Glu Lys Phe Ile
            595                 600                 605

Thr Val Asn Ala Val Met Pro Val Ala Glu Phe Val Gly Thr Pro Thr
        610                 615                 620

Glu Ile Glu Glu Gly Gln Thr Val Ser Phe Gln Asn Gln Ser Thr Asn
625                 630                 635                 640

Ala Thr Asn Tyr Val Trp Ile Phe Asp Gly Gly Thr Pro Ala Thr Ser
                645                 650                 655

Glu Asp Glu Asn Pro Thr Val Leu Tyr Ser Lys Ala Gly Gln Tyr Asp
            660                 665                 670

Val Thr Leu Lys Ala Ile Ser Ala Ser Gly Glu Thr Val Lys Thr Lys
        675                 680                 685

Glu Lys Tyr Ile Thr Val Lys Lys Ala Pro Val Pro Ala Pro Val Ala
690                 695                 700

Asp Phe Glu Gly Thr Pro Arg Lys Val Lys Lys Gly Gly Thr Val Thr
705                 710                 715                 720

Phe Lys Asp Leu Ser Thr Asn Asn Pro Thr Ser Trp Leu Trp Val Phe
                725                 730                 735

Glu Gly Gly Ser Pro Ala Thr Ser Thr Glu Gln Asn Pro Val Val Thr
            740                 745                 750

Tyr Asn Glu Thr Gly Lys Tyr Asp Val Gln Leu Thr Ala Thr Asn Glu
            755                 760                 765

Gly Gly Ser Asn Val Lys Lys Ala Glu Asp Tyr Ile Glu Val Ile Leu
        770                 775                 780

Asp Asp Ser Val Glu Asp Ile Val Ala Gln Thr Gly Ile Val Ile Arg
785                 790                 795                 800

Pro Gln Asn Gly Thr Lys Gln Ile Leu Ile Glu Ala Asn Ala Ala Ile
                805                 810                 815

Lys Ala Ile Val Leu Tyr Asp Ile Asn Gly Arg Val Val Leu Lys Thr
            820                 825                 830

Thr Pro Asn Gln Leu Arg Ser Thr Val Asp Leu Ser Ile Leu Pro Glu
        835                 840                 845

Gly Ile Tyr Thr Ile Asn Ile Lys Thr Glu Lys Ser Ala Arg Thr Glu
    850                 855                 860

Lys Ile His Ile Gly
865

<210> SEQ ID NO 86
<211> LENGTH: 106
<212> TYPE: PRT
<213> ORGANISM: Porphyromonas gingivalis

<400> SEQUENCE: 86
```

```
Leu Ser Tyr Ser Gly Glu Ser Asp Ala Lys Glu Ser Asp Gln Asn Cys
1               5                   10                  15

Arg Lys Cys Thr Phe Ile Gly Phe Glu Lys Arg Val Asn Thr Met Arg
                20                  25                  30

Leu Ile Lys Ala Phe Leu Val Gln Leu Leu Leu Pro Ile Phe Phe
            35                  40                  45

Tyr Lys Arg Phe Ile Ser Pro Leu Thr Pro Pro Ser Cys Arg Phe Thr
    50                  55                  60

Pro Ser Cys Ser Ser Tyr Ala Ile Glu Ala Leu Arg Lys Tyr Gly Pro
65                  70                  75                  80

Gly Lys Gly Leu Leu Leu Ser Ile Lys Arg Ile Leu Arg Cys His Pro
                85                  90                  95

Trp Gly Gly Ser Gly Tyr Asp Pro Val Pro
                100                 105

<210> SEQ ID NO 87
<211> LENGTH: 456
<212> TYPE: PRT
<213> ORGANISM: Porphyromonas gingivalis

<400> SEQUENCE: 87

Arg Gly Gly Gln Ile Arg Arg His His Thr Asp Ser Ser Arg Gly Ser
1               5                   10                  15

Asp Ser Lys Ala Cys Arg Phe Ser Phe His Ala Glu Thr Ile Gly Phe
                20                  25                  30

Ser Asn His Gln Arg Ala Lys Met Asn Tyr Leu Tyr Ile Leu Ile Thr
            35                  40                  45

Leu Leu Leu Ser Gly Phe Phe Ser Gly Ala Glu Ile Ala Phe Leu Ser
    50                  55                  60

Ser Asp Lys Leu Arg Leu Glu Leu Asp Arg Asn Arg Gly Asp Leu Thr
65                  70                  75                  80

Gly Arg Ala Leu Asn Leu Leu Tyr Arg His Pro Asp Gln Leu Val Thr
                85                  90                  95

Thr Leu Leu Val Gly Asn Asn Ile Val Leu Val Val Tyr Gly Leu Leu
                100                 105                 110

Met Ala Gly Leu Leu Ala Ala Pro Leu Ala Gln Trp Ile Asp Asn Asp
            115                 120                 125

Ala Met Ile Val Val Leu Gln Ser Val Leu Ser Thr Ile Ile Ile Leu
130                 135                 140

Phe Thr Gly Glu Phe Leu Pro Lys Ala Ile Phe Lys Thr Asn Ala Asn
145                 150                 155                 160

Met Met Met Arg Val Phe Ala Leu Pro Ile Val Ala Ile Tyr Tyr Leu
                165                 170                 175

Leu Tyr Pro Leu Ser Lys Leu Phe Thr Gly Leu Ser Arg Ser Phe Ile
            180                 185                 190

Arg Leu Val Asp Lys Asn Tyr Val Pro Thr Thr Val Gly Leu Gly Arg
        195                 200                 205

Val Asp Leu Asp His Tyr Leu Ala Glu Asn Met Ser Gly Glu Asn Glu
    210                 215                 220

Gln Asn Asp Leu Thr Thr Glu Val Lys Ile Gln Asn Ala Leu Asp
225                 230                 235                 240

Phe Ser Gly Ile Gln Val Arg Asp Cys Met Ile Pro Arg Asn Glu Met
                245                 250                 255

Ile Ala Cys Glu Leu Gln Thr Asp Ile Glu Val Leu Lys Thr Thr Phe
                260                 265                 270
```

```
Ile Asp Thr Gly Leu Ser Lys Ile Ile Tyr Arg Gln Asn Ile Asp
        275                 280                 285

Asp Val Val Gly Tyr Ile His Ser Ser Glu Met Phe Arg Gly Gln Asp
290                 295                 300

Trp Gln Lys Arg Ile Asn Thr Thr Val Phe Val Pro Glu Ser Met Tyr
305                 310                 315                 320

Ala Asn Lys Leu Met Arg Leu Leu Met Gln Arg Lys Lys Ser Ile Ala
                325                 330                 335

Ile Val Ile Asp Glu Leu Gly Gly Thr Ala Gly Met Val Thr Leu Glu
            340                 345                 350

Asp Leu Val Glu Glu Ile Phe Gly Asp Ile Glu Asp Glu His Asp Thr
        355                 360                 365

Arg Lys Ile Ile Ala Lys Gln Leu Gly Pro His Thr Tyr Leu Val Ser
    370                 375                 380

Gly Arg Met Glu Ile Asp Asp Val Asn Glu Arg Phe Gly Leu Ser Leu
385                 390                 395                 400

Pro Glu Ser Asp Asp Tyr Leu Thr Val Ala Gly Phe Ile Leu Asn Ser
                405                 410                 415

His Gln Asn Ile Pro Gln Ala Asn Glu Val Val Glu Ile Ala Pro Tyr
            420                 425                 430

Thr Phe Thr Ile Leu Arg Ser Ser Ser Thr Lys Ile Glu Leu Val Lys
        435                 440                 445

Met Ser Ile Asp Asp Gln Ser Asn
    450                 455

<210> SEQ ID NO 88
<211> LENGTH: 299
<212> TYPE: PRT
<213> ORGANISM: Porphyromonas gingivalis

<400> SEQUENCE: 88

Leu Lys Lys Glu Ile Thr Met Lys Gln Asn Tyr Phe Lys Arg Val Cys
1               5                   10                  15

Ser Leu Leu Trp Leu Val Leu Pro Met Leu Ile Met Pro Leu Glu Val
            20                  25                  30

Ala Ala Gln Glu Ile Ile Pro Asn Glu Glu Val Leu Glu Ser Leu Thr
        35                  40                  45

Phe Val Ala Pro Val Glu Glu Thr Asp Ala Ile Glu Ala Glu Val Glu
50                  55                  60

Ala Leu Gln Glu Ile Val Ala Thr Glu Glu Ile Ala Glu Gln Ala Val
65                  70                  75                  80

Arg Ser Tyr Thr Tyr Thr Val Tyr Arg Asp Gly Val Lys Ile Ala Ser
                85                  90                  95

Gly Leu Thr Glu Pro Thr Phe Leu Asp Glu Asp Val Pro Ala Gly Glu
            100                 105                 110

His Thr Tyr Cys Val Glu Val Gln Tyr Gln Gly Gly Val Ser Asp Lys
        115                 120                 125

Val Cys Val Asp Val Glu Val Lys Asp Phe Lys Pro Val Thr Asn Leu
    130                 135                 140

Thr Gly Thr Ala Ser Asn Asp Glu Val Ser Leu Asp Trp Asp Gly Val
145                 150                 155                 160

Glu Glu Lys Ala Glu Glu Pro Ala Ser Asp Lys Ala Val Ser Tyr Asn
                165                 170                 175

Val Tyr Lys Asn Gly Thr Leu Ile Gly Asn Thr Ala Glu Thr His Tyr
            180                 185                 190
```

```
Val Glu Thr Gly Val Ala Asn Gly Thr Tyr Ile Tyr Glu Val Glu Val
                195                 200                 205

Lys Tyr Pro Asp Gly Val Ser Pro Lys Val Ala Val Thr Val Thr Val
            210                 215                 220

Thr Asn Ser Ser Leu Ser Asn Val Asp Gly Gln Ala Pro Tyr Thr Leu
225                 230                 235                 240

Arg Val Glu Gly Lys Lys Ile Ile Ala Glu Ala His Gly Met Ile Thr
                245                 250                 255

Leu Tyr Asp Ile Asn Gly Arg Thr Val Ala Val Ala Pro Asn Arg Leu
            260                 265                 270

Glu Tyr Met Ala Gln Thr Gly Phe Tyr Ala Val Arg Phe Asp Val Gly
                275                 280                 285

Asn Lys His His Val Ser Lys Ile Gln Val Arg
            290                 295

<210> SEQ ID NO 89
<211> LENGTH: 377
<212> TYPE: PRT
<213> ORGANISM: Porphyromonas gingivalis

<400> SEQUENCE: 89

Leu Phe Asn His Lys Lys Ser Trp Tyr Glu Thr Phe Gln Phe Tyr Leu
1               5                   10                  15

Val Val Phe Arg Ser Gly Phe Ile Leu Leu Cys Glu Asn Thr Leu Ala
                20                  25                  30

Gln Gln Lys Thr Glu Glu Phe Ala Pro Val Ser Asp Leu Arg Ala Glu
            35                  40                  45

Ala Tyr Gly Ser Thr Val Phe Leu His Trp Thr Pro Pro Tyr Asp Asn
        50                  55                  60

Pro Met Ile Pro Leu Ser Glu Ser Phe Glu Ser Gly Ile Pro Ala Ile
65                  70                  75                  80

Trp Lys Thr Ile Asp Ala Asp Gly Asp Gly Tyr Asn Trp Met His Leu
                85                  90                  95

Thr Asn Phe Thr Gly Gln Ser Gly Leu Cys Val Ser Ser Ala Ser Tyr
            100                 105                 110

Ile Gly Gly Val Gly Ala Leu Thr Pro Asp Asn Tyr Leu Ile Thr Pro
        115                 120                 125

Glu Leu Lys Leu Pro Thr Asp Ala Leu Val Glu Ile Ile Tyr Trp Val
130                 135                 140

Cys Thr Gln Asp Leu Thr Ala Pro Ser Glu His Tyr Ala Val Tyr Ser
145                 150                 155                 160

Ser Ser Thr Gly Asn Asn Ala Ala Asp Phe Val Asn Leu Leu Tyr Glu
                165                 170                 175

Glu Thr Leu Thr Ala Lys Arg Ile Gln Ser Pro Glu Leu Ile Arg Gly
            180                 185                 190

Asn Arg Thr Gln Gly Val Trp Tyr Gln Arg Lys Val Val Leu Pro Asn
        195                 200                 205

Asp Thr Lys Tyr Val Ala Phe Arg His Phe Asn Ser Thr Asp Asn Phe
    210                 215                 220

Trp Leu Asn Leu Asp Glu Val Ser Ile Leu Tyr Thr Pro Leu Pro Arg
225                 230                 235                 240

Arg Ala Pro Cys Pro His Pro Gly Gly Tyr Thr Tyr Ser Val Phe Arg
                245                 250                 255

Asp Gly Gln Lys Ile Ala Ser Gly Leu Ser Ala Leu Ala Tyr Ile Asp
            260                 265                 270
```

```
Thr Asp Val Pro Tyr Gly Thr Gln Asp Tyr Cys Val Gln Val Asn Tyr
        275                 280                 285

Leu Gln Gly Asp Ser Tyr Lys Val Cys Lys Asn Ile Val Ala Asn
        290                 295                 300

Ser Ala Asn Ile Tyr Gly Ala Asp Lys Pro Phe Ala Leu Thr Val Val
305                 310                 315                 320

Gly Lys Thr Ile Val Ala Ser Ala Phe Lys Gly Glu Ile Thr Leu Tyr
                    325                 330                 335

Asp Ile Arg Gly Arg Leu Ile Ala Ser Gly Cys Asp Thr Leu Arg Tyr
                    340                 345                 350

Lys Ala Glu Asn Gly Phe Tyr Leu Ile Lys Ile Gln Val Asn Gly Thr
                355                 360                 365

Val Tyr Thr Glu Lys Ile Gln Ile Gln
                370                 375

<210> SEQ ID NO 90
<211> LENGTH: 849
<212> TYPE: PRT
<213> ORGANISM: Porphyromonas gingivalis

<400> SEQUENCE: 90

Phe Gly Ile Ser Pro Ser Met Lys Lys Ser Phe Leu Leu Ala Ile Val
1               5                   10                  15

Met Leu Phe Gly Ile Ala Met Gln Gly His Ser Ala Pro Val Thr Lys
                20                  25                  30

Glu Arg Ala Leu Ser Leu Ala Arg Leu Ala Leu Arg Gln Val Ser Leu
            35                  40                  45

Arg Met Gly Gln Thr Ala Val Ser Asp Lys Ile Ser Ile Asp Tyr Val
50                  55                  60

Tyr Arg Gln Gly Asp Ala Glu Arg Gly Ile Thr Ser Gln Glu Glu Gly
65                  70                  75                  80

Ser Pro Ala Tyr Phe Tyr Val Ala Asn Arg Gly Asn Asn Glu Gly Tyr
                85                  90                  95

Ala Leu Val Ala Ala Asp Asp Arg Ile Pro Thr Ile Leu Ala Tyr Ser
            100                 105                 110

Pro Ile Gly Arg Phe Asp Met Asp Ser Met Pro Asp Asn Leu Arg Met
        115                 120                 125

Trp Leu Gln Ile Tyr Asp Gln Glu Ile Gly Leu Ile Leu Ser Gly Lys
130                 135                 140

Ala Gln Leu Asn Glu Glu Ile Leu Arg Thr Glu Gly Val Pro Ala Glu
145                 150                 155                 160

Val His Ala Leu Met Asp Asn Gly His Phe Ala Asn Asp Pro Met Arg
                165                 170                 175

Trp Asn Gln Gly Tyr Pro Trp Asn Asn Lys Glu Pro Leu Leu Pro Asn
            180                 185                 190

Gly Asn His Ala Tyr Thr Gly Cys Val Ala Thr Ala Ala Ala Gln Ile
        195                 200                 205

Met Arg Tyr His Ser Trp Pro Leu Gln Gly Glu Gly Ser Phe Asp Tyr
210                 215                 220

His Ala Gly Ser Leu Val Gly Asn Trp Ser Gly Thr Phe Gly Glu Met
225                 230                 235                 240

Tyr Asp Trp Ile Asn Met Pro Gly Asn Pro Asp Leu Asp Asn Leu Thr
                245                 250                 255

Gln Ser Gln Val Asp Ala Tyr Ala Thr Leu Met Arg Asp Val Ser Ala
            260                 265                 270
```

```
Ser Val Ser Met Ser Phe Tyr Glu Asn Gly Ser Gly Thr Tyr Ser Val
        275                 280                 285

Tyr Val Val Gly Ala Leu Arg Asn Asn Phe Arg Tyr Lys Arg Ser Leu
        290                 295                 300

Gln Leu His Val Arg Ala Leu Tyr Thr Ser Gln Glu Trp His Asp Met
305                 310                 315                 320

Ile Arg Gly Glu Leu Ala Ser Gly Arg Pro Val Tyr Tyr Ala Gly Asn
                325                 330                 335

Asn Gln Ser Ile Gly His Ala Phe Val Cys Asp Gly Tyr Ala Ser Asp
            340                 345                 350

Gly Thr Phe His Phe Asn Trp Gly Trp Gly Val Ser Asn Gly Phe
            355                 360                 365

Tyr Lys Leu Thr Leu Leu Ser Pro Thr Ser Leu Gly Ile Gly Gly Glu
        370                 375                 380

Gly Ile Gly Phe Thr Ile Tyr Gln Glu Ile Ile Thr Gly Ile Glu Pro
385                 390                 395                 400

Ala Lys Thr Pro Ala Glu Ala Gly Thr Asp Ala Leu Pro Ile Leu Ala
                405                 410                 415

Leu Lys Asp Ile Glu Ala Glu Tyr Lys Ser Glu Ser Gly Leu Asn Val
                420                 425                 430

Gly Tyr Ser Ile Tyr Asn Thr Gly Glu Glu Gln Ser Asn Leu Asp Leu
            435                 440                 445

Gly Tyr Arg Leu Asn Lys Ala Asp Gly Glu Val Ile Glu Val Lys Thr
        450                 455                 460

Ser Ser Ile Asn Ile Ser Trp Tyr Gly Tyr Gly Glu His Pro Glu Ser
465                 470                 475                 480

Phe Ser Leu Ala Pro Asn Gln Leu Ser Gln Gly Ile Asn Thr Ile Thr
                485                 490                 495

Leu Leu Tyr Arg Arg Thr Gly Thr Glu Gln Trp Glu Pro Val Arg His
            500                 505                 510

Ala Gln Gly Gly Tyr Val Asn Ser Ile Lys Val Asn Thr Thr Asp Pro
        515                 520                 525

Asn Asn Val Val Thr Val Asp Asn Glu Gly Lys Leu Ser Ile
530                 535                 540

Val Pro Asn Ser Phe Val Ala Asp Leu Asn Ser Tyr Glu His Ser Thr
545                 550                 555                 560

Ile Thr Val Gln Phe Asn Ser Asp Ser Pro Asp Glu Ile Arg Thr Pro
                565                 570                 575

Val Ala Phe Ala Leu Ser Thr Gly Ala Thr Ala Asp Asp Val Ile Ser
                580                 585                 590

Leu Gly Trp Val Met Ala Glu Val Pro Gly Gly Ser Ser Asn Tyr Pro
        595                 600                 605

Val Val Trp Ser Lys Asp Val Leu Thr Leu Ser Glu Gly Asp Tyr Thr
        610                 615                 620

Leu Trp Tyr Arg Phe Ser Ile Asn Asn Gln Lys Asp Glu Trp Lys Lys
625                 630                 635                 640

Ile Gly Ser Val Ser Val Lys Thr Pro Thr Glu Tyr Thr His Pro Leu
                645                 650                 655

Phe Glu Val Gly His Asn Gln Thr Ser Thr Tyr Thr Leu Asp Met Ala
                660                 665                 670

His Asn Arg Val Leu Pro Asp Phe Thr Leu Lys Asn Leu Gly Leu Pro
            675                 680                 685

Phe Asn Gly Glu Leu Val Val Val Phe Arg Gln Thr Gln Ser Ser Ser
```

-continued

```
                690                 695                 700
Gly Ser Leu Trp Ala Ala Gln Glu Thr Val His Ile Lys Gln Gly Glu
705                 710                 715                 720

Thr Phe Val Tyr Lys Pro Val Val Glu Gly Pro Ile Pro Asp Gly Ser
                725                 730                 735

Tyr Arg Ala Thr Leu His Ala Phe Val Asn Gly Gln Gln Leu Tyr
                740                 745                 750

Leu Lys Gly Lys Arg Asn Tyr Thr Val Lys Ile Val Asn Gly Thr Ala
                755                 760                 765

Val Glu Ala Ile Glu Ser Ser Glu Gly Ile Arg Val Phe Pro Asn Pro
770                 775                 780

Ala Arg Asp Tyr Val Glu Ile Ser Ala Pro Cys Ile Pro Gln Glu Thr
785                 790                 795                 800

Ser Ile Ile Leu Phe Asp Leu Ser Gly Lys Ile Val Met Lys Asn Ser
                805                 810                 815

Leu Ser Ala Gly His Gly Arg Met Asp Val Ser Arg Leu Pro Asn Gly
                820                 825                 830

Ala Tyr Ile Leu Lys Val Asp Gly Tyr Thr Thr Lys Ile Asn Ile Val
                835                 840                 845

His

<210> SEQ ID NO 91
<211> LENGTH: 295
<212> TYPE: PRT
<213> ORGANISM: Porphyromonas gingivalis

<400> SEQUENCE: 91

Thr Lys Lys Thr Leu Met Lys Lys Leu Phe Leu Ser Leu Thr Ser Leu
1               5                   10                  15

Val Met Val Phe Ala Val Ala Ser Cys Asp Ile Ile Asp Lys Asp Gln
                20                  25                  30

Thr Leu Leu Pro Ala Pro Thr Asn Val Thr Pro Asp Asn Pro Asp Asp
                35                  40                  45

Asn Pro Ser Glu Ile Asp Ile Thr Gln Thr His Thr Glu Lys Tyr Val
50                  55                  60

Leu Ala Glu Glu Phe Thr Gly Gln Lys Cys Leu Asn Cys Pro Lys Gly
65                  70                  75                  80

His Arg Lys Leu Ala Ala Leu Lys Glu Gln Tyr Gly Lys Arg Leu Thr
                85                  90                  95

Val Val Gly Ile His Ala Gly Pro Gly Ser Leu Val Pro Pro Leu Phe
                100                 105                 110

Arg Thr Glu Ala Gly Asp Ala Tyr Tyr Ser Lys Phe Ala Asn Asn Thr
                115                 120                 125

Pro Leu Pro Ala Leu Met Val Ser Arg Lys Lys Phe Gly Ser Ser Tyr
130                 135                 140

Val Tyr Asp Lys Ser Tyr Lys Thr Trp Asp Val Pro Ile Ala Glu Gln
145                 150                 155                 160

Met Glu Gln Lys Ala Lys Ile Asn Ile Phe Ala Val Ala Glu Tyr Thr
                165                 170                 175

Asp Thr Gln Lys Ile Lys Val Thr Val Lys Gly Lys Ile Leu Glu Gly
                180                 185                 190

Asn Thr Leu Pro Lys Ser Met Val Gln Val Tyr Leu Leu Glu Asp Lys
                195                 200                 205

Leu Ile Ala Pro Gln Val Asp Gly Asn Thr Thr Val Glu Asn Tyr Glu
                210                 215                 220
```

His Asn His Val Leu Arg Gly Ala Val Asn Gly Ile Trp Gly Glu Glu
225                 230                 235                 240

Phe Val Asn Leu Lys Asp Tyr Leu Tyr Thr Tyr Ala Val Glu Pro Leu
            245                 250                 255

Ser Gly Met Ser Phe Val Ala Glu Asn Tyr Ser Ile Val Ala Phe Val
        260                 265                 270

Tyr Asp Val Gln Thr Phe Glu Val Tyr Asp Val Val His Val Lys Ile
    275                 280                 285

Asn Pro Gln Ser Asp Gly Lys
    290                 295

<210> SEQ ID NO 92
<211> LENGTH: 230
<212> TYPE: PRT
<213> ORGANISM: Porphyromonas gingivalis

<400> SEQUENCE: 92

Thr Asn Lys Lys Glu Glu Thr Met Lys Lys Ser Ser Val Val Ala Ser
1               5                   10                  15

Val Leu Ala Val Ala Leu Val Phe Ala Gly Cys Gly Leu Asn Asn Met
            20                  25                  30

Ala Lys Gly Gly Leu Ile Gly Ala Gly Val Gly Gly Ala Ile Gly Ala
        35                  40                  45

Gly Val Gly Asn Val Ala Gly Asn Thr Ala Gly Ala Ile Val Gly
    50                  55                  60

Thr Ala Val Gly Gly Ala Ala Gly Ala Leu Ile Gly Lys Lys Met Asp
65                  70                  75                  80

Lys Gln Lys Lys Glu Leu Glu Ala Ala Val Pro Asp Ala Thr Ile Gln
            85                  90                  95

Thr Val Asn Asp Gly Glu Ala Ile Leu Val Thr Phe Asp Ser Gly Ile
        100                 105                 110

Leu Phe Ala Thr Asn Ser Ser Thr Leu Ser Pro Asn Ser Arg Thr Ala
    115                 120                 125

Leu Thr Lys Phe Ala Ala Asn Met Asn Lys Asn Pro Asp Thr Asp Ile
130                 135                 140

Arg Ile Val Gly His Thr Asp Asn Thr Gly Ser Asp Lys Ile Asn Asp
145                 150                 155                 160

Pro Leu Ser Glu Arg Arg Ala Ala Ser Val Tyr Ser Phe Leu Asn Ser
            165                 170                 175

Gln Gly Val Ser Met Ser Arg Met Ala Ala Glu Gly Arg Gly Ser His
        180                 185                 190

Glu Pro Val Ala Asp Asn Ser Thr Val Ala Gly Arg Ser Ala Asn Arg
    195                 200                 205

Arg Val Glu Val Tyr Ile Leu Pro Asn Ala Lys Met Ile Glu Gln Ala
210                 215                 220

Gln Gln Gly Thr Leu Lys
225                 230

<210> SEQ ID NO 93
<211> LENGTH: 679
<212> TYPE: PRT
<213> ORGANISM: Porphyromonas gingivalis

<400> SEQUENCE: 93

Pro Ile Pro Phe Leu Leu Asn Met Tyr Ser Gly His Lys Ile His
1               5                   10                  15

-continued

Tyr Pro Phe Leu Ile Leu Leu Val Cys Leu Ala Phe Ala Ala Cys Lys
         20                  25                  30

Ser Val Lys Leu Lys Asp Ala Glu Lys Ala His Asp Arg Gln Glu Tyr
             35                  40                  45

Thr Lys Ala Ala Asp Met Tyr Asn Thr Leu Tyr Arg Arg Thr Arg Arg
 50                  55                  60

Lys Gln Val Glu Met Lys Ala Tyr Thr Ala Phe Arg Ser Gly Glu Asn
 65                  70                  75                  80

Tyr Arg Ala Ala Gly Arg Gln Ala Lys Ala Leu Arg Gly Tyr Leu Asn
                 85                  90                  95

Ala Arg Arg Tyr Gly Tyr Pro Asp Ser Val Val Leu Arg Leu Ala
                100                 105                 110

Gln Thr Tyr Gln Gln Gly Gly Asn Tyr Lys Glu Ala Glu Val Leu Phe
                115                 120                 125

Arg Gly Tyr Leu Glu Ala Tyr Pro Lys Ser Tyr Phe Ala Ala Ile Gly
            130                 135                 140

Leu Glu Gly Cys Leu Phe Ala Arg Gln Gln Lys Glu Tyr Pro Thr Arg
145                 150                 155                 160

Tyr Arg Ile Arg Arg Ala Ala Glu Trp Asn Ser Ala Arg Gly Asp Phe
                165                 170                 175

Gly Pro Ala Tyr Ala Pro Asp Ala Ser Ala Leu Tyr Phe Thr Ser Ser
            180                 185                 190

Arg Ser Lys Asp Asp Gly Leu Asp Asn Ser Ser Ile Thr Gly Leu Lys
            195                 200                 205

Pro Asn Asp Ile Tyr Ile Lys Arg Asp Ala Gln Gly Arg Trp Gly
            210                 215                 220

Arg Pro Asp Ser Val Ser Gly Ile Asn Thr Pro Trp Asp Glu Gly
225                 230                 235                 240

Val Pro Thr Ile Thr Pro Asp Gly Ser Thr Ile Tyr Tyr Thr Leu Ala
                245                 250                 255

Gln Gln Gly Ala Asp Tyr Asp Arg Thr Val Gln Ile Tyr Ser Ala Ala
            260                 265                 270

Arg Ser Gly Glu Gly Gly Trp Ser Asn Gly Ser Leu Val Asp Ile Met
            275                 280                 285

Arg Asp Ser Leu Arg Met Ala Ala His Pro Ser Met Ser Ala Ser Gly
            290                 295                 300

Asp Tyr Leu Tyr Phe Val Ser Asn Ile Gly Gly Ser Tyr Gly Gly Lys
305                 310                 315                 320

Asp Ile Tyr Arg Val Lys Val Ser Asp Arg Ser Tyr Gly Ser Pro Glu
                325                 330                 335

Asn Leu Gly Pro Asp Ile Asn Thr Pro Gly Asp Glu Met Phe Pro Phe
            340                 345                 350

Ile Asp Gly Asp Ser Thr Leu Phe Phe Ala Ser Asp Gly His Ala Gly
            355                 360                 365

Leu Gly Gly Leu Asp Ile Phe Lys Ala Thr Leu Asp Ser Thr Gly Gln
            370                 375                 380

Trp His Val Val Asn Met Gly Gln Pro Val Asn Ser Ser Ala Asp Asp
385                 390                 395                 400

Phe Gly Leu Ala Val Glu Pro Lys Gly Lys Asn Lys Glu Glu Ala Leu
                405                 410                 415

Pro Asp Asn Gly Val Lys Gly Val Phe Cys Ser Asn Arg Gly Asp Ala
            420                 425                 430

Arg Gly Trp Pro His Leu Phe His Phe Glu Leu Pro Ala Ile Tyr Thr
            435                 440                 445

Glu Ile Gln Gly Tyr Val Met Asp Arg Glu Glu Asn Pro Ile Ala Gly
            450                 455                 460

Ala Thr Val Arg Ile Val Gly Glu Arg Gly Pro Val Gly Gln Gly Phe
465                 470                 475                 480

Val Thr Thr Arg Asp Asp Gly Ser Tyr Lys Met Ser Val Gln Gly Asp
                485                 490                 495

Thr Arg Tyr Val Met Leu Ala Gly Ala Ser Gly Tyr Leu Asn Gln Tyr
            500                 505                 510

Val Glu Leu Lys Thr Asp Thr Ala Lys Gln Ser Glu Thr Tyr Tyr Val
            515                 520                 525

Asp Phe Phe Leu Ala Ser Arg Glu Lys Ala Glu Gly Leu Gln Asn Ile
            530                 535                 540

Phe Tyr Asp Phe Asp Lys Ala Thr Leu Arg Pro Glu Ser Met Lys Ser
545                 550                 555                 560

Leu Asp Glu Leu Ile Arg Ile Leu Thr Asp Asn Pro Asp Ile Arg Ile
                565                 570                 575

Glu Leu Gly Ser His Ala Asp Arg Lys Gly Pro Asp Ala Tyr Asn Leu
            580                 585                 590

Gly Leu Ser Asp Arg Arg Ala Lys Ser Val Val Asp Tyr Leu Thr Ser
            595                 600                 605

Arg Gly Ile Ala Ala Asp Arg Leu Thr Trp Lys Gly Tyr Gly Lys Ser
            610                 615                 620

Val Pro Lys Thr Val Thr Ala Lys Ile Ala Glu Arg His Asp Phe Leu
625                 630                 635                 640

Lys Glu Gly Asp Val Leu Thr Glu Glu Phe Val Ala Pro Leu Thr Glu
                645                 650                 655

Glu Gln Gln Ser Val Cys Asp Leu Asn Arg Arg Thr Glu Phe Arg
            660                 665                 670

Val Ile Glu Glu Glu Leu Arg
            675

<210> SEQ ID NO 94
<211> LENGTH: 329
<212> TYPE: PRT
<213> ORGANISM: Porphyromonas gingivalis

<400> SEQUENCE: 94

Asn Leu Arg Thr Gln Pro Phe Phe Leu Val Asp Leu Gln Ser Met Ile
1               5                   10                  15

Arg Thr Ile Leu Ser Arg Tyr Val Ser Ser Asn Phe Trp Ser Arg Gly
            20                  25                  30

Ala Thr Phe Phe Phe Thr Ile Phe Pro Ala Phe Ile Leu Ala Ala Thr
            35                  40                  45

Ala Leu Pro Ala Cys Gly Gly Thr Ala Ser Gly Ser Asp Arg Thr
50                  55                  60

Leu Ala Val Thr Ile Glu Pro Gln Lys Tyr Phe Ile Glu Ser Ile Ala
65                  70                  75                  80

Asp Lys Ser Val Gln Val Ala Leu Val Pro Ala Gly Ser Asn Pro
            85                  90                  95

Glu Glu Tyr Asp Pro Ser Pro Thr Val Met Lys Arg Leu Ser Glu Ala
            100                 105                 110

Asp Ala Tyr Phe Tyr Ile Gly Gly Leu Gly Phe Glu Gln Arg Asn Leu
            115                 120                 125

Ala Ala Ile Arg Asp Asn Asn Pro Lys Leu Pro Leu Phe Glu Met Gly
130                 135                 140

```
Lys Ala Leu Ala Asp Ala Gly Ser Ala Asp Leu His Gly Ser Cys Thr
145                 150                 155                 160

Asp His Ser His Thr Asp Leu His Ala His Asp Pro His Tyr Trp Ser
                165                 170                 175

Ser Val Val Gly Ala Lys Ala Leu Ser Arg Ala Ala Tyr Asp Ala Leu
            180                 185                 190

Val Glu Leu Tyr Pro Asn Glu Lys Asp Lys Trp Asp Lys Gly His Asp
        195                 200                 205

Arg Leu Asn Gly Arg Ile Asp Ser Val Lys Arg Leu Val Asp Thr Met
    210                 215                 220

Phe Ala Asn Gly Lys Ala Asp Lys Ala Phe Val Ile Tyr His Pro Ser
225                 230                 235                 240

Leu Ser Phe Phe Ala Gln Glu Phe Gly Leu Arg Gln Ile Val Ile Glu
                245                 250                 255

Glu Asp Gly Lys Glu Pro Thr Ala Ala His Leu Arg Arg Val Ile Asp
            260                 265                 270

Gln Ala Arg Ala Asp Gly Val Arg Ile Val Phe Ile Gln Pro Glu Phe
        275                 280                 285

Glu Thr Arg Gln Ala Glu Asp Ile Ala Arg Glu Ile Gly Ala Arg Pro
    290                 295                 300

Val Arg Ile Asn Pro Leu Arg Ser Ser Trp Glu Glu Ile Leu His
305                 310                 315                 320

Ile Ala Arg Ala Leu Ala His Glu Arg
                325

<210> SEQ ID NO 95
<211> LENGTH: 962
<212> TYPE: PRT
<213> ORGANISM: Porphyromonas gingivalis

<400> SEQUENCE: 95

Ala Ile Phe Val Val Ser Leu Gln Ile Glu Lys Ile Thr Glu Asn Lys
1               5                   10                  15

Tyr Asn Ser Asp Lys Ser Met Asn Lys Phe Tyr Lys Ser Leu Leu Gln
            20                  25                  30

Ser Gly Leu Ala Ala Phe Val Ser Met Ala Thr Ala Leu Thr Ala Ser
        35                  40                  45

Ala Gln Ile Ser Phe Gly Gly Glu Pro Leu Ser Phe Ser Ser Arg Ser
    50                  55                  60

Ala Gly Thr His Ser Phe Asp Asp Ala Met Thr Ile Arg Leu Thr Pro
65                  70                  75                  80

Asp Phe Asn Pro Glu Asp Leu Ile Ala Gln Ser Arg Trp Gln Ser Gln
                85                  90                  95

Arg Asp Gly Arg Pro Val Arg Ile Gly Gln Val Ile Pro Val Asp Val
            100                 105                 110

Asp Phe Ala Ser Lys Ala Ser His Ile Ser Ser Ile Gly Asp Val Asp
        115                 120                 125

Val Tyr Arg Leu Gln Phe Lys Leu Glu Gly Ala Lys Ala Ile Thr Leu
    130                 135                 140

Tyr Tyr Asp Ala Phe Asn Ile Pro Glu Gly Gly Arg Leu Tyr Ile Tyr
145                 150                 155                 160

Thr Pro Asp His Glu Ile Val Leu Gly Ala Tyr Thr Asn Ala Thr His
                165                 170                 175

Arg Arg Asn Gly Ala Phe Ala Thr Glu Pro Val Pro Gly Ser Glu Leu
            180                 185                 190
```

```
Ile Met Asp Tyr Glu Val Ser Arg Gly Gly Thr Leu Pro Asp Ile Lys
            195                 200                 205

Ile Ser Gly Ala Gly Tyr Ile Phe Asp Lys Val Gly Arg Pro Val
    210                 215                 220

Thr Asp Asn His Tyr Gly Ile Gly Glu Asp Ser Asp Ser Asp Cys
225                 230                 235                 240

Glu Ile Asn Ile Asn Cys Pro Glu Gly Ala Asp Trp Gln Ala Glu Lys
                245                 250                 255

Asn Gly Val Val Gln Met Ile Met Val Lys Gly Gln Tyr Ile Ser Met
            260                 265                 270

Cys Ser Gly Asn Leu Leu Asn Asn Thr Lys Gly Asp Phe Thr Pro Leu
        275                 280                 285

Ile Ile Ser Ala Gly His Cys Ala Ser Ile Thr Thr Asn Phe Gly Val
    290                 295                 300

Thr Gln Ser Glu Leu Asp Lys Trp Ile Phe Thr Phe His Tyr Glu Lys
305                 310                 315                 320

Arg Gly Cys Ser Asn Gly Thr Leu Ala Ile Phe Arg Gly Asn Ser Ile
                325                 330                 335

Ile Gly Ala Ser Met Lys Ala Phe Leu Pro Ile Lys Gly Lys Ser Asp
            340                 345                 350

Gly Leu Leu Leu Gln Leu Asn Asp Glu Val Pro Leu Arg Tyr Arg Val
        355                 360                 365

Tyr Tyr Asn Gly Trp Asp Ser Thr Pro Asp Ile Pro Ser Ser Gly Ala
    370                 375                 380

Gly Ile His His Pro Ala Gly Asp Ala Met Lys Ile Ser Ile Leu Lys
385                 390                 395                 400

Lys Thr Pro Ala Leu Asn Thr Trp Ile Ser Ser Gly Ser Gly Gly
                405                 410                 415

Thr Asp Asp His Phe Tyr Phe Lys Tyr Asp Gln Gly Gly Thr Glu Gly
            420                 425                 430

Gly Ser Ser Gly Ser Ser Leu Phe Asn Gln Asn Lys His Val Val Gly
        435                 440                 445

Thr Leu Thr Gly Gly Ala Gly Asn Cys Gly Gly Thr Glu Phe Tyr Gly
    450                 455                 460

Arg Leu Asn Ser His Trp Asn Glu Tyr Ala Ser Asp Gly Asn Thr Ser
465                 470                 475                 480

Arg Met Asp Ile Tyr Leu Asp Pro Gln Asn Asn Gly Gln Thr Thr Ile
                485                 490                 495

Leu Asn Gly Thr Tyr Arg Asp Gly Tyr Lys Pro Leu Pro Ser Val Pro
            500                 505                 510

Arg Leu Leu Leu Gln Ser Thr Gly Asp Gln Val Glu Leu Asn Trp Thr
        515                 520                 525

Ala Val Pro Ala Asp Gln Tyr Pro Ser Ser Tyr Gln Val Glu Tyr His
    530                 535                 540

Ile Phe Arg Asn Gly Lys Glu Ile Ala Thr Thr Lys Glu Leu Ser Tyr
545                 550                 555                 560

Ser Asp Ala Ile Asp Glu Ser Ile Ile Gly Ser Gly Ile Ile Arg Tyr
                565                 570                 575

Glu Val Ser Ala Arg Phe Ile Tyr Pro Ser Pro Leu Asp Gly Val Glu
            580                 585                 590

Ser Tyr Lys Asp Thr Asp Lys Thr Ser Ala Asp Leu Ala Ile Gly Asp
        595                 600                 605

Ile Gln Thr Lys Leu Lys Pro Asp Val Thr Pro Leu Pro Gly Gly Gly
```

```
               610                 615                 620
Val Ser Leu Ser Trp Lys Val Pro Phe Leu Ser Gln Leu Val Ser Arg
625                 630                 635                 640

Phe Gly Glu Ser Pro Asn Pro Val Phe Lys Thr Phe Glu Val Pro Tyr
                645                 650                 655

Val Ser Ala Ala Ala Ala Gln Thr Pro Asn Pro Val Gly Val Val
                660                 665                 670

Ile Ala Asp Lys Phe Met Ala Gly Thr Tyr Pro Glu Lys Ala Ala Ile
                675                 680                 685

Ala Ala Val Tyr Val Met Pro Ser Ala Pro Asp Ser Thr Phe His Leu
        690                 695                 700

Phe Leu Lys Ser Asn Thr Asn Arg Arg Leu Gln Lys Val Thr Thr Pro
705                 710                 715                 720

Ser Asp Trp Gln Ala Gly Thr Trp Leu Arg Ile Asn Leu Asp Lys Pro
                725                 730                 735

Phe Pro Val Asn Asn Asp His Met Leu Phe Ala Gly Ile Arg Met Pro
                740                 745                 750

Asn Lys Tyr Lys Leu Asn Arg Ala Ile Arg Tyr Val Arg Asn Pro Asp
            755                 760                 765

Asn Leu Phe Ser Ile Thr Gly Lys Lys Ile Ser Tyr Asn Asn Gly Val
770                 775                 780

Ser Phe Glu Gly Tyr Gly Ile Pro Ser Leu Leu Gly Tyr Met Ala Ile
785                 790                 795                 800

Lys Tyr Leu Val Val Asn Thr Asp Ala Pro Lys Ile Asp Met Ser Leu
                805                 810                 815

Val Gln Glu Pro Tyr Ala Lys Gly Thr Asn Val Ala Pro Phe Pro Glu
            820                 825                 830

Leu Val Gly Ile Tyr Val Tyr Lys Asn Gly Thr Phe Ile Gly Thr Gln
            835                 840                 845

Asp Pro Ser Val Thr Thr Tyr Ser Val Ser Asp Gly Thr Glu Ser Asp
        850                 855                 860

Glu Tyr Glu Ile Lys Leu Val Tyr Lys Gly Ser Gly Ile Ser Asn Gly
865                 870                 875                 880

Val Ala Gln Ile Glu Asn Asn Asn Ala Val Ala Tyr Pro Ser Val
            885                 890                 895

Val Thr Asp Arg Phe Ser Ile Lys Asn Ala His Met Val His Ala Ala
            900                 905                 910

Ala Leu Tyr Ser Leu Asp Gly Lys Gln Val Arg Ser Trp Asn Asn Leu
            915                 920                 925

Arg Asn Gly Val Thr Phe Ser Val Gln Gly Leu Thr Ala Gly Thr Tyr
    930                 935                 940

Met Leu Val Met Gln Thr Ala Asn Gly Pro Val Ser Gln Lys Ile Val
945                 950                 955                 960

Lys Gln

<210> SEQ ID NO 96
<211> LENGTH: 938
<212> TYPE: PRT
<213> ORGANISM: Porphyromonas gingivalis

<400> SEQUENCE: 96

Ser Glu Asn Tyr Arg Tyr Gly Lys Ile Thr Asn Gln Ile Met Ala Ile
1               5                   10                  15

Met Met Lys Ser Ile Val Phe Arg Ala Phe Leu Thr Ile Leu Leu Ser
            20                  25                  30
```

```
Trp Ala Ala Ile Thr Asn Pro Thr Ala Gln Glu Ile Ser Gly Met Asn
             35                  40                  45

Ala Ser Cys Leu Ala Ala Pro Ala Gln Pro Asp Thr Ile Leu Tyr Glu
 50                  55                  60

Ser Phe Glu Asn Gly Pro Val Pro Asn Gly Trp Leu Glu Ile Asp Ala
 65                  70                  75                  80

Asp Ala Asp Gly Ala Thr Trp Gly Ser Pro Ser Gly Ser Phe Ser Val
                 85                  90                  95

Pro Tyr Gly His Asn Gly Leu Cys Thr Tyr Ser His Ile Arg Ser Gly
                100                 105                 110

Ile Ser Thr Ala Gly Asn Tyr Leu Ile Thr Pro Asn Ile Glu Gly Ala
            115                 120                 125

Lys Arg Val Lys Tyr Trp Val Cys Asn Gln Tyr Ser Thr Asn Pro Glu
            130                 135                 140

His Tyr Ala Val Met Val Ser Thr Thr Gly Thr Ala Ile Glu Asp Phe
145                 150                 155                 160

Val Leu Leu Phe Asp Asp Ser Ile Thr Gly Lys Pro Thr Pro Leu Val
                165                 170                 175

Trp Arg Arg Arg Ile Val Asp Leu Pro Glu Gly Thr Lys Tyr Ile Ala
                180                 185                 190

Trp Arg His Tyr Lys Val Thr Asp Ser His Thr Glu Phe Leu Lys Leu
            195                 200                 205

Asp Asp Val Thr Val Tyr Arg Ser Ile Glu Gly Pro Glu Pro Ala Thr
            210                 215                 220

Asp Phe Thr Val Ile Asn Ile Gly Gln Asn Val Gly Arg Leu Thr Trp
225                 230                 235                 240

Asn Tyr Pro Glu Asp Tyr Gln Pro Glu Gly Lys Gly Asn Glu Glu Leu
                245                 250                 255

Gln Leu Ser Gly Tyr Asn Ile Tyr Ala Asn Gly Thr Leu Leu Ala Gln
                260                 265                 270

Ile Lys Asp Val Ser Ile Leu Glu Tyr Val Asp Ser Thr Tyr Ser Leu
            275                 280                 285

Arg Asp Asn Pro Leu Gln Val Glu Tyr Cys Val Thr Ala Val Tyr Asp
            290                 295                 300

Glu Ser Ile Glu Ser Ser Thr Val Cys Gly Thr Leu His Tyr Ala Thr
305                 310                 315                 320

Asp Ala Ile Leu Tyr Glu Asn Phe Glu Asn Gly Pro Val Pro Asn Gly
                325                 330                 335

Trp Leu Val Ile Asp Ala Asp Gly Asp Gly Phe Ser Trp Gly His Tyr
                340                 345                 350

Leu Asn Ala Tyr Asp Ala Phe Pro Gly His Asn Gly Gly His Cys Ser
            355                 360                 365

Leu Ser Ala Ser Tyr Val Pro Gly Ile Gly Pro Val Thr Pro Asp Asn
370                 375                 380

Tyr Leu Ile Thr Pro Lys Val Glu Gly Ala Lys Arg Val Lys Tyr Trp
385                 390                 395                 400

Val Ser Thr Gln Asp Ala Asn Trp Ala Ala Glu His Tyr Ala Val Met
                405                 410                 415

Ala Ser Thr Thr Gly Thr Ala Val Gly Asp Phe Val Ile Leu Phe Glu
                420                 425                 430

Glu Thr Met Thr Ala Lys Pro Thr Gly Ala Trp Tyr Glu Arg Thr Ile
            435                 440                 445

Asn Leu Pro Glu Gly Thr Lys Tyr Ile Ala Trp Arg His Tyr Asn Cys
```

```
                      450           455           460
Thr Asp Ile Tyr Phe Leu Lys Leu Asp Asp Ile Thr Val Phe Gly Thr
465                 470                 475                 480

Pro Ala Ser Glu Pro Glu Pro Val Thr Asp Phe Val Val Ser Leu Ile
                485                 490                 495

Glu Asn Asn Lys Gly Arg Leu Lys Trp Asn Tyr Pro Asn Gly Tyr Glu
                500                 505                 510

Pro Asp Lys Thr Asp Asp Lys Asp Pro Leu Gln Leu Ala Gly Tyr Asn
                515                 520                 525

Ile Tyr Ala Asn Gly Ser Leu Leu Val His Ile Gln Asp Pro Thr Val
530                 535                 540

Leu Glu Tyr Ile Asp Glu Thr Tyr Ser Ser Arg Asp Asp Gln Val Glu
545                 550                 555                 560

Val Glu Tyr Cys Val Thr Ala Val Tyr Asn Asp Asn Ile Glu Ser Gln
                565                 570                 575

Ser Val Cys Asp Lys Leu Ile Tyr Asp Ser Gln Ser Asp Ile Ile Leu
                580                 585                 590

Tyr Glu Gly Phe Glu Ala Gly Ser Ile Pro Glu Gly Trp Leu Leu Ile
                595                 600                 605

Asp Ala Asp Gly Asp Asn Val Asn Trp Asp Tyr Tyr Pro Trp Thr Met
610                 615                 620

Tyr Gly His Asp Ser Glu Lys Cys Ile Ala Ser Pro Ser Tyr Leu Pro
625                 630                 635                 640

Met Ile Gly Val Leu Thr Pro Asp Asn Tyr Leu Val Thr Pro Arg Leu
                645                 650                 655

Glu Gly Ala Lys Leu Val Lys Tyr Trp Val Ser Ala Gln Asp Ala Val
                660                 665                 670

Tyr Ser Ala Glu His Tyr Ala Val Met Val Ser Thr Gly Thr Ala
                675                 680                 685

Val Glu Asp Phe Val Leu Leu Phe Glu Glu Thr Met Thr Ala Lys Ala
                690                 695                 700

Asn Gly Ala Trp Tyr Glu Arg Thr Ile Thr Leu Pro Ala Gly Thr Lys
705                 710                 715                 720

Tyr Ile Ala Trp Arg His Tyr Asp Cys Thr Asp Met Phe Phe Leu Leu
                725                 730                 735

Leu Asp Asp Ile Thr Val Tyr Arg Ser Thr Glu Thr Val Pro Glu Pro
                740                 745                 750

Val Thr Asp Phe Val Val Ser Leu Ile Glu Asn Asn Lys Gly Arg Leu
                755                 760                 765

Lys Trp Asn Tyr Pro Asn Gly Tyr Glu Pro Asp Lys Thr Asp Asp Lys
770                 775                 780

Lys Pro Leu Gln Leu Thr Gly Tyr Asn Ile Tyr Ala Asn Gly Ser Leu
785                 790                 795                 800

Leu Val His Ile Gln Asp Pro Thr Val Leu Glu Tyr Ile Asp Glu Thr
                805                 810                 815

Tyr Ser Ser Arg Asp Gly Gln Val Glu Met Glu Tyr Cys Val Thr Ala
                820                 825                 830

Val Tyr Asn Asp Asn Ile Glu Ser Gln Ser Val Cys Asp Lys Leu Asn
                835                 840                 845

Tyr Thr Ile Thr Ser Leu Asp Asn Ile Gln Ser Asp Thr Ser Leu Lys
                850                 855                 860

Ile Tyr Pro Asn Pro Ala Ser Tyr Val Val Arg Ile Glu Gly Leu Ser
865                 870                 875                 880
```

```
Arg Ser Lys Ser Thr Ile Glu Leu Tyr Asn Ala Leu Gly Ile Cys Ile
                885                 890                 895

Leu Arg Glu Glu Thr His Ser Glu Lys Thr Glu Ile Asp Val Ser Arg
            900                 905                 910

Leu Asn Asp Gly Val Tyr Leu Ile Lys Val Val Gly Gly Asn Lys Thr
            915                 920                 925

Thr Thr Glu Lys Val Glu Ile Lys Arg Pro
        930                 935

<210> SEQ ID NO 97
<211> LENGTH: 337
<212> TYPE: PRT
<213> ORGANISM: Porphyromonas gingivalis

<400> SEQUENCE: 97

Pro Gln Pro Val Gly Leu Lys Glu Ile Thr Ile Lys Pro Met Cys Leu
1               5                   10                  15

Glu Pro Ile Ile Ala Pro Ile Ser Ser Glu Leu Leu Glu Gln Glu Leu
            20                  25                  30

Thr Ala Asp Arg Phe Leu Arg Met Thr Asn Lys Ala Gly Asn Glu Ile
        35                  40                  45

Tyr Val Phe Thr Ala Glu Glu Ala Pro His Cys Met Lys Glu Val Gly
50                  55                  60

Arg Leu Arg Glu Glu Ala Phe Arg His Tyr Gly Gly Thr Gly Lys
65                  70                  75                  80

Ala Ile Asp Ile Asp Glu Phe Asp Thr Met Pro Gly Ser Tyr Lys Gln
                85                  90                  95

Leu Ile Val Trp Asp Pro Gln Asn Lys Ala Ile Leu Gly Gly Tyr Arg
            100                 105                 110

Phe Ile Tyr Gly Arg Asp Val Ala Phe Asp Thr Asp Gly Lys Pro Leu
        115                 120                 125

Leu Ala Thr Ala Glu Met Phe Arg Phe Ser Asp Ala Phe Leu His Asp
    130                 135                 140

Tyr Leu Pro Tyr Thr Val Glu Leu Gly Arg Ser Phe Val Ser Leu Gln
145                 150                 155                 160

Tyr Gln Ser Thr Arg Met Gly Thr Lys Ala Ile Phe Val Leu Asp Asn
                165                 170                 175

Leu Trp Asp Gly Ile Gly Ala Leu Thr Val Val Asn Pro Glu Ala Leu
            180                 185                 190

Tyr Phe Tyr Gly Lys Val Thr Met Tyr Lys Asp Tyr Asp Arg Arg Ala
        195                 200                 205

Arg Asn Leu Ile Leu Tyr Phe Leu Arg Lys His Phe Ser Asp Pro Glu
    210                 215                 220

Gly Leu Val Lys Pro Ile His Pro Leu Pro Ile Glu Ile Ser Ala Glu
225                 230                 235                 240

Asp Glu Ala Leu Phe Ser Ser Asp Phe Asp Thr Asn Tyr Lys Thr
                245                 250                 255

Leu Asn Ile Glu Val Arg Lys Leu Gly Ile Asn Ile Pro Pro Leu Val
            260                 265                 270

Ser Ala Tyr Ile Ala Leu Ser Pro Glu Met Arg Val Phe Gly Thr Ala
        275                 280                 285

Val Asn Glu Ser Phe Gly Glu Val Glu Glu Thr Gly Ile Phe Ile Ala
    290                 295                 300

Val Gly Lys Ile Leu Glu Glu Lys Lys Gln Arg His Ile Glu Ser Phe
305                 310                 315                 320
```

Ile Leu Ser Arg Asn Glu Lys Lys Gly Leu Asp Ser Ser Asn Gly Arg
                325                 330                 335

Ser

<210> SEQ ID NO 98
<211> LENGTH: 1251
<212> TYPE: PRT
<213> ORGANISM: Porphyromonas gingivalis
<220> FEATURE:
<221> NAME/KEY: misc_feature
<222> LOCATION: (1008)..(1008)
<223> OTHER INFORMATION: Xaa can be any naturally occurring amino acid

<400> SEQUENCE: 98

Lys Trp Lys Leu Ala Cys Ala Phe Asp Cys Ala Cys Cys Phe Asp Pro
1               5                   10                  15

Phe Val Val Thr Asn Glu Val Ile Ile Met Met Lys Arg Tyr Thr Ile
                20                  25                  30

Ile Leu Ala Val Phe Leu Leu Phe Cys Thr Val Phe Thr Phe Gln Ile
            35                  40                  45

Lys Ala Arg Pro Tyr Glu Arg Phe Ala Asp Val Glu Lys Pro Trp Ile
    50                  55                  60

Gln Lys His Ser Met Asp Ser Lys Leu Val Pro Ala Asn Lys Gly Asn
65                  70                  75                  80

Leu Ile Gln Ala Glu Ile Val Tyr Gln Ser Val Ser Glu His Ser Asp
                85                  90                  95

Leu Val Ile Ser Pro Val Asn Glu Ile Arg Pro Ala Asn Arg Phe Pro
            100                 105                 110

Ser His Arg Lys Ser Phe Phe Ala Glu Asn Leu Arg Ala Ser Pro Pro
        115                 120                 125

Val Val Pro Val Ala Val Asp Lys Tyr Ala Val Pro Val Ala Asn Pro
130                 135                 140

Met Asp Pro Glu Asn Pro Asn Ala Trp Asp Val Thr Leu Lys Ile Thr
145                 150                 155                 160

Thr Lys Ala Val Thr Val Pro Val Asp Val Met Val Ile Asp Gln
                165                 170                 175

Ser Ser Ser Met Gly Gly Gln Asn Ile Ala Arg Leu Lys Ser Ala Ile
            180                 185                 190

Ala Ser Gly Gln Arg Phe Val Lys Lys Met Leu Pro Lys Gly Thr Ala
        195                 200                 205

Thr Glu Gly Val Arg Ile Ala Leu Val Ser Tyr Asp His Glu Pro His
    210                 215                 220

Arg Leu Ser Asp Phe Thr Lys Asp Thr Ala Phe Leu Cys Gln Lys Ile
225                 230                 235                 240

Arg Ala Leu Thr Pro Ile Trp Gly Thr His Thr Gln Gly Gly Leu Lys
                245                 250                 255

Met Ala Arg Asn Ile Met Ala Thr Ser Thr Ala Val Asp Lys His Ile
            260                 265                 270

Ile Leu Met Ser Asp Gly Leu Ala Thr Glu Gln Tyr Pro Val Lys Asn
        275                 280                 285

Val Thr Thr Ala Asp Phe Ile Gly Lys Thr Gly Asn Ala Asn Asp Pro
    290                 295                 300

Ile Asp Leu Val Ile Gln Gly Ala Ile Asn Phe Pro Thr Asn Tyr Val
305                 310                 315                 320

Ser Asn Asn Pro Ser Thr Pro Leu Thr Pro Asn Tyr Pro Thr His Ser
                325                 330                 335

```
Ser Lys Val Gly Arg Arg Asn Leu Pro Glu Ser Lys Phe Asp Tyr Ser
            340                 345                 350

Asn Leu Ser Ala Arg Ile Thr Phe Asp Gly Val Ala Gly Ala Leu Val
            355                 360                 365

Tyr Glu Pro Arg Phe Pro His Pro Tyr Tyr Tyr Phe Pro Cys Asn
        370                 375                 380

Ala Ala Ile Asn Glu Ala Gln Phe Ala Lys Asn Ser Gly Tyr Thr Ile
385                 390                 395                 400

His Thr Ile Gly Tyr Asp Leu Gly Asp Phe Ala Leu Ala Asn Asn Ser
                405                 410                 415

Leu Lys Leu Thr Ala Thr Asp Glu Asn His Phe Phe Thr Ala Thr Pro
            420                 425                 430

Ala Asn Leu Ala Ala Ala Phe Asp Asn Ile Ala Gln Thr Ile Asn Ile
            435                 440                 445

Gly Ile Gln Arg Gly Glu Val Thr Asp Phe Val Ala Pro Gly Phe Ile
            450                 455                 460

Val Lys Asn Leu Thr Gln Ser Gly Asp Val Thr His Leu Leu Asn Val
465                 470                 475                 480

Ser Asn Gly Thr Val His Tyr Asp Val Ser Thr Lys Lys Leu Thr Trp
                485                 490                 495

Thr Thr Gly Thr Ile Leu Ser Ser Glu Ala Thr Ile Thr Tyr Arg
            500                 505                 510

Ile Tyr Ala Asp Leu Asp Tyr Ile Gln Asn Asn Asp Ile Pro Val Asn
        515                 520                 525

Thr Thr Ser Ala Ile Gly Pro Asp Leu Gly Gly Phe Asp Thr Asn Thr
            530                 535                 540

Glu Ala Lys Leu Thr Tyr Thr Asn Ser Asn Gly Glu Pro Asn Gln Gln
545                 550                 555                 560

Leu Ile Phe Pro Arg Pro Thr Val Lys Leu Gly Tyr Gly Val Ile Lys
                565                 570                 575

Arg His Tyr Val Leu Val Asn Lys Asp Gly Gln Pro Ile Gln Ala Asn
            580                 585                 590

Gly Thr Val Val Ser Ser Leu Ser Glu Ala His Val Leu Gln Ser Gln
            595                 600                 605

Asp Phe Phe Leu Pro Ser Gly Gly His Ile Val Pro Lys Trp Ile
        610                 615                 620

Lys Leu Asp Lys Thr Thr Glu Ala Leu Gln Tyr Tyr Ser Val Pro Pro
625                 630                 635                 640

Thr Asn Thr Val Ile Thr Thr Ala Asp Gly Lys Arg Tyr Arg Phe Val
                645                 650                 655

Glu Val Pro Gly Ser Thr Pro Asn Pro Gly Gln Ile Gly Ile Ser Trp
            660                 665                 670

Lys Lys Pro Ala Gly Asn Ala Tyr Phe Ala Tyr Lys Leu Leu Asn Tyr
            675                 680                 685

Trp Met Gly Gly Thr Thr Asp Gln Gln Ser Glu Trp Asp Val Thr Ser
        690                 695                 700

Asn Trp Thr Gly Ala Gln Val Pro Leu Thr Gly Glu Asp Val Glu Phe
705                 710                 715                 720

Ala Thr Thr Glu Asn Phe Gly Ser Pro Ala Val Ala Asp Leu His Val
                725                 730                 735

Pro Thr Thr Asn Pro Lys Ile Ile Gly Asn Leu Ile Asn Asn Ser Asp
            740                 745                 750

Lys Asp Leu Val Val Thr Thr Ser Ser Gln Leu Thr Ile Asn Gly Val
            755                 760                 765
```

Val Glu Asp Asn Asn Pro Asn Val Gly Thr Ile Val Val Lys Ser Ser
770                 775                 780

Lys Asp Asn Pro Thr Gly Thr Leu Leu Phe Ala Asn Pro Gly Tyr Asn
785                 790                 795                 800

Gln Asn Val Gly Gly Thr Val Glu Phe Tyr Asn Gln Gly Tyr Asp Cys
                805                 810                 815

Ala Asp Cys Gly Met Tyr Arg Arg Ser Trp Gln Tyr Phe Gly Ile Pro
            820                 825                 830

Val Asn Glu Ser Gly Phe Pro Ile Asn Asp Val Gly Gly Asn Glu Thr
        835                 840                 845

Val Asn Gln Trp Val Glu Pro Phe Asn Gly Asp Lys Trp Arg Pro Ala
850                 855                 860

Pro Tyr Ala Pro Asp Thr Glu Leu Gln Lys Phe Lys Gly Tyr Gln Ile
865                 870                 875                 880

Thr Asn Asp Val Gln Ala Gln Pro Thr Gly Val Tyr Ser Phe Lys Gly
                885                 890                 895

Met Ile Cys Val Cys Asp Ala Phe Leu Asn Leu Thr Arg Thr Ser Gly
                900                 905                 910

Val Asn Tyr Ser Gly Ala Asn Leu Ile Gly Asn Ser Tyr Thr Gly Ala
                915                 920                 925

Ile Asp Ile Lys Gln Gly Ile Val Phe Pro Pro Glu Val Glu Gln Thr
        930                 935                 940

Val Tyr Leu Phe Asn Thr Gly Thr Arg Asp Gln Trp Arg Lys Leu Asn
945                 950                 955                 960

Gly Ser Thr Val Ser Gly Tyr Arg Ala Gly Gln Tyr Leu Ser Val Pro
                965                 970                 975

Lys Asn Thr Ala Gly Gln Asp Asn Leu Pro Asp Arg Ile Pro Ser Met
            980                 985                 990

His Ser Phe Leu Val Lys Met Gln Asn Gly Ala Ser Cys Thr Leu Xaa
        995                 1000                1005

Ile Leu Tyr Asp Lys Leu Leu Lys Asn Thr Thr Val Asn Asn Gly
    1010                1015                1020

Asn Gly Thr Gln Ile Thr Trp Arg Ser Gly Asn Ser Gly Ser Ala
    1025                1030                1035

Asn Met Pro Ser Leu Val Met Asp Val Leu Gly Asn Glu Ser Ala
    1040                1045                1050

Asp Arg Leu Trp Ile Phe Thr Asp Gly Gly Leu Ser Phe Gly Phe
    1055                1060                1065

Asp Asn Gly Trp Asp Gly Arg Lys Leu Thr Glu Lys Gly Leu Ser
    1070                1075                1080

Gln Leu Tyr Ala Met Ser Asp Ile Gly Asn Asp Lys Phe Gln Val
    1085                1090                1095

Ala Gly Val Pro Glu Leu Asn Asn Leu Leu Ile Gly Phe Asp Ala
    1100                1105                1110

Asp Lys Asp Gly Gln Tyr Thr Leu Glu Phe Ala Leu Ser Asp His
    1115                1120                1125

Phe Ala Lys Gly Ala Val Tyr Leu His Asp Leu Gln Ser Gly Ala
    1130                1135                1140

Lys His Arg Ile Thr Asn Ser Thr Ser Tyr Ser Phe Asp Ala Lys
    1145                1150                1155

Arg Gly Asp Ser Gly Ala Arg Phe Arg Leu Ser Tyr Gly Cys Asp
    1160                1165                1170

Glu Asn Val Asp Asp Ser His Val Val Ser Thr Asn Gly Arg Glu

```
              1175                1180                1185
Ile  Ile  Ile  Leu  Asn  Gln  Asp  Ala  Leu  Asp  Cys  Thr  Val  Thr  Leu
         1190                1195                1200

Phe  Thr  Ile  Glu  Gly  Lys  Leu  Leu  Arg  Arg  Leu  Lys  Val  Leu  Ala
         1205                1210                1215

Gly  His  Arg  Glu  Val  Met  Lys  Val  Gln  Thr  Gly  Gly  Ala  Tyr  Ile
         1220                1225                1230

Val  His  Leu  Gln  Asn  Ala  Phe  Thr  Asn  Asp  Val  His  Lys  Val  Leu
         1235                1240                1245

Val  Glu  Tyr
         1250

<210> SEQ ID NO 99
<211> LENGTH: 406
<212> TYPE: PRT
<213> ORGANISM: Porphyromonas gingivalis

<400> SEQUENCE: 99

Ile  Phe  Ile  Asp  Pro  Asp  Lys  Asn  Thr  Lys  Gln  Asn  Glu  Arg  Asn  Met
1                   5                   10                  15

Ile  Ile  Lys  Lys  Met  Leu  Lys  Asn  Lys  Leu  Ala  Pro  Leu  Ala  Ile  Leu
             20                  25                  30

Phe  Leu  Phe  Ala  Pro  Lys  Ala  Met  Lys  Ala  Gln  Glu  Gln  Leu  Asn  Val
             35                  40                  45

Val  His  Thr  Ser  Val  Pro  Ser  Leu  Asn  Ile  Ser  Pro  Asp  Ala  Arg  Ala
        50                  55                  60

Ala  Gly  Met  Gly  Asp  Ile  Gly  Val  Ala  Thr  Thr  Pro  Asp  Ala  Tyr  Ser
65                  70                  75                  80

Gln  Tyr  Trp  Asn  Pro  Ser  Lys  Tyr  Ala  Phe  Met  Asp  Thr  Lys  Ala  Gly
                85                  90                  95

Ile  Ser  Phe  Ser  Tyr  Thr  Pro  Trp  Leu  Ser  Lys  Leu  Val  Asn  Asp  Ile
            100                 105                 110

Ala  Leu  Met  Gln  Met  Thr  Gly  Phe  Tyr  Lys  Leu  Gly  Thr  Asp  Glu  Asn
            115                 120                 125

Gln  Ala  Ile  Ser  Ala  Ser  Leu  Arg  Tyr  Phe  Thr  Leu  Gly  Lys  Leu  Glu
        130                 135                 140

Thr  Phe  Asp  Glu  Leu  Gly  Glu  Ser  Met  Gly  Glu  Ala  His  Pro  Asn  Glu
145                 150                 155                 160

Phe  Ala  Val  Asp  Leu  Gly  Tyr  Ser  Arg  Gln  Leu  Ser  Glu  Asn  Phe  Ser
                165                 170                 175

Met  Ala  Val  Ala  Leu  Arg  Tyr  Ile  Arg  Ser  Asp  Gln  Ser  Thr  His  Asn
            180                 185                 190

Thr  Gly  Glu  Asn  Gln  Ala  Gly  Asn  Ala  Phe  Ala  Ala  Asp  Ile  Ala  Gly
            195                 200                 205

Tyr  Leu  Gln  Lys  Tyr  Val  Leu  Leu  Gly  Asn  Ala  Glu  Ser  Leu  Trp  Ser
        210                 215                 220

Leu  Gly  Phe  Asn  Val  Lys  Asn  Ile  Gly  Thr  Lys  Ile  Ser  Tyr  Asp  Gly
225                 230                 235                 240

Gly  Val  Thr  Ser  Phe  Phe  Ile  Pro  Thr  Ser  Leu  Asn  Leu  Gly  Thr  Gly
                245                 250                 255

Leu  Leu  Tyr  Pro  Ile  Asp  Asp  Tyr  Asn  Ser  Ile  Asn  Phe  Asn  Leu  Glu
            260                 265                 270

Leu  Ser  Lys  Leu  Leu  Val  Pro  Thr  Pro  Ile  Met  Asp  Gln  Asn  Asp
            275                 280                 285

Gln  Ala  Gly  Tyr  Glu  Ala  Ala  Leu  Lys  Lys  Tyr  Gln  Glu  Thr  Ser  Ser
```

```
                290                 295                 300
Ile Ser Gly Ile Phe Ser Ser Phe Gly Asp Ala Pro Gly Gly Leu Lys
305                 310                 315                 320

Glu Glu Phe Arg Glu Ile Thr Trp Gly Leu Gly Ala Glu Tyr Ser Tyr
                325                 330                 335

Asp Asp Lys Phe Phe Val Arg Ala Gly Tyr Ser Tyr Leu His Pro Thr
                340                 345                 350

Lys Gly Asn Leu Gln Tyr Phe Thr Ala Gly Ala Gly Phe Lys Met Asn
                355                 360                 365

Ile Phe Arg Ile Asp Ala Ser Tyr Leu Leu Ser Thr Ile Gln Ser Asn
                370                 375                 380

Pro Leu Asp Gln Thr Leu Arg Phe Thr Leu Ala Phe Asp Met Asp Gly
385                 390                 395                 400

Leu Arg Asn Leu Phe His
                405

<210> SEQ ID NO 100
<211> LENGTH: 452
<212> TYPE: PRT
<213> ORGANISM: Porphyromonas gingivalis

<400> SEQUENCE: 100

Leu Ile Ile Glu Lys Glu Met Lys Thr Val Gln Gln Ile Ile Leu
1                 5                   10                  15

Cys Leu Ala Leu Met Met Ser Gly Val Leu Gly Gly Asn Ala Gln Ser
                20                  25                  30

Phe Trp Glu Glu Ile Ala Pro Pro Phe Ile Ser Asn Glu Pro Asn Val
                35                  40                  45

Lys Tyr Ile Ile Pro Asn Met Gly Ile Asp Ser Lys Gly Thr Ile Tyr
50                  55                  60

Val Thr Val Thr Lys Arg Ile Gln Gln Gly Ala Asn Tyr Thr Ser Glu
65                  70                  75                  80

Gln Leu Gly Met Tyr Tyr Arg Pro Leu Gly Asp Asn Glu Gln Trp Trp
                85                  90                  95

Lys His Asp Pro Tyr Phe Asp Asp Lys Ile Val Ala Asp Ile Gln Thr
                100                 105                 110

Asp Ala Tyr Gly Arg Val Tyr Val Cys Thr Thr Ser Ser Arg Asp Gln
                115                 120                 125

Glu Tyr Gln Leu Tyr Ile Asn Glu Gln Asn Glu Trp Arg Cys Ile Phe
                130                 135                 140

Lys Thr Ser Val Ser Thr Tyr Glu His Gly Met Ala Val Phe Arg Ser
145                 150                 155                 160

Ser Thr Gly Val Thr Tyr Ile Gly Thr Arg His His Ile Phe Ala Ser
                165                 170                 175

Gly Val Asn Asp Phe Glu Phe Asn Thr Ile Tyr Glu Asp Ser Thr Pro
                180                 185                 190

Met Ser Cys Arg Phe Ala Glu Ala Thr Asn Ser Gly Thr Ile Tyr Leu
                195                 200                 205

Ala Leu Met His Glu Thr Thr Met Ser Thr Thr Ile Leu Thr Tyr Gln
                210                 215                 220

Asn Gly Glu Phe Val Asp Ile Ser Glu Ser Leu Ser Asn Ser Ile
225                 230                 235                 240

Ile Ala Ser Met Cys Ser Asn Lys Glu Gly Asp Ile Ile Ala Leu Val
                245                 250                 255

Thr Ser Tyr Thr Gly Phe Met Ser Gly Thr Leu Ala Ile Arg Lys Ala
```

```
                 260                 265                 270
Asp Glu Gly Lys Trp Gln Leu Val Gly Gly Asp Ile Gln Asn Ala Ile
            275                 280                 285

Val Gln Asn Ile Cys Met Met Asp Asp Asn Lys Ile Ala Cys Glu Val
            290                 295                 300

Phe Gly Thr Pro Asn Gly Val Asp Gly Arg Thr Arg Val Cys Val Ser
305                 310                 315                 320

Asp Ala Ser Val Phe Asp Phe Glu Trp Tyr Glu Asp Glu Ile Tyr Gly
                325                 330                 335

Gly Leu Ile Phe Asp Thr Phe Phe Tyr Ser Pro Trp Asp Lys Leu Leu
            340                 345                 350

Tyr Ala Lys Phe Gly Gly Ile Met Leu Arg Ser Lys Glu Ser Phe Ile
            355                 360                 365

Thr Ser Phe Ile Ser Pro Thr Val Val Gln Gly Val Asp Val Tyr Thr
        370                 375                 380

Leu Ala Gly Lys Ile Arg Ile Glu Ser Glu Thr Pro Val Ser Glu Val
385                 390                 395                 400

Leu Leu Phe Asp Leu Ala Gly Arg Met Val Leu Arg Gln Thr Ile Asp
                405                 410                 415

Asn Lys Ile Tyr Ser Asp Ile Asp Thr Asn Gly Leu Lys Arg Ser Gly
            420                 425                 430

Ile Tyr Val Val Ser Val Arg Leu Ser Ser Gly Gln Val Phe Ser His
            435                 440                 445

Lys Val Gln Val
        450

<210> SEQ ID NO 101
<211> LENGTH: 614
<212> TYPE: PRT
<213> ORGANISM: Porphyromonas gingivalis

<400> SEQUENCE: 101

Pro Tyr Asn Val Gln Ser Ile Ser Asn Lys Thr Ile Lys Lys Gln Met
1               5                   10                  15

Glu Asn Leu Lys Asn Ile Gln Pro Arg Glu Asp Phe Asn Trp Glu Glu
            20                  25                  30

Phe Glu Ala Gly Gly Val His Ala Ala Val Ser Arg Gln Glu Gln Glu
        35                  40                  45

Ala Ala Tyr Asp Lys Thr Leu Asn Thr Ile Lys Glu Lys Glu Val Val
    50                  55                  60

Met Gly Arg Val Thr Ala Ile Asn Lys Arg Glu Val Val Ile Asn Val
65                  70                  75                  80

Gly Tyr Lys Ser Glu Gly Val Val Pro Ala Thr Glu Phe Arg Tyr Asn
                85                  90                  95

Pro Glu Leu Lys Val Gly Asp Glu Val Glu Val Tyr Ile Glu Asn Gln
            100                 105                 110

Glu Asp Lys Lys Gly Gln Leu Val Leu Ser His Arg Lys Gly Arg Ala
        115                 120                 125

Ala Arg Ser Trp Glu Arg Val Asn Glu Ala Leu Glu Lys Asp Glu Ile
    130                 135                 140

Val Lys Gly Tyr Val Lys Cys Arg Thr Lys Gly Gly Met Ile Val Asp
145                 150                 155                 160

Val Phe Gly Ile Glu Ala Phe Leu Pro Gly Ser Gln Ile Asp Val Arg
                165                 170                 175

Pro Ile Arg Asp Tyr Asp Ala Phe Val Glu Lys Thr Met Glu Phe Lys
```

-continued

```
                180                 185                 190
Ile Val Lys Ile Asn Gln Glu Tyr Lys Asn Val Val Ser His Lys
            195                 200                 205
Val Leu Ile Glu Ala Glu Leu Glu Gln Gln Lys Lys Glu Ile Ile Gly
    210                 215                 220
Lys Leu Glu Lys Gly Gln Val Leu Glu Gly Ile Val Lys Asn Ile Thr
225                 230                 235                 240
Ser Tyr Gly Val Phe Ile Asp Leu Gly Gly Val Asp Gly Leu Ile His
                245                 250                 255
Ile Thr Asp Leu Ser Trp Gly Arg Val Ala His Pro Glu Glu Ile Val
            260                 265                 270
Gln Leu Asp Gln Lys Ile Asn Val Val Ile Leu Asp Phe Asp Glu Asp
        275                 280                 285
Arg Lys Arg Ile Ala Leu Gly Leu Lys Gln Leu Met Pro His Pro Trp
    290                 295                 300
Asp Ala Leu Asp Ser Glu Leu Lys Val Gly Asp Lys Val Lys Gly Lys
305                 310                 315                 320
Val Val Val Met Ala Asp Tyr Gly Ala Phe Val Glu Ile Ala Gln Gly
                325                 330                 335
Val Glu Gly Leu Ile His Val Ser Glu Met Ser Trp Thr Gln His Leu
            340                 345                 350
Arg Ser Ala Gln Asp Phe Leu His Val Gly Asp Glu Val Glu Ala Val
        355                 360                 365
Ile Leu Thr Leu Asp Arg Glu Glu Arg Lys Met Ser Leu Gly Leu Lys
    370                 375                 380
Gln Leu Lys Pro Asp Pro Trp Ala Asp Ile Glu Thr Arg Phe Pro Val
385                 390                 395                 400
Gly Ser Arg His His Ala Arg Val Arg Asn Phe Thr Asn Phe Gly Val
                405                 410                 415
Phe Val Glu Ile Glu Glu Gly Val Asp Gly Leu Ile His Ile Ser Asp
            420                 425                 430
Leu Ser Trp Thr Lys Lys Ile Lys His Pro Ser Glu Phe Thr Glu Val
        435                 440                 445
Gly Ala Asp Ile Glu Val Gln Val Ile Glu Ile Asp Lys Glu Asn Arg
    450                 455                 460
Arg Leu Ser Leu Gly His Lys Gln Leu Glu Glu Asn Pro Trp Asp Val
465                 470                 475                 480
Phe Glu Thr Val Phe Thr Val Gly Ser Ile His Glu Gly Thr Val Ile
                485                 490                 495
Glu Val Met Asp Lys Gly Ala Val Val Ser Leu Pro Tyr Gly Val Glu
            500                 505                 510
Gly Phe Ala Thr Pro Lys His Met Val Lys Glu Asp Gly Ser Gln Ala
        515                 520                 525
Val Leu Glu Glu Lys Leu Pro Phe Lys Val Ile Glu Phe Asn Lys Asp
    530                 535                 540
Ala Lys Arg Ile Ile Val Ser His Ser Arg Val Phe Glu Asp Glu Gln
545                 550                 555                 560
Lys Met Ala Gln Arg Glu Ala Asn Ala Glu Arg Lys Ala Glu Ala Lys
                565                 570                 575
Ala Ala Gln Lys Glu Ala Ala Glu Ala Ala Asn Pro Ala Gln Ala
            580                 585                 590
Val Glu Lys Ala Thr Leu Gly Asp Leu Gly Glu Leu Ala Ala Leu Lys
    595                 600                 605
```

```
Glu Lys Leu Ser Glu Asn
            610

<210> SEQ ID NO 102
<211> LENGTH: 563
<212> TYPE: PRT
<213> ORGANISM: Porphyromonas gingivalis

<400> SEQUENCE: 102

Ser Leu Ile Asn Asn Ser Arg Asp Trp Arg Ala Pro Val Arg Leu Ser
1               5                   10                  15

Leu Lys Lys Lys Thr Lys Thr Met Lys Thr Lys Val Leu Arg Lys Phe
            20                  25                  30

Val Val Ala Ala Phe Ala Val Ala Thr Leu Cys Pro Leu Ala Gln Ala
        35                  40                  45

Gln Thr Met Gly Gly Asp Asp Val Lys Val Val Gln Tyr Asn Gln Glu
    50                  55                  60

Lys Leu Val Gln Thr Arg Met Ser Val Ala Asp Asn Gly Trp Ile Tyr
65                  70                  75                  80

Val Met Thr His Ser Gly Tyr Asp Thr Gly Asn Ser Asn Val Lys Ile
                85                  90                  95

Phe Arg Ser Lys Asp Gln Gly Ala Thr Tyr Gln Lys Leu Arg Asp Trp
            100                 105                 110

Asp Pro Ser Asp Asp Tyr Gln Phe Gln Asp Phe Asp Ile Val Val Thr
        115                 120                 125

Gly Lys Asn Glu Ser Asp Ile Lys Ile Trp Ser Val Glu Leu Met Asn
    130                 135                 140

Lys Pro Gly Gly Tyr Lys Ser Arg Val Ala Val Phe Ser Arg Asp Ala
145                 150                 155                 160

Asn Ala Gln Asn Ala Lys Leu Val Tyr Lys Glu Asp Phe Ser Asn Val
                165                 170                 175

Gln Leu Tyr Asp Val Asp Ile Ala Ser Asn Tyr Arg Ser Pro Ser Ser
            180                 185                 190

Leu Asn Asn Gly Gly Asn Pro Phe Ala Leu Ala Phe Ala Tyr Thr Gly
        195                 200                 205

Phe Asn Asn Thr His Lys Ile Ser Phe Val Asp Tyr Val Phe Ser Leu
    210                 215                 220

Asn Gly Gly Gln Asn Phe Asn Lys Asn Leu Leu Phe Ser Gln Asp Gly
225                 230                 235                 240

Glu Lys Lys Ile Asp Lys Val Asp Leu Ser Leu Gly Ser Thr Ser Glu
                245                 250                 255

Ser Met Gly His Asn Ala Trp Pro Leu Met Gly Val Val Phe Glu Met
            260                 265                 270

Asn Lys Gln Gly Gly Lys Ser Asp Ile Gly Phe Leu Ser Asn Phe Val
        275                 280                 285

Asp Asn Asp Pro Glu Phe Gln Trp Ser Gly Pro Ile Lys Val Ser Glu
    290                 295                 300

Ser Asp Met Ser Phe Ser Pro Lys Ile Gln Met Leu Leu Asp Glu Asp
305                 310                 315                 320

Asn Asn Thr Ile Asn Gly Glu Ser Cys His Asn Phe Met Ile Thr Tyr
                325                 330                 335

Ser Asp Tyr Asp Ser Glu Tyr Ser Asp Trp Asp Ile Arg Tyr Val Tyr
            340                 345                 350

Pro Lys Lys Ser Phe Lys Tyr Glu Lys Gly Lys Thr Pro Thr Met Asp
        355                 360                 365
```

```
Asp Leu Val Glu Ala Phe Leu Thr Ala Ser Tyr Gln Ser Glu Thr Asn
        370                 375                 380

Ser Gly Leu Gly Tyr Asp Lys Asn Ala Asn His Tyr Leu Ile Thr Tyr
385                 390                 395                 400

Ala Lys Lys Glu Glu Asn Gly Thr Asn Thr Leu Lys Tyr Arg Trp Ala
                405                 410                 415

Asn Tyr Asp Lys Ile His Asn Lys Asp Leu Trp Ser Asp Thr Phe Thr
            420                 425                 430

Tyr Thr Ser Ser Ala Asn Ala Leu Tyr Thr Pro Gln Val Asp Ile Asn
        435                 440                 445

Pro Thr Lys Gly Leu Val Cys Trp Ser Trp Val Glu Tyr Leu Pro Gly
    450                 455                 460

Lys Arg Ile Val Trp Ser Asp Thr Gln Trp Thr His Ala Asn Gly Val
465                 470                 475                 480

Glu Asp Ile Val Met Gln Gly Ser Met Lys Leu Tyr Pro Asn Pro
                485                 490                 495

Ala Gln Glu Tyr Ala Val Ile Ser Leu Pro Thr Ala Ala Asn Cys Lys
                500                 505                 510

Ala Val Val Tyr Asp Met Gln Gly Arg Val Val Ala Glu Ala Ser Phe
            515                 520                 525

Ser Gly Asn Glu Tyr Arg Leu Asn Val Gln His Leu Ala Lys Gly Thr
    530                 535                 540

Tyr Ile Leu Lys Val Val Ser Asp Thr Glu Arg Phe Val Glu Lys Leu
545                 550                 555                 560

Ile Val Glu

<210> SEQ ID NO 103
<211> LENGTH: 1162
<212> TYPE: PRT
<213> ORGANISM: Porphyromonas gingivalis

<400> SEQUENCE: 103

Ala Ile Ser Gln Met Lys Arg Ile Leu Pro Ile Val Ala Phe Leu Ser
1               5                   10                  15

Leu Phe Leu Ala Leu Ala Leu Pro Ala Lys Ala Gln Arg Ala Met Gly
                20                  25                  30

Lys Thr Ala Asp Arg Ser Leu Met Ala Ser Gly His Trp Val Lys Ile
            35                  40                  45

Arg Val Asp Ala Ser Gly Val Tyr Arg Leu Thr Asp Glu Gln Leu Arg
        50                  55                  60

Ala Asn Gly Phe Ser Asp Pro Ser Lys Val Gly Val Phe Gly Tyr Gly
65                  70                  75                  80

Gly Gly Val Leu Pro Glu Asp Leu Ser Arg Ile Thr Thr Asp Asp Leu
                85                  90                  95

Pro Pro Val Pro Val Leu Arg Gln Gly Asn Ala Leu Tyr Phe Tyr Ala
            100                 105                 110

Val Gly Pro Val Thr Trp Phe Tyr Asn Pro Ala Lys Thr Thr Met Glu
        115                 120                 125

His Thr Val Asn Thr Tyr Ser Thr His Gly Tyr Tyr Phe Leu Ser Asp
    130                 135                 140

Ala Ala Gly Ala Pro Leu Gln Met Ser Gln Tyr Thr Gly Gly Gly Ala
145                 150                 155                 160

Ser Ala Glu Ala Leu Ile Asp Tyr Tyr Asp Glu Leu Met Leu His Glu
                165                 170                 175

Gln Glu Leu Tyr Ser Pro Lys Glu Ser Gly Arg Asp Leu Tyr Gly Glu
```

-continued

```
                180                 185                 190
Ser Phe Ser Ala Val Asn Thr Arg Thr Val Lys Phe Pro Leu Arg Gly
            195                 200                 205

Asn Thr Arg Ser Ser Gly Glu Leu Gly Thr Val Phe Ser Tyr Ile Ala
        210                 215                 220

Lys Ala Arg Ser Ala Gly Gly Arg Glu Met Ser Leu Ser Ala Asn
225                 230                 235                 240

Gly Ile Leu Ile Phe Ser Asp Pro Phe Ser Met Thr Ser Asn Glu Val
                245                 250                 255

Ser Asn Ser Tyr Leu Ala Gly Lys Lys Arg Arg Leu Tyr His Ser Thr
            260                 265                 270

Pro Met Asn Ser Leu Val Asn Glu Leu Arg Leu Asp Ala Asn Tyr Ser
        275                 280                 285

Met Thr Gly Asp Ala Val Asn Leu Asp Phe Ile Glu Val Ala Thr Gln
    290                 295                 300

Asn Asp Leu Arg Tyr Asp Gly Ala Pro Met His Ile Arg Arg Phe Ser
305                 310                 315                 320

Asn Leu Pro Val Leu Gly Gly Glu Ser Cys Arg Phe Val Ile Ser Glu
                325                 330                 335

Val Pro Glu Ser Leu Val Val Leu Gln Ala Asn Ser Ser Leu Thr Ala
            340                 345                 350

Ser Leu Val Pro Val Lys Thr Val Gly Asp Lys Thr Ile Glu Phe Val
        355                 360                 365

Ala Pro Pro Lys Gly Gln Asp Arg Arg Thr Ile Asn Thr Phe Tyr Ala
    370                 375                 380

Val Asp Leu Ser Gln Ala Ser Ala Pro Glu Ile Leu Gly Ala Val Pro
385                 390                 395                 400

Asn Gln Asn Leu His Gly Glu Ile Pro Asp Leu Ile Ile Val Ser
                405                 410                 415

Thr Gln Ala Leu Leu Glu Ala Asp Arg Leu Ala Thr Tyr Arg Arg
            420                 425                 430

Glu Lys Asn Gly Leu Lys Val Leu Val Val Leu Gln Glu Gln Val Phe
        435                 440                 445

Asn Glu Phe Ser Gly Gly Thr Pro Asp Ala Thr Ala Tyr Arg Leu Phe
    450                 455                 460

Ala Lys Met Phe Tyr Asp Arg Trp Lys Ala Asn Ala Pro Val Gly Glu
465                 470                 475                 480

Thr Phe Pro Met Gln Met Leu Leu Phe Gly Asp Gly Ala His Asp Asn
                485                 490                 495

Arg Lys Val Ser Val Ala Trp Gln Lys Pro Tyr Leu Gln Gln Thr Glu
            500                 505                 510

Phe Leu Leu Thr Phe Gln Ala Val Asn Ser Thr Asn Val Asn Ser Tyr
        515                 520                 525

Val Thr Asp Asp Tyr Phe Gly Leu Leu Asp Gln Pro Ala Ser Val
    530                 535                 540

Asn Ile Gly Trp Arg Asn Tyr Asn Met Ala Val Gly Arg Phe Pro Val
545                 550                 555                 560

Arg Thr Pro Ala Glu Ala Arg Ile Ala Val Asp Lys Thr Ile Arg Tyr
                565                 570                 575

Glu Glu Asp Arg Glu Ser Gly Ala Trp Arg Ile Arg Ala Cys Phe Ala
            580                 585                 590

Ala Asp Asn Gly Asp Lys His Ala Thr Glu Thr Ser Arg Leu Ile Asp
        595                 600                 605
```

-continued

Thr Val Lys Arg Tyr Ala Pro Ala Ile Met Pro Val Arg Ala Phe Gln
610                 615                 620

Asp Val Tyr Pro His Val Ile Glu Asn Gly Leu His Ser Ile Pro Gly
625                 630                 635                 640

Ala Lys Lys Met Leu Glu Thr Leu Gln Ser Gly Ile Ile Leu Leu
            645                 650                 655

Asn Tyr Ala Gly His Gly Gly Pro Ala Gly Trp Ser Asp Glu His Leu
            660                 665                 670

Leu Thr Leu Asn Asp Ile His Lys Phe Asn Tyr Lys His Met Pro Ile
            675                 680                 685

Trp Ile Thr Ala Thr Cys Asp Phe Ala Asn Tyr Asp Ser Gln Thr Thr
            690                 695                 700

Ser Ala Gly Glu Glu Val Phe Leu His Glu Lys Ser Gly Thr Pro Ile
705                 710                 715                 720

Met Phe Ser Thr Thr Arg Val Val Tyr Asn Thr Gln Asn Glu Lys Ile
                725                 730                 735

Asn Gly Phe Met Leu Arg Arg Met Phe Glu Lys Ala Lys Asp Gly Arg
            740                 745                 750

Tyr Arg Thr Met Gly Glu Ile Ile Arg Ser Ala Lys Gln Gly Met Leu
            755                 760                 765

Ser Thr Val Phe Pro Asp Ser Ile Asn Gln Leu Ser Phe Phe Leu Met
770                 775                 780

Gly Asp Pro Ser Val Arg Met Asn Leu Pro Thr His Lys Val Gln Leu
785                 790                 795                 800

Thr Ala Ile Asn Gly Gln Asp Pro Glu Gly Gln Gly Tyr Gly Thr Ile Met
            805                 810                 815

Leu Lys Ser Leu Glu Arg Val Ala Leu Lys Gly Lys Val Thr Asp Glu
            820                 825                 830

Lys Gly Thr Phe Asp Glu Thr Phe Ser Gly Lys Val Phe Leu Thr Val
            835                 840                 845

Phe Asp Gly Arg Lys Lys Met Thr Ala Leu Glu Glu Glu Gly Asn Asp
850                 855                 860

Leu Ser Leu Val Tyr Tyr Asp Tyr Pro Asn Val Met Tyr Ala Gly Ile
865                 870                 875                 880

Ala Glu Val Lys Asp Gly Leu Phe Glu Thr Ser Phe Ile Val Pro Lys
            885                 890                 895

Asp Val Asn Tyr Ser Glu His Glu Gly Arg Ile Asn Leu Tyr Ala Tyr
            900                 905                 910

Asn Glu Ser Thr Lys Ala Glu Ala Met Gly Val Asp Phe Ser Ile Arg
            915                 920                 925

Val Gln Pro Gly Ile Pro Asp Glu Val Thr Glu Asp Asn Thr Pro Pro
930                 935                 940

Glu Ile Ile Ser Cys Phe Leu Asn Asp Ser Thr Phe Arg Ser Gly Asp
945                 950                 955                 960

Glu Val Asn Pro Thr Pro Leu Phe Met Ala Glu Val Phe Asp Leu Asn
                965                 970                 975

Gly Ile Asn Ile Thr Gly Ser Gly Val Gly His Asp Ile Thr Leu Cys
            980                 985                 990

Ile Asp Gly Arg Ala Asp Leu Thr  Tyr Asn Leu Asn Ala  Tyr Phe Thr
            995                 1000                1005

Ser Ser  Ala Thr Asp Ala Gly  Val Gly Thr Ile Leu  Phe Met Ile
    1010                1015                1020

Pro Ala  Leu Ala Glu Gly Asp  His Thr Ala Arg Leu  Thr Val Trp
    1025                1030                1035

```
Asp Ile Phe Asn Asn Ala Val His His Asp Phe Ser Phe Arg Val
    1040                1045                1050

Val Asp Gly Ile Ala Pro Asp Val Ala Asp Val Ile Leu Phe Pro
    1055                1060                1065

Asn Pro Val Arg Glu Ser Ala Thr Phe Arg Ile Phe His Asn Arg
    1070                1075                1080

Pro Gly Ser Asp Leu Asn Val Ala Val Glu Ile Tyr Asp Phe Thr
    1085                1090                1095

Gly Arg Leu Val Asn Ser Leu Pro Val Lys Thr Tyr Ser Ser Ser
    1100                1105                1110

Tyr Gly Glu Pro Ile Glu Ile Lys Trp Asp Leu Thr Ser Lys Tyr
    1115                1120                1125

Gly Val Lys Ile Gly Asn Gly Phe Tyr Leu Tyr Arg Cys Val Val
    1130                1135                1140

Asn Ser Pro Gly Gly Gln Thr Ala Ser Met Ala Lys Lys Met Ile
    1145                1150                1155

Val Val Gly Gln
    1160

<210> SEQ ID NO 104
<211> LENGTH: 563
<212> TYPE: PRT
<213> ORGANISM: Porphyromonas gingivalis

<400> SEQUENCE: 104

His His Lys Thr Tyr Gln Thr Met Lys Lys Leu Leu Gln Ala Lys Ala
1               5                   10                  15

Leu Ile Leu Ala Leu Gly Leu Phe Gln Leu Pro Ala Ile Ala Gln Thr
            20                  25                  30

Gln Met Gln Ala Asp Arg Thr Asn Gly Gln Phe Ala Thr Glu Glu Met
        35                  40                  45

Gln Arg Ala Phe Gln Glu Thr Asn Pro Pro Ala Gly Pro Val Arg Ala
    50                  55                  60

Ile Ala Glu Tyr Glu Arg Ser Ala Ala Val Leu Val Arg Tyr Pro Phe
65                  70                  75                  80

Gly Ile Pro Met Glu Leu Ile Lys Glu Leu Ala Lys Asn Asp Lys Val
                85                  90                  95

Ile Thr Ile Val Ala Ser Glu Ser Gln Lys Asn Thr Val Ile Thr Gln
            100                 105                 110

Tyr Thr Gln Ser Gly Val Asn Leu Ser Asn Cys Asp Phe Ile Ile Ala
        115                 120                 125

Lys Thr Asp Ser Tyr Trp Thr Arg Asp Tyr Thr Gly Trp Phe Ala Met
    130                 135                 140

Tyr Asp Thr Asn Lys Val Gly Leu Val Asp Phe Ile Tyr Asn Arg Pro
145                 150                 155                 160

Arg Pro Asn Asp Asp Glu Phe Pro Lys Tyr Glu Ala Gln Tyr Leu Gly
                165                 170                 175

Ile Glu Met Phe Gly Met Lys Leu Lys Gln Thr Gly Gly Asn Tyr Met
            180                 185                 190

Thr Asp Gly Tyr Gly Ser Ala Val Gln Ser His Ile Ala Tyr Thr Glu
        195                 200                 205

Asn Ser Ser Leu Ser Gln Ala Gln Val Asn Gly Lys Met Lys Asp Tyr
    210                 215                 220

Leu Gly Ile Thr His His Asp Val Val Gln Asp Pro Asn Gly Glu Tyr
225                 230                 235                 240
```

```
Ile Asn His Val Asp Cys Trp Gly Lys Tyr Leu Ala Pro Asn Lys Ile
            245                 250                 255

Leu Ile Arg Lys Val Pro Asp Asn His Pro Gln His Gln Ala Leu Glu
            260                 265                 270

Asp Met Ala Ala Tyr Phe Ala Ala Gln Thr Cys Ala Trp Gly Thr Lys
            275                 280                 285

Tyr Glu Val Tyr Arg Ala Leu Ala Thr Asn Glu Gln Pro Tyr Thr Asn
            290                 295                 300

Ser Leu Ile Leu Asn Asn Arg Val Phe Val Pro Val Asn Gly Pro Ala
305                 310                 315                 320

Ser Val Asp Asn Asp Ala Leu Asn Val Tyr Lys Thr Ala Met Pro Gly
                325                 330                 335

Tyr Glu Ile Ile Gly Val Lys Gly Ala Ser Gly Thr Pro Trp Leu Gly
                340                 345                 350

Thr Asp Ala Leu His Cys Arg Thr His Glu Val Ala Asp Lys Gly Tyr
                355                 360                 365

Leu Tyr Ile Lys His Tyr Pro Ile Leu Gly Glu Gln Ala Gly Pro Asp
            370                 375                 380

Tyr Lys Ile Glu Ala Asp Val Val Ser Cys Ala Asn Ala Thr Ile Ser
385                 390                 395                 400

Pro Val Gln Cys Tyr Tyr Arg Ile Asn Gly Ser Gly Ser Phe Lys Ala
                405                 410                 415

Ala Asp Met Thr Met Glu Ser Thr Gly His Tyr Thr Tyr Ser Phe Thr
                420                 425                 430

Gly Leu Asn Lys Asn Asp Lys Val Glu Tyr Tyr Ile Ser Ala Ala Asp
            435                 440                 445

Asn Ser Gly Arg Lys Glu Thr Tyr Pro Phe Ile Gly Glu Pro Asp Pro
            450                 455                 460

Phe Lys Phe Thr Cys Met Asn Glu Thr Asn Thr Cys Thr Val Thr Gly
465                 470                 475                 480

Ala Ala Lys Ala Leu Arg Ala Trp Phe Asn Ala Gly Arg Ser Glu Leu
                485                 490                 495

Ala Val Ser Val Ser Leu Asn Ile Ala Gly Thr Tyr Arg Ile Lys Leu
                500                 505                 510

Tyr Asn Thr Ala Gly Glu Glu Val Ala Ala Met Thr Lys Glu Leu Val
            515                 520                 525

Ala Gly Thr Ser Val Phe Ser Met Asp Val Tyr Ser Gln Ala Pro Gly
            530                 535                 540

Thr Tyr Val Leu Val Val Glu Gly Asn Gly Ile Arg Glu Thr Met Lys
545                 550                 555                 560

Ile Leu Lys

<210> SEQ ID NO 105
<211> LENGTH: 437
<212> TYPE: PRT
<213> ORGANISM: Porphyromonas gingivalis

<400> SEQUENCE: 105

Thr Thr Asn Arg Lys Pro Asn Thr Asn Met Lys Leu Ser Ser Lys Lys
1               5                   10                  15

Ile Leu Ala Ile Ile Ala Leu Leu Thr Met Gly His Ala Val Gln Ala
            20                  25                  30

Gln Phe Val Pro Ala Pro Thr Thr Gly Ile Arg Met Ser Val Thr Thr
        35                  40                  45
```

-continued

| | | | | | | | | | | | | | | |
|---|---|---|---|---|---|---|---|---|---|---|---|---|---|---|
|Thr|Lys|Ala|Val|Gly|Glu|Lys|Ile|Glu|Leu|Leu|Val|His|Ser|Ile|Glu|
| |50| | | |55| | | |60| | | | | | |
|Lys|Lys|Gly|Ile|Trp|Ile|Asp|Leu|Asn|Gly|Asp|Ala|Thr|Tyr|Gln|Gln|
|65| | | | |70| | | |75| | | | |80| |
|Gly|Glu|Glu|Ile|Thr|Val|Phe|Asp|Glu|Ala|Tyr|His|Glu|Tyr|Thr|Ile|
| | | | |85| | | |90| | | | |95| | |
|Gly|Thr|Gln|Thr|Leu|Thr|Ile|Tyr|Gly|Asn|Thr|Thr|Arg|Leu|Gly|Cys|
| | |100| | | | |105| | | | |110| | | |
|Arg|Ser|Thr|Gly|Ala|Thr|Ala|Val|Asp|Val|Thr|Lys|Asn|Pro|Asn|Leu|
| | |115| | | |120| | | | |125| | | | |
|Thr|Tyr|Leu|Ala|Cys|Pro|Lys|Asn|Asn|Leu|Lys|Ser|Leu|Asp|Leu|Thr|
| |130| | | | |135| | | |140| | | | | |
|Gln|Asn|Pro|Lys|Leu|Leu|Arg|Val|Trp|Cys|Asp|Ser|Asn|Glu|Ile|Glu|
|145| | | | |150| | | |155| | | | |160| |
|Ser|Leu|Asp|Leu|Ser|Gly|Asn|Pro|Ala|Leu|Ile|Ile|Leu|Gly|Cys|Asp|
| | | | |165| | | |170| | | | |175| | |
|Arg|Asn|Lys|Leu|Thr|Glu|Leu|Lys|Thr|Asp|Asn|Asn|Pro|Lys|Leu|Ala|
| | | |180| | | | |185| | | | |190| | |
|Ser|Leu|Trp|Cys|Ser|Asp|Asn|Leu|Thr|Glu|Leu|Glu|Leu|Ser|Ala|
| | |195| | | | |200| | | | |205| | | |
|Asn|Pro|Arg|Leu|Asn|Asp|Leu|Trp|Cys|Phe|Gly|Asn|Arg|Ile|Thr|Lys|
| |210| | | | |215| | | | |220| | | | |
|Leu|Asp|Leu|Ser|Ala|Asn|Pro|Leu|Leu|Val|Thr|Leu|Trp|Cys|Ser|Asp|
|225| | | | |230| | | |235| | | | |240| |
|Asn|Glu|Leu|Ser|Thr|Leu|Asp|Leu|Ser|Lys|Asn|Ser|Asp|Val|Ala|Tyr|
| | | | |245| | | |250| | | | |255| | |
|Leu|Trp|Cys|Ser|Ser|Asn|Lys|Leu|Thr|Ser|Leu|Asn|Leu|Ser|Gly|Val|
| | |260| | | | |265| | | | |270| | | |
|Lys|Gly|Leu|Ser|Val|Leu|Val|Cys|His|Ser|Asn|Gln|Ile|Ala|Gly|Glu|
| | |275| | | | |280| | | | |285| | | |
|Glu|Met|Thr|Lys|Val|Val|Asn|Ala|Leu|Pro|Thr|Leu|Ser|Pro|Gly|Ala|
| |290| | | | |295| | | |300| | | | | |
|Gly|Ala|Gln|Ser|Lys|Phe|Val|Val|Asp|Leu|Lys|Asp|Thr|Asp|Glu|
|305| | | | |310| | | | |315| | | | |320|
|Lys|Asn|Ile|Cys|Thr|Val|Lys|Asp|Val|Glu|Lys|Ala|Lys|Ser|Lys|Asn|
| | | |325| | | | |330| | | | |335| | |
|Trp|Arg|Val|Phe|Asp|Phe|Asn|Gly|Asp|Ser|Asp|Asn|Met|Leu|Pro|Tyr|
| | |340| | | | |345| | | | |350| | | |
|Glu|Gly|Ser|Pro|Thr|Ser|Asn|Leu|Ala|Val|Asp|Ala|Pro|Thr|Val|Arg|
| | |355| | | | |360| | | | |365| | | |
|Ile|Tyr|Pro|Asn|Pro|Val|Gly|Arg|Tyr|Ala|Leu|Val|Glu|Ile|Pro|Glu|
| |370| | | | |375| | | | |380| | | | |
|Ser|Leu|Leu|Gly|Gln|Glu|Ala|Ala|Leu|Tyr|Asp|Met|Asn|Gly|Val|Lys|
|385| | | | |390| | | |395| | | | |400| |
|Val|Tyr|Ser|Phe|Ala|Val|Glu|Ser|Leu|Arg|Gln|Asn|Ile|Asp|Leu|Thr|
| | | | |405| | | |410| | | | |415| | |
|His|Leu|Pro|Asp|Gly|Thr|Tyr|Phe|Phe|Arg|Leu|Asp|Asn|Tyr|Thr|Thr|
| | |420| | | | |425| | | | |430| | | |
|Lys|Leu|Ile|Lys|Gln|
| | |435| | | | | | | | | | | | | |

<210> SEQ ID NO 106
<211> LENGTH: 318
<212> TYPE: PRT
<213> ORGANISM: Porphyromonas gingivalis

<400> SEQUENCE: 106

```
Asn His Leu Lys Thr Asn Ile Lys Met Arg Lys Thr Ile Ile Phe Cys
1               5                   10                  15

Leu Leu Leu Ala Leu Phe Gly Cys Ser Trp Ala Gln Glu Arg Val Asp
            20                  25                  30

Glu Lys Val Phe Ser Ala Gly Thr Ser Ile Phe Arg Gly Ile Leu Glu
        35                  40                  45

Lys Val Lys Ala Pro Leu Met Tyr Gly Asp Arg Glu Val Trp Gly Met
    50                  55                  60

Ala Arg Ala Ser Glu Asp Phe Phe Ile Leu Pro Val Thr Asp Asp
65                  70                  75                  80

Leu Thr Pro Val Leu Phe Tyr Asn Arg Leu Thr Asn Glu Pro Cys Phe
                85                  90                  95

Val Ser Asp Gln Gly Ile Thr Glu Tyr Phe Lys Phe Ala Gln Glu Gly
            100                 105                 110

Asp Tyr Ile Glu Val Glu Gly Ser Val Phe Met Ala Asn Leu Leu
        115                 120                 125

Tyr Tyr Arg Phe Phe Pro Thr Arg Ile Thr Ser Tyr Asn Ala Pro Ile
130                 135                 140

Glu Gly Val Val Ser Lys Thr Gly Asn Pro Ala Phe Thr Ile Pro Met
145                 150                 155                 160

Leu Pro Gly Val Ser Asp Cys Ile Glu Ile Ser Asn Asn Arg Lys Val
                165                 170                 175

Phe Leu Thr Asn Gln Leu Gly Val Val Asn Ile Thr Asp Gly Met Glu
            180                 185                 190

Pro Pro Ile Ile Ala Gly Val Ser Ala Ser Tyr Gly Ser Ser Val Arg
        195                 200                 205

Val Tyr Gly His Val Ser Gln Arg Trp Asp Ile Gly His Cys Tyr
    210                 215                 220

Leu Asp Ile Tyr Pro Thr Asn Cys Tyr Pro Leu Ser Thr Lys Pro Val
225                 230                 235                 240

Ala Gly Asp Asp Glu Val Phe Val Lys Gln Gln Gly Arg Gln Ile Glu
                245                 250                 255

Ile Asp Ser Asn Ser Pro Ile Val Gln Val Val Tyr Asp Leu Glu
            260                 265                 270

Gly Lys Ser Val Phe Arg Lys Arg Met Thr Glu Asn Ala Tyr Thr Leu
        275                 280                 285

Ser Phe Arg Ala Pro Met Leu Gly Phe Met Thr Ile Met Ile Glu Thr
290                 295                 300

Gln Asn Ser Ile Ile Asn Lys Lys Leu Asn Val Thr Gln Leu
305                 310                 315
```

<210> SEQ ID NO 107
<211> LENGTH: 461
<212> TYPE: PRT
<213> ORGANISM: Porphyromonas gingivalis

<400> SEQUENCE: 107

```
Arg Arg Ala Val Lys Ile Arg Ser Pro Pro His Ile His Ser Leu Phe
1               5                   10                  15

Val Arg Lys Cys Leu Phe Ser Asp Phe Lys Tyr Leu Tyr Leu Ser Arg
            20                  25                  30

Lys Ile Thr Gln Glu Arg Leu Gly Arg Leu Ser Ile Arg Leu Lys Ser
        35                  40                  45
```

```
Tyr Asn Pro Ile Ile Ile Glu Met Lys Lys Thr Thr Ile Ile Ser
 50                  55                  60

Leu Ile Val Phe Gly Ala Phe Ala Ala Val Gly Gln Thr Lys Asp
 65                  70                  75                  80

Asn Ser Ser Tyr Lys Pro Phe Ser Lys Glu Asp Ile Ala Gly Val
                 85                  90                  95

Tyr Ser Leu Pro Thr Gln Asn Arg Ala Gln Lys Asp Asn Ala Glu Trp
                100                 105                 110

Leu Leu Thr Ala Thr Val Ser Thr Asn Gln Ser Ala Asp Thr His Phe
                115                 120                 125

Ile Phe Asp Glu Asn Asn Arg Tyr Ile Ala Arg Asp Ile Lys Ala Asn
                130                 135                 140

Gly Val Arg Lys Ser Thr Asp Ser Ile Tyr Tyr Asp Ala Asn Gly Arg
145                 150                 155                 160

Ile Ser His Val Asp Leu Tyr Ile Ser Phe Ser Gly Gly Glu Pro Ala
                165                 170                 175

Leu Asp Thr Arg Phe Lys Tyr Thr Tyr Asp Asp Glu Gly Lys Met Thr
                180                 185                 190

Val Arg Glu Val Phe Met Leu Val Met Asp Pro Asn Thr Pro Ile Ser
                195                 200                 205

Arg Leu Glu Tyr His Tyr Asp Ala Gln Gly Arg Leu Thr His Trp Ile
                210                 215                 220

Ser Phe Ala Phe Gly Ala Glu Ser Gln Lys Asn Thr Tyr His Tyr Asn
225                 230                 235                 240

Glu Lys Gly Leu Leu Val Ser Glu Val Leu Ser Asn Ala Met Gly Thr
                245                 250                 255

Thr Tyr Ser Asp Thr Gly Lys Thr Glu Tyr Ser Tyr Asp Asp Ala Asp
                260                 265                 270

Asn Met Val Lys Ala Glu Tyr Phe Val Gln Gln Gly Lys Ala Trp
                275                 280                 285

Gln Val Leu Lys Arg Glu Glu Tyr Thr Tyr Glu Asp Asn Ile Cys Ile
                290                 295                 300

Gln Tyr Leu Ala Ile Asn Gly Thr Asp Thr Lys Val Tyr Lys Arg Asp
305                 310                 315                 320

Ile Glu Ser Asp Lys Ser Ile Ser Ala Asn Val Ile Asp Ile Pro Ser
                325                 330                 335

Met Pro Glu Gln Thr Trp Pro Asn Met Tyr Gly Phe Asn Ala Lys Arg
                340                 345                 350

Leu Lys Glu Thr Tyr Ser Ser Tyr Glu Gly Asp Val Ala Thr Pro Ile
                355                 360                 365

Phe Asp Tyr Ile Tyr Thr Tyr Lys Ala Leu Thr Ser Met Ala Thr Pro
370                 375                 380

Ser Thr Glu Ala Gln Val Ala Val Tyr Leu Asn Pro Ser Thr Asp Arg
385                 390                 395                 400

Leu Val Ile Leu Ala Asn Gly Ile Thr His Leu Ser Met Tyr Asp Leu
                405                 410                 415

Gln Gly Lys Leu Ile Arg Asp Cys Ala Leu Ser Gly Asp Lys Val Glu
                420                 425                 430

Met Gly Val Gly Ser Leu Thr Lys Gly Thr Tyr Leu Leu Lys Val Asn
                435                 440                 445

Thr Asp Gln Gly Ala Phe Val Arg Lys Val Val Ile Arg
450                 455                 460

<210> SEQ ID NO 108
```

```
<211> LENGTH: 451
<212> TYPE: PRT
<213> ORGANISM: Porphyromonas gingivalis

<400> SEQUENCE: 108
```

| | | | | | | | | | | | | | | | |
|---|---|---|---|---|---|---|---|---|---|---|---|---|---|---|---|
| Met | Ala | Lys | Val | Ile | Lys | Thr | Lys | Lys | Gly | Leu | Ala | Leu | Asn | Leu | Lys |
| 1 | | | | 5 | | | | | 10 | | | | | 15 | |
| Gly | Lys | Pro | Leu | Pro | Glu | Met | Leu | Ala | Glu | Pro | Ala | Gln | Ser | Pro | Thr |
| | | | 20 | | | | | 25 | | | | | 30 | | |
| Tyr | Ala | Val | Val | Pro | Asp | Asp | Phe | Glu | Gly | Val | Ile | Pro | Lys | Val | Thr |
| | | | 35 | | | | | 40 | | | | | 45 | | |
| Ala | Arg | Pro | Gly | Asp | Lys | Val | Arg | Ala | Gly | Ser | Ala | Leu | Met | His | His |
| | 50 | | | | | 55 | | | | | 60 | | | | |
| Lys | Ala | Tyr | Pro | Glu | Met | Lys | Phe | Thr | Ser | Pro | Val | Ser | Gly | Glu | Val |
| 65 | | | | | 70 | | | | | 75 | | | | | 80 |
| Ile | Ala | Val | Asn | Arg | Gly | Ala | Lys | Arg | Lys | Val | Leu | Ser | Ile | Glu | Val |
| | | | | 85 | | | | | 90 | | | | | 95 | |
| Lys | Pro | Asp | Gly | Leu | Asn | Glu | Tyr | Glu | Ser | Phe | Pro | Val | Gly | Asp | Pro |
| | | | 100 | | | | | 105 | | | | | 110 | | |
| Ser | Ala | Leu | Ser | Ala | Glu | Gln | Ile | Lys | Glu | Leu | Leu | Leu | Ser | Ser | Gly |
| | | | 115 | | | | | 120 | | | | | 125 | | |
| Met | Trp | Gly | Phe | Ile | Lys | Gln | Arg | Pro | Tyr | Asp | Ile | Val | Ala | Thr | Pro |
| | | | 130 | | | | | 135 | | | | | 140 | | |
| Asp | Ile | Ala | Pro | Arg | Asp | Ile | Tyr | Ile | Thr | Ala | Asn | Phe | Thr | Ala | Pro |
| 145 | | | | | 150 | | | | | 155 | | | | | 160 |
| Leu | Ala | Pro | Asp | Phe | Asp | Phe | Ile | Val | Arg | Gly | Glu | Glu | Arg | Ala | Leu |
| | | | | 165 | | | | | 170 | | | | | 175 | |
| Gln | Thr | Ala | Ile | Asp | Ala | Leu | Ala | Lys | Leu | Thr | Thr | Gly | Lys | Val | Tyr |
| | | | 180 | | | | | 185 | | | | | 190 | | |
| Val | Gly | Leu | Lys | Pro | Gly | Ser | Ser | Leu | Gly | Leu | His | Asn | Ala | Glu | Ile |
| | | | 195 | | | | | 200 | | | | | 205 | | |
| Val | Glu | Val | His | Gly | Pro | His | Pro | Ala | Gly | Asn | Val | Gly | Val | Leu | Ile |
| | | | 210 | | | | | 215 | | | | | 220 | | |
| Asn | His | Thr | Lys | Pro | Ile | Asn | Arg | Gly | Glu | Thr | Val | Trp | Thr | Leu | Lys |
| 225 | | | | | 230 | | | | | 235 | | | | | 240 |
| Ala | Thr | Asp | Leu | Ile | Val | Ile | Gly | Arg | Phe | Leu | Leu | Thr | Gly | Lys | Ala |
| | | | | 245 | | | | | 250 | | | | | 255 | |
| Asp | Phe | Thr | Arg | Met | Ile | Ala | Met | Thr | Gly | Ser | Asp | Ala | Ala | Ala | His |
| | | | 260 | | | | | 265 | | | | | 270 | | |
| Gly | Tyr | Val | Arg | Ile | Met | Pro | Gly | Cys | Asn | Val | Phe | Ala | Ser | Phe | Pro |
| | | | 275 | | | | | 280 | | | | | 285 | | |
| Gly | Arg | Leu | Thr | Ile | Lys | Glu | Ser | His | Glu | Arg | Val | Ile | Asp | Gly | Asn |
| | | | 290 | | | | | 295 | | | | | 300 | | |
| Val | Leu | Thr | Gly | Lys | Lys | Leu | Cys | Glu | Lys | Glu | Pro | Phe | Leu | Ser | Ala |
| 305 | | | | | 310 | | | | | 315 | | | | | 320 |
| Arg | Cys | Asp | Gln | Ile | Thr | Val | Ile | Pro | Glu | Gly | Asp | Val | Asp | Glu |
| | | | | 325 | | | | | 330 | | | | | 335 |
| Leu | Phe | Gly | Trp | Ala | Ala | Pro | Arg | Leu | Asp | Gln | Tyr | Ser | Met | Ser | Arg |
| | | | 340 | | | | | 345 | | | | | 350 | | |
| Ala | Tyr | Phe | Ser | Trp | Leu | Gln | Gly | Lys | Asn | Lys | Glu | Tyr | Val | Leu | Asp |
| | | | 355 | | | | | 360 | | | | | 365 | | |
| Ala | Arg | Ile | Lys | Gly | Gly | Glu | Arg | Ala | Met | Ile | Met | Ser | Asn | Glu | Tyr |
| | | 370 | | | | | 375 | | | | | 380 | | | |
| Asp | Arg | Val | Phe | Pro | Met | Asp | Ile | Tyr | Pro | Glu | Tyr | Leu | Leu | Lys | Ala |
| 385 | | | | | 390 | | | | | 395 | | | | | 400 |

```
Ile Ile Ala Phe Asp Ile Asp Lys Met Glu Asp Leu Gly Ile Tyr Glu
            405                 410                 415

Val Ala Pro Glu Asp Phe Ala Thr Cys Glu Phe Val Asp Thr Ser Lys
            420                 425                 430

Ile Glu Leu Gln Arg Ile Val Arg Glu Gly Leu Asp Met Leu Tyr Lys
            435                 440                 445

Glu Met Asn
    450

<210> SEQ ID NO 109
<211> LENGTH: 195
<212> TYPE: PRT
<213> ORGANISM: Porphyromonas gingivalis

<400> SEQUENCE: 109

Met Asp Lys Val Ser Tyr Ala Leu Gly Leu Ser Ile Gly Asn Asn Phe
1               5                   10                  15

Lys Ser Ser Gly Ile Asp Ser Val Val Met Asp Asp Phe Met Gln Gly
            20                  25                  30

Leu Ser Asp Val Leu Glu Glu Lys Ala Pro Gln Leu Ser Tyr Asp Glu
        35                  40                  45

Ala Lys Arg Glu Ile Glu Ala Tyr Phe Met Asp Leu Gln Gln Lys Ala
    50                  55                  60

Val Lys Leu Asn Lys Glu Ala Gly Glu Glu Phe Leu Lys Ile Asn Ala
65                  70                  75                  80

His Lys Glu Gly Val Thr Thr Leu Pro Ser Gly Leu Gln Tyr Glu Val
                85                  90                  95

Ile Lys Met Gly Glu Gly Pro Lys Pro Thr Leu Ser Asp Thr Val Thr
            100                 105                 110

Cys His Tyr His Gly Thr Leu Ile Asn Gly Ile Val Phe Asp Ser Ser
        115                 120                 125

Met Asp Arg Gly Glu Pro Ala Ser Phe Pro Leu Arg Gly Val Ile Ala
    130                 135                 140

Gly Trp Thr Glu Ile Leu Gln Leu Met Pro Val Gly Ser Lys Trp Lys
145                 150                 155                 160

Val Thr Ile Pro Ser Asp Leu Ala Tyr Gly Asp Arg Gly Ala Gly Glu
                165                 170                 175

His Ile Lys Pro Gly Ser Thr Leu Ile Phe Ile Ile Glu Leu Leu Ser
            180                 185                 190

Ile Asn Lys
    195

<210> SEQ ID NO 110
<211> LENGTH: 273
<212> TYPE: PRT
<213> ORGANISM: Porphyromonas gingivalis

<400> SEQUENCE: 110

Met Lys Lys Ala Leu Leu Ile Gly Ala Ala Leu Leu Gly Ala Val Ser
1               5                   10                  15

Phe Ala Ser Ala Gln Ser Leu Ser Thr Ile Lys Val Gln Asn Asn Ser
            20                  25                  30

Val Gln Gln Pro Arg Glu Glu Ala Thr Ile Gln Val Cys Gly Glu Leu
        35                  40                  45

Ala Glu Gln Val Asp Cys Ile Gly Thr Gly Asn Ser Ala Ile Ile Ala
    50                  55                  60
```

```
Ala Ala Ala Lys Phe Glu Ser Asp Asp Leu Glu Ser Tyr Val Gly Trp
 65                  70                  75                  80

Glu Ile Met Ser Val Asp Phe Pro Gly Tyr Lys Ala Cys Lys Tyr
             85                  90                  95

Thr Ser Ala Val Trp Ala Asp Asp Met Thr Ile Leu Gly Gln Ser Glu
            100                 105                 110

Asp Ser Asp Pro Glu Met Gln Thr Ile Asn Asn Leu Ala Leu Lys Thr
            115                 120                 125

Ser Val Lys Ile Glu Ala Gly Lys Asn Tyr Ile Val Gly Tyr Ile Ala
            130                 135                 140

Asn Thr Ala Gly Gly His Pro Ile Gly Cys Asp Gln Gly Pro Ala Val
145                 150                 155                 160

Asp Gly Tyr Gly Asp Leu Val Ser Ile Ser Glu Asp Gly Gly Ala Thr
            165                 170                 175

Phe Pro Pro Phe Glu Ser Leu His Gln Ala Val Pro Thr Leu Asn Tyr
            180                 185                 190

Asn Ile Tyr Val Val His Leu Lys Lys Gly Glu Gly Val Glu Ala
            195                 200                 205

Val Leu Thr Asn Asp Lys Ala Asn Ala Tyr Val Gln Asn Gly Val Ile
210                 215                 220

Tyr Val Ala Gly Ala Asn Gly Arg Gln Val Ser Leu Phe Asp Met Asn
225                 230                 235                 240

Gly Lys Val Val Tyr Thr Gly Val Ser Glu Thr Ile Ala Ala Pro Gln
            245                 250                 255

Lys Gly Met Tyr Ile Leu Arg Val Gly Ala Lys Ser Ile Lys Leu Ala
            260                 265                 270

Ile
```

<210> SEQ ID NO 111
<211> LENGTH: 554
<212> TYPE: PRT
<213> ORGANISM: Porphyromonas gingivalis

<400> SEQUENCE: 111

```
Met Pro Arg Ile Met Lys Leu Lys Ile Ala Leu Arg Leu Leu Leu Ala
  1               5                  10                  15

Thr Phe Ala Ile Val Leu Phe Ser Pro Leu Ala Lys Ala Gln Met Asp
             20                  25                  30

Ile Gly Gly Asp Asp Val Leu Ile Glu Thr Met Ser Thr Leu Ser Gly
         35                  40                  45

Tyr Ser Glu Asp Phe Tyr Tyr Lys Met Ala Val Ala Asp Asn Gly Trp
 50                  55                  60

Ile Tyr Val Met Leu Asp Phe Ser Arg Ile Tyr Phe Asp Val Arg
 65                  70                  75                  80

Leu Tyr Arg Ser Lys Asp Gly Gly Ala Thr Tyr Gln Lys Leu Gly Ser
             85                  90                  95

Leu Gly Ser Leu Val Pro Tyr Asp Phe Asp Val Ser His Cys Asp Phe
            100                 105                 110

Ile Val Thr Gly Lys Asp Glu Asp Ile Asn Val Trp Thr Val Met
            115                 120                 125

Thr Ala Phe Glu Tyr Val Gly Thr Ile Gly Asn Gly Val Leu Leu
            130                 135                 140

Met His Arg His Asp Ala Asp Ile Asn Asn Thr Glu Cys Val Tyr Lys
145                 150                 155                 160

Lys Asp Phe Pro Asn Asn Arg Leu Met Gly Val Ala Ile Ala Ser Asn
```

```
                        165                 170                 175
Tyr Arg Ala Pro Ser Pro Tyr Gly Leu Gly Gly Asp Pro Phe Ala Leu
                    180                 185                 190

Ala Val Ala Val Ser Gly Ser Gly Ser Asp His Ser Phe Leu Asp Tyr
                    195                 200                 205

Ile Phe Ser Leu Asp Gly Gly Val His Phe Glu Gln Lys Arg Ile Tyr
                    210                 215                 220

Thr Arg Pro Gln Lys Leu Thr Ile Asn Arg Val Asp Leu Ser Leu Gly
225                 230                 235                 240

Ser Thr Ser Pro Ser Leu Gly Phe Asn Thr Trp Pro Leu Met Gly Val
                    245                 250                 255

Val Phe Glu Met Asn Lys Asn Leu Asp Gly Phe Asp Ile Gly Phe Ile
                260                 265                 270

Ser Asn Phe Val Asp Tyr Asp Pro Arg Tyr Ala Trp Ser Glu Pro Ile
                275                 280                 285

Ile Ile Glu Glu Asp Cys Gly Trp Thr Asp Phe Asn Pro Leu Gly Ala
                290                 295                 300

Leu Ser Ile Glu Ile Gln Met Met Leu Asp Asp Asn Ser Asp Asn Thr
305                 310                 315                 320

Val Gly Gly Glu Arg Ser His Asn Phe Leu Ile Thr Tyr Pro Gly His
                    325                 330                 335

Tyr Val Tyr Pro Lys Gln Ser Phe Asn Tyr Ser Pro Gly His Thr Pro
                340                 345                 350

Thr Lys Lys Asp Leu Val Phe Lys His Cys Ile Gly Ile Pro Ala Leu
                355                 360                 365

Ala Tyr Asp Lys Glu Gly Asp Arg Tyr Leu Thr Thr Phe Gln Asp His
                370                 375                 380

Asn Leu Met Arg Tyr Arg Trp Ile Lys Tyr Asp Asp Ile Asn Ser Phe
385                 390                 395                 400

Tyr Gly Trp Ser Trp Pro Tyr Val Tyr Ala Lys Glu Ala Lys Asp Lys
                    405                 410                 415

Lys Arg Arg Arg Pro Gln Val Ala Leu Asn Pro Thr Asn Gly Lys Ala
                420                 425                 430

Cys Trp Val Trp His Thr Arg Lys Ser Pro Tyr Asp Glu Thr Lys Pro
                435                 440                 445

His Pro Thr Pro Val Ile Ile Lys His Phe Leu Trp Ser Asp Thr Glu
                450                 455                 460

Trp Val His Ala Leu Asp Val Gly Asp Val Leu Gln Lys Glu Gly Ser
465                 470                 475                 480

Met Lys Leu Tyr Pro Asn Pro Ala Lys Glu Tyr Val Leu Ile Asn Leu
                    485                 490                 495

Pro Lys Glu Gly Gly His Glu Ala Val Val Tyr Asp Met Gln Gly Arg
                500                 505                 510

Ile Val Glu Lys Val Ser Phe Ser Gly Lys Tyr Lys Leu Asn Val
                515                 520                 525

Gln Tyr Leu Ser Lys Gly Thr Tyr Met Leu Lys Val Val Ala Asp Thr
530                 535                 540

Glu Tyr Phe Val Glu Lys Ile Ile Val Glu
545                 550

<210> SEQ ID NO 112
<211> LENGTH: 550
<212> TYPE: PRT
<213> ORGANISM: Porphyromonas gingivalis
```

<400> SEQUENCE: 112

```
Met Lys Leu Lys Ile Ala Leu Arg Leu Leu Ala Thr Phe Ala Ile
1               5                   10                  15

Val Leu Phe Ser Pro Leu Ala Lys Ala Gln Met Asp Ile Gly Gly
            20                  25                  30

Asp Val Leu Ile Glu Thr Met Ser Thr Leu Ser Gly Tyr Ser Glu Asp
        35                  40                  45

Phe Tyr Tyr Lys Met Ala Val Ala Asp Asn Gly Trp Ile Tyr Val Met
    50                  55                  60

Leu Asp Phe Ser Arg Ile Tyr Phe Asp Val Arg Leu Tyr Arg Ser
65                  70                  75                  80

Lys Asp Gly Gly Ala Thr Tyr Gln Lys Leu Gly Ser Leu Gly Ser Leu
                85                  90                  95

Val Pro Tyr Asp Phe Asp Val Ser His Cys Asp Phe Ile Val Thr Gly
            100                 105                 110

Lys Asp Glu Asp Asp Ile Asn Val Trp Thr Val Met Thr Ala Phe Glu
            115                 120                 125

Tyr Val Gly Gly Thr Ile Gly Asn Gly Val Leu Leu Met His Arg His
        130                 135                 140

Asp Ala Asp Ile Asn Asn Thr Glu Cys Val Tyr Lys Lys Asp Phe Pro
145                 150                 155                 160

Asn Asn Arg Leu Met Gly Val Ala Ile Ala Ser Asn Tyr Arg Ala Pro
                165                 170                 175

Ser Pro Tyr Gly Leu Gly Gly Asp Pro Phe Ala Leu Ala Val Ala Val
            180                 185                 190

Ser Gly Ser Gly Ser Asp His Ser Phe Leu Asp Tyr Ile Phe Ser Leu
        195                 200                 205

Asp Gly Gly Val His Phe Glu Gln Lys Arg Ile Tyr Thr Arg Pro Gln
210                 215                 220

Lys Leu Thr Ile Asn Arg Val Asp Leu Ser Leu Gly Thr Ser Pro
225                 230                 235                 240

Ser Leu Gly Phe Asn Thr Trp Pro Leu Met Gly Val Val Phe Glu Met
                245                 250                 255

Asn Lys Asn Leu Asp Gly Phe Asp Ile Gly Phe Ile Ser Asn Phe Val
            260                 265                 270

Asp Tyr Asp Pro Arg Tyr Ala Trp Ser Glu Pro Ile Ile Glu Glu
        275                 280                 285

Asp Cys Gly Trp Thr Asp Phe Asn Pro Leu Gly Ala Leu Ser Ile Glu
    290                 295                 300

Ile Gln Met Met Leu Asp Asp Asn Ser Asp Asn Thr Val Gly Gly Glu
305                 310                 315                 320

Arg Ser His Asn Phe Leu Ile Thr Tyr Pro Gly His Tyr Val Tyr Pro
                325                 330                 335

Lys Gln Ser Phe Asn Tyr Ser Pro Gly His Thr Pro Thr Lys Lys Asp
            340                 345                 350

Leu Val Phe Lys His Cys Ile Gly Ile Pro Ala Leu Ala Tyr Asp Lys
        355                 360                 365

Glu Gly Asp Arg Tyr Leu Thr Thr Phe Gln Asp His Asn Leu Met Arg
    370                 375                 380

Tyr Arg Trp Ile Lys Tyr Asp Asp Ile Asn Ser Phe Tyr Gly Trp Ser
385                 390                 395                 400

Trp Pro Tyr Val Tyr Ala Lys Glu Ala Lys Asp Lys Lys Arg Arg
                405                 410                 415
```

```
Pro Gln Val Ala Leu Asn Pro Thr Asn Gly Lys Ala Cys Trp Val Trp
            420                 425                 430

His Thr Arg Lys Ser Pro Tyr Asp Glu Thr Lys Pro His Pro Thr Pro
            435                 440                 445

Val Ile Ile Lys His Phe Leu Trp Ser Asp Thr Glu Trp Val His Ala
        450                 455                 460

Leu Asp Val Gly Asp Val Leu Gln Lys Glu Gly Ser Met Lys Leu Tyr
465                 470                 475                 480

Pro Asn Pro Ala Lys Glu Tyr Val Leu Ile Asn Leu Pro Lys Glu Gly
                485                 490                 495

Gly His Glu Ala Val Val Tyr Asp Met Gln Gly Arg Ile Val Glu Lys
            500                 505                 510

Val Ser Phe Ser Gly Lys Glu Tyr Lys Leu Asn Val Gln Tyr Leu Ser
        515                 520                 525

Lys Gly Thr Tyr Met Leu Lys Val Val Ala Asp Thr Glu Tyr Phe Val
530                 535                 540

Glu Lys Ile Ile Val Glu
545                 550

<210> SEQ ID NO 113
<211> LENGTH: 390
<212> TYPE: PRT
<213> ORGANISM: Porphyromonas gingivalis

<400> SEQUENCE: 113

Met Lys Arg Leu Leu Pro Phe Leu Leu Leu Ala Gly Leu Val Ala Val
1               5                   10                  15

Gly Asn Val Ser Ala Gln Ser Pro Arg Ile Pro Gln Val Asp Val His
            20                  25                  30

Thr Arg Ile Ala Arg Asn Ala Arg Tyr Arg Leu Asp Lys Ile Ser Val
        35                  40                  45

Pro Asp Ser Arg Gln Ile Phe Asp Tyr Phe Tyr Lys Glu Glu Thr Ile
    50                  55                  60

Pro Thr Lys Ile Gln Thr Thr Gly Gly Ala Ile Thr Ser Ile Asp
65                  70                  75                  80

Ser Leu Phe Tyr Glu Asp Asp Arg Leu Val Gln Val Arg Tyr Phe Asp
                85                  90                  95

Asn Asn Leu Glu Leu Lys Gln Ala Glu Lys Tyr Val Tyr Asp Gly Ser
            100                 105                 110

Lys Leu Val Leu Arg Glu Ile Arg Lys Ser Pro Thr Asp Glu Thr Pro
        115                 120                 125

Ile Lys Lys Val Ser Tyr His Tyr Leu Cys Gly Ser Asp Met Pro Phe
    130                 135                 140

Glu Ile Thr Thr Glu Met Ser Asp Gly Tyr Phe Glu Ser His Thr Leu
145                 150                 155                 160

Asn Tyr Leu Asn Gly Lys Ile Ala Arg Ile Asp Ile Met Thr Gln Gln
                165                 170                 175

Asn Pro Ser Ala Glu Leu Ile Glu Thr Gly Arg Met Val Tyr Glu Phe
            180                 185                 190

Asp Ala Asn Asn Asp Ala Val Leu Leu Arg Asp Ser Val Phe Leu Pro
        195                 200                 205

Leu Gln Asn Lys Trp Val Glu Met Phe Thr His Arg Tyr Thr Tyr Asp
    210                 215                 220

Asn Lys His Asn Cys Ile Arg Trp Glu Gln Asp Glu Phe Gly Thr Leu
225                 230                 235                 240
```

```
Thr Leu Ala Asn Asn Phe Glu Tyr Asp Thr Thr Ile Pro Leu Ser Ser
                245                 250                 255

Val Leu Phe Pro Thr His Glu Glu Phe Phe Arg Pro Leu Leu Pro Asn
            260                 265                 270

Phe Met Lys His Met Arg Thr Lys Gln Thr Tyr Phe Asn Asn Ser Gly
        275                 280                 285

Glu Gly Leu Ser Glu Val Cys Asp Tyr Asn Tyr Phe Tyr Thr Asp Met
    290                 295                 300

Gln Gly Asn Ala Leu Thr Asp Val Ala Val Asn Glu Ser Ile Lys Ile
305                 310                 315                 320

Tyr Pro Arg Pro Ala Thr Asp Phe Leu Arg Ile Glu Gly Ser Gln Leu
                325                 330                 335

Leu Arg Leu Ser Leu Phe Asp Met Asn Gly Lys Leu Ile Arg Ala Thr
            340                 345                 350

Glu Leu Thr Gly Asp Leu Ala Ile Ile Gly Val Ala Ser Leu Pro Arg
        355                 360                 365

Gly Thr Tyr Ile Ala Glu Ile Thr Ala Ala Asn Ser Lys Thr Ile Arg
    370                 375                 380

Ala Lys Val Ser Leu Arg
385                 390

<210> SEQ ID NO 114
<211> LENGTH: 313
<212> TYPE: PRT
<213> ORGANISM: Porphyromonas gingivalis

<400> SEQUENCE: 114

Met Arg Ala Asn Ile Trp Gln Ile Leu Ser Val Ser Val Leu Phe Phe
1               5                   10                  15

Phe Gly Thr Ala Ile Gly Gln Ala Gln Ser Arg Asn Arg Thr Tyr Glu
            20                  25                  30

Ala Tyr Val Lys Gln Tyr Ala Asp Glu Ala Ile Arg Gln Met Ser Arg
        35                  40                  45

Tyr Asn Ile Pro Ala Ser Ile Thr Ile Ala Gln Ala Leu Val Glu Thr
    50                  55                  60

Gly Ala Gly Ala Ser Thr Leu Ala Ser Val His Asn Asn His Phe Gly
65                  70                  75                  80

Ile Lys Cys His Lys Ser Trp Thr Gly Lys Arg Thr Tyr Arg Thr Asp
                85                  90                  95

Asp Ala Pro Asn Glu Cys Phe Arg Ser Tyr Ser Ala Ala Arg Glu Ser
            100                 105                 110

Tyr Glu Asp His Ser Arg Phe Leu Leu Gln Pro Arg Tyr Arg Pro Leu
        115                 120                 125

Phe Lys Leu Asp Arg Glu Asp Tyr Arg Gly Trp Ala Thr Gly Leu Gln
    130                 135                 140

Arg Cys Gly Tyr Ala Thr Asn Arg Gly Tyr Ala Asn Leu Leu Ile Lys
145                 150                 155                 160

Met Val Glu Leu Tyr Glu Leu Tyr Ala Leu Asp Arg Glu Lys Tyr Pro
                165                 170                 175

Ser Trp Phe His Lys Ser Tyr Pro Gly Ser Asn Lys Lys Ser His Gln
            180                 185                 190

Thr Thr Lys Gln Lys Gln Ser Gly Leu Lys His Glu Ala Tyr Phe Ser
        195                 200                 205

Tyr Gly Leu Leu Tyr Ile Ile Ala Lys Gln Gly Asp Thr Phe Asp Ser
    210                 215                 220
```

-continued

Leu Ala Glu Glu Phe Asp Met Arg Ala Ser Lys Leu Ala Lys Tyr Asn
225                 230                 235                 240

Asp Ala Pro Val Asp Phe Pro Ile Glu Lys Gly Asp Val Ile Tyr Leu
                245                 250                 255

Glu Lys Lys His Ala Cys Ser Ile Ser Lys His Thr Gln His Val Val
            260                 265                 270

Arg Val Gly Asp Ser Met His Ser Ile Ser Gln Arg Tyr Gly Ile Arg
        275                 280                 285

Met Lys Asn Leu Tyr Lys Leu Asn Asp Lys Asp Gly Glu Tyr Ile Pro
    290                 295                 300

Gln Glu Gly Asp Ile Leu Arg Leu Arg
305                 310

<210> SEQ ID NO 115
<211> LENGTH: 271
<212> TYPE: PRT
<213> ORGANISM: Porphyromonas gingivalis

<400> SEQUENCE: 115

Met Asn Ser Arg His Leu Thr Ile Thr Ile Ala Gly Leu Ser Leu
1               5                   10                  15

Phe Val Leu Thr Leu Gly Gly Cys Ser Val Ala Gln Gln Asp Thr Gln
                20                  25                  30

Trp Thr Leu Gly Gly Lys Leu Phe Thr Ser Ala Trp Ile Gln Arg Ser
            35                  40                  45

Ala Glu Tyr Gln Ala Leu Cys Ile Gln Ala Tyr Asn Ile Ala Thr Glu
        50                  55                  60

Arg Val Asp Ala Leu Pro Ala Glu Arg Lys Gln Gly Asp Arg Pro Tyr
65                  70                  75                  80

Ala Ile Val Thr Asp Ile Asp Glu Thr Ile Leu Asp Asn Thr Pro Asn
                85                  90                  95

Ser Val Tyr Gln Ala Leu Arg Gly Lys Asp Tyr Asp Glu Glu Thr Trp
                100                 105                 110

Gly Lys Trp Cys Ala Gln Ala Asp Ala Asp Thr Leu Ala Gly Ala Leu
            115                 120                 125

Ser Phe Phe Leu His Ala Ala Asn Lys Gly Ile Glu Val Phe Tyr Val
130                 135                 140

Thr Asn Arg Arg Asp Asn Leu Arg Glu Ala Thr Leu Gln Asn Leu Gln
145                 150                 155                 160

Arg Tyr Gly Phe Pro Phe Ala Asp Glu Glu His Leu Leu Thr Thr His
                165                 170                 175

Gly Pro Ser Asp Lys Glu Pro Arg Arg Leu Lys Ile Gln Glu Gln Tyr
                180                 185                 190

Glu Ile Val Leu Leu Ile Gly Asp Asn Leu Gly Asp Phe His His Phe
            195                 200                 205

Phe Asn Thr Lys Glu Glu Ser Gly Arg Lys Gln Ala Leu Gly Leu Thr
        210                 215                 220

Ala Gly Glu Phe Gly Arg His Phe Ile Met Leu Pro Asn Pro Asn Tyr
225                 230                 235                 240

Gly Ser Trp Glu Pro Ala Trp Tyr Gly Lys Tyr Pro Pro Leu Pro
                245                 250                 255

Glu Arg Asp Lys Ala Leu Lys Gln Leu His Ser Gln Asn Ser Arg
            260                 265                 270

<210> SEQ ID NO 116
<211> LENGTH: 757

```
<212> TYPE: PRT
<213> ORGANISM: Porphyromonas gingivalis

<400> SEQUENCE: 116

Met Arg Thr Lys Thr Ile Phe Phe Ala Ile Ile Ser Phe Ile Ala Leu
1               5                   10                  15

Leu Ser Ser Ser Leu Ser Ala Gln Ser Lys Ala Val Leu Thr Gly Ser
            20                  25                  30

Val Ser Asp Ala Glu Thr Gly Glu Pro Leu Ala Gly Ala Arg Ile Glu
        35                  40                  45

Val Lys His Thr Asn Ile Val Ala Gly Ala Asp Ala Gly Gly His Phe
    50                  55                  60

Glu Ile Lys Asn Leu Pro Ala Gly Gln His Thr Ile Ile Cys Ser Leu
65              70                  75                  80

Gly Gly Tyr Gly Gln Lys Glu Val Val Ala Ile Glu Ala Gly Gln
                85                  90                  95

Thr Lys Thr Ile Ser Phe Ala Leu Arg Leu Arg Thr Asn Asn Leu Glu
            100                 105                 110

Glu Val Val Thr Gly Thr Gly Thr Arg Tyr Arg Leu Val Asp Ala
        115                 120                 125

Pro Val Ala Thr Glu Val Leu Thr Ala Lys Asp Ile Ala Ser Phe Ser
    130                 135                 140

Ala Pro Thr Ser Glu Ala Leu Leu Gln Gly Leu Ser Pro Ser Phe Asp
145                 150                 155                 160

Phe Gly Pro Asn Leu Met Gly Ser Phe Met Gln Leu Asn Gly Leu Ser
                165                 170                 175

Ser Lys Tyr Ile Leu Ile Leu Ile Asp Gly Lys Arg Val Tyr Gly Asp
            180                 185                 190

Val Gly Gly Gln Ala Asp Leu Ser Arg Ile Ser Pro Asp Gln Ile Glu
        195                 200                 205

Arg Ile Glu Leu Val Lys Gly Ala Ser Ser Leu Tyr Gly Ser Asp
    210                 215                 220

Ala Ile Ala Gly Val Ile Asn Val Ile Thr Lys Lys Asn Thr Asn Arg
225                 230                 235                 240

Leu Ser Ala Tyr Thr Ser His Arg Ile Ser Lys Tyr Asn Asp Arg Gln
                245                 250                 255

Thr Asn Thr Ser Leu Asp Ile Asn Ile Gly Lys Phe Ser Ser Asn Thr
            260                 265                 270

Asn Tyr Phe Phe Tyr His Thr Asp Gly Trp Gln Asn Ser Pro Phe Glu
        275                 280                 285

Ile Lys Lys Lys Lys Gly Ser Gly Glu Pro Val Leu Glu Glu Thr Tyr
    290                 295                 300

Lys Lys Thr Phe Arg Ala Gln Glu Asn Gln Gly Val Ser Gln Ser Leu
305                 310                 315                 320

Ser Tyr Tyr Ala Thr Asn Asn Leu Ser Phe Ser Gly Asn Val Gln Tyr
                325                 330                 335

Asn Lys Arg Gln Ile Phe Thr Pro Thr Phe Ser Glu Lys Lys Ala Tyr
            340                 345                 350

Asp Met Asp Tyr Arg Ala Leu Thr Ala Ser Leu Gly Thr Asn Tyr Leu
        355                 360                 365

Phe Pro Asn Gly Leu His Thr Leu Ser Phe Asp Ala Val Tyr Asp Arg
    370                 375                 380

Phe Arg Phe Gly Tyr Leu Tyr His Asp Lys Asp Ser Ser Glu Ser Leu
385                 390                 395                 400
```

Ile Asn Asn Gln Gly Gln Thr Glu Gln Pro Thr Phe Phe Pro Gly Gln
                405                 410                 415

Leu Arg Asn Lys Asn Asp Gln Ile Arg Tyr Thr Ala Glu Ala Arg Gly
            420                 425                 430

Val Phe Thr Leu Pro Tyr Ala Gln Lys Leu Thr Gly Gly Leu Glu Tyr
        435                 440                 445

Phe Arg Glu Glu Leu Ile Ser Pro Tyr Asn Leu Ile Thr Asp Lys Ala
    450                 455                 460

Asp Ala Ser Thr Leu Ser Ala Tyr Val Gln Asp Glu Trp Lys Pro Leu
465                 470                 475                 480

Asp Trp Phe Asn Met Thr Ala Gly Phe Arg Leu Val His His Gln Glu
                485                 490                 495

Phe Gly Thr Arg Met Thr Pro Lys Val Ser Ile Leu Ala Lys Tyr Gly
            500                 505                 510

Pro Leu Asn Phe Arg Ala Thr Tyr Ala Asn Gly Tyr Lys Thr Pro Thr
        515                 520                 525

Leu Lys Glu Leu Phe Ala Arg Asn Glu Leu Thr Thr Met Gly Ser His
    530                 535                 540

Asn Leu Tyr Leu Gly Asn Ala Asp Leu Lys Pro Gln Met Ser Asp Tyr
545                 550                 555                 560

Tyr Ala Leu Gly Leu Glu Tyr Asn Gln Gly Pro Ile Ser Phe Ser Ala
                565                 570                 575

Thr Val Tyr Asp Asn Glu Leu Arg Asn Leu Ile Ser Phe Met Asp Ile
            580                 585                 590

Pro Thr Ser Pro Glu His Glu Ala Gln Gly Ile Lys Lys Thr Lys Gln
        595                 600                 605

Tyr Ala Asn Ile Gly Lys Ala Arg Ser Arg Gly Leu Asp Val Leu Cys
    610                 615                 620

Asp Ala Ser Ile Gly Trp Gly Ile Lys Leu Gly Ala Gly Tyr Ser Leu
625                 630                 635                 640

Val Glu Ala Lys Asn Leu Gln Thr Asp Glu Trp Leu Glu Gly Ala Ala
                645                 650                 655

Arg His Arg Ala Asn Val His Ala Asp Trp Val His Tyr Trp Gly Gln
            660                 665                 670

Tyr Arg Leu Gly Val Ser Leu Phe Gly Arg Ile Gln Ser Glu Arg Tyr
        675                 680                 685

Tyr Lys Asp Gly Asn Ala Pro Asp Tyr Thr Leu Trp Arg Leu Ala Thr
    690                 695                 700

Ser His Arg Phe Ala His Phe Arg His Ile Ile Leu Asp Gly Thr Leu
705                 710                 715                 720

Gly Ile Asp Asn Leu Phe Asp Tyr Val Asp Asp Arg Pro Met Gly Val
                725                 730                 735

Asn Tyr Ala Thr Val Thr Pro Gly Arg Thr Phe Phe Ala Gln Ile Ala
            740                 745                 750

Ile Arg Phe Asn Asn
        755

<210> SEQ ID NO 117
<211> LENGTH: 331
<212> TYPE: PRT
<213> ORGANISM: Porphyromonas gingivalis

<400> SEQUENCE: 117

Met Thr Asp Asn Lys Gln Arg Asn Ile Val Phe Pro Ala Phe Leu Leu
1               5                   10                  15

```
Leu Leu Gly Val Ile Ala Val Val Thr Ile Val Gly Phe Phe Met Leu
             20                  25                  30

Arg Pro Ala Glu Glu Ile Ile Gln Gly Gln Ile Glu Val Thr Glu Tyr
         35                  40                  45

Arg Val Ser Ser Lys Val Pro Gly Arg Ile Lys Glu Leu Arg Val Ser
 50                  55                  60

Glu Gly Gln Gln Val Gln Ala Gly Asp Thr Leu Ala Val Ile Glu Ala
 65                  70                  75                  80

Pro Asp Val Ala Ala Lys Met Glu Gln Ala Lys Ala Ala Glu Ala Ala
                 85                  90                  95

Ala Gln Ala Gln Asn Ala Lys Ala Leu Lys Gly Ala Arg Ser Glu Gln
            100                 105                 110

Ile Gln Ala Ala Tyr Glu Met Trp Gln Lys Ala Gln Ala Gly Val Ala
        115                 120                 125

Ile Ala Thr Lys Thr His Gln Arg Val Gln Asn Leu Tyr Asp Gln Gly
130                 135                 140

Val Val Pro Ala Gln Lys Leu Asp Glu Ala Thr Ala Gln Arg Asp Ala
145                 150                 155                 160

Ala Ile Ala Thr Gln Lys Ala Glu Ala Gln Tyr Asn Met Ala Arg
                165                 170                 175

Asn Gly Ala Glu Arg Glu Asp Lys Leu Ala Ala Ser Ala Leu Val Asp
            180                 185                 190

Arg Ala Arg Gly Ala Val Ala Glu Val Glu Ser Tyr Ile Asn Glu Thr
        195                 200                 205

Tyr Leu Ile Ala Pro Arg Ala Gly Glu Val Ser Glu Ile Phe Pro Lys
    210                 215                 220

Ala Gly Glu Leu Val Gly Thr Gly Ala Pro Ile Met Asn Ile Ala Glu
225                 230                 235                 240

Met Gly Asp Met Trp Ala Ser Phe Ala Val Arg Glu Asp Phe Leu Ser
                245                 250                 255

Ser Met Thr Met Gly Ala Val Leu Glu Thr Val Pro Ala Leu Asn
            260                 265                 270

Glu Glu Lys Val Arg Phe Lys Ile Thr Phe Ile Lys Asn Met Gly Thr
        275                 280                 285

Tyr Ala Ala Trp Lys Ala Thr Lys Thr Thr Gly Gln Tyr Asp Leu Lys
    290                 295                 300

Thr Phe Glu Val Lys Ala Thr Leu Ala Asp Lys Asp Lys Ala Gln Lys
305                 310                 315                 320

Leu Arg Pro Gly Met Ser Val Ile Ile Arg Lys
                325                 330

<210> SEQ ID NO 118
<211> LENGTH: 1017
<212> TYPE: PRT
<213> ORGANISM: Porphyromonas gingivalis

<400> SEQUENCE: 118

Met Lys Arg Met Thr Leu Phe Phe Leu Cys Leu Leu Thr Ser Ile Gly
 1               5                  10                  15

Trp Ala Met Ala Gln Asn Arg Thr Val Lys Gly Thr Val Ile Ser Ser
             20                  25                  30

Glu Asp Asn Glu Pro Leu Ile Gly Ala Asn Val Val Val Gly Asn
         35                  40                  45

Thr Thr Ile Gly Ala Ala Thr Asp Leu Asp Gly Asn Phe Thr Leu Ser
 50                  55                  60
```

```
Val Pro Ala Asn Ala Lys Met Leu Arg Val Ser Tyr Ser Gly Met Thr
 65                  70                  75                  80

Thr Lys Glu Val Ala Ile Ala Asn Val Met Lys Ile Val Leu Asp Pro
                 85                  90                  95

Asp Ser Lys Val Leu Glu Gln Val Val Leu Gly Tyr Gly Thr Gly
            100                 105                 110

Gln Lys Leu Ser Thr Val Ser Gly Val Ala Lys Val Ser Ser Glu
            115                 120                 125

Lys Leu Ala Glu Lys Pro Val Ala Asn Ile Met Asp Ala Leu Gln Gly
130                 135                 140

Gln Val Ala Gly Met Gln Val Met Thr Thr Ser Gly Asp Pro Thr Ala
145                 150                 155                 160

Val Ala Ser Val Glu Ile His Gly Thr Gly Ser Leu Gly Ala Ser Ser
                165                 170                 175

Ala Pro Leu Tyr Ile Val Asp Gly Met Gln Thr Ser Leu Asp Val Val
                180                 185                 190

Ala Thr Met Asn Pro Asn Asp Phe Glu Ser Met Ser Val Leu Lys Asp
                195                 200                 205

Ala Ser Ala Thr Ser Ile Tyr Gly Ala Arg Ala Ala Asn Gly Val Val
210                 215                 220

Phe Ile Gln Thr Lys Lys Gly Lys Met Ser Glu Arg Gly Arg Ile Thr
225                 230                 235                 240

Phe Asn Ala Ser Tyr Gly Ile Ser Gln Ile Leu Asn Thr Lys Pro Leu
                245                 250                 255

Asp Asn Met Met Thr Gly Asp Glu Leu Leu Asp Phe Gln Val Lys Ala
                260                 265                 270

Gly Phe Trp Gly Asn Asn Gln Thr Val Gln Lys Val Lys Asp Met Ile
                275                 280                 285

Leu Ala Gly Ala Glu Asp Leu Tyr Gly Asn Tyr Asp Ser Leu Lys Asp
290                 295                 300

Glu Tyr Gly Lys Thr Leu Phe Pro Val Asp Phe Asn His Asp Ala Asp
305                 310                 315                 320

Trp Leu Lys Ala Leu Phe Lys Thr Ala Pro Thr Ser Gln Gly Asp Ile
                325                 330                 335

Ser Phe Ser Gly Gly Ser Gln Gly Thr Ser Tyr Tyr Ala Ser Ile Gly
                340                 345                 350

Tyr Phe Asp Gln Glu Gly Met Ala Arg Glu Pro Ala Asn Phe Lys Arg
                355                 360                 365

Tyr Ser Gly Arg Leu Asn Phe Glu Ser Arg Ile Asn Glu Trp Leu Lys
                370                 375                 380

Val Gly Ala Asn Leu Ser Gly Ala Ile Ala Asn Arg Arg Ser Ala Asp
385                 390                 395                 400

Tyr Phe Gly Lys Tyr Tyr Met Gly Ser Gly Thr Phe Gly Val Leu Thr
                405                 410                 415

Met Pro Arg Tyr Tyr Asn Pro Phe Asp Val Asn Gly Asp Leu Ala Asp
                420                 425                 430

Val Tyr Tyr Met Tyr Gly Ala Thr Arg Pro Ser Met Thr Glu Pro Tyr
                435                 440                 445

Phe Ala Lys Met Arg Pro Phe Ser Ser Glu Ser His Gln Ala Asn Val
                450                 455                 460

Asn Gly Phe Ala Gln Ile Thr Pro Ile Lys Gly Leu Thr Leu Lys Ala
465                 470                 475                 480

Gln Ala Gly Val Asp Ile Thr Asn Thr Arg Thr Ser Ser Lys Arg Met
                485                 490                 495
```

```
Pro Asn Asn Pro Tyr Asp Ser Thr Pro Leu Gly Glu Arg Glu Arg
            500                 505                 510

Ala Tyr Arg Asp Val Ser Lys Ser Phe Thr Asn Thr Ala Glu Tyr Lys
            515                 520                 525

Phe Ser Ile Asp Glu Lys His Asp Leu Thr Ala Leu Met Gly His Glu
            530                 535                 540

Tyr Ile Glu Tyr Glu Gly Asp Val Ile Gly Ala Ser Ser Lys Gly Phe
545                 550                 555                 560

Glu Ser Asp Lys Leu Met Leu Leu Ser Gln Gly Lys Thr Gly Asn Ser
                565                 570                 575

Leu Ser Leu Pro Glu His Arg Val Ala Glu Tyr Ala Tyr Leu Ser Phe
            580                 585                 590

Phe Ser Arg Phe Asn Tyr Gly Phe Asp Lys Trp Met Tyr Ile Asp Phe
            595                 600                 605

Ser Val Arg Asn Asp Gln Ser Ser Arg Phe Gly Ser Asn Asn Arg Ser
            610                 615                 620

Ala Trp Phe Tyr Ser Val Gly Met Phe Asp Ile Tyr Asn Lys Phe
625                 630                 635                 640

Ile Gln Glu Ser Asn Trp Leu Ser Asp Leu Arg Leu Lys Met Ser Tyr
                645                 650                 655

Gly Thr Thr Gly Asn Ser Glu Ile Gly Asn Tyr Asn His Gln Ala Leu
            660                 665                 670

Val Thr Val Asn Asn Tyr Thr Glu Asp Ala Met Gly Leu Ser Ile Ser
            675                 680                 685

Thr Ala Gly Asn Pro Asp Leu Ser Trp Glu Lys Gln Ser Gln Phe Asn
690                 695                 700

Phe Gly Leu Ala Ala Gly Ala Phe Asn Asn Arg Leu Ser Ala Glu Val
705                 710                 715                 720

Asp Phe Tyr Val Arg Thr Thr Asn Asp Met Leu Ile Asp Val Pro Met
            725                 730                 735

Pro Tyr Ile Ser Gly Phe Phe Ser Gln Tyr Gln Asn Val Gly Ser Met
            740                 745                 750

Lys Asn Thr Gly Val Asp Leu Ser Leu Lys Gly Thr Ile Tyr Gln Asn
            755                 760                 765

Lys Asp Trp Asn Val Tyr Ala Ser Ala Asn Phe Asn Tyr Asn Arg Gln
770                 775                 780

Glu Ile Thr Lys Leu Phe Phe Gly Leu Asn Lys Tyr Met Leu Pro Asn
785                 790                 795                 800

Thr Gly Thr Ile Trp Glu Ile Gly Tyr Pro Asn Ser Phe Tyr Met Ala
            805                 810                 815

Glu Tyr Ala Gly Ile Asp Lys Lys Thr Gly Lys Gln Leu Trp Tyr Val
            820                 825                 830

Pro Gly Gln Val Asp Ala Asp Gly Asn Lys Val Thr Thr Ser Gln Tyr
            835                 840                 845

Ser Ala Asp Leu Glu Thr Arg Ile Asp Lys Ser Val Thr Pro Pro Ile
850                 855                 860

Thr Gly Gly Phe Ser Leu Gly Ala Ser Trp Lys Gly Leu Ser Leu Asp
865                 870                 875                 880

Ala Asp Phe Ala Tyr Ile Val Gly Lys Trp Met Ile Asn Asn Asp Arg
            885                 890                 895

Tyr Phe Thr Glu Asn Ala Gly Gly Leu Met Gln Leu Asn Lys Asp Lys
            900                 905                 910

Met Leu Leu Asn Ala Trp Thr Glu Asp Asn Lys Glu Thr Asp Val Pro
```

```
                915                 920                 925
Lys Leu Gly Gln Ser Pro Gln Phe Asp Thr His Leu Leu Glu Asn Ala
        930                 935                 940

Ser Phe Leu Arg Leu Lys Asn Leu Lys Leu Thr Tyr Val Leu Pro Asn
945                 950                 955                 960

Ser Leu Phe Ala Gly Gln Asn Val Ile Gly Ala Arg Val Tyr Leu
                965                 970                 975

Met Ala Arg Asn Leu Leu Thr Val Thr Lys Tyr Lys Gly Phe Asp Pro
        980                 985                 990

Glu Ala Gly Gly Asn Val Gly Lys Asn Gln Tyr Pro Asn Ser Lys Gln
        995                 1000                1005

Tyr Val Ala Gly Ile Gln Leu Ser Phe
        1010                1015

<210> SEQ ID NO 119
<211> LENGTH: 1014
<212> TYPE: PRT
<213> ORGANISM: Porphyromonas gingivalis

<400> SEQUENCE: 119

Met Thr Leu Phe Phe Leu Cys Leu Leu Thr Ser Ile Gly Trp Ala Met
1               5                   10                  15

Ala Gln Asn Arg Thr Val Lys Gly Thr Val Ile Ser Ser Glu Asp Asn
            20                  25                  30

Glu Pro Leu Ile Gly Ala Asn Val Val Val Gly Asn Thr Thr Ile
            35                  40                  45

Gly Ala Ala Thr Asp Leu Asp Gly Asn Phe Thr Leu Ser Val Pro Ala
    50                  55                  60

Asn Ala Lys Met Leu Arg Val Ser Tyr Ser Gly Met Thr Thr Lys Glu
65                  70                  75                  80

Val Ala Ile Ala Asn Val Met Lys Ile Val Leu Asp Pro Asp Ser Lys
                85                  90                  95

Val Leu Glu Gln Val Val Val Leu Gly Tyr Gly Thr Gly Gln Lys Leu
            100                 105                 110

Ser Thr Val Ser Gly Ser Val Ala Lys Val Ser Ser Glu Lys Leu Ala
        115                 120                 125

Glu Lys Pro Val Ala Asn Ile Met Asp Ala Leu Gln Gly Gln Val Ala
    130                 135                 140

Gly Met Gln Val Met Thr Thr Ser Gly Asp Pro Thr Ala Val Ala Ser
145                 150                 155                 160

Val Glu Ile His Gly Thr Gly Ser Leu Gly Ala Ser Ser Ala Pro Leu
                165                 170                 175

Tyr Ile Val Asp Gly Met Gln Thr Ser Leu Asp Val Val Ala Thr Met
            180                 185                 190

Asn Pro Asn Asp Phe Glu Ser Met Ser Val Leu Lys Asp Ala Ser Ala
        195                 200                 205

Thr Ser Ile Tyr Gly Ala Arg Ala Ala Asn Gly Val Val Phe Ile Gln
    210                 215                 220

Thr Lys Lys Gly Lys Met Ser Glu Arg Gly Arg Ile Thr Phe Asn Ala
225                 230                 235                 240

Ser Tyr Gly Ile Ser Gln Ile Leu Asn Thr Lys Pro Leu Asp Asn Met
                245                 250                 255

Met Thr Gly Asp Glu Leu Leu Asp Phe Gln Val Lys Ala Gly Phe Trp
            260                 265                 270

Gly Asn Asn Gln Thr Val Gln Lys Val Lys Asp Met Ile Leu Ala Gly
```

-continued

```
                275                 280                 285
Ala Glu Asp Leu Tyr Gly Asn Tyr Asp Ser Leu Lys Asp Glu Tyr Gly
290                 295                 300
Lys Thr Leu Phe Pro Val Asp Phe Asn His Asp Ala Asp Trp Leu Lys
305                 310                 315                 320
Ala Leu Phe Lys Thr Ala Pro Thr Ser Gln Gly Asp Ile Ser Phe Ser
            325                 330                 335
Gly Gly Ser Gln Gly Thr Ser Tyr Ala Ser Ile Gly Tyr Phe Asp
        340                 345                 350
Gln Glu Gly Met Ala Arg Glu Pro Ala Asn Phe Lys Arg Tyr Ser Gly
            355                 360                 365
Arg Leu Asn Phe Glu Ser Arg Ile Asn Glu Trp Leu Lys Val Gly Ala
370                 375                 380
Asn Leu Ser Gly Ala Ile Ala Asn Arg Arg Ser Ala Asp Tyr Phe Gly
385                 390                 395                 400
Lys Tyr Tyr Met Gly Ser Gly Thr Phe Gly Val Leu Thr Met Pro Arg
                405                 410                 415
Tyr Tyr Asn Pro Phe Asp Val Asn Gly Asp Leu Ala Asp Val Tyr Tyr
            420                 425                 430
Met Tyr Gly Ala Thr Arg Pro Ser Met Thr Glu Pro Tyr Phe Ala Lys
            435                 440                 445
Met Arg Pro Phe Ser Ser Ser Glu Ser His Gln Ala Asn Val Asn Gly Phe
450                 455                 460
Ala Gln Ile Thr Pro Ile Lys Gly Leu Thr Leu Lys Ala Gln Ala Gly
465                 470                 475                 480
Val Asp Ile Thr Asn Thr Arg Thr Ser Ser Lys Arg Met Pro Asn Asn
                485                 490                 495
Pro Tyr Asp Ser Thr Pro Leu Gly Glu Arg Arg Glu Arg Ala Tyr Arg
            500                 505                 510
Asp Val Ser Lys Ser Phe Thr Asn Thr Ala Glu Tyr Lys Phe Ser Ile
            515                 520                 525
Asp Glu Lys His Asp Leu Thr Ala Leu Met Gly His Glu Tyr Ile Glu
530                 535                 540
Tyr Glu Gly Asp Val Ile Gly Ala Ser Ser Lys Gly Phe Glu Ser Asp
545                 550                 555                 560
Lys Leu Met Leu Leu Ser Gln Gly Lys Thr Gly Asn Ser Leu Ser Leu
                565                 570                 575
Pro Glu His Arg Val Ala Glu Tyr Ala Tyr Leu Ser Phe Phe Ser Arg
            580                 585                 590
Phe Asn Tyr Gly Phe Asp Lys Trp Met Tyr Ile Asp Phe Ser Val Arg
            595                 600                 605
Asn Asp Gln Ser Ser Arg Phe Gly Ser Asn Asn Arg Ser Ala Trp Phe
610                 615                 620
Tyr Ser Val Gly Gly Met Phe Asp Ile Tyr Asn Lys Phe Ile Gln Glu
625                 630                 635                 640
Ser Asn Trp Leu Ser Asp Leu Arg Leu Lys Met Ser Tyr Gly Thr Thr
                645                 650                 655
Gly Asn Ser Glu Ile Gly Asn Tyr Asn His Gln Ala Leu Val Thr Val
            660                 665                 670
Asn Asn Tyr Thr Glu Asp Ala Met Gly Leu Ser Ile Ser Thr Ala Gly
            675                 680                 685
Asn Pro Asp Leu Ser Trp Glu Lys Gln Ser Gln Phe Asn Phe Gly Leu
690                 695                 700
```

```
Ala Ala Gly Ala Phe Asn Asn Arg Leu Ser Ala Glu Val Asp Phe Tyr
705                 710                 715                 720

Val Arg Thr Thr Asn Asp Met Leu Ile Asp Val Pro Met Pro Tyr Ile
            725                 730                 735

Ser Gly Phe Phe Ser Gln Tyr Gln Asn Val Gly Ser Met Lys Asn Thr
        740                 745                 750

Gly Val Asp Leu Ser Leu Lys Gly Thr Ile Tyr Gln Asn Lys Asp Trp
    755                 760                 765

Asn Val Tyr Ala Ser Ala Asn Phe Asn Tyr Asn Arg Gln Glu Ile Thr
770                 775                 780

Lys Leu Phe Phe Gly Leu Asn Lys Tyr Met Leu Pro Asn Thr Gly Thr
785                 790                 795                 800

Ile Trp Glu Ile Gly Tyr Pro Asn Ser Phe Tyr Met Ala Glu Tyr Ala
                805                 810                 815

Gly Ile Asp Lys Lys Thr Gly Lys Gln Leu Trp Tyr Val Pro Gly Gln
            820                 825                 830

Val Asp Ala Asp Gly Asn Lys Val Thr Thr Ser Gln Tyr Ser Ala Asp
        835                 840                 845

Leu Glu Thr Arg Ile Asp Lys Ser Val Thr Pro Pro Ile Thr Gly Gly
    850                 855                 860

Phe Ser Leu Gly Ala Ser Trp Lys Gly Leu Ser Leu Asp Ala Asp Phe
865                 870                 875                 880

Ala Tyr Ile Val Gly Lys Trp Met Ile Asn Asn Asp Arg Tyr Phe Thr
                885                 890                 895

Glu Asn Ala Gly Gly Leu Met Gln Leu Asn Lys Asp Lys Met Leu Leu
            900                 905                 910

Asn Ala Trp Thr Glu Asp Asn Lys Glu Thr Asp Val Pro Lys Leu Gly
        915                 920                 925

Gln Ser Pro Gln Phe Asp Thr His Leu Leu Glu Asn Ala Ser Phe Leu
    930                 935                 940

Arg Leu Lys Asn Leu Lys Leu Thr Tyr Val Leu Pro Asn Ser Leu Phe
945                 950                 955                 960

Ala Gly Gln Asn Val Ile Gly Gly Ala Arg Val Tyr Leu Met Ala Arg
                965                 970                 975

Asn Leu Leu Thr Val Thr Lys Tyr Lys Gly Phe Asp Pro Glu Ala Gly
            980                 985                 990

Gly Asn Val Gly Lys Asn Gln Tyr  Pro Asn Ser Lys Gln Tyr Val Ala
        995                 1000                1005

Gly Ile  Gln Leu Ser Phe
    1010

<210> SEQ ID NO 120
<211> LENGTH: 821
<212> TYPE: PRT
<213> ORGANISM: Porphyromonas gingivalis

<400> SEQUENCE: 120

Met Lys Lys Lys Asn Phe Leu Leu Gly Ile Phe Val Ala Leu Leu
1               5                   10                  15

Thr Phe Ile Gly Ser Met Gln Ala Gln Gln Ala Lys Asp Tyr Phe Asn
            20                  25                  30

Phe Asp Glu Arg Gly Glu Ala Tyr Phe Ser Phe Lys Val Pro Asp Arg
        35                  40                  45

Ala Val Leu Gln Glu Leu Ala Leu Ile Met Ser Ile Asp Glu Phe Asp
    50                  55                  60
```

```
Pro Val Thr Asn Glu Ala Ile Ala Tyr Ala Ser Glu Glu Glu Phe Glu
 65                  70                  75                  80

Ala Phe Leu Arg Tyr Gly Leu Lys Pro Thr Phe Leu Thr Pro Pro Ser
                 85                  90                  95

Met Gln Arg Ala Val Glu Met Phe Asp Tyr Arg Ser Gly Glu Lys Tyr
            100                 105                 110

Glu Trp Asn Ala Tyr Pro Thr Tyr Glu Ala Tyr Ile Ser Met Met Glu
        115                 120                 125

Glu Phe Gln Thr Lys Tyr Pro Ser Leu Cys Thr Thr Ser Val Ile Gly
    130                 135                 140

Lys Ser Val Lys Asp Arg Lys Leu Met Ile Cys Lys Leu Thr Ser Ser
145                 150                 155                 160

Ala Asn Thr Gly Lys Lys Pro Arg Val Leu Tyr Thr Ser Thr Met His
                165                 170                 175

Gly Asp Glu Thr Thr Gly Tyr Val Val Leu Leu Arg Leu Ile Asp His
            180                 185                 190

Leu Leu Ser Asn Tyr Glu Ser Asp Pro Arg Ile Lys Asn Ile Leu Asp
        195                 200                 205

Lys Thr Glu Val Trp Ile Cys Pro Leu Thr Asn Pro Asp Gly Ala Tyr
    210                 215                 220

Arg Ala Gly Asn His Thr Val Gln Gly Ala Thr Arg Tyr Asn Ala Asn
225                 230                 235                 240

Asn Val Asp Leu Asn Arg Asn Phe Lys Asp Val Ala Gly Asp His
                245                 250                 255

Pro Asp Gly Lys Pro Trp Gln Pro Glu Ala Thr Ala Phe Met Asp Leu
                260                 265                 270

Glu Gly Asn Thr Ser Phe Val Leu Gly Ala Asn Ile His Gly Gly Thr
            275                 280                 285

Glu Val Val Asn Tyr Pro Trp Asp Asn Lys Lys Glu Arg His Ala Asp
        290                 295                 300

Asp Glu Trp Tyr Lys Leu Ile Ser Arg Asn Tyr Ala Ala Ala Cys Gln
305                 310                 315                 320

Ser Ile Ser Ala Ser Tyr Met Thr Ser Glu Thr Asn Ser Gly Ile Ile
                325                 330                 335

Asn Gly Ser Asp Trp Tyr Val Ile Arg Gly Ser Arg Gln Asp Asn Ala
            340                 345                 350

Asn Tyr Phe His Arg Leu Arg Glu Ile Thr Leu Glu Ile Ser Asn Thr
        355                 360                 365

Lys Leu Val Pro Ala Ser Gln Leu Pro Lys Tyr Trp Asn Leu Asn Lys
    370                 375                 380

Glu Ser Leu Leu Ala Leu Ile Glu Glu Ser Leu Tyr Gly Ile His Gly
385                 390                 395                 400

Thr Val Thr Ser Ala Ala Asn Gly Gln Pro Leu Lys Cys Gln Ile Leu
                405                 410                 415

Ile Glu Asn His Asp Lys Arg Asn Ser Asp Val Tyr Ser Asp Ala Thr
            420                 425                 430

Thr Gly Tyr Tyr Val Arg Pro Ile Lys Ala Gly Thr Tyr Thr Val Lys
        435                 440                 445

Tyr Lys Ala Glu Gly Tyr Pro Glu Ala Thr Arg Thr Ile Thr Ile Lys
    450                 455                 460

Asp Lys Glu Thr Val Ile Met Asp Ile Ala Leu Gly Asn Ser Val Pro
465                 470                 475                 480

Leu Pro Val Pro Asp Phe Thr Ala Ser Pro Met Thr Ile Ser Val Gly
                485                 490                 495
```

-continued

Glu Ser Val Gln Phe Gln Asp Gln Thr Thr Asn Asn Pro Thr Asn Trp
            500                 505                 510

Glu Trp Thr Phe Glu Gly Gly Gln Pro Ala Met Ser Thr Glu Gln Asn
            515                 520                 525

Pro Leu Val Ser Tyr Ser His Pro Gly Gln Tyr Asp Val Thr Leu Lys
            530                 535                 540

Val Trp Asn Ala Ser Gly Ser Asn Thr Ile Thr Lys Glu Lys Phe Ile
545                 550                 555                 560

Thr Val Asn Ala Val Met Pro Val Ala Glu Phe Val Gly Thr Pro Thr
            565                 570                 575

Glu Ile Glu Glu Gly Gln Thr Val Ser Phe Gln Asn Gln Ser Thr Asn
            580                 585                 590

Ala Thr Asn Tyr Val Trp Ile Phe Asp Gly Gly Thr Pro Ala Thr Ser
            595                 600                 605

Glu Asp Glu Asn Pro Thr Val Leu Tyr Ser Lys Ala Gly Gln Tyr Asp
            610                 615                 620

Val Thr Leu Lys Ala Ile Ser Ala Ser Gly Glu Thr Val Lys Thr Lys
625                 630                 635                 640

Glu Lys Tyr Ile Thr Val Lys Lys Ala Pro Val Pro Ala Pro Val Ala
            645                 650                 655

Asp Phe Glu Gly Thr Pro Arg Lys Val Lys Lys Gly Glu Thr Val Thr
            660                 665                 670

Phe Lys Asp Leu Ser Thr Asn Asn Pro Thr Ser Trp Leu Trp Val Phe
            675                 680                 685

Glu Gly Gly Ser Pro Ala Thr Ser Thr Glu Gln Asn Pro Val Val Thr
            690                 695                 700

Tyr Asn Glu Thr Gly Lys Tyr Asp Val Gln Leu Thr Ala Thr Asn Glu
705                 710                 715                 720

Gly Gly Ser Asn Val Lys Lys Ala Glu Asp Tyr Ile Glu Val Ile Leu
            725                 730                 735

Asp Asp Ser Val Glu Asp Ile Val Ala Gln Thr Gly Ile Val Ile Arg
            740                 745                 750

Pro Gln Asn Gly Thr Lys Gln Ile Leu Ile Glu Ala Asn Ala Ala Ile
            755                 760                 765

Lys Ala Ile Val Leu Tyr Asp Ile Asn Gly Arg Val Val Leu Lys Thr
            770                 775                 780

Thr Pro Asn Gln Leu Arg Ser Thr Val Asp Leu Ser Ile Leu Pro Glu
785                 790                 795                 800

Gly Ile Tyr Thr Ile Asn Ile Lys Thr Glu Lys Ser Ala Arg Thr Glu
            805                 810                 815

Lys Ile His Ile Gly
            820

<210> SEQ ID NO 121
<211> LENGTH: 76
<212> TYPE: PRT
<213> ORGANISM: Porphyromonas gingivalis

<400> SEQUENCE: 121

Met Arg Leu Ile Lys Ala Phe Leu Val Gln Leu Leu Leu Leu Pro Ile
1               5                   10                  15

Phe Phe Tyr Lys Arg Phe Ile Ser Pro Leu Thr Pro Pro Ser Cys Arg
                20                  25                  30

Phe Thr Pro Ser Cys Ser Ser Tyr Ala Ile Glu Ala Leu Arg Lys Tyr
            35                  40                  45

```
Gly Pro Gly Lys Gly Leu Leu Leu Ser Ile Lys Arg Ile Leu Arg Cys
    50                  55                  60

His Pro Trp Gly Gly Ser Gly Tyr Asp Pro Val Pro
65                  70                  75

<210> SEQ ID NO 122
<211> LENGTH: 417
<212> TYPE: PRT
<213> ORGANISM: Porphyromonas gingivalis

<400> SEQUENCE: 122

Met Asn Tyr Leu Tyr Ile Leu Ile Thr Leu Leu Ser Gly Phe Phe
1               5                   10                  15

Ser Gly Ala Glu Ile Ala Phe Leu Ser Ser Asp Lys Leu Arg Leu Glu
                20                  25                  30

Leu Asp Arg Asn Arg Gly Asp Leu Thr Gly Arg Ala Leu Asn Leu Leu
            35                  40                  45

Tyr Arg His Pro Asp Gln Leu Val Thr Thr Leu Leu Val Gly Asn Asn
        50                  55                  60

Ile Val Leu Val Val Tyr Gly Leu Leu Met Ala Gly Leu Ala Ala
65                  70                  75                  80

Pro Leu Ala Gln Trp Ile Asp Asn Asp Ala Met Ile Val Val Leu Gln
                85                  90                  95

Ser Val Leu Ser Thr Ile Ile Leu Phe Thr Gly Glu Phe Leu Pro
            100                 105                 110

Lys Ala Ile Phe Lys Thr Asn Ala Asn Met Met Met Arg Val Phe Ala
        115                 120                 125

Leu Pro Ile Val Ala Ile Tyr Tyr Leu Leu Tyr Pro Leu Ser Lys Leu
    130                 135                 140

Phe Thr Gly Leu Ser Arg Ser Phe Ile Arg Leu Val Asp Lys Asn Tyr
145                 150                 155                 160

Val Pro Thr Thr Val Gly Leu Gly Arg Val Asp Leu Asp His Tyr Leu
                165                 170                 175

Ala Glu Asn Met Ser Gly Glu Asn Glu Gln Asn Asp Leu Thr Thr Glu
            180                 185                 190

Val Lys Ile Ile Gln Asn Ala Leu Asp Phe Ser Gly Ile Gln Val Arg
        195                 200                 205

Asp Cys Met Ile Pro Arg Asn Glu Met Ile Ala Cys Glu Leu Gln Thr
    210                 215                 220

Asp Ile Glu Val Leu Lys Thr Thr Phe Ile Asp Thr Gly Leu Ser Lys
225                 230                 235                 240

Ile Ile Ile Tyr Arg Gln Asn Ile Asp Asp Val Val Gly Tyr Ile His
                245                 250                 255

Ser Ser Glu Met Phe Arg Gly Gln Asp Trp Gln Lys Arg Ile Asn Thr
            260                 265                 270

Thr Val Phe Val Pro Glu Ser Met Tyr Ala Asn Lys Leu Met Arg Leu
        275                 280                 285

Leu Met Gln Arg Lys Lys Ser Ile Ala Ile Val Ile Asp Glu Leu Gly
    290                 295                 300

Gly Thr Ala Gly Met Val Thr Leu Glu Asp Leu Val Glu Glu Ile Phe
305                 310                 315                 320

Gly Asp Ile Glu Asp Glu His Asp Thr Arg Lys Ile Ile Ala Lys Gln
                325                 330                 335

Leu Gly Pro His Thr Tyr Leu Val Ser Gly Arg Met Glu Ile Asp Asp
            340                 345                 350
```

```
Val Asn Glu Arg Phe Gly Leu Ser Leu Pro Glu Ser Asp Asp Tyr Leu
            355                 360                 365

Thr Val Ala Gly Phe Ile Leu Asn Ser His Gln Asn Ile Pro Gln Ala
            370                 375                 380

Asn Glu Val Val Glu Ile Ala Pro Tyr Thr Phe Thr Ile Leu Arg Ser
385                 390                 395                 400

Ser Ser Thr Lys Ile Glu Leu Val Lys Met Ser Ile Asp Asp Gln Ser
            405                 410                 415

Asn
```

<210> SEQ ID NO 123
<211> LENGTH: 293
<212> TYPE: PRT
<213> ORGANISM: Porphyromonas gingivalis

<400> SEQUENCE: 123

```
Met Lys Gln Asn Tyr Phe Lys Arg Val Cys Ser Leu Leu Trp Leu Val
1               5                   10                  15

Leu Pro Met Leu Ile Met Pro Leu Glu Val Ala Ala Gln Glu Ile Ile
            20                  25                  30

Pro Asn Glu Glu Val Leu Glu Ser Leu Thr Phe Val Ala Pro Val Glu
            35                  40                  45

Glu Thr Asp Ala Ile Glu Ala Glu Val Glu Ala Leu Gln Glu Ile Val
        50                  55                  60

Ala Thr Glu Glu Ile Ala Glu Gln Ala Val Arg Ser Tyr Thr Tyr Thr
65                  70                  75                  80

Val Tyr Arg Asp Gly Val Lys Ile Ala Ser Gly Leu Thr Glu Pro Thr
                85                  90                  95

Phe Leu Asp Glu Asp Val Pro Ala Gly Glu His Thr Tyr Cys Val Glu
            100                 105                 110

Val Gln Tyr Gln Gly Gly Val Ser Asp Lys Val Cys Val Asp Val Glu
            115                 120                 125

Val Lys Asp Phe Lys Pro Val Thr Asn Leu Thr Gly Thr Ala Ser Asn
130                 135                 140

Asp Glu Val Ser Leu Asp Trp Asp Gly Val Glu Glu Lys Ala Glu Glu
145                 150                 155                 160

Pro Ala Ser Asp Lys Ala Val Ser Tyr Asn Val Tyr Lys Asn Gly Thr
                165                 170                 175

Leu Ile Gly Asn Thr Ala Glu Ser His Tyr Val Glu Thr Gly Val Ala
            180                 185                 190

Asn Gly Thr Tyr Ile Tyr Glu Val Glu Val Lys Tyr Pro Asp Gly Val
            195                 200                 205

Ser Pro Lys Val Ala Val Thr Val Thr Val Thr Asn Ser Ser Leu Ser
210                 215                 220

Asn Val Asp Gly Gln Ala Pro Tyr Thr Leu Arg Val Glu Gly Lys Lys
225                 230                 235                 240

Ile Ile Ala Glu Ala His Gly Met Ile Thr Leu Tyr Asp Ile Asn Gly
                245                 250                 255

Arg Thr Val Ala Val Ala Pro Asn Arg Leu Glu Tyr Met Ala Gln Thr
            260                 265                 270

Gly Phe Tyr Ala Val Arg Phe Asp Val Gly Asn Lys His His Val Ser
            275                 280                 285

Lys Ile Gln Val Arg
    290
```

<210> SEQ ID NO 124
<211> LENGTH: 312
<212> TYPE: PRT
<213> ORGANISM: Porphyromonas gingivalis

<400> SEQUENCE: 124

Met Ile Pro Leu Ser Glu Ser Phe Glu Ser Gly Ile Pro Ala Ile Trp
1               5                   10                  15

Lys Thr Ile Asp Ala Asp Gly Asp Gly Tyr Asn Trp Met His Leu Thr
            20                  25                  30

Asn Phe Thr Gly Gln Ser Gly Leu Cys Val Ser Ser Ala Ser Tyr Ile
        35                  40                  45

Gly Gly Val Gly Ala Leu Thr Pro Asp Asn Tyr Leu Ile Thr Pro Glu
    50                  55                  60

Leu Lys Leu Pro Thr Asp Ala Leu Val Glu Ile Tyr Trp Val Cys
65                  70                  75                  80

Thr Gln Asp Leu Thr Ala Pro Ser Glu His Tyr Ala Val Tyr Ser Ser
                85                  90                  95

Ser Thr Gly Asn Asn Ala Ala Asp Phe Val Asn Leu Tyr Glu Glu
            100                 105                 110

Thr Leu Thr Ala Lys Arg Ile Gln Ser Pro Glu Leu Ile Arg Gly Asn
        115                 120                 125

Arg Thr Gln Gly Val Trp Tyr Gln Arg Lys Val Val Leu Pro Asn Asp
    130                 135                 140

Thr Lys Tyr Val Ala Phe Arg His Phe Asn Ser Thr Asp Asn Phe Trp
145                 150                 155                 160

Leu Asn Leu Asp Glu Val Ser Ile Leu Tyr Thr Pro Leu Pro Arg Arg
                165                 170                 175

Ala Pro Cys Pro His Pro Gly Gly Tyr Thr Tyr Ser Val Phe Arg Asp
            180                 185                 190

Gly Gln Lys Ile Ala Ser Gly Leu Ser Ala Leu Ala Tyr Ile Asp Thr
        195                 200                 205

Asp Val Pro Tyr Gly Thr Gln Asp Tyr Cys Val Gln Val Asn Tyr Leu
    210                 215                 220

Gln Gly Asp Ser Tyr Lys Val Cys Lys Asn Ile Val Val Ala Asn Ser
225                 230                 235                 240

Ala Asn Ile Tyr Gly Ala Asp Lys Pro Phe Ala Leu Thr Val Val Gly
                245                 250                 255

Lys Thr Ile Val Ala Ser Ala Phe Lys Gly Glu Ile Thr Leu Tyr Asp
            260                 265                 270

Ile Arg Gly Arg Leu Ile Ala Ser Gly Cys Asp Thr Leu Arg Tyr Lys
        275                 280                 285

Ala Glu Asn Gly Phe Tyr Leu Ile Lys Ile Gln Val Asn Gly Thr Val
    290                 295                 300

Tyr Thr Glu Lys Ile Gln Ile Gln
305                 310

<210> SEQ ID NO 125
<211> LENGTH: 843
<212> TYPE: PRT
<213> ORGANISM: Porphyromonas gingivalis

<400> SEQUENCE: 125

Met Lys Lys Ser Phe Leu Leu Ala Ile Val Met Leu Phe Gly Ile Ala
1               5                   10                  15

Met Gln Gly His Ser Ala Pro Val Thr Lys Glu Arg Ala Leu Ser Leu

```
                    20                  25                  30
Ala Arg Leu Ala Leu Arg Gln Val Ser Leu Arg Met Gly Gln Thr Ala
                35                  40                  45

Val Ser Asp Lys Ile Ser Ile Asp Tyr Val Tyr Arg Gln Gly Asp Ala
 50                  55                  60

Glu Arg Gly Ile Thr Ser Gln Glu Glu Gly Ser Pro Ala Tyr Phe Tyr
 65                  70                  75                  80

Val Ala Asn Arg Gly Asn Asn Glu Gly Tyr Ala Leu Val Ala Ala Asp
                 85                  90                  95

Asp Arg Ile Pro Thr Ile Leu Ala Tyr Ser Pro Ile Gly Arg Phe Asp
                100                 105                 110

Met Asp Ser Met Pro Asp Asn Leu Arg Met Trp Leu Gln Ile Tyr Asp
                115                 120                 125

Gln Glu Ile Gly Leu Ile Leu Ser Gly Lys Ala Gln Leu Asn Glu Glu
                130                 135                 140

Ile Leu Arg Thr Glu Gly Val Pro Ala Glu Val His Ala Leu Met Asp
145                 150                 155                 160

Asn Gly His Phe Ala Asn Asp Pro Met Arg Trp Asn Gln Gly Tyr Pro
                165                 170                 175

Trp Asn Asn Lys Glu Pro Leu Leu Pro Asn Gly Asn His Ala Tyr Thr
                180                 185                 190

Gly Cys Val Ala Thr Ala Ala Gln Ile Met Arg Tyr His Ser Trp
                195                 200                 205

Pro Leu Gln Gly Glu Gly Ser Phe Asp Tyr His Ala Gly Ser Leu Val
                210                 215                 220

Gly Asn Trp Ser Gly Thr Phe Gly Glu Met Tyr Asp Trp Ile Asn Met
225                 230                 235                 240

Pro Gly Asn Pro Asp Leu Asp Asn Leu Thr Gln Ser Gln Val Asp Ala
                245                 250                 255

Tyr Ala Thr Leu Met Arg Asp Val Ser Ala Ser Val Ser Met Ser Phe
                260                 265                 270

Tyr Glu Asn Gly Ser Gly Thr Tyr Ser Val Tyr Val Gly Ala Leu
                275                 280                 285

Arg Asn Asn Phe Arg Tyr Lys Arg Ser Leu Gln Leu His Val Arg Ala
                290                 295                 300

Leu Tyr Thr Ser Gln Glu Trp His Asp Met Ile Arg Gly Glu Leu Ala
305                 310                 315                 320

Ser Gly Arg Pro Val Tyr Tyr Ala Gly Asn Asn Gln Ser Ile Gly His
                325                 330                 335

Ala Phe Val Cys Asp Gly Tyr Ala Ser Asp Gly Thr Phe His Phe Asn
                340                 345                 350

Trp Gly Trp Gly Gly Val Ser Asn Gly Phe Tyr Lys Leu Thr Leu Leu
                355                 360                 365

Ser Pro Thr Ser Leu Gly Ile Gly Gly Glu Gly Ile Gly Phe Thr Ile
                370                 375                 380

Tyr Gln Glu Ile Ile Thr Gly Ile Glu Pro Ala Lys Thr Pro Ala Glu
385                 390                 395                 400

Ala Gly Thr Asp Ala Leu Pro Ile Leu Ala Leu Lys Asp Ile Glu Ala
                405                 410                 415

Glu Tyr Lys Ser Glu Ser Gly Leu Asn Val Gly Tyr Ser Ile Tyr Asn
                420                 425                 430

Thr Gly Glu Glu Gln Ser Asn Leu Asp Leu Gly Tyr Arg Leu Asn Lys
                435                 440                 445
```

Ala Asp Gly Glu Val Ile Glu Val Lys Thr Ser Ser Ile Asn Ile Ser
        450                 455                 460

Trp Tyr Gly Tyr Gly Glu His Pro Glu Ser Phe Ser Leu Ala Pro Asn
465                 470                 475                 480

Gln Leu Ser Gln Gly Ile Asn Thr Ile Thr Leu Leu Tyr Arg Arg Thr
                485                 490                 495

Gly Thr Glu Gln Trp Glu Pro Val Arg His Ala Gln Gly Gly Tyr Val
            500                 505                 510

Asn Ser Ile Lys Val Asn Thr Thr Asp Pro Asn Asn Val Val Val Thr
        515                 520                 525

Val Asp Asn Asn Glu Gly Lys Leu Ser Ile Val Pro Asn Ser Phe Val
530                 535                 540

Ala Asp Leu Asn Ser Tyr Glu His Ser Thr Ile Thr Val Gln Phe Asn
545                 550                 555                 560

Ser Asp Ser Pro Asp Glu Ile Arg Thr Pro Val Ala Phe Ala Leu Ser
                565                 570                 575

Thr Gly Ala Thr Ala Asp Asp Val Ile Ser Leu Gly Trp Val Met Ala
            580                 585                 590

Glu Val Pro Gly Gly Ser Ser Asn Tyr Pro Val Val Trp Ser Lys Asp
        595                 600                 605

Val Leu Thr Leu Ser Glu Gly Asp Tyr Thr Leu Trp Tyr Arg Phe Ser
610                 615                 620

Ile Asn Asn Gln Lys Asp Glu Trp Lys Lys Ile Gly Ser Val Ser Val
625                 630                 635                 640

Lys Thr Pro Thr Glu Tyr Thr His Pro Leu Phe Glu Val Gly His Asn
                645                 650                 655

Gln Thr Ser Thr Tyr Thr Leu Asp Met Ala His Asn Arg Val Leu Pro
            660                 665                 670

Asp Phe Thr Leu Lys Asn Leu Gly Leu Pro Phe Asn Gly Glu Leu Val
        675                 680                 685

Val Val Phe Arg Gln Thr Gln Ser Ser Gly Ser Leu Trp Ala Ala
690                 695                 700

Gln Glu Thr Val His Ile Lys Gln Gly Glu Thr Phe Val Tyr Lys Pro
705                 710                 715                 720

Val Val Glu Gly Pro Ile Pro Asp Gly Ser Tyr Arg Ala Thr Leu His
                725                 730                 735

Ala Phe Val Asn Gly Gln Gln Leu Tyr Leu Lys Gly Lys Arg Asn
            740                 745                 750

Tyr Thr Val Lys Ile Val Asn Gly Thr Ala Val Glu Ala Ile Glu Ser
        755                 760                 765

Ser Glu Glu Ile Arg Val Phe Pro Asn Pro Ala Arg Asp Tyr Val Glu
770                 775                 780

Ile Ser Ala Pro Cys Ile Pro Gln Glu Thr Ser Ile Ile Leu Phe Asp
785                 790                 795                 800

Leu Ser Gly Lys Ile Val Met Lys Asn Ser Leu Ser Ala Gly His Gly
                805                 810                 815

Arg Met Asp Val Ser Arg Leu Pro Asn Gly Ala Tyr Ile Leu Lys Val
            820                 825                 830

Asp Gly Tyr Thr Thr Lys Ile Asn Ile Val His
        835                 840

<210> SEQ ID NO 126
<211> LENGTH: 290
<212> TYPE: PRT
<213> ORGANISM: Porphyromonas gingivalis

```
<400> SEQUENCE: 126

Met Lys Lys Leu Phe Leu Ser Leu Thr Ser Leu Val Met Val Phe Ala
1               5                   10                  15

Val Ala Ser Cys Asp Ile Ile Asp Lys Asp Gln Thr Leu Leu Pro Ala
            20                  25                  30

Pro Thr Asn Val Thr Pro Asp Asn Pro Asp Asn Pro Ser Glu Ile
        35                  40                  45

Asp Ile Thr Gln Thr His Thr Glu Lys Tyr Val Leu Ala Glu Glu Phe
50                  55                  60

Thr Gly Gln Lys Cys Leu Asn Cys Pro Lys Gly His Arg Lys Leu Ala
65                  70                  75                  80

Ala Leu Lys Glu Gln Tyr Gly Lys Arg Leu Thr Val Val Gly Ile His
                85                  90                  95

Ala Gly Pro Gly Ser Leu Val Pro Pro Leu Phe Arg Thr Glu Ala Gly
            100                 105                 110

Asp Ala Tyr Tyr Ser Lys Phe Ala Asn Asn Thr Pro Leu Pro Ala Leu
        115                 120                 125

Met Val Ser Arg Lys Lys Phe Gly Ser Ser Tyr Val Tyr Asp Lys Ser
130                 135                 140

Tyr Lys Thr Trp Asp Val Pro Ile Ala Glu Gln Met Glu Gln Lys Ala
145                 150                 155                 160

Lys Ile Asn Ile Phe Ala Val Ala Glu Tyr Thr Asp Thr Gln Lys Ile
                165                 170                 175

Lys Val Thr Val Lys Gly Lys Ile Leu Glu Gly Asn Thr Leu Pro Lys
            180                 185                 190

Ser Met Val Gln Val Tyr Leu Leu Glu Asp Lys Leu Ile Ala Pro Gln
        195                 200                 205

Val Asp Gly Asn Thr Thr Val Glu Asn Tyr Glu His Asn His Val Leu
210                 215                 220

Arg Gly Ala Val Asn Gly Ile Trp Gly Glu Glu Phe Val Asn Leu Lys
225                 230                 235                 240

Asp Tyr Leu Tyr Thr Tyr Ala Val Glu Pro Leu Ser Gly Met Ser Phe
                245                 250                 255

Val Ala Glu Asn Tyr Ser Ile Val Ala Phe Val Tyr Asp Val Gln Thr
            260                 265                 270

Phe Glu Val Tyr Asp Val Val His Val Lys Ile Asn Pro Gln Ser Asp
        275                 280                 285

Gly Lys
    290

<210> SEQ ID NO 127
<211> LENGTH: 223
<212> TYPE: PRT
<213> ORGANISM: Porphyromonas gingivalis

<400> SEQUENCE: 127

Met Lys Lys Ser Ser Val Val Ala Ser Val Leu Ala Val Ala Leu Val
1               5                   10                  15

Phe Ala Gly Cys Gly Leu Asn Asn Met Ala Lys Gly Gly Leu Ile Gly
            20                  25                  30

Ala Gly Val Gly Gly Ala Ile Gly Ala Gly Val Gly Gly Asn Val Ala Gly
        35                  40                  45

Asn Thr Ala Val Gly Ala Ile Gly Thr Ala Val Gly Gly Ala Ala
50                  55                  60
```

```
Gly Ala Leu Ile Gly Lys Lys Met Asp Lys Gln Lys Glu Leu Glu
 65                  70                  75                  80

Ala Ala Val Pro Asp Ala Thr Ile Gln Thr Val Asn Asp Gly Glu Ala
                 85                  90                  95

Ile Leu Val Thr Phe Asp Ser Gly Ile Leu Phe Ala Thr Asn Ser Ser
                100                 105                 110

Thr Leu Ser Pro Asn Ser Arg Thr Ala Leu Thr Lys Phe Ala Ala Asn
            115                 120                 125

Met Asn Lys Asn Pro Asp Thr Asp Ile Arg Ile Val Gly His Thr Asp
        130                 135                 140

Asn Thr Gly Ser Asp Lys Ile Asn Asp Pro Leu Ser Glu Arg Arg Ala
145                 150                 155                 160

Ala Ser Val Tyr Ser Phe Leu Asn Ser Gln Gly Val Ser Met Ser Arg
                165                 170                 175

Met Ala Ala Glu Gly Arg Gly Ser His Glu Pro Val Ala Asp Asn Ser
                180                 185                 190

Thr Val Ala Gly Arg Ser Ala Asn Arg Arg Val Glu Val Tyr Ile Leu
            195                 200                 205

Pro Asn Ala Lys Met Ile Glu Gln Ala Gln Gln Gly Thr Leu Lys
        210                 215                 220

<210> SEQ ID NO 128
<211> LENGTH: 672
<212> TYPE: PRT
<213> ORGANISM: Porphyromonas gingivalis

<400> SEQUENCE: 128

Met Tyr Ser Gly His His Lys Ile His Tyr Pro Phe Leu Ile Leu Leu
  1               5                  10                  15

Val Cys Leu Ala Phe Ala Ala Cys Lys Ser Val Lys Leu Lys Asp Ala
                 20                  25                  30

Glu Lys Ala His Asp Arg Gln Glu Tyr Thr Lys Ala Ala Asp Met Tyr
             35                  40                  45

Asn Thr Leu Tyr Arg Arg Thr Arg Arg Lys Gln Val Glu Met Lys Ala
 50                  55                  60

Tyr Thr Ala Phe Arg Ser Gly Glu Asn Tyr Arg Ala Ala Gly Arg Gln
 65                  70                  75                  80

Ala Lys Ala Leu Arg Gly Tyr Leu Asn Ala Arg Arg Tyr Gly Tyr Pro
                 85                  90                  95

Asp Ser Val Leu Leu Arg Leu Ala Gln Thr Tyr Gln Gln Gly Gly
                100                 105                 110

Asn Tyr Lys Glu Ala Glu Val Leu Phe Arg Gly Tyr Leu Glu Ala Tyr
            115                 120                 125

Pro Lys Ser Tyr Phe Ala Ala Ile Gly Leu Glu Gly Cys Leu Phe Ala
        130                 135                 140

Arg Gln Gln Lys Glu Tyr Pro Thr Arg Tyr Arg Ile Arg Arg Ala Ala
145                 150                 155                 160

Glu Trp Asn Ser Ala Arg Gly Asp Phe Gly Pro Ala Tyr Ala Pro Asp
                165                 170                 175

Ala Ser Ala Leu Tyr Phe Thr Ser Ser Arg Ser Lys Asp Asp Gly Leu
                180                 185                 190

Asp Asn Ser Ser Ile Thr Gly Leu Lys Pro Asn Asp Ile Tyr Ile Ile
            195                 200                 205

Lys Arg Asp Ala Gln Gly Arg Trp Gly Arg Pro Asp Ser Val Ser Gly
        210                 215                 220
```

```
Gly Ile Asn Thr Pro Trp Asp Glu Gly Val Pro Thr Ile Thr Pro Asp
225                 230                 235                 240

Gly Ser Thr Ile Tyr Tyr Thr Leu Ala Gln Gln Gly Ala Asp Tyr Asp
            245                 250                 255

Arg Thr Val Gln Ile Tyr Ser Ala Ala Arg Ser Gly Glu Gly Gly Trp
                260                 265                 270

Ser Asn Gly Ser Leu Val Asp Ile Met Arg Asp Ser Leu Arg Met Ala
            275                 280                 285

Ala His Pro Ser Met Ser Ala Ser Gly Asp Tyr Leu Tyr Phe Val Ser
            290                 295                 300

Asn Ile Gly Gly Ser Tyr Gly Gly Lys Asp Ile Tyr Arg Val Lys Val
305                 310                 315                 320

Ser Asp Arg Ser Tyr Gly Ser Pro Glu Asn Leu Gly Pro Asp Ile Asn
                325                 330                 335

Thr Pro Gly Asp Glu Met Phe Pro Phe Ile Asp Gly Asp Ser Thr Leu
            340                 345                 350

Phe Phe Ala Ser Asp Gly His Ala Gly Leu Gly Gly Leu Asp Ile Phe
            355                 360                 365

Lys Ala Thr Leu Asp Ser Thr Gly Gln Trp His Val Val Asn Met Gly
370                 375                 380

Gln Pro Val Asn Ser Ser Ala Asp Asp Phe Gly Leu Ala Val Glu Pro
385                 390                 395                 400

Lys Gly Lys Asn Lys Glu Glu Ala Leu Pro Asp Asn Gly Val Lys Gly
                405                 410                 415

Val Phe Cys Ser Asn Arg Gly Asp Ala Arg Gly Trp Pro His Leu Phe
            420                 425                 430

His Phe Glu Leu Pro Ala Ile Tyr Thr Glu Ile Gln Gly Tyr Val Met
            435                 440                 445

Asp Arg Glu Glu Asn Pro Ile Ala Gly Ala Thr Val Arg Ile Val Gly
450                 455                 460

Glu Arg Gly Pro Val Gly Gln Gly Phe Val Thr Arg Asp Asp Gly
465                 470                 475                 480

Ser Tyr Lys Met Ser Val Gln Gly Asp Thr Arg Tyr Val Met Leu Ala
                485                 490                 495

Gly Ala Ser Gly Tyr Leu Asn Gln Tyr Val Glu Leu Lys Thr Asp Thr
            500                 505                 510

Ala Lys Gln Ser Glu Thr Tyr Tyr Val Asp Phe Phe Leu Ala Ser Arg
            515                 520                 525

Glu Lys Ala Glu Gly Leu Gln Asn Ile Phe Tyr Asp Phe Asp Lys Ala
            530                 535                 540

Thr Leu Arg Pro Glu Ser Met Lys Ser Leu Asp Glu Leu Ile Arg Ile
545                 550                 555                 560

Leu Thr Asp Asn Pro Asp Ile Arg Ile Glu Leu Gly Ser His Ala Asp
                565                 570                 575

Arg Lys Gly Pro Asp Ala Tyr Asn Leu Gly Leu Ser Asp Arg Arg Ala
            580                 585                 590

Lys Ser Val Val Asp Tyr Leu Thr Ser Arg Gly Ile Ala Ala Asp Arg
            595                 600                 605

Leu Thr Trp Lys Gly Tyr Gly Lys Ser Val Pro Lys Thr Val Thr Ala
            610                 615                 620

Lys Ile Ala Glu Arg His Asp Phe Leu Lys Glu Gly Asp Val Leu Thr
625                 630                 635                 640

Glu Glu Phe Val Ala Pro Leu Thr Glu Glu Gln Gln Ser Val Cys Asp
                645                 650                 655
```

```
Gln Leu Asn Arg Arg Thr Glu Phe Arg Val Ile Glu Glu Glu Leu Arg
            660                 665                 670
```

<210> SEQ ID NO 129
<211> LENGTH: 315
<212> TYPE: PRT
<213> ORGANISM: Porphyromonas gingivalis

<400> SEQUENCE: 129

```
Met Ile Arg Thr Ile Leu Ser Arg Tyr Val Ser Asn Phe Trp Ser
1               5                   10                  15

Arg Gly Ala Thr Phe Phe Thr Ile Phe Pro Ala Phe Ile Leu Ala
            20                  25                  30

Ala Thr Ala Leu Pro Ala Cys Gly Gly Thr Ala Ser Gly Ser Asp
            35                  40                  45

Arg Thr Leu Ala Val Thr Ile Glu Pro Gln Lys Tyr Phe Ile Glu Ser
50                  55                  60

Ile Ala Asp Lys Ser Val Gln Val Val Ala Leu Val Pro Ala Gly Ser
65                  70                  75                  80

Asn Pro Glu Glu Tyr Asp Pro Ser Pro Thr Val Met Lys Arg Leu Ser
                85                  90                  95

Glu Ala Asp Ala Tyr Phe Tyr Ile Gly Gly Leu Gly Phe Glu Gln Arg
            100                 105                 110

Asn Leu Ala Ala Ile Arg Asp Asn Asn Pro Lys Leu Pro Leu Phe Glu
            115                 120                 125

Met Gly Lys Ala Leu Ala Asp Ala Gly Ser Ala Asp Leu His Gly Ser
130                 135                 140

Cys Thr Asp His Ser His Thr Asp Leu His Ala His Asp Pro His Tyr
145                 150                 155                 160

Trp Ser Ser Val Val Gly Ala Lys Ala Leu Ser Arg Ala Ala Tyr Asp
                165                 170                 175

Ala Leu Val Glu Leu Tyr Pro Asn Glu Lys Asp Lys Trp Asp Lys Gly
            180                 185                 190

His Asp Arg Leu Asn Gly Arg Ile Asp Ser Val Lys Arg Leu Val Asp
            195                 200                 205

Thr Met Phe Ala Asn Gly Lys Ala Asp Lys Ala Phe Val Ile Tyr His
210                 215                 220

Pro Ser Leu Ser Phe Phe Ala Gln Glu Phe Gly Leu Arg Gln Ile Val
225                 230                 235                 240

Ile Glu Glu Asp Gly Lys Glu Pro Thr Ala Ala His Leu Arg Arg Val
                245                 250                 255

Ile Asp Gln Ala Arg Ala Asp Gly Val Arg Ile Val Phe Ile Gln Pro
            260                 265                 270

Glu Phe Glu Thr Arg Gln Ala Glu Asp Ile Ala Arg Glu Ile Gly Ala
            275                 280                 285

Arg Pro Val Arg Ile Asn Pro Leu Arg Ser Ser Trp Glu Glu Glu Ile
290                 295                 300

Leu His Ile Ala Arg Ala Leu Ala His Glu Arg
305                 310                 315
```

<210> SEQ ID NO 130
<211> LENGTH: 940
<212> TYPE: PRT
<213> ORGANISM: Porphyromonas gingivalis

<400> SEQUENCE: 130

```
Met Asn Lys Phe Tyr Lys Ser Leu Leu Gln Ser Gly Leu Ala Ala Phe
1               5                   10                  15

Val Ser Met Ala Thr Ala Leu Thr Ala Ser Ala Gln Ile Ser Phe Gly
            20                  25                  30

Gly Glu Pro Leu Ser Phe Ser Ser Arg Ser Ala Gly Thr His Ser Phe
        35                  40                  45

Asp Asp Ala Met Thr Ile Arg Leu Thr Pro Asp Phe Asn Pro Glu Asp
    50                  55                  60

Leu Ile Ala Gln Ser Arg Trp Gln Ser Gln Arg Asp Gly Arg Pro Val
65                  70                  75                  80

Arg Ile Gly Gln Val Ile Pro Val Asp Val Phe Ala Ser Lys Ala
                85                  90                  95

Ser His Ile Ser Ser Ile Gly Asp Val Asp Val Tyr Arg Leu Gln Phe
                100                 105                 110

Lys Leu Glu Gly Ala Lys Ala Ile Thr Leu Tyr Tyr Asp Ala Phe Asn
            115                 120                 125

Ile Pro Glu Gly Gly Arg Leu Tyr Ile Tyr Thr Pro Asp His Glu Ile
        130                 135                 140

Val Leu Gly Ala Tyr Thr Asn Ala Thr His Arg Arg Asn Gly Ala Phe
145                 150                 155                 160

Ala Thr Glu Pro Val Pro Gly Ser Glu Leu Ile Met Asp Tyr Glu Val
                165                 170                 175

Ser Arg Gly Gly Thr Leu Pro Asp Ile Lys Ile Ser Gly Ala Gly Tyr
                180                 185                 190

Ile Phe Asp Lys Val Gly Gly Arg Pro Val Thr Asp Asn His Tyr Gly
        195                 200                 205

Ile Gly Glu Asp Asp Ser Asp Ser Asp Cys Glu Ile Asn Ile Asn Cys
210                 215                 220

Pro Glu Gly Ala Asp Trp Gln Ala Glu Lys Asn Gly Val Val Gln Met
225                 230                 235                 240

Ile Met Val Lys Gly Gln Tyr Ile Ser Met Cys Ser Gly Asn Leu Leu
                245                 250                 255

Asn Asn Thr Lys Gly Asp Phe Thr Pro Leu Ile Ile Ser Ala Gly His
            260                 265                 270

Cys Ala Ser Ile Thr Thr Asn Phe Gly Val Thr Gln Ser Glu Leu Asp
    275                 280                 285

Lys Trp Ile Phe Thr Phe His Tyr Glu Lys Arg Gly Cys Ser Asn Gly
290                 295                 300

Thr Leu Ala Ile Phe Arg Gly Asn Ser Ile Ile Gly Ala Ser Met Lys
305                 310                 315                 320

Ala Phe Leu Pro Ile Lys Gly Lys Ser Asp Gly Leu Leu Gln Leu
                325                 330                 335

Asn Asp Glu Val Pro Leu Arg Tyr Arg Val Tyr Tyr Asn Gly Trp Asp
            340                 345                 350

Ser Thr Pro Asp Ile Pro Ser Ser Gly Ala Gly Ile His His Pro Ala
        355                 360                 365

Gly Asp Ala Met Lys Ile Ser Ile Leu Lys Lys Thr Pro Ala Leu Asn
    370                 375                 380

Thr Trp Ile Ser Ser Ser Gly Ser Gly Thr Asp Asp His Phe Tyr
385                 390                 395                 400

Phe Lys Tyr Asp Gln Gly Gly Thr Glu Gly Gly Ser Ser Gly Ser Ser
                405                 410                 415

Leu Phe Asn Gln Asn Lys His Val Val Gly Thr Leu Thr Gly Gly Ala
            420                 425                 430
```

```
Gly Asn Cys Gly Gly Thr Glu Phe Tyr Gly Arg Leu Asn Ser His Trp
            435                 440                 445

Asn Glu Tyr Ala Ser Asp Gly Asn Thr Ser Arg Met Asp Ile Tyr Leu
450                 455                 460

Asp Pro Gln Asn Asn Gly Gln Thr Thr Ile Leu Asn Gly Thr Tyr Arg
465                 470                 475                 480

Asp Gly Tyr Lys Pro Leu Pro Ser Val Pro Arg Leu Leu Gln Ser
                485                 490                 495

Thr Gly Asp Gln Val Glu Leu Asn Trp Thr Ala Val Pro Ala Asp Gln
            500                 505                 510

Tyr Pro Ser Ser Tyr Gln Val Glu Tyr His Ile Phe Arg Asn Gly Lys
        515                 520                 525

Glu Ile Ala Thr Thr Lys Glu Leu Ser Tyr Ser Asp Ala Ile Asp Glu
    530                 535                 540

Ser Ile Ile Gly Ser Gly Ile Ile Arg Tyr Glu Val Ser Ala Arg Phe
545                 550                 555                 560

Ile Tyr Pro Ser Pro Leu Asp Gly Val Glu Ser Tyr Lys Asp Thr Asp
                565                 570                 575

Lys Thr Ser Ala Asp Leu Ala Ile Gly Asp Ile Gln Thr Lys Leu Lys
            580                 585                 590

Pro Asp Val Thr Pro Leu Pro Gly Gly Val Ser Leu Ser Trp Lys
        595                 600                 605

Val Pro Phe Leu Ser Gln Leu Val Ser Arg Phe Gly Glu Ser Pro Asn
    610                 615                 620

Pro Val Phe Lys Thr Phe Glu Val Pro Tyr Val Ser Ala Ala Ala Ala
625                 630                 635                 640

Gln Thr Pro Asn Pro Pro Val Gly Val Val Ile Ala Asp Lys Phe Met
                645                 650                 655

Ala Gly Thr Tyr Pro Glu Lys Ala Ala Ile Ala Ala Val Tyr Val Met
            660                 665                 670

Pro Ser Ala Pro Asp Ser Thr Phe His Leu Phe Leu Lys Ser Asn Thr
        675                 680                 685

Asn Arg Arg Leu Gln Lys Val Thr Thr Pro Ser Asp Trp Gln Ala Gly
    690                 695                 700

Thr Trp Leu Arg Ile Asn Leu Asp Lys Pro Phe Pro Val Asn Asn Asp
705                 710                 715                 720

His Met Leu Phe Ala Gly Ile Arg Met Pro Asn Lys Tyr Lys Leu Asn
                725                 730                 735

Arg Ala Ile Arg Tyr Val Arg Asn Pro Asp Asn Leu Phe Ser Ile Thr
            740                 745                 750

Gly Lys Lys Ile Ser Tyr Asn Asn Gly Val Ser Phe Glu Gly Tyr Gly
        755                 760                 765

Ile Pro Ser Leu Leu Gly Tyr Met Ala Ile Lys Tyr Leu Val Val Asn
    770                 775                 780

Thr Asp Ala Pro Lys Ile Asp Met Ser Leu Val Gln Glu Pro Tyr Ala
785                 790                 795                 800

Lys Gly Thr Asn Val Ala Pro Phe Pro Glu Leu Val Gly Ile Tyr Val
                805                 810                 815

Tyr Lys Asn Gly Thr Phe Ile Gly Thr Gln Asp Pro Ser Val Thr Thr
            820                 825                 830

Tyr Ser Val Ser Asp Gly Thr Glu Ser Asp Glu Tyr Glu Ile Lys Leu
        835                 840                 845

Val Tyr Lys Gly Ser Gly Ile Ser Asn Gly Val Ala Gln Ile Glu Asn
```

-continued

```
                850              855              860
Asn Asn Ala Val Val Ala Tyr Pro Ser Val Val Thr Asp Arg Phe Ser
865              870              875              880

Ile Lys Asn Ala His Met Val His Ala Ala Leu Tyr Ser Leu Asp
             885              890              895

Gly Lys Gln Val Arg Ser Trp Asn Asn Leu Arg Asn Gly Val Thr Phe
             900              905              910

Ser Val Gln Gly Leu Thr Ala Gly Thr Tyr Met Leu Val Met Gln Thr
             915              920              925

Ala Asn Gly Pro Val Ser Gln Lys Ile Val Lys Gln
             930              935              940

<210> SEQ ID NO 131
<211> LENGTH: 925
<212> TYPE: PRT
<213> ORGANISM: Porphyromonas gingivalis

<400> SEQUENCE: 131

Met Ala Ile Met Met Lys Ser Ile Val Phe Arg Ala Phe Leu Thr Ile
1               5                   10                  15

Leu Leu Ser Trp Ala Ala Ile Thr Asn Pro Thr Ala Gln Glu Ile Ser
            20                  25                  30

Gly Met Asn Ala Ser Cys Leu Ala Ala Pro Ala Gln Pro Asp Thr Ile
        35                  40                  45

Leu Tyr Glu Ser Phe Glu Asn Gly Pro Val Pro Asn Gly Trp Leu Glu
    50                  55                  60

Ile Asp Ala Asp Ala Asp Gly Ala Thr Trp Gly Ser Pro Ser Gly Ser
65                  70                  75                  80

Phe Ser Val Pro Tyr Gly His Asn Gly Leu Cys Thr Tyr Ser His Ile
                85                  90                  95

Arg Ser Gly Ile Ser Thr Ala Gly Asn Tyr Leu Ile Thr Pro Asn Ile
            100                 105                 110

Glu Gly Ala Lys Arg Val Lys Tyr Trp Val Cys Asn Gln Tyr Ser Thr
        115                 120                 125

Asn Pro Glu His Tyr Ala Val Met Val Ser Thr Thr Gly Thr Ala Ile
    130                 135                 140

Glu Asp Phe Val Leu Leu Phe Asp Asp Ser Ile Thr Gly Lys Pro Thr
145                 150                 155                 160

Pro Leu Val Trp Arg Arg Arg Ile Val Asp Leu Pro Glu Gly Thr Lys
                165                 170                 175

Tyr Ile Ala Trp Arg His Tyr Lys Val Thr Asp Ser His Thr Glu Phe
            180                 185                 190

Leu Lys Leu Asp Asp Val Thr Val Tyr Arg Ser Ile Glu Gly Pro Glu
        195                 200                 205

Pro Ala Thr Asp Phe Thr Val Ile Asn Ile Gly Gln Asn Val Gly Arg
    210                 215                 220

Leu Thr Trp Asn Tyr Pro Glu Asp Tyr Gln Pro Glu Gly Lys Gly Asn
225                 230                 235                 240

Glu Glu Leu Gln Leu Ser Gly Tyr Asn Ile Tyr Ala Asn Gly Thr Leu
                245                 250                 255

Leu Ala Gln Ile Lys Asp Val Ser Ile Leu Glu Tyr Val Asp Ser Thr
            260                 265                 270

Tyr Ser Leu Arg Asp Asn Pro Leu Gln Val Glu Tyr Cys Val Thr Ala
        275                 280                 285

Val Tyr Asp Glu Ser Ile Glu Ser Ser Thr Val Cys Gly Thr Leu His
```

```
            290                 295                 300
Tyr Ala Thr Asp Ala Ile Leu Tyr Glu Asn Phe Glu Asn Gly Pro Val
305                 310                 315                 320

Pro Asn Gly Trp Leu Val Ile Asp Ala Asp Gly Asp Gly Phe Ser Trp
            325                 330                 335

Gly His Tyr Leu Asn Ala Tyr Asp Ala Phe Pro Gly His Asn Gly Gly
            340                 345                 350

His Cys Ser Leu Ser Ala Ser Tyr Val Pro Gly Ile Gly Pro Val Thr
            355                 360                 365

Pro Asp Asn Tyr Leu Ile Thr Pro Lys Val Glu Gly Ala Lys Arg Val
370                 375                 380

Lys Tyr Trp Val Ser Thr Gln Asp Ala Asn Trp Ala Ala Glu His Tyr
385                 390                 395                 400

Ala Val Met Ala Ser Thr Thr Gly Thr Ala Val Gly Asp Phe Val Ile
            405                 410                 415

Leu Phe Glu Glu Thr Met Thr Ala Lys Pro Thr Gly Ala Trp Tyr Glu
            420                 425                 430

Arg Thr Ile Asn Leu Pro Glu Gly Thr Lys Tyr Ile Ala Trp Arg His
            435                 440                 445

Tyr Asn Cys Thr Asp Ile Tyr Phe Leu Lys Leu Asp Asp Ile Thr Val
450                 455                 460

Phe Gly Thr Pro Ala Ser Glu Pro Glu Pro Val Thr Asp Phe Val Val
465                 470                 475                 480

Ser Leu Ile Glu Asn Asn Lys Gly Arg Leu Lys Trp Asn Tyr Pro Asn
            485                 490                 495

Gly Tyr Glu Pro Asp Lys Thr Asp Lys Asp Pro Leu Gln Leu Ala
            500                 505                 510

Gly Tyr Asn Ile Tyr Ala Asn Gly Ser Leu Leu Val His Ile Gln Asp
            515                 520                 525

Pro Thr Val Leu Glu Tyr Ile Asp Glu Thr Tyr Ser Ser Arg Asp Asp
            530                 535                 540

Gln Val Glu Val Glu Tyr Cys Val Thr Ala Val Tyr Asn Asp Asn Ile
545                 550                 555                 560

Glu Ser Gln Ser Val Cys Asp Lys Leu Ile Tyr Asp Ser Gln Ser Asp
            565                 570                 575

Ile Ile Leu Tyr Glu Gly Phe Glu Ala Gly Ser Ile Pro Glu Gly Trp
            580                 585                 590

Leu Leu Ile Asp Ala Asp Gly Asp Asn Val Asn Trp Asp Tyr Tyr Pro
            595                 600                 605

Trp Thr Met Tyr Gly His Asp Ser Glu Lys Cys Ile Ala Ser Pro Ser
610                 615                 620

Tyr Leu Pro Met Ile Gly Val Leu Thr Pro Asp Asn Tyr Leu Val Thr
625                 630                 635                 640

Pro Arg Leu Glu Gly Ala Lys Leu Val Lys Tyr Trp Val Ser Ala Gln
            645                 650                 655

Asp Ala Val Tyr Ser Ala Glu His Tyr Ala Val Met Val Ser Thr Thr
            660                 665                 670

Gly Thr Ala Val Glu Asp Phe Val Leu Leu Phe Glu Glu Thr Met Thr
            675                 680                 685

Ala Lys Ala Asn Gly Ala Trp Tyr Glu Arg Thr Ile Thr Leu Pro Ala
            690                 695                 700

Gly Thr Lys Tyr Ile Ala Trp Arg His Tyr Asp Cys Thr Asp Met Phe
705                 710                 715                 720
```

```
Phe Leu Leu Leu Asp Asp Ile Thr Val Tyr Arg Ser Thr Glu Thr Val
                725                 730                 735

Pro Glu Pro Val Thr Asp Phe Val Val Ser Leu Ile Glu Asn Asn Lys
            740                 745                 750

Gly Arg Leu Lys Trp Asn Tyr Pro Asn Gly Tyr Glu Pro Asp Lys Thr
        755                 760                 765

Asp Asp Lys Lys Pro Leu Gln Leu Thr Gly Tyr Asn Ile Tyr Ala Asn
    770                 775                 780

Gly Ser Leu Leu Val His Ile Gln Asp Pro Thr Val Leu Glu Tyr Ile
785                 790                 795                 800

Asp Glu Thr Tyr Ser Ser Arg Asp Gly Gln Val Glu Met Glu Tyr Cys
                805                 810                 815

Val Thr Ala Val Tyr Asn Asp Asn Ile Glu Ser Gln Ser Val Cys Asp
            820                 825                 830

Lys Leu Asn Tyr Thr Ile Thr Ser Leu Asp Asn Ile Gln Ser Asp Thr
        835                 840                 845

Ser Leu Lys Ile Tyr Pro Asn Pro Ala Ser Tyr Val Val Arg Ile Glu
    850                 855                 860

Gly Leu Ser Arg Ser Lys Ser Thr Ile Glu Leu Tyr Asn Ala Leu Gly
865                 870                 875                 880

Ile Cys Ile Leu Arg Glu Glu Thr His Ser Glu Lys Thr Glu Ile Asp
                885                 890                 895

Val Ser Arg Leu Asn Asp Gly Val Tyr Leu Ile Lys Val Val Gly Gly
            900                 905                 910

Asn Lys Thr Thr Thr Glu Lys Val Glu Ile Lys Arg Pro
        915                 920                 925

<210> SEQ ID NO 132
<211> LENGTH: 922
<212> TYPE: PRT
<213> ORGANISM: Porphyromonas gingivalis

<400> SEQUENCE: 132

Met Met Lys Ser Ile Val Phe Arg Ala Phe Leu Thr Ile Leu Leu Ser
1               5                   10                  15

Trp Ala Ala Ile Thr Asn Pro Thr Ala Gln Glu Ile Ser Gly Met Asn
            20                  25                  30

Ala Ser Cys Leu Ala Ala Pro Ala Gln Pro Asp Thr Ile Leu Tyr Glu
        35                  40                  45

Ser Phe Glu Asn Gly Pro Val Pro Asn Gly Trp Leu Glu Ile Asp Ala
    50                  55                  60

Asp Ala Asp Gly Ala Thr Trp Gly Ser Pro Ser Gly Ser Phe Ser Val
65                  70                  75                  80

Pro Tyr Gly His Asn Gly Leu Cys Thr Tyr Ser His Ile Arg Ser Gly
                85                  90                  95

Ile Ser Thr Ala Gly Asn Tyr Leu Ile Thr Pro Asn Ile Glu Gly Ala
            100                 105                 110

Lys Arg Val Lys Tyr Trp Val Cys Asn Gln Tyr Ser Thr Asn Pro Glu
        115                 120                 125

His Tyr Ala Val Met Val Ser Thr Gly Thr Ala Ile Glu Asp Phe
    130                 135                 140

Val Leu Leu Phe Asp Asp Ser Ile Thr Gly Lys Pro Thr Pro Leu Val
145                 150                 155                 160

Trp Arg Arg Arg Ile Val Asp Leu Pro Glu Gly Thr Lys Tyr Ile Ala
                165                 170                 175
```

```
Trp Arg His Tyr Lys Val Thr Asp Ser His Thr Glu Phe Leu Lys Leu
            180                 185                 190

Asp Asp Val Thr Val Tyr Arg Ser Ile Glu Gly Pro Glu Pro Ala Thr
            195                 200                 205

Asp Phe Thr Val Ile Asn Ile Gly Gln Asn Val Gly Arg Leu Thr Trp
            210                 215                 220

Asn Tyr Pro Glu Asp Tyr Gln Pro Glu Gly Lys Gly Asn Glu Glu Leu
225                 230                 235                 240

Gln Leu Ser Gly Tyr Asn Ile Tyr Ala Asn Gly Thr Leu Leu Ala Gln
                245                 250                 255

Ile Lys Asp Val Ser Ile Leu Glu Tyr Val Asp Ser Thr Tyr Ser Leu
                260                 265                 270

Arg Asp Asn Pro Leu Gln Val Glu Tyr Cys Val Thr Ala Val Tyr Asp
                275                 280                 285

Glu Ser Ile Glu Ser Ser Thr Val Cys Gly Thr Leu His Tyr Ala Thr
            290                 295                 300

Asp Ala Ile Leu Tyr Glu Asn Phe Glu Asn Gly Pro Val Pro Asn Gly
305                 310                 315                 320

Trp Leu Val Ile Asp Ala Asp Gly Asp Gly Phe Ser Trp Gly His Tyr
                325                 330                 335

Leu Asn Ala Tyr Asp Ala Phe Pro Gly His Asn Gly Gly His Cys Ser
                340                 345                 350

Leu Ser Ala Ser Tyr Val Pro Gly Ile Gly Pro Val Thr Pro Asp Asn
            355                 360                 365

Tyr Leu Ile Thr Pro Lys Val Glu Gly Ala Lys Arg Val Lys Tyr Trp
                370                 375                 380

Val Ser Thr Gln Asp Ala Asn Trp Ala Ala Glu His Tyr Ala Val Met
385                 390                 395                 400

Ala Ser Thr Thr Gly Thr Ala Val Gly Asp Phe Val Ile Leu Phe Glu
                405                 410                 415

Glu Thr Met Thr Ala Lys Pro Thr Gly Ala Trp Tyr Glu Arg Thr Ile
                420                 425                 430

Asn Leu Pro Glu Gly Thr Lys Tyr Ile Ala Trp Arg His Tyr Asn Cys
                435                 440                 445

Thr Asp Ile Tyr Phe Leu Lys Leu Asp Asp Ile Thr Val Phe Gly Thr
450                 455                 460

Pro Ala Ser Glu Pro Glu Pro Val Thr Asp Phe Val Val Ser Leu Ile
465                 470                 475                 480

Glu Asn Asn Lys Gly Arg Leu Lys Trp Asn Tyr Pro Asn Gly Tyr Glu
                485                 490                 495

Pro Asp Lys Thr Asp Asp Lys Pro Leu Gln Leu Ala Gly Tyr Asn
                500                 505                 510

Ile Tyr Ala Asn Gly Ser Leu Leu Val His Ile Gln Asp Pro Thr Val
                515                 520                 525

Leu Glu Tyr Ile Asp Glu Thr Tyr Ser Ser Arg Asp Asp Gln Val Glu
            530                 535                 540

Val Glu Tyr Cys Val Thr Ala Val Tyr Asn Asp Asn Ile Glu Ser Gln
545                 550                 555                 560

Ser Val Cys Asp Lys Leu Ile Tyr Asp Ser Gln Ser Asp Ile Ile Leu
                565                 570                 575

Tyr Glu Gly Phe Glu Ala Gly Ser Ile Pro Glu Gly Trp Leu Leu Ile
                580                 585                 590

Asp Ala Asp Gly Asp Asn Val Asn Trp Asp Tyr Tyr Pro Trp Thr Met
                595                 600                 605
```

Tyr Gly His Asp Ser Glu Lys Cys Ile Ala Ser Pro Ser Tyr Leu Pro
    610                 615                 620

Met Ile Gly Val Leu Thr Pro Asp Asn Tyr Leu Val Thr Pro Arg Leu
625                 630                 635                 640

Glu Gly Ala Lys Leu Val Lys Tyr Trp Val Ser Ala Gln Asp Ala Val
                645                 650                 655

Tyr Ser Ala Glu His Tyr Ala Val Met Val Ser Thr Thr Gly Thr Ala
                660                 665                 670

Val Glu Asp Phe Val Leu Leu Phe Glu Glu Thr Met Thr Ala Lys Ala
            675                 680                 685

Asn Gly Ala Trp Tyr Glu Arg Thr Ile Thr Leu Pro Ala Gly Thr Lys
690                 695                 700

Tyr Ile Ala Trp Arg His Tyr Asp Cys Thr Asp Met Phe Phe Leu Leu
705                 710                 715                 720

Leu Asp Asp Ile Thr Val Tyr Arg Ser Thr Glu Thr Val Pro Glu Pro
                725                 730                 735

Val Thr Asp Phe Val Val Ser Leu Ile Glu Asn Asn Lys Gly Arg Leu
            740                 745                 750

Lys Trp Asn Tyr Pro Asn Gly Tyr Glu Pro Asp Lys Thr Asp Asp Lys
            755                 760                 765

Lys Pro Leu Gln Leu Thr Gly Tyr Asn Ile Tyr Ala Asn Gly Ser Leu
770                 775                 780

Leu Val His Ile Gln Asp Pro Thr Val Leu Glu Tyr Ile Asp Glu Thr
785                 790                 795                 800

Tyr Ser Ser Arg Asp Gly Gln Val Glu Met Glu Tyr Cys Val Thr Ala
                805                 810                 815

Val Tyr Asn Asp Asn Ile Glu Ser Gln Ser Val Cys Asp Lys Leu Asn
            820                 825                 830

Tyr Thr Ile Thr Ser Leu Asp Asn Ile Gln Ser Asp Thr Ser Leu Lys
            835                 840                 845

Ile Tyr Pro Asn Pro Ala Ser Tyr Val Val Arg Ile Glu Gly Leu Ser
850                 855                 860

Arg Ser Lys Ser Thr Ile Glu Leu Tyr Asn Ala Leu Gly Ile Cys Ile
865                 870                 875                 880

Leu Arg Glu Glu Thr His Ser Glu Lys Thr Glu Ile Asp Val Ser Arg
                885                 890                 895

Leu Asn Asp Gly Val Tyr Leu Ile Lys Val Val Gly Gly Asn Lys Thr
            900                 905                 910

Thr Thr Glu Lys Val Glu Ile Lys Arg Pro
            915                 920

<210> SEQ ID NO 133
<211> LENGTH: 921
<212> TYPE: PRT
<213> ORGANISM: Porphyromonas gingivalis

<400> SEQUENCE: 133

Met Lys Ser Ile Val Phe Arg Ala Phe Leu Thr Ile Leu Leu Ser Trp
1               5                   10                  15

Ala Ala Ile Thr Asn Pro Thr Ala Gln Glu Ile Ser Gly Met Asn Ala
                20                  25                  30

Ser Cys Leu Ala Ala Pro Ala Gln Pro Asp Thr Ile Leu Tyr Glu Ser
            35                  40                  45

Phe Glu Asn Gly Pro Val Pro Asn Gly Trp Leu Glu Ile Asp Ala Asp
        50                  55                  60

```
Ala Asp Gly Ala Thr Trp Gly Ser Pro Ser Gly Ser Phe Ser Val Pro
 65                  70                  75                  80

Tyr Gly His Asn Gly Leu Cys Thr Tyr Ser His Ile Arg Ser Gly Ile
             85                  90                  95

Ser Thr Ala Gly Asn Tyr Leu Ile Thr Pro Asn Ile Glu Gly Ala Lys
             100                 105                 110

Arg Val Lys Tyr Trp Val Cys Asn Gln Tyr Ser Thr Asn Pro Glu His
             115                 120                 125

Tyr Ala Val Met Val Ser Thr Thr Gly Thr Ala Ile Glu Asp Phe Val
 130                 135                 140

Leu Leu Phe Asp Asp Ser Ile Thr Gly Lys Pro Thr Pro Leu Val Trp
 145                 150                 155                 160

Arg Arg Arg Ile Val Asp Leu Pro Glu Gly Thr Lys Tyr Ile Ala Trp
             165                 170                 175

Arg His Tyr Lys Val Thr Asp Ser His Thr Glu Phe Leu Lys Leu Asp
             180                 185                 190

Asp Val Thr Val Tyr Arg Ser Ile Glu Gly Pro Glu Pro Ala Thr Asp
             195                 200                 205

Phe Thr Val Ile Asn Ile Gly Gln Asn Val Gly Arg Leu Thr Trp Asn
 210                 215                 220

Tyr Pro Glu Asp Tyr Gln Pro Glu Gly Lys Gly Asn Glu Glu Leu Gln
225                  230                 235                 240

Leu Ser Gly Tyr Asn Ile Tyr Ala Asn Gly Thr Leu Leu Ala Gln Ile
             245                 250                 255

Lys Asp Val Ser Ile Leu Glu Tyr Val Asp Ser Thr Tyr Ser Leu Arg
             260                 265                 270

Asp Asn Pro Leu Gln Val Glu Tyr Cys Val Thr Ala Val Tyr Asp Glu
             275                 280                 285

Ser Ile Glu Ser Ser Thr Val Cys Gly Thr Leu His Tyr Ala Thr Asp
 290                 295                 300

Ala Ile Leu Tyr Glu Asn Phe Glu Asn Gly Pro Val Pro Asn Gly Trp
305                  310                 315                 320

Leu Val Ile Asp Ala Asp Gly Asp Gly Phe Ser Trp Gly His Tyr Leu
             325                 330                 335

Asn Ala Tyr Asp Ala Phe Pro Gly His Asn Gly Gly His Cys Ser Leu
             340                 345                 350

Ser Ala Ser Tyr Val Pro Gly Ile Gly Pro Val Thr Pro Asp Asn Tyr
             355                 360                 365

Leu Ile Thr Pro Lys Val Glu Gly Ala Lys Arg Val Lys Tyr Trp Val
 370                 375                 380

Ser Thr Gln Asp Ala Asn Trp Ala Ala Glu His Tyr Ala Val Met Ala
385                  390                 395                 400

Ser Thr Thr Gly Thr Ala Val Gly Asp Phe Val Ile Leu Phe Glu Glu
             405                 410                 415

Thr Met Thr Ala Lys Pro Thr Gly Ala Trp Tyr Glu Arg Thr Ile Asn
             420                 425                 430

Leu Pro Glu Gly Thr Lys Tyr Ile Ala Trp Arg His Tyr Asn Cys Thr
             435                 440                 445

Asp Ile Tyr Phe Leu Lys Leu Asp Asp Ile Thr Val Phe Gly Thr Pro
             450                 455                 460

Ala Ser Glu Pro Glu Pro Val Thr Asp Phe Val Val Ser Leu Ile Glu
465                  470                 475                 480

Asn Asn Lys Gly Arg Leu Lys Trp Asn Tyr Pro Asn Gly Tyr Glu Pro
```

```
                485                 490                 495
Asp Lys Thr Asp Asp Lys Asp Pro Leu Gln Leu Ala Gly Tyr Asn Ile
                500                 505                 510

Tyr Ala Asn Gly Ser Leu Leu Val His Ile Gln Asp Pro Thr Val Leu
                515                 520                 525

Glu Tyr Ile Asp Glu Thr Tyr Ser Ser Arg Asp Asp Gln Val Glu Val
                530                 535                 540

Glu Tyr Cys Val Thr Ala Val Tyr Asn Asp Asn Ile Glu Ser Gln Ser
545                 550                 555                 560

Val Cys Asp Lys Leu Ile Tyr Asp Ser Gln Ser Asp Ile Ile Leu Tyr
                565                 570                 575

Glu Gly Phe Glu Ala Gly Ser Ile Pro Glu Gly Trp Leu Leu Ile Asp
                580                 585                 590

Ala Asp Gly Asp Asn Val Asn Trp Asp Tyr Tyr Pro Trp Thr Met Tyr
                595                 600                 605

Gly His Asp Ser Glu Lys Cys Ile Ala Ser Pro Ser Tyr Leu Pro Met
                610                 615                 620

Ile Gly Val Leu Thr Pro Asp Asn Tyr Leu Val Thr Pro Arg Leu Glu
625                 630                 635                 640

Gly Ala Lys Leu Val Lys Tyr Trp Val Ser Ala Gln Asp Ala Val Tyr
                645                 650                 655

Ser Ala Glu His Tyr Ala Val Met Val Ser Thr Thr Gly Thr Ala Val
                660                 665                 670

Glu Asp Phe Val Leu Leu Phe Glu Glu Thr Met Thr Ala Lys Ala Asn
                675                 680                 685

Gly Ala Trp Tyr Glu Arg Thr Ile Thr Leu Pro Ala Gly Thr Lys Tyr
                690                 695                 700

Ile Ala Trp Arg His Tyr Asp Cys Thr Asp Met Phe Phe Leu Leu Leu
705                 710                 715                 720

Asp Asp Ile Thr Val Tyr Arg Ser Thr Glu Thr Val Pro Glu Pro Val
                725                 730                 735

Thr Asp Phe Val Val Ser Leu Ile Glu Asn Asn Lys Gly Arg Leu Lys
                740                 745                 750

Trp Asn Tyr Pro Asn Gly Tyr Glu Pro Asp Lys Thr Asp Asp Lys Lys
                755                 760                 765

Pro Leu Gln Leu Thr Gly Tyr Asn Ile Tyr Ala Asn Gly Ser Leu Leu
                770                 775                 780

Val His Ile Gln Asp Pro Thr Val Leu Glu Tyr Ile Asp Glu Thr Tyr
785                 790                 795                 800

Ser Ser Arg Asp Gly Gln Val Glu Met Glu Tyr Cys Val Thr Ala Val
                805                 810                 815

Tyr Asn Asp Asn Ile Glu Ser Gln Ser Val Cys Asp Lys Leu Asn Tyr
                820                 825                 830

Thr Ile Thr Ser Leu Asp Asn Ile Gln Ser Asp Thr Ser Leu Lys Ile
                835                 840                 845

Tyr Pro Asn Pro Ala Ser Tyr Val Val Arg Ile Glu Gly Leu Ser Arg
850                 855                 860

Ser Lys Ser Thr Ile Glu Leu Tyr Asn Ala Leu Gly Ile Cys Ile Leu
865                 870                 875                 880

Arg Glu Glu Thr His Ser Glu Lys Thr Glu Ile Asp Val Ser Arg Leu
                885                 890                 895

Asn Asp Gly Val Tyr Leu Ile Lys Val Val Gly Gly Asn Lys Thr Thr
                900                 905                 910
```

```
Thr Glu Lys Val Glu Ile Lys Arg Pro
        915                 920
```

<210> SEQ ID NO 134
<211> LENGTH: 324
<212> TYPE: PRT
<213> ORGANISM: Porphyromonas gingivalis

<400> SEQUENCE: 134

```
Met Cys Leu Glu Pro Ile Ile Ala Pro Ile Ser Glu Leu Leu Glu
 1               5                  10                  15

Gln Glu Leu Thr Ala Asp Arg Phe Leu Arg Met Thr Asn Lys Ala Gly
             20                  25                  30

Asn Glu Ile Tyr Val Phe Thr Ala Glu Glu Ala Pro His Cys Met Lys
             35                  40                  45

Glu Val Gly Arg Leu Arg Glu Glu Ala Phe Arg His Tyr Gly Gly
         50                  55                  60

Thr Gly Lys Ala Ile Asp Ile Asp Glu Phe Asp Thr Met Pro Gly Ser
 65                  70                  75                  80

Tyr Lys Gln Leu Ile Val Trp Asp Pro Gln Asn Lys Ala Ile Leu Gly
                 85                  90                  95

Gly Tyr Arg Phe Ile Tyr Gly Arg Asp Val Ala Phe Asp Thr Asp Gly
                100                 105                 110

Lys Pro Leu Leu Ala Thr Ala Glu Met Phe Arg Phe Ser Asp Ala Phe
                115                 120                 125

Leu His Asp Tyr Leu Pro Tyr Thr Val Glu Leu Gly Arg Ser Phe Val
130                 135                 140

Ser Leu Gln Tyr Gln Ser Thr Arg Met Gly Thr Lys Ala Ile Phe Val
145                 150                 155                 160

Leu Asp Asn Leu Trp Asp Gly Ile Gly Ala Leu Thr Val Val Asn Pro
                165                 170                 175

Glu Ala Leu Tyr Phe Tyr Gly Lys Val Thr Met Tyr Lys Asp Tyr Asp
                180                 185                 190

Arg Arg Ala Arg Asn Leu Ile Leu Tyr Phe Leu Arg Lys His Phe Ser
            195                 200                 205

Asp Pro Glu Gly Leu Val Lys Pro Ile His Pro Leu Pro Ile Glu Ile
        210                 215                 220

Ser Ala Glu Asp Glu Ala Leu Phe Ser Ser Ser Asp Phe Asp Thr Asn
225                 230                 235                 240

Tyr Lys Thr Leu Asn Ile Glu Val Arg Lys Leu Gly Ile Asn Ile Pro
                245                 250                 255

Pro Leu Val Ser Ala Tyr Ile Ala Leu Ser Pro Glu Met Arg Val Phe
            260                 265                 270

Gly Thr Ala Val Asn Glu Ser Phe Gly Glu Val Glu Thr Gly Ile
        275                 280                 285

Phe Ile Ala Val Gly Lys Ile Leu Glu Glu Lys Lys Gln Arg His Ile
        290                 295                 300

Glu Ser Phe Ile Leu Ser Arg Asn Glu Lys Lys Gly Leu Asp Ser Ser
305                 310                 315                 320

Asn Gly Arg Ser
```

<210> SEQ ID NO 135
<211> LENGTH: 1226
<212> TYPE: PRT
<213> ORGANISM: Porphyromonas gingivalis
<220> FEATURE:
<221> NAME/KEY: misc_feature
<222> LOCATION: (983)..(983)
<223> OTHER INFORMATION: Xaa can be any naturally occurring amino acid

<400> SEQUENCE: 135

```
Met Met Lys Arg Tyr Thr Ile Ile Leu Ala Val Phe Leu Leu Phe Cys
1               5                   10                  15

Thr Val Phe Thr Phe Gln Ile Lys Ala Arg Pro Tyr Glu Arg Phe Ala
            20                  25                  30

Asp Val Glu Lys Pro Trp Ile Gln Lys His Ser Met Asp Ser Lys Leu
        35                  40                  45

Val Pro Ala Asn Lys Gly Asn Leu Ile Gln Ala Glu Ile Val Tyr Gln
    50                  55                  60

Ser Val Ser Glu His Ser Asp Leu Val Ile Ser Pro Val Asn Glu Ile
65                  70                  75                  80

Arg Pro Ala Asn Arg Phe Pro Ser His Arg Lys Ser Phe Phe Ala Glu
                85                  90                  95

Asn Leu Arg Ala Ser Pro Pro Val Val Pro Val Ala Val Asp Lys Tyr
            100                 105                 110

Ala Val Pro Val Ala Asn Pro Met Asp Pro Glu Asn Pro Asn Ala Trp
        115                 120                 125

Asp Val Thr Leu Lys Ile Thr Thr Lys Ala Val Thr Val Pro Val Asp
    130                 135                 140

Val Val Met Val Ile Asp Gln Ser Ser Ser Met Gly Gly Gln Asn Ile
145                 150                 155                 160

Ala Arg Leu Lys Ser Ala Ile Ala Ser Gly Gln Arg Phe Val Lys Lys
                165                 170                 175

Met Leu Pro Lys Gly Thr Ala Thr Glu Gly Val Arg Ile Ala Leu Val
            180                 185                 190

Ser Tyr Asp His Glu Pro His Arg Leu Ser Asp Phe Thr Lys Asp Thr
        195                 200                 205

Ala Phe Leu Cys Gln Lys Ile Arg Ala Leu Thr Pro Ile Trp Gly Thr
    210                 215                 220

His Thr Gln Gly Gly Leu Lys Met Ala Arg Asn Ile Met Ala Thr Ser
225                 230                 235                 240

Thr Ala Val Asp Lys His Ile Ile Leu Met Ser Asp Gly Leu Ala Thr
                245                 250                 255

Glu Gln Tyr Pro Val Lys Asn Val Thr Thr Ala Asp Phe Ile Gly Lys
            260                 265                 270

Thr Gly Asn Ala Asn Asp Pro Ile Asp Leu Val Ile Gln Gly Ala Ile
        275                 280                 285

Asn Phe Pro Thr Asn Tyr Val Ser Asn Pro Ser Thr Pro Leu Thr
    290                 295                 300

Pro Asn Tyr Pro Thr His Ser Ser Lys Val Gly Arg Arg Asn Leu Pro
305                 310                 315                 320

Glu Ser Lys Phe Asp Tyr Ser Asn Leu Ser Ala Arg Ile Thr Phe Asp
                325                 330                 335

Gly Val Ala Gly Ala Leu Val Tyr Glu Pro Arg Phe Pro His Pro Tyr
            340                 345                 350

Tyr Tyr Tyr Phe Pro Cys Asn Ala Ala Ile Asn Glu Ala Gln Phe Ala
        355                 360                 365

Lys Asn Ser Gly Tyr Thr Ile His Thr Ile Gly Tyr Asp Leu Gly Asp
    370                 375                 380

Phe Ala Leu Ala Asn Asn Ser Leu Lys Leu Thr Ala Thr Asp Glu Asn
385                 390                 395                 400
```

-continued

```
His Phe Phe Thr Ala Thr Pro Ala Asn Leu Ala Ala Ala Phe Asp Asn
                405                 410                 415

Ile Ala Gln Thr Ile Asn Ile Gly Ile Gln Arg Gly Glu Val Thr Asp
            420                 425                 430

Phe Val Ala Pro Gly Phe Ile Val Lys Asn Leu Thr Gln Ser Gly Asp
        435                 440                 445

Val Thr His Leu Leu Asn Val Ser Asn Gly Thr Val His Tyr Asp Val
    450                 455                 460

Ser Thr Lys Lys Leu Thr Trp Thr Gly Thr Ile Leu Ser Ser Ser
465                 470                 475                 480

Glu Ala Thr Ile Thr Tyr Arg Ile Tyr Ala Asp Leu Asp Tyr Ile Gln
                485                 490                 495

Asn Asn Asp Ile Pro Val Asn Thr Thr Ser Ala Ile Gly Pro Asp Leu
            500                 505                 510

Gly Gly Phe Asp Thr Asn Thr Glu Ala Lys Leu Thr Tyr Thr Asn Ser
        515                 520                 525

Asn Gly Glu Pro Asn Gln Gln Leu Ile Phe Pro Arg Pro Thr Val Lys
    530                 535                 540

Leu Gly Tyr Gly Val Ile Lys Arg His Tyr Val Leu Val Asn Lys Asp
545                 550                 555                 560

Gly Gln Pro Ile Gln Ala Asn Gly Thr Val Val Ser Ser Leu Ser Glu
                565                 570                 575

Ala His Val Leu Gln Ser Gln Asp Phe Phe Leu Pro Ser Gly Gly Gly
            580                 585                 590

His Ile Val Pro Lys Trp Ile Lys Leu Asp Lys Thr Thr Glu Ala Leu
        595                 600                 605

Gln Tyr Tyr Ser Val Pro Pro Thr Asn Thr Val Ile Thr Thr Ala Asp
    610                 615                 620

Gly Lys Arg Tyr Arg Phe Val Glu Val Pro Gly Ser Thr Pro Asn Pro
625                 630                 635                 640

Gly Gln Ile Gly Ile Ser Trp Lys Lys Pro Ala Gly Asn Ala Tyr Phe
                645                 650                 655

Ala Tyr Lys Leu Leu Asn Tyr Trp Met Gly Gly Thr Thr Asp Gln Gln
            660                 665                 670

Ser Glu Trp Asp Val Thr Ser Asn Trp Thr Gly Ala Gln Val Pro Leu
        675                 680                 685

Thr Gly Glu Asp Val Glu Phe Ala Thr Thr Glu Asn Phe Gly Ser Pro
    690                 695                 700

Ala Val Ala Asp Leu His Val Pro Thr Thr Asn Pro Lys Ile Ile Gly
705                 710                 715                 720

Asn Leu Ile Asn Asn Ser Asp Lys Asp Leu Val Val Thr Thr Ser Ser
                725                 730                 735

Gln Leu Thr Ile Asn Gly Val Val Glu Asp Asn Asn Pro Asn Val Gly
            740                 745                 750

Thr Ile Val Val Lys Ser Ser Lys Asp Asn Pro Thr Gly Thr Leu Leu
        755                 760                 765

Phe Ala Asn Pro Gly Tyr Asn Gln Asn Val Gly Gly Thr Val Glu Phe
    770                 775                 780

Tyr Asn Gln Gly Tyr Asp Cys Ala Asp Cys Gly Met Tyr Arg Arg Ser
785                 790                 795                 800

Trp Gln Tyr Phe Gly Ile Pro Val Asn Glu Ser Gly Phe Pro Ile Asn
                805                 810                 815

Asp Val Gly Gly Asn Glu Thr Val Asn Gln Trp Val Glu Pro Phe Asn
            820                 825                 830
```

Gly Asp Lys Trp Arg Pro Ala Pro Tyr Ala Pro Asp Thr Glu Leu Gln
    835                 840                 845

Lys Phe Lys Gly Tyr Gln Ile Thr Asn Asp Val Gln Ala Gln Pro Thr
    850                 855                 860

Gly Val Tyr Ser Phe Lys Gly Met Ile Cys Val Cys Asp Ala Phe Leu
865                 870                 875                 880

Asn Leu Thr Arg Thr Ser Gly Val Asn Tyr Ser Gly Ala Asn Leu Ile
                885                 890                 895

Gly Asn Ser Tyr Thr Gly Ala Ile Asp Ile Lys Gln Gly Ile Val Phe
            900                 905                 910

Pro Pro Glu Val Glu Gln Thr Val Tyr Leu Phe Asn Thr Gly Thr Arg
        915                 920                 925

Asp Gln Trp Arg Lys Leu Asn Gly Ser Thr Val Ser Gly Tyr Arg Ala
    930                 935                 940

Gly Gln Tyr Leu Ser Val Pro Lys Asn Thr Ala Gly Gln Asp Asn Leu
945                 950                 955                 960

Pro Asp Arg Ile Pro Ser Met His Ser Phe Leu Val Lys Met Gln Asn
                965                 970                 975

Gly Ala Ser Cys Thr Leu Xaa Ile Leu Tyr Asp Lys Leu Leu Lys Asn
            980                 985                 990

Thr Thr Val Asn Asn Gly Asn Gly  Thr Gln Ile Thr Trp  Arg Ser Gly
        995                 1000                1005

Asn Ser  Gly Ser Ala Asn Met  Pro Ser Leu Val Met  Asp Val Leu
    1010                1015                1020

Gly Asn  Glu Ser Ala Asp Arg  Leu Trp Ile Phe Thr  Asp Gly Gly
    1025                1030                1035

Leu Ser  Phe Gly Phe Asp Asn  Gly Trp Asp Gly Arg  Lys Leu Thr
    1040                1045                1050

Glu Lys  Gly Leu Ser Gln Leu  Tyr Ala Met Ser Asp  Ile Gly Asn
    1055                1060                1065

Asp Lys  Phe Gln Val Ala Gly  Val Pro Glu Leu Asn  Asn Leu Leu
    1070                1075                1080

Ile Gly  Phe Asp Ala Asp Lys  Asp Gly Gln Tyr Thr  Leu Glu Phe
    1085                1090                1095

Ala Leu  Ser Asp His Phe Ala  Lys Gly Ala Val Tyr  Leu His Asp
    1100                1105                1110

Leu Gln  Ser Gly Ala Lys His  Arg Ile Thr Asn Ser  Thr Ser Tyr
    1115                1120                1125

Ser Phe  Asp Ala Lys Arg Gly  Asp Ser Gly Ala Arg  Phe Arg Leu
    1130                1135                1140

Ser Tyr  Gly Cys Asp Glu Asn  Val Asp Asp Ser His  Val Val Ser
    1145                1150                1155

Thr Asn  Gly Arg Glu Ile Ile  Ile Leu Asn Gln Asp  Ala Leu Asp
    1160                1165                1170

Cys Thr  Val Thr Leu Phe Thr  Ile Glu Gly Lys Leu  Leu Arg Arg
    1175                1180                1185

Leu Lys  Val Leu Ala Gly His  Arg Glu Val Met Lys  Val Gln Thr
    1190                1195                1200

Gly Gly  Ala Tyr Ile Val His  Leu Gln Asn Ala Phe  Thr Asn Asp
    1205                1210                1215

Val His  Lys Val Leu Val Glu  Tyr
    1220                1225

```
<210> SEQ ID NO 136
<211> LENGTH: 1225
<212> TYPE: PRT
<213> ORGANISM: Porphyromonas gingivalis
<220> FEATURE:
<221> NAME/KEY: misc_feature
<222> LOCATION: (982)..(982)
<223> OTHER INFORMATION: Xaa can be any naturally occurring amino acid

<400> SEQUENCE: 136

Met Lys Arg Tyr Thr Ile Ile Leu Ala Val Phe Leu Leu Phe Cys Thr
1               5                   10                  15

Val Phe Thr Phe Gln Ile Lys Ala Arg Pro Tyr Glu Arg Phe Ala Asp
            20                  25                  30

Val Glu Lys Pro Trp Ile Gln Lys His Ser Met Asp Ser Lys Leu Val
        35                  40                  45

Pro Ala Asn Lys Gly Asn Leu Ile Gln Ala Glu Ile Val Tyr Gln Ser
    50                  55                  60

Val Ser Glu His Ser Asp Leu Val Ile Ser Pro Val Asn Glu Ile Arg
65                  70                  75                  80

Pro Ala Asn Arg Phe Pro Ser His Arg Lys Ser Phe Phe Ala Glu Asn
                85                  90                  95

Leu Arg Ala Ser Pro Pro Val Val Pro Val Ala Val Asp Lys Tyr Ala
            100                 105                 110

Val Pro Val Ala Asn Pro Met Asp Pro Glu Asn Pro Asn Ala Trp Asp
        115                 120                 125

Val Thr Leu Lys Ile Thr Thr Lys Ala Val Thr Val Pro Val Asp Val
    130                 135                 140

Val Met Val Ile Asp Gln Ser Ser Met Gly Gly Gln Asn Ile Ala
145                 150                 155                 160

Arg Leu Lys Ser Ala Ile Ala Ser Gly Gln Arg Phe Val Lys Lys Met
                165                 170                 175

Leu Pro Lys Gly Thr Ala Thr Glu Gly Val Arg Ile Ala Leu Val Ser
            180                 185                 190

Tyr Asp His Glu Pro His Arg Leu Ser Asp Phe Thr Lys Asp Thr Ala
        195                 200                 205

Phe Leu Cys Gln Lys Ile Arg Ala Leu Thr Pro Ile Trp Gly Thr His
    210                 215                 220

Thr Gln Gly Gly Leu Lys Met Ala Arg Asn Ile Met Ala Thr Ser Thr
225                 230                 235                 240

Ala Val Asp Lys His Ile Ile Leu Met Ser Asp Gly Leu Ala Thr Glu
                245                 250                 255

Gln Tyr Pro Val Lys Asn Val Thr Thr Ala Asp Phe Ile Gly Lys Thr
            260                 265                 270

Gly Asn Ala Asn Asp Pro Ile Asp Leu Val Ile Gln Gly Ala Ile Asn
        275                 280                 285

Phe Pro Thr Asn Tyr Val Ser Asn Asn Pro Ser Thr Pro Leu Thr Pro
    290                 295                 300

Asn Tyr Pro Thr His Ser Ser Lys Val Gly Arg Arg Asn Leu Pro Glu
305                 310                 315                 320

Ser Lys Phe Asp Tyr Ser Asn Leu Ser Ala Arg Ile Thr Phe Asp Gly
                325                 330                 335

Val Ala Gly Ala Leu Val Tyr Glu Pro Arg Phe Pro His Pro Tyr Tyr
            340                 345                 350

Tyr Tyr Phe Pro Cys Asn Ala Ala Ile Asn Glu Ala Gln Phe Ala Lys
        355                 360                 365
```

-continued

Asn Ser Gly Tyr Thr Ile His Thr Ile Gly Tyr Asp Leu Gly Asp Phe
    370                 375                 380

Ala Leu Ala Asn Asn Ser Leu Lys Leu Thr Ala Thr Asp Glu Asn His
385                 390                 395                 400

Phe Phe Thr Ala Thr Pro Ala Asn Leu Ala Ala Phe Asp Asn Ile
            405                 410                 415

Ala Gln Thr Ile Asn Ile Gly Ile Gln Arg Gly Glu Val Thr Asp Phe
            420                 425                 430

Val Ala Pro Gly Phe Ile Val Lys Asn Leu Thr Gln Ser Gly Asp Val
            435                 440                 445

Thr His Leu Leu Asn Val Ser Asn Gly Thr Val His Tyr Asp Val Ser
    450                 455                 460

Thr Lys Lys Leu Thr Trp Thr Thr Gly Thr Ile Leu Ser Ser Ser Glu
465                 470                 475                 480

Ala Thr Ile Thr Tyr Arg Ile Tyr Ala Asp Leu Asp Tyr Ile Gln Asn
                485                 490                 495

Asn Asp Ile Pro Val Asn Thr Thr Ser Ala Ile Gly Pro Asp Leu Gly
            500                 505                 510

Gly Phe Asp Thr Asn Thr Glu Ala Lys Leu Thr Tyr Thr Asn Ser Asn
            515                 520                 525

Gly Glu Pro Asn Gln Gln Leu Ile Phe Pro Arg Pro Thr Val Lys Leu
    530                 535                 540

Gly Tyr Gly Val Ile Lys Arg His Tyr Val Leu Val Asn Lys Asp Gly
545                 550                 555                 560

Gln Pro Ile Gln Ala Asn Gly Thr Val Val Ser Ser Leu Ser Glu Ala
                565                 570                 575

His Val Leu Gln Ser Gln Asp Phe Phe Leu Pro Ser Gly Gly His
            580                 585                 590

Ile Val Pro Lys Trp Ile Lys Leu Asp Lys Thr Thr Glu Ala Leu Gln
            595                 600                 605

Tyr Tyr Ser Val Pro Pro Thr Asn Thr Val Ile Thr Thr Ala Asp Gly
    610                 615                 620

Lys Arg Tyr Arg Phe Val Glu Val Pro Gly Ser Thr Asn Pro Gly
625                 630                 635                 640

Gln Ile Gly Ile Ser Trp Lys Lys Pro Ala Gly Asn Ala Tyr Phe Ala
                645                 650                 655

Tyr Lys Leu Leu Asn Tyr Trp Met Gly Gly Thr Thr Asp Gln Gln Ser
            660                 665                 670

Glu Trp Asp Val Thr Ser Asn Trp Thr Gly Ala Gln Val Pro Leu Thr
            675                 680                 685

Gly Glu Asp Val Glu Phe Ala Thr Thr Glu Asn Phe Gly Ser Pro Ala
    690                 695                 700

Val Ala Asp Leu His Val Pro Thr Thr Asn Pro Lys Ile Ile Gly Asn
705                 710                 715                 720

Leu Ile Asn Asn Ser Asp Lys Asp Leu Val Val Thr Ser Ser Gln
                725                 730                 735

Leu Thr Ile Asn Gly Val Val Glu Asp Asn Pro Asn Val Gly Thr
            740                 745                 750

Ile Val Val Lys Ser Ser Lys Asp Asn Pro Thr Gly Thr Leu Leu Phe
            755                 760                 765

Ala Asn Pro Gly Tyr Asn Gln Asn Val Gly Gly Thr Val Glu Phe Tyr
    770                 775                 780

Asn Gln Gly Tyr Asp Cys Ala Asp Cys Gly Met Tyr Arg Arg Ser Trp
785                 790                 795                 800

-continued

Gln Tyr Phe Gly Ile Pro Val Asn Glu Ser Gly Phe Pro Ile Asn Asp
            805                 810                 815

Val Gly Gly Asn Glu Thr Val Asn Gln Trp Val Glu Pro Phe Asn Gly
            820                 825                 830

Asp Lys Trp Arg Pro Ala Pro Tyr Ala Pro Asp Thr Glu Leu Gln Lys
            835                 840                 845

Phe Lys Gly Tyr Gln Ile Thr Asn Asp Val Gln Ala Gln Pro Thr Gly
850                 855                 860

Val Tyr Ser Phe Lys Gly Met Ile Cys Val Cys Asp Ala Phe Leu Asn
865                 870                 875                 880

Leu Thr Arg Thr Ser Gly Val Asn Tyr Ser Gly Ala Asn Leu Ile Gly
            885                 890                 895

Asn Ser Tyr Thr Gly Ala Ile Asp Ile Lys Gln Gly Ile Val Phe Pro
            900                 905                 910

Pro Glu Val Glu Gln Thr Val Tyr Leu Phe Asn Thr Gly Thr Arg Asp
            915                 920                 925

Gln Trp Arg Lys Leu Asn Gly Ser Thr Val Ser Gly Tyr Arg Ala Gly
            930                 935                 940

Gln Tyr Leu Ser Val Pro Lys Asn Thr Ala Gly Gln Asp Asn Leu Pro
945                 950                 955                 960

Asp Arg Ile Pro Ser Met His Ser Phe Leu Val Lys Met Gln Asn Gly
            965                 970                 975

Ala Ser Cys Thr Leu Xaa Ile Leu Tyr Asp Lys Leu Leu Lys Asn Thr
            980                 985                 990

Thr Val Asn Asn Gly Asn Gly Thr Gln Ile Thr Trp Arg Ser Gly Asn
            995                 1000                1005

Ser Gly Ser Ala Asn Met Pro Ser Leu Val Met Asp Val Leu Gly
    1010                1015                1020

Asn Glu Ser Ala Asp Arg Leu Trp Ile Phe Thr Asp Gly Gly Leu
    1025                1030                1035

Ser Phe Gly Phe Asp Asn Gly Trp Asp Gly Arg Lys Leu Thr Glu
    1040                1045                1050

Lys Gly Leu Ser Gln Leu Tyr Ala Met Ser Asp Ile Gly Asn Asp
    1055                1060                1065

Lys Phe Gln Val Ala Gly Val Pro Glu Leu Asn Asn Leu Leu Ile
    1070                1075                1080

Gly Phe Asp Ala Asp Lys Asp Gly Gln Tyr Thr Leu Glu Phe Ala
    1085                1090                1095

Leu Ser Asp His Phe Ala Lys Gly Ala Val Tyr Leu His Asp Leu
    1100                1105                1110

Gln Ser Gly Ala Lys His Arg Ile Thr Asn Ser Thr Ser Tyr Ser
    1115                1120                1125

Phe Asp Ala Lys Arg Gly Asp Ser Gly Ala Arg Phe Arg Leu Ser
    1130                1135                1140

Tyr Gly Cys Asp Glu Asn Val Asp Asp Ser His Val Val Ser Thr
    1145                1150                1155

Asn Gly Arg Glu Ile Ile Ile Leu Asn Gln Asp Ala Leu Asp Cys
    1160                1165                1170

Thr Val Thr Leu Phe Thr Ile Glu Gly Lys Leu Leu Arg Arg Leu
    1175                1180                1185

Lys Val Leu Ala Gly His Arg Glu Val Met Lys Val Gln Thr Gly
    1190                1195                1200

Gly Ala Tyr Ile Val His Leu Gln Asn Ala Phe Thr Asn Asp Val

```
              1205                1210                1215

His Lys  Val Leu Val Glu Tyr
      1220             1225

<210> SEQ ID NO 137
<211> LENGTH: 391
<212> TYPE: PRT
<213> ORGANISM: Porphyromonas gingivalis

<400> SEQUENCE: 137

Met Ile Ile Lys Lys Met Leu Lys Asn Lys Leu Ala Pro Leu Ala Ile
1               5                   10                  15

Leu Phe Leu Phe Ala Pro Lys Ala Met Lys Ala Gln Glu Gln Leu Asn
            20                  25                  30

Val Val His Thr Ser Val Pro Ser Leu Asn Ile Ser Pro Asp Ala Arg
        35                  40                  45

Ala Ala Gly Met Gly Asp Ile Gly Val Ala Thr Thr Pro Asp Ala Tyr
    50                  55                  60

Ser Gln Tyr Trp Asn Pro Ser Lys Tyr Ala Phe Met Asp Thr Lys Ala
65                  70                  75                  80

Gly Ile Ser Phe Ser Tyr Thr Pro Trp Leu Ser Lys Leu Val Asn Asp
                85                  90                  95

Ile Ala Leu Met Gln Met Thr Gly Phe Tyr Lys Leu Gly Thr Asp Glu
            100                 105                 110

Asn Gln Ala Ile Ser Ala Ser Leu Arg Tyr Phe Thr Leu Gly Lys Leu
        115                 120                 125

Glu Thr Phe Asp Glu Leu Gly Glu Ser Met Gly Glu Ala His Pro Asn
130                 135                 140

Glu Phe Ala Val Asp Leu Gly Tyr Ser Arg Gln Leu Ser Glu Asn Phe
145                 150                 155                 160

Ser Met Ala Val Ala Leu Arg Tyr Ile Arg Ser Asp Gln Ser Thr His
                165                 170                 175

Asn Thr Gly Glu Asn Gln Ala Gly Asn Ala Phe Ala Ala Asp Ile Ala
            180                 185                 190

Gly Tyr Leu Gln Lys Tyr Val Leu Leu Gly Asn Ala Glu Ser Leu Trp
        195                 200                 205

Ser Leu Gly Phe Asn Val Lys Asn Ile Gly Thr Lys Ile Ser Tyr Asp
210                 215                 220

Gly Gly Val Thr Ser Phe Phe Ile Pro Thr Ser Leu Asn Leu Gly Thr
225                 230                 235                 240

Gly Leu Leu Tyr Pro Ile Asp Asp Tyr Asn Ser Ile Asn Phe Asn Leu
                245                 250                 255

Glu Leu Ser Lys Leu Leu Val Pro Thr Pro Ile Met Asp Gln Asn
            260                 265                 270

Asp Gln Ala Gly Tyr Glu Ala Ala Leu Lys Lys Tyr Gln Glu Thr Ser
        275                 280                 285

Ser Ile Ser Gly Ile Phe Ser Ser Phe Gly Asp Ala Pro Gly Gly Leu
    290                 295                 300

Lys Glu Glu Phe Arg Glu Ile Thr Trp Gly Leu Gly Ala Glu Tyr Ser
305                 310                 315                 320

Tyr Asp Asp Lys Phe Phe Val Arg Ala Gly Tyr Ser Tyr Leu His Pro
                325                 330                 335

Thr Lys Gly Asn Leu Gln Tyr Phe Thr Ala Gly Ala Gly Phe Lys Met
            340                 345                 350

Asn Ile Phe Arg Ile Asp Ala Ser Tyr Leu Leu Ser Thr Ile Gln Ser
```

```
            355                 360                 365
Asn Pro Leu Asp Gln Thr Leu Arg Phe Thr Leu Ala Phe Asp Met Asp
370                 375                 380

Gly Leu Arg Asn Leu Phe His
385                 390

<210> SEQ ID NO 138
<211> LENGTH: 446
<212> TYPE: PRT
<213> ORGANISM: Porphyromonas gingivalis

<400> SEQUENCE: 138

Met Lys Thr Thr Val Gln Gln Ile Ile Leu Cys Leu Ala Leu Met Met
1               5                   10                  15

Ser Gly Val Leu Gly Gly Asn Ala Gln Ser Phe Trp Glu Glu Ile Ala
            20                  25                  30

Pro Pro Phe Ile Ser Asn Glu Pro Asn Val Lys Tyr Ile Ile Pro Asn
        35                  40                  45

Met Gly Ile Asp Ser Lys Gly Thr Ile Tyr Val Thr Val Thr Lys Arg
    50                  55                  60

Ile Gln Gln Gly Ala Asn Tyr Thr Ser Glu Gln Leu Gly Met Tyr Tyr
65                  70                  75                  80

Arg Pro Leu Gly Asp Asn Glu Gln Trp Trp Lys His Asp Pro Tyr Phe
                85                  90                  95

Asp Asp Lys Ile Val Ala Asp Ile Gln Thr Asp Ala Tyr Gly Arg Val
            100                 105                 110

Tyr Val Cys Thr Thr Ser Ser Arg Asp Gln Glu Tyr Gln Leu Tyr Ile
        115                 120                 125

Asn Glu Gln Asn Glu Trp Arg Cys Ile Phe Lys Thr Ser Val Ser Thr
    130                 135                 140

Tyr Glu His Gly Met Ala Val Phe Arg Ser Ser Thr Gly Val Thr Tyr
145                 150                 155                 160

Ile Gly Thr Arg His His Ile Phe Ala Ser Gly Val Asn Asp Phe Glu
                165                 170                 175

Phe Asn Thr Ile Tyr Glu Asp Ser Thr Pro Met Ser Cys Arg Phe Ala
            180                 185                 190

Glu Ala Thr Asn Ser Gly Thr Ile Tyr Leu Ala Leu Met His Glu Thr
        195                 200                 205

Thr Met Ser Thr Thr Ile Leu Thr Tyr Gln Asn Gly Glu Phe Val Asp
    210                 215                 220

Ile Ser Glu Ser Glu Leu Ser Asn Ser Ile Ile Ala Ser Met Cys Ser
225                 230                 235                 240

Asn Lys Glu Gly Asp Ile Ile Ala Leu Val Thr Ser Tyr Thr Gly Phe
                245                 250                 255

Met Ser Gly Thr Leu Ala Ile Arg Lys Ala Asp Glu Gly Lys Trp Gln
            260                 265                 270

Leu Val Gly Gly Asp Ile Gln Asn Ala Ile Val Gln Asn Ile Cys Met
        275                 280                 285

Met Asp Asp Asn Lys Ile Ala Cys Glu Val Phe Gly Thr Pro Asn Gly
    290                 295                 300

Val Asp Gly Arg Thr Arg Val Cys Val Ser Asp Ala Ser Val Phe Asp
305                 310                 315                 320

Phe Glu Trp Tyr Glu Asp Glu Ile Tyr Gly Gly Leu Ile Phe Asp Thr
                325                 330                 335

Phe Phe Tyr Ser Pro Trp Asp Lys Leu Leu Tyr Ala Lys Phe Gly Gly
```

340                 345                 350
Ile Met Leu Arg Ser Lys Glu Ser Phe Ile Thr Ser Phe Ile Ser Pro
                355                 360                 365

Thr Val Val Gln Gly Val Asp Val Tyr Thr Leu Ala Gly Lys Ile Arg
        370                 375                 380

Ile Glu Ser Glu Thr Pro Val Ser Glu Val Leu Leu Phe Asp Leu Ala
385                 390                 395                 400

Gly Arg Met Val Leu Arg Gln Thr Ile Asp Asn Lys Ile Tyr Ser Asp
                405                 410                 415

Ile Asp Thr Asn Gly Leu Lys Arg Ser Gly Ile Tyr Val Val Ser Val
                420                 425                 430

Arg Leu Ser Ser Gly Gln Val Phe Ser His Lys Val Gln Val
                435                 440                 445

<210> SEQ ID NO 139
<211> LENGTH: 599
<212> TYPE: PRT
<213> ORGANISM: Porphyromonas gingivalis

<400> SEQUENCE: 139

Met Glu Asn Leu Lys Asn Ile Gln Pro Arg Glu Asp Phe Asn Trp Glu
1               5                   10                  15

Glu Phe Glu Ala Gly Gly Val His Ala Ala Val Ser Arg Gln Glu Gln
                20                  25                  30

Glu Ala Ala Tyr Asp Lys Thr Leu Asn Thr Ile Lys Glu Lys Glu Val
                35                  40                  45

Val Met Gly Arg Val Thr Ala Ile Asn Lys Arg Glu Val Val Ile Asn
        50                  55                  60

Val Gly Tyr Lys Ser Glu Gly Val Val Pro Ala Thr Glu Phe Arg Tyr
65              70                  75                  80

Asn Pro Glu Leu Lys Val Gly Asp Glu Val Glu Val Tyr Ile Glu Asn
                85                  90                  95

Gln Glu Asp Lys Lys Gly Gln Leu Val Leu Ser His Arg Lys Gly Arg
                100                 105                 110

Ala Ala Arg Ser Trp Glu Arg Val Asn Glu Ala Leu Glu Lys Asp Glu
                115                 120                 125

Ile Val Lys Gly Tyr Val Lys Cys Arg Thr Lys Gly Gly Met Ile Val
                130                 135                 140

Asp Val Phe Gly Ile Glu Ala Phe Leu Pro Gly Ser Gln Ile Asp Val
145                 150                 155                 160

Arg Pro Ile Arg Asp Tyr Asp Ala Phe Val Glu Lys Thr Met Glu Phe
                165                 170                 175

Lys Ile Val Lys Ile Asn Gln Glu Tyr Lys Asn Val Val Ser His
                180                 185                 190

Lys Val Leu Ile Glu Ala Glu Leu Gln Gln Lys Lys Glu Ile Ile
                195                 200                 205

Gly Lys Leu Glu Lys Gly Gln Val Leu Glu Gly Ile Val Lys Asn Ile
                210                 215                 220

Thr Ser Tyr Gly Val Phe Ile Asp Leu Gly Gly Val Asp Gly Leu Ile
225                 230                 235                 240

His Ile Thr Asp Leu Ser Trp Gly Arg Val Ala His Pro Glu Glu Ile
                245                 250                 255

Val Gln Leu Asp Gln Lys Ile Asn Val Val Ile Leu Asp Phe Asp Glu
                260                 265                 270

Asp Arg Lys Arg Ile Ala Leu Gly Leu Lys Gln Leu Met Pro His Pro

```
                    275                 280                 285
Trp Asp Ala Leu Asp Ser Glu Leu Lys Val Gly Asp Lys Val Lys Gly
290                 295                 300

Lys Val Val Met Ala Asp Tyr Gly Ala Phe Val Glu Ile Ala Gln
305                 310                 315                 320

Gly Val Glu Gly Leu Ile His Val Ser Glu Met Ser Trp Thr Gln His
                325                 330                 335

Leu Arg Ser Ala Gln Asp Phe Leu His Val Gly Asp Glu Val Glu Ala
                340                 345                 350

Val Ile Leu Thr Leu Asp Arg Glu Arg Lys Met Ser Leu Gly Leu
                355                 360                 365

Lys Gln Leu Lys Pro Asp Pro Trp Ala Asp Ile Glu Thr Arg Phe Pro
370                 375                 380

Val Gly Ser Arg His His Ala Arg Val Arg Asn Phe Thr Asn Phe Gly
385                 390                 395                 400

Val Phe Val Glu Ile Glu Glu Gly Val Asp Gly Leu Ile His Ile Ser
                405                 410                 415

Asp Leu Ser Trp Thr Lys Lys Ile Lys His Pro Ser Glu Phe Thr Glu
                420                 425                 430

Val Gly Ala Asp Ile Glu Val Gln Val Ile Glu Ile Asp Lys Glu Asn
                435                 440                 445

Arg Arg Leu Ser Leu Gly His Lys Gln Leu Glu Glu Asn Pro Trp Asp
450                 455                 460

Val Phe Glu Thr Val Phe Thr Val Gly Ser Ile His Glu Gly Thr Val
465                 470                 475                 480

Ile Glu Val Met Asp Lys Gly Ala Val Val Ser Leu Pro Tyr Gly Val
                485                 490                 495

Glu Gly Phe Ala Thr Pro Lys His Met Val Lys Glu Asp Gly Ser Gln
                500                 505                 510

Ala Val Leu Glu Glu Lys Leu Pro Phe Lys Val Ile Glu Phe Asn Lys
                515                 520                 525

Asp Ala Lys Arg Ile Ile Val Ser His Ser Arg Val Phe Glu Asp Glu
                530                 535                 540

Gln Lys Met Ala Gln Arg Glu Ala Asn Ala Glu Arg Lys Ala Glu Ala
545                 550                 555                 560

Lys Ala Ala Gln Lys Glu Ala Ala Glu Ala Ala Asn Pro Ala Gln
                565                 570                 575

Ala Val Glu Lys Ala Thr Leu Gly Asp Leu Gly Glu Leu Ala Ala Leu
                580                 585                 590

Lys Glu Lys Leu Ser Glu Asn
                595

<210> SEQ ID NO 140
<211> LENGTH: 550
<212> TYPE: PRT
<213> ORGANISM: Porphyromonas gingivalis

<400> SEQUENCE: 140

Met Gly Arg Val Thr Ala Ile Asn Lys Arg Glu Val Val Ile Asn Val
1               5                   10                  15

Gly Tyr Lys Ser Glu Gly Val Pro Ala Thr Glu Phe Arg Tyr Asn
                20                  25                  30

Pro Glu Leu Lys Val Gly Asp Glu Val Glu Val Tyr Ile Glu Asn Gln
                35                  40                  45

Glu Asp Lys Lys Gly Gln Leu Val Leu Ser His Arg Lys Gly Arg Ala
```

```
             50                  55                  60
Ala Arg Ser Trp Glu Arg Val Asn Glu Ala Leu Glu Lys Asp Glu Ile
 65                  70                  75                  80

Val Lys Gly Tyr Val Lys Cys Arg Thr Lys Gly Gly Met Ile Val Asp
                     85                  90                  95

Val Phe Gly Ile Glu Ala Phe Leu Pro Gly Ser Gln Ile Asp Val Arg
                100                 105                 110

Pro Ile Arg Asp Tyr Asp Ala Phe Val Glu Lys Thr Met Glu Phe Lys
                115                 120                 125

Ile Val Lys Ile Asn Gln Glu Tyr Lys Asn Val Val Ser His Lys
130                 135                 140

Val Leu Ile Glu Ala Glu Leu Glu Gln Gln Lys Lys Glu Ile Ile Gly
145                 150                 155                 160

Lys Leu Glu Lys Gly Gln Val Leu Glu Gly Ile Val Lys Asn Ile Thr
                165                 170                 175

Ser Tyr Gly Val Phe Ile Asp Leu Gly Gly Val Asp Gly Leu Ile His
                180                 185                 190

Ile Thr Asp Leu Ser Trp Gly Arg Val Ala His Pro Glu Glu Ile Val
                195                 200                 205

Gln Leu Asp Gln Lys Ile Asn Val Val Ile Leu Asp Phe Asp Glu Asp
210                 215                 220

Arg Lys Arg Ile Ala Leu Gly Leu Lys Gln Leu Met Pro His Pro Trp
225                 230                 235                 240

Asp Ala Leu Asp Ser Glu Leu Lys Val Gly Asp Lys Val Lys Gly Lys
                245                 250                 255

Val Val Val Met Ala Asp Tyr Gly Ala Phe Val Glu Ile Ala Gln Gly
                260                 265                 270

Val Glu Gly Leu Ile His Val Ser Glu Met Ser Trp Thr Gln His Leu
                275                 280                 285

Arg Ser Ala Gln Asp Phe Leu His Val Gly Asp Glu Val Glu Ala Val
290                 295                 300

Ile Leu Thr Leu Asp Arg Glu Glu Arg Lys Met Ser Leu Gly Leu Lys
305                 310                 315                 320

Gln Leu Lys Pro Asp Pro Trp Ala Asp Ile Glu Thr Arg Phe Pro Val
                325                 330                 335

Gly Ser Arg His His Ala Arg Val Arg Asn Phe Thr Asn Phe Gly Val
                340                 345                 350

Phe Val Glu Ile Glu Glu Gly Val Asp Gly Leu Ile His Ile Ser Asp
                355                 360                 365

Leu Ser Trp Thr Lys Lys Ile Lys His Pro Ser Glu Phe Thr Glu Val
370                 375                 380

Gly Ala Asp Ile Glu Val Gln Val Ile Glu Ile Asp Lys Glu Asn Arg
385                 390                 395                 400

Arg Leu Ser Leu Gly His Lys Gln Leu Glu Glu Asn Pro Trp Asp Val
                405                 410                 415

Phe Glu Thr Val Phe Thr Val Gly Ser Ile His Glu Gly Thr Val Ile
                420                 425                 430

Glu Val Met Asp Lys Gly Ala Val Val Ser Leu Pro Tyr Gly Val Glu
                435                 440                 445

Gly Phe Ala Thr Pro Lys His Met Val Lys Glu Asp Gly Ser Gln Ala
                450                 455                 460

Val Leu Glu Glu Lys Leu Pro Phe Lys Val Ile Glu Phe Asn Lys Asp
465                 470                 475                 480
```

```
Ala Lys Arg Ile Ile Val Ser His Ser Arg Val Phe Glu Asp Glu Gln
            485                 490                 495

Lys Met Ala Gln Arg Glu Ala Asn Ala Glu Arg Lys Ala Glu Ala Lys
            500                 505                 510

Ala Ala Gln Lys Glu Ala Ala Glu Ala Ala Asn Pro Ala Gln Ala
        515                 520                 525

Val Glu Lys Ala Thr Leu Gly Asp Leu Gly Glu Leu Ala Ala Leu Lys
            530                 535                 540

Glu Lys Leu Ser Glu Asn
545             550

<210> SEQ ID NO 141
<211> LENGTH: 458
<212> TYPE: PRT
<213> ORGANISM: Porphyromonas gingivalis

<400> SEQUENCE: 141

Met Ile Val Asp Val Phe Gly Ile Glu Ala Phe Leu Pro Gly Ser Gln
1               5                   10                  15

Ile Asp Val Arg Pro Ile Arg Asp Tyr Asp Ala Phe Val Glu Lys Thr
            20                  25                  30

Met Glu Phe Lys Ile Val Lys Ile Asn Gln Glu Tyr Lys Asn Val Val
        35                  40                  45

Val Ser His Lys Val Leu Ile Glu Ala Glu Leu Gln Gln Lys Lys
    50                  55                  60

Glu Ile Ile Gly Lys Leu Glu Lys Gly Gln Val Leu Glu Gly Ile Val
65                  70                  75                  80

Lys Asn Ile Thr Ser Tyr Gly Val Phe Ile Asp Leu Gly Gly Val Asp
                85                  90                  95

Gly Leu Ile His Ile Thr Asp Leu Ser Trp Gly Arg Val Ala His Pro
            100                 105                 110

Glu Glu Ile Val Gln Leu Asp Gln Lys Ile Asn Val Val Ile Leu Asp
        115                 120                 125

Phe Asp Glu Asp Arg Lys Arg Ile Ala Leu Gly Leu Lys Gln Leu Met
130                 135                 140

Pro His Pro Trp Asp Ala Leu Asp Ser Glu Leu Lys Val Gly Asp Lys
145                 150                 155                 160

Val Lys Gly Lys Val Val Met Ala Asp Tyr Gly Ala Phe Val Glu
                165                 170                 175

Ile Ala Gln Gly Val Glu Gly Leu Ile His Val Ser Gly Met Ser Trp
            180                 185                 190

Thr Gln His Leu Arg Ser Ala Gln Asp Phe Leu His Val Gly Asp Glu
        195                 200                 205

Val Glu Ala Val Ile Leu Thr Leu Asp Arg Glu Glu Arg Lys Met Ser
    210                 215                 220

Leu Gly Leu Lys Gln Leu Lys Pro Asp Pro Trp Ala Asp Ile Glu Thr
225                 230                 235                 240

Arg Phe Pro Val Gly Ser Arg His His Ala Arg Val Arg Asn Phe Thr
                245                 250                 255

Asn Phe Gly Val Phe Val Glu Ile Glu Glu Gly Val Asp Gly Leu Ile
            260                 265                 270

His Ile Ser Asp Leu Ser Trp Thr Lys Lys Ile Lys His Pro Ser Glu
        275                 280                 285

Phe Thr Glu Val Gly Ala Asp Ile Glu Val Gln Val Ile Glu Ile Asp
    290                 295                 300
```

```
Lys Glu Asn Arg Arg Leu Ser Leu Gly His Lys Gln Leu Glu Glu Asn
305                 310                 315                 320

Pro Trp Asp Val Phe Glu Thr Val Phe Thr Val Gly Ser Ile His Glu
            325                 330                 335

Gly Thr Val Ile Glu Val Met Asp Lys Gly Ala Val Val Ser Leu Pro
        340                 345                 350

Tyr Gly Val Glu Gly Phe Ala Thr Pro Lys His Met Val Lys Glu Asp
    355                 360                 365

Gly Ser Gln Ala Val Leu Glu Glu Lys Leu Pro Phe Lys Val Ile Glu
370                 375                 380

Phe Asn Lys Asp Ala Lys Arg Ile Ile Val Ser His Ser Arg Val Phe
385                 390                 395                 400

Glu Asp Glu Gln Lys Met Ala Gln Arg Glu Ala Asn Ala Glu Arg Lys
                405                 410                 415

Ala Glu Ala Lys Ala Ala Gln Lys Glu Ala Ala Glu Ala Ala Asn
            420                 425                 430

Pro Ala Gln Ala Val Glu Lys Ala Thr Leu Gly Asp Leu Gly Glu Leu
        435                 440                 445

Ala Ala Leu Lys Glu Lys Leu Ser Glu Asn
    450                 455

<210> SEQ ID NO 142
<211> LENGTH: 426
<212> TYPE: PRT
<213> ORGANISM: Porphyromonas gingivalis

<400> SEQUENCE: 142

Met Glu Phe Lys Ile Val Lys Ile Asn Gln Glu Tyr Lys Asn Val Val
1               5                   10                  15

Val Ser His Lys Val Leu Ile Glu Ala Glu Leu Glu Gln Gln Lys Lys
            20                  25                  30

Glu Ile Ile Gly Lys Leu Glu Lys Gly Gln Val Leu Glu Gly Ile Val
        35                  40                  45

Lys Asn Ile Thr Ser Tyr Gly Val Phe Ile Asp Leu Gly Gly Val Asp
50                  55                  60

Gly Leu Ile His Ile Thr Asp Leu Ser Trp Gly Arg Val Ala His Pro
65                  70                  75                  80

Glu Glu Ile Val Gln Leu Asp Gln Lys Ile Asn Val Val Ile Leu Asp
                85                  90                  95

Phe Asp Glu Asp Arg Lys Arg Ile Ala Leu Gly Leu Lys Gln Leu Met
            100                 105                 110

Pro His Pro Trp Asp Ala Leu Asp Ser Glu Leu Lys Val Gly Asp Lys
        115                 120                 125

Val Lys Gly Lys Val Val Met Ala Asp Tyr Gly Ala Phe Val Glu
130                 135                 140

Ile Ala Gln Gly Val Glu Gly Leu Ile His Val Ser Glu Met Ser Trp
145                 150                 155                 160

Thr Gln His Leu Arg Ser Ala Gln Asp Phe Leu His Val Gly Asp Glu
                165                 170                 175

Val Glu Ala Val Ile Leu Thr Leu Asp Arg Glu Glu Arg Lys Met Ser
            180                 185                 190

Leu Gly Leu Lys Gln Leu Lys Pro Asp Pro Trp Ala Asp Ile Glu Thr
        195                 200                 205

Arg Phe Pro Val Gly Ser Arg His Ala Arg Val Arg Asn Phe Thr
210                 215                 220
```

-continued

Asn Phe Gly Val Phe Val Glu Ile Glu Glu Gly Val Asp Gly Leu Ile
225                 230                 235                 240

His Ile Ser Asp Leu Ser Trp Thr Lys Lys Ile Lys His Pro Ser Glu
            245                 250                 255

Phe Thr Glu Val Gly Ala Asp Ile Glu Val Gln Val Ile Glu Ile Asp
        260                 265                 270

Lys Glu Asn Arg Arg Leu Ser Leu Gly His Lys Gln Leu Glu Glu Asn
    275                 280                 285

Pro Trp Asp Val Phe Glu Thr Val Phe Thr Val Gly Ser Ile His Glu
290                 295                 300

Gly Thr Val Ile Glu Val Met Asp Lys Gly Ala Val Val Ser Leu Pro
305                 310                 315                 320

Tyr Gly Val Glu Gly Phe Ala Thr Pro Lys His Met Val Lys Glu Asp
            325                 330                 335

Gly Ser Gln Ala Val Leu Glu Glu Lys Leu Pro Phe Lys Val Ile Glu
        340                 345                 350

Phe Asn Lys Asp Ala Lys Arg Ile Ile Val Ser His Ser Arg Val Phe
    355                 360                 365

Glu Asp Glu Gln Lys Met Ala Gln Arg Glu Ala Asn Ala Glu Arg Lys
370                 375                 380

Ala Glu Ala Lys Ala Ala Gln Lys Glu Ala Ala Glu Ala Ala Asn
385                 390                 395                 400

Pro Ala Gln Ala Val Glu Lys Ala Thr Leu Gly Asp Leu Gly Glu Leu
            405                 410                 415

Ala Ala Leu Lys Glu Lys Leu Ser Glu Asn
        420                 425

<210> SEQ ID NO 143
<211> LENGTH: 540
<212> TYPE: PRT
<213> ORGANISM: Porphyromonas gingivalis

<400> SEQUENCE: 143

Met Lys Thr Lys Val Leu Arg Lys Phe Val Val Ala Ala Phe Ala Val
1               5                   10                  15

Ala Thr Leu Cys Pro Leu Ala Gln Ala Gln Thr Met Gly Gly Asp Asp
            20                  25                  30

Val Lys Val Val Gln Tyr Asn Gln Glu Lys Leu Val Gln Thr Arg Met
        35                  40                  45

Ser Val Ala Asp Asn Gly Trp Ile Tyr Val Met Thr His Ser Gly Tyr
    50                  55                  60

Asp Thr Gly Asn Ser Asn Val Lys Ile Phe Arg Ser Lys Asp Gln Gly
65                  70                  75                  80

Ala Thr Tyr Gln Lys Leu Arg Asp Trp Asp Pro Ser Asp Tyr Gln
            85                  90                  95

Phe Gln Asp Phe Asp Ile Val Val Thr Gly Lys Asn Glu Ser Asp Ile
        100                 105                 110

Lys Ile Trp Ser Val Glu Leu Met Asn Lys Pro Gly Gly Tyr Lys Ser
    115                 120                 125

Arg Val Ala Val Phe Ser Arg Asp Ala Asn Ala Gln Asn Ala Lys Leu
130                 135                 140

Val Tyr Lys Glu Asp Phe Ser Asn Val Gln Leu Tyr Asp Val Asp Ile
145                 150                 155                 160

Ala Ser Asn Tyr Arg Ser Pro Ser Ser Leu Asn Asn Gly Gly Asn Pro
            165                 170                 175

```
Phe Ala Leu Ala Phe Ala Tyr Thr Gly Phe Asn Asn Thr His Lys Ile
                180                 185                 190

Ser Phe Val Asp Tyr Val Phe Ser Leu Asn Gly Gln Asn Phe Asn
            195                 200                 205

Lys Asn Leu Leu Phe Ser Gln Asp Gly Glu Lys Lys Ile Asp Lys Val
            210                 215                 220

Asp Leu Ser Leu Gly Ser Thr Ser Glu Ser Met Gly His Asn Ala Trp
225                 230                 235                 240

Pro Leu Met Gly Val Val Phe Glu Met Asn Lys Gln Gly Gly Lys Ser
                245                 250                 255

Asp Ile Gly Phe Leu Ser Asn Phe Val Asp Asn Asp Pro Glu Phe Gln
            260                 265                 270

Trp Ser Gly Pro Ile Lys Val Ser Glu Ser Asp Met Ser Phe Ser Pro
            275                 280                 285

Lys Ile Gln Met Leu Leu Asp Glu Asp Asn Asn Thr Ile Asn Gly Glu
            290                 295                 300

Ser Cys His Asn Phe Met Ile Thr Tyr Ser Asp Tyr Asp Ser Glu Tyr
305                 310                 315                 320

Ser Asp Trp Asp Ile Arg Tyr Val Tyr Pro Lys Lys Ser Phe Lys Tyr
                325                 330                 335

Glu Lys Gly Lys Thr Pro Thr Met Asp Asp Leu Val Glu Ala Phe Leu
            340                 345                 350

Thr Ala Ser Tyr Gln Ser Glu Thr Asn Ser Gly Leu Gly Tyr Asp Lys
            355                 360                 365

Asn Ala Asn His Tyr Leu Ile Thr Tyr Ala Lys Lys Glu Glu Asn Gly
            370                 375                 380

Thr Asn Thr Leu Lys Tyr Arg Trp Ala Asn Tyr Asp Lys Ile His Asn
385                 390                 395                 400

Lys Asp Leu Trp Ser Asp Thr Phe Thr Tyr Thr Ser Ser Ala Asn Ala
                405                 410                 415

Leu Tyr Thr Pro Gln Val Asp Ile Asn Pro Thr Lys Gly Leu Val Cys
            420                 425                 430

Trp Ser Trp Val Glu Tyr Leu Pro Gly Lys Arg Ile Val Trp Ser Asp
            435                 440                 445

Thr Gln Trp Thr His Ala Asn Gly Val Glu Asp Ile Val Met Gln Glu
            450                 455                 460

Gly Ser Met Lys Leu Tyr Pro Asn Pro Ala Gln Glu Tyr Ala Val Ile
465                 470                 475                 480

Ser Leu Pro Thr Ala Ala Asn Cys Lys Ala Val Val Tyr Asp Met Gln
                485                 490                 495

Gly Arg Val Val Ala Glu Ala Ser Phe Ser Gly Asn Glu Tyr Arg Leu
            500                 505                 510

Asn Val Gln His Leu Ala Lys Gly Thr Tyr Ile Leu Lys Val Val Ser
            515                 520                 525

Asp Thr Glu Arg Phe Val Glu Lys Leu Ile Val Glu
            530                 535                 540

<210> SEQ ID NO 144
<211> LENGTH: 1158
<212> TYPE: PRT
<213> ORGANISM: Porphyromonas gingivalis

<400> SEQUENCE: 144

Met Lys Arg Ile Leu Pro Ile Val Ala Phe Leu Ser Leu Phe Leu Ala
1               5                   10                  15
```

-continued

```
Leu Ala Leu Pro Ala Lys Ala Gln Arg Ala Met Gly Lys Thr Ala Asp
             20                  25                  30

Arg Ser Leu Met Ala Ser Gly His Trp Val Lys Ile Arg Val Asp Ala
         35                  40                  45

Ser Gly Val Tyr Arg Leu Thr Asp Glu Gln Leu Arg Ala Asn Gly Phe
 50                  55                  60

Ser Asp Pro Ser Lys Val Gly Val Phe Gly Tyr Gly Gly Val Leu
 65                  70                  75                  80

Pro Glu Asp Leu Ser Arg Ile Thr Thr Asp Asp Leu Pro Pro Val Pro
                 85                  90                  95

Val Leu Arg Gln Gly Asn Ala Leu Tyr Phe Tyr Ala Val Gly Pro Val
            100                 105                 110

Thr Trp Phe Tyr Asn Pro Ala Lys Thr Thr Met Glu His Thr Val Asn
        115                 120                 125

Thr Tyr Ser Thr His Gly Tyr Tyr Phe Leu Ser Asp Ala Ala Gly Ala
    130                 135                 140

Pro Leu Gln Met Ser Gln Tyr Thr Gly Gly Gly Ala Ser Ala Glu Ala
145                 150                 155                 160

Leu Ile Asp Tyr Tyr Asp Glu Leu Met Leu His Glu Gln Glu Leu Tyr
                165                 170                 175

Ser Pro Lys Glu Ser Gly Arg Asp Leu Tyr Gly Glu Ser Phe Ser Ala
            180                 185                 190

Val Asn Thr Arg Thr Val Lys Phe Pro Leu Arg Gly Asn Thr Arg Ser
        195                 200                 205

Ser Gly Glu Leu Gly Thr Val Phe Ser Tyr Ile Ala Lys Ala Arg Ser
    210                 215                 220

Ala Gly Gly Arg Glu Met Ser Leu Ser Ala Asn Gly Ile Leu Ile
225                 230                 235                 240

Phe Ser Asp Pro Phe Ser Met Thr Ser Asn Glu Val Ser Asn Ser Tyr
                245                 250                 255

Leu Ala Gly Lys Lys Arg Arg Leu Tyr His Ser Thr Pro Met Asn Ser
            260                 265                 270

Leu Val Asn Glu Leu Arg Leu Asp Ala Asn Tyr Ser Met Thr Gly Asp
        275                 280                 285

Ala Val Asn Leu Asp Phe Ile Glu Val Ala Thr Gln Asn Asp Leu Arg
    290                 295                 300

Tyr Asp Gly Ala Pro Met His Ile Arg Arg Phe Ser Asn Leu Pro Val
305                 310                 315                 320

Leu Gly Gly Glu Ser Cys Arg Phe Val Ile Ser Glu Val Pro Glu Ser
                325                 330                 335

Leu Val Val Leu Gln Ala Asn Ser Ser Leu Thr Ala Ser Leu Val Pro
            340                 345                 350

Val Lys Thr Val Gly Asp Lys Thr Ile Glu Phe Val Ala Pro Pro Lys
        355                 360                 365

Gly Gln Asp Arg Arg Thr Ile Asn Thr Phe Tyr Ala Val Asp Leu Ser
    370                 375                 380

Gln Ala Ser Ala Pro Glu Ile Leu Gly Ala Val Pro Asn Gln Asn Leu
385                 390                 395                 400

His Gly Glu Glu Ile Pro Asp Leu Ile Ile Val Ser Thr Gln Ala Leu
                405                 410                 415

Leu Leu Glu Ala Asp Arg Leu Ala Thr Tyr Arg Arg Glu Lys Asn Gly
            420                 425                 430

Leu Lys Val Leu Val Val Leu Gln Glu Gln Val Phe Asn Glu Phe Ser
        435                 440                 445
```

```
Gly Gly Thr Pro Asp Ala Thr Ala Tyr Arg Leu Phe Ala Lys Met Phe
    450                 455                 460

Tyr Asp Arg Trp Lys Ala Asn Ala Pro Val Gly Glu Thr Phe Pro Met
465                 470                 475                 480

Gln Met Leu Leu Phe Gly Asp Gly Ala His Asp Asn Arg Lys Val Ser
                485                 490                 495

Val Ala Trp Gln Lys Pro Tyr Leu Gln Gln Thr Glu Phe Leu Leu Thr
            500                 505                 510

Phe Gln Ala Val Asn Ser Thr Asn Val Asn Ser Tyr Val Thr Asp Asp
        515                 520                 525

Tyr Phe Gly Leu Leu Asp Asp Gln Pro Ala Ser Val Asn Ile Gly Trp
    530                 535                 540

Arg Asn Tyr Asn Met Ala Val Gly Arg Phe Pro Val Arg Thr Pro Ala
545                 550                 555                 560

Glu Ala Arg Ile Ala Val Asp Lys Thr Ile Arg Tyr Glu Glu Asp Arg
                565                 570                 575

Glu Ser Gly Ala Trp Arg Ile Arg Ala Cys Phe Ala Ala Asp Asn Gly
            580                 585                 590

Asp Lys His Ala Thr Glu Thr Ser Arg Leu Ile Asp Thr Val Lys Arg
        595                 600                 605

Tyr Ala Pro Ala Ile Met Pro Val Arg Ala Phe Gln Asp Val Tyr Pro
    610                 615                 620

His Val Ile Glu Asn Gly Leu His Ser Ile Pro Gly Ala Lys Lys Lys
625                 630                 635                 640

Met Leu Glu Thr Leu Gln Ser Gly Ile Ile Leu Leu Asn Tyr Ala Gly
                645                 650                 655

His Gly Gly Pro Ala Gly Trp Ser Asp Glu His Leu Leu Thr Leu Asn
            660                 665                 670

Asp Ile His Lys Phe Asn Tyr Lys His Met Pro Ile Trp Ile Thr Ala
        675                 680                 685

Thr Cys Asp Phe Ala Asn Tyr Asp Ser Gln Thr Thr Ser Ala Gly Glu
    690                 695                 700

Glu Val Phe Leu His Glu Lys Ser Gly Thr Pro Ile Met Phe Ser Thr
705                 710                 715                 720

Thr Arg Val Val Tyr Asn Thr Gln Asn Glu Lys Ile Asn Gly Phe Met
                725                 730                 735

Leu Arg Arg Met Phe Glu Lys Ala Lys Asp Gly Arg Tyr Arg Thr Met
            740                 745                 750

Gly Glu Ile Ile Arg Ser Ala Lys Gln Gly Met Leu Ser Thr Val Phe
        755                 760                 765

Pro Asp Ser Ile Asn Gln Leu Ser Phe Phe Leu Met Gly Asp Pro Ser
    770                 775                 780

Val Arg Met Asn Leu Pro Thr His Lys Val Gln Leu Thr Ala Ile Asn
785                 790                 795                 800

Gly Gln Asp Pro Glu Gly Gln Tyr Gly Thr Ile Met Leu Lys Ser Leu
                805                 810                 815

Glu Arg Val Ala Leu Lys Gly Lys Val Thr Asp Glu Lys Gly Thr Phe
            820                 825                 830

Asp Glu Thr Phe Ser Gly Lys Val Phe Leu Thr Val Phe Asp Gly Arg
        835                 840                 845

Lys Lys Met Thr Ala Leu Glu Glu Gly Asn Asp Leu Ser Leu Val
    850                 855                 860

Tyr Tyr Asp Tyr Pro Asn Val Met Tyr Ala Gly Ile Ala Glu Val Lys
```

-continued

```
                865                 870                 875                 880

Asp Gly Leu Phe Glu Thr Ser Phe Ile Val Pro Lys Asp Val Asn Tyr
                    885                 890                 895

Ser Glu His Glu Gly Arg Ile Asn Leu Tyr Ala Tyr Asn Glu Ser Thr
                    900                 905                 910

Lys Ala Glu Ala Met Gly Val Asp Phe Ser Ile Arg Val Gln Pro Gly
                    915                 920                 925

Ile Pro Asp Glu Val Thr Glu Asp Asn Thr Pro Glu Ile Ile Ser
    930                 935                 940

Cys Phe Leu Asn Asp Ser Thr Phe Arg Ser Gly Asp Glu Val Asn Pro
945                 950                 955                 960

Thr Pro Leu Phe Met Ala Glu Val Phe Asp Leu Asn Gly Ile Asn Ile
                    965                 970                 975

Thr Gly Ser Gly Val Gly His Asp Ile Thr Leu Cys Ile Asp Gly Arg
                    980                 985                 990

Ala Asp Leu Thr Tyr Asn Leu Asn  Ala Tyr Phe Thr Ser  Ser Ala Thr
                    995                 1000                1005

Asp Ala  Gly Val Gly Thr Ile  Leu Phe Met Ile Pro  Ala Leu Ala
    1010                1015                1020

Glu Gly  Asp His Thr Ala Arg  Leu Thr Val Trp Asp  Ile Phe Asn
    1025                1030                1035

Asn Ala  Val His His Asp Phe  Ser Phe Arg Val Val  Asp Gly Ile
    1040                1045                1050

Ala Pro  Asp Val Ala Asp Val  Ile Leu Phe Pro Asn  Pro Val Arg
    1055                1060                1065

Glu Ser  Ala Thr Phe Arg Ile  Phe His Asn Arg Pro  Gly Ser Asp
    1070                1075                1080

Leu Asn  Val Ala Val Glu Ile  Tyr Asp Phe Thr Gly  Arg Leu Val
    1085                1090                1095

Asn Ser  Leu Pro Val Lys Thr  Tyr Ser Ser Ser Tyr  Gly Glu Pro
    1100                1105                1110

Ile Glu  Ile Lys Trp Asp Leu  Thr Ser Lys Tyr Gly  Val Lys Ile
    1115                1120                1125

Gly Asn  Gly Phe Tyr Leu Tyr  Arg Cys Val Val Asn  Ser Pro Gly
    1130                1135                1140

Gly Gln  Thr Ala Ser Met Ala  Lys Lys Met Ile Val  Val Gly Gln
    1145                1150                1155

<210> SEQ ID NO 145
<211> LENGTH: 556
<212> TYPE: PRT
<213> ORGANISM: Porphyromonas gingivalis

<400> SEQUENCE: 145

Met Lys Lys Leu Leu Gln Ala Lys Ala Leu Ile Leu Ala Leu Gly Leu
1               5                   10                  15

Phe Gln Leu Pro Ala Ile Ala Gln Thr Gln Met Gln Ala Asp Arg Thr
                20                  25                  30

Asn Gly Gln Phe Ala Thr Glu Glu Met Gln Arg Ala Phe Gln Glu Thr
            35                  40                  45

Asn Pro Pro Ala Gly Pro Val Arg Ala Ile Ala Glu Tyr Glu Arg Ser
        50                  55                  60

Ala Ala Val Leu Val Arg Tyr Pro Phe Gly Ile Pro Met Glu Leu Ile
65                  70                  75                  80

Lys Glu Leu Ala Lys Asn Asp Lys Val Ile Thr Ile Val Ala Ser Glu
```

```
                    85                  90                  95
Ser Gln Lys Asn Thr Val Ile Thr Gln Tyr Thr Gln Ser Gly Val Asn
                100                 105                 110

Leu Ser Asn Cys Asp Phe Ile Ile Ala Lys Thr Asp Ser Tyr Trp Thr
            115                 120                 125

Arg Asp Tyr Thr Gly Trp Phe Ala Met Tyr Asp Thr Asn Lys Val Gly
        130                 135                 140

Leu Val Asp Phe Ile Tyr Asn Arg Pro Arg Pro Asn Asp Asp Glu Phe
145                 150                 155                 160

Pro Lys Tyr Glu Ala Gln Tyr Leu Gly Ile Glu Met Phe Gly Met Lys
                165                 170                 175

Leu Lys Gln Thr Gly Gly Asn Tyr Met Thr Asp Gly Tyr Gly Ser Ala
                180                 185                 190

Val Gln Ser His Ile Ala Tyr Thr Glu Asn Ser Ser Leu Ser Gln Ala
            195                 200                 205

Gln Val Asn Gln Lys Met Lys Asp Tyr Leu Gly Ile Thr His His Asp
        210                 215                 220

Val Val Gln Asp Pro Asn Gly Glu Tyr Ile Asn His Val Asp Cys Trp
225                 230                 235                 240

Gly Lys Tyr Leu Ala Pro Asn Lys Ile Leu Ile Arg Lys Val Pro Asp
                245                 250                 255

Asn His Pro Gln His Gln Ala Leu Glu Asp Met Ala Ala Tyr Phe Ala
                260                 265                 270

Ala Gln Thr Cys Ala Trp Gly Thr Lys Tyr Glu Val Tyr Arg Ala Leu
            275                 280                 285

Ala Thr Asn Glu Gln Pro Tyr Thr Asn Ser Leu Ile Leu Asn Asn Arg
        290                 295                 300

Val Phe Val Pro Val Asn Gly Pro Ala Ser Val Asp Asn Asp Ala Leu
305                 310                 315                 320

Asn Val Tyr Lys Thr Ala Met Pro Gly Tyr Ile Ile Gly Val Lys
                325                 330                 335

Gly Ala Ser Gly Thr Pro Trp Leu Gly Thr Asp Ala Leu His Cys Arg
            340                 345                 350

Thr His Glu Val Ala Asp Lys Gly Tyr Leu Tyr Ile Lys His Tyr Pro
        355                 360                 365

Ile Leu Gly Glu Gln Ala Gly Pro Asp Tyr Lys Ile Glu Ala Asp Val
    370                 375                 380

Val Ser Cys Ala Asn Ala Thr Ile Ser Pro Val Gln Cys Tyr Tyr Arg
385                 390                 395                 400

Ile Asn Gly Ser Gly Ser Phe Lys Ala Ala Asp Met Thr Met Glu Ser
                405                 410                 415

Thr Gly His Tyr Thr Tyr Ser Phe Thr Gly Leu Asn Lys Asn Asp Lys
            420                 425                 430

Val Glu Tyr Tyr Ile Ser Ala Ala Asp Asn Ser Gly Arg Lys Glu Thr
        435                 440                 445

Tyr Pro Phe Ile Gly Glu Pro Asp Pro Phe Lys Phe Thr Cys Met Asn
    450                 455                 460

Glu Thr Asn Thr Cys Thr Val Thr Gly Ala Ala Lys Ala Leu Arg Ala
465                 470                 475                 480

Trp Phe Asn Ala Gly Arg Ser Glu Leu Ala Val Ser Val Ser Leu Asn
                485                 490                 495

Ile Ala Gly Thr Tyr Arg Ile Lys Leu Tyr Asn Thr Ala Gly Glu Glu
            500                 505                 510
```

```
Val Ala Ala Met Thr Lys Glu Leu Val Ala Gly Thr Ser Val Phe Ser
        515                 520                 525

Met Asp Val Tyr Ser Gln Ala Pro Gly Thr Tyr Val Leu Val Val Glu
530                 535                 540

Gly Asn Gly Ile Arg Glu Thr Met Lys Ile Leu Lys
545                 550                 555

<210> SEQ ID NO 146
<211> LENGTH: 428
<212> TYPE: PRT
<213> ORGANISM: Porphyromonas gingivalis

<400> SEQUENCE: 146

Met Lys Leu Ser Ser Lys Lys Ile Leu Ala Ile Ala Leu Leu Thr
1               5                   10                  15

Met Gly His Ala Val Gln Ala Gln Phe Val Pro Ala Pro Thr Thr Gly
                20                  25                  30

Ile Arg Met Ser Val Thr Thr Lys Ala Val Gly Glu Lys Ile Glu
            35                  40                  45

Leu Leu Val His Ser Ile Glu Lys Lys Gly Ile Trp Ile Asp Leu Asn
50                  55                  60

Gly Asp Ala Thr Tyr Gln Gln Gly Glu Glu Ile Thr Val Phe Asp Glu
65                  70                  75                  80

Ala Tyr His Glu Tyr Thr Ile Gly Thr Gln Thr Leu Thr Ile Tyr Gly
                85                  90                  95

Asn Thr Thr Arg Leu Gly Cys Arg Ser Thr Gly Ala Thr Ala Val Asp
                100                 105                 110

Val Thr Lys Asn Pro Asn Leu Thr Tyr Leu Ala Cys Pro Lys Asn Asn
            115                 120                 125

Leu Lys Ser Leu Asp Leu Thr Gln Asn Pro Lys Leu Leu Arg Val Trp
        130                 135                 140

Cys Asp Ser Asn Glu Ile Glu Ser Leu Asp Leu Ser Gly Asn Pro Ala
145                 150                 155                 160

Leu Ile Ile Leu Gly Cys Asp Arg Asn Lys Leu Thr Glu Leu Lys Thr
                165                 170                 175

Asp Asn Asn Pro Lys Leu Ala Ser Leu Trp Cys Ser Asp Asn Asn Leu
            180                 185                 190

Thr Glu Leu Glu Leu Ser Ala Asn Pro Arg Leu Asn Asp Leu Trp Cys
        195                 200                 205

Phe Gly Asn Arg Ile Thr Lys Leu Asp Leu Ser Ala Asn Pro Leu Leu
210                 215                 220

Val Thr Leu Trp Cys Ser Asp Asn Glu Leu Ser Thr Leu Asp Leu Ser
225                 230                 235                 240

Lys Asn Ser Asp Val Ala Tyr Leu Trp Cys Ser Ser Asn Lys Leu Thr
                245                 250                 255

Ser Leu Asn Leu Ser Gly Val Lys Gly Leu Ser Val Leu Val Cys His
            260                 265                 270

Ser Asn Gln Ile Ala Gly Glu Glu Met Thr Lys Val Val Asn Ala Leu
        275                 280                 285

Pro Thr Leu Ser Pro Gly Ala Gly Ala Gln Ser Lys Phe Val Val Val
    290                 295                 300

Asp Leu Lys Asp Thr Asp Glu Lys Asn Ile Cys Thr Val Lys Asp Val
305                 310                 315                 320

Glu Lys Ala Lys Ser Lys Asn Trp Arg Val Phe Asp Phe Asn Gly Asp
                325                 330                 335
```

```
Ser Asp Asn Met Leu Pro Tyr Glu Gly Ser Pro Thr Ser Asn Leu Ala
            340                 345                 350

Val Asp Ala Pro Thr Val Arg Ile Tyr Pro Asn Pro Val Gly Arg Tyr
            355                 360                 365

Ala Leu Val Glu Ile Pro Glu Ser Leu Leu Gly Gln Glu Ala Ala Leu
            370                 375                 380

Tyr Asp Met Asn Gly Val Lys Val Tyr Ser Phe Ala Val Glu Ser Leu
385                 390                 395                 400

Arg Gln Asn Ile Asp Leu Thr His Leu Pro Asp Gly Thr Tyr Phe Phe
            405                 410                 415

Arg Leu Asp Asn Tyr Thr Thr Lys Leu Ile Lys Gln
            420                 425

<210> SEQ ID NO 147
<211> LENGTH: 310
<212> TYPE: PRT
<213> ORGANISM: Porphyromonas gingivalis

<400> SEQUENCE: 147

Met Arg Lys Thr Ile Ile Phe Cys Leu Leu Ala Leu Phe Gly Cys
1               5                   10                  15

Ser Trp Ala Gln Glu Arg Val Asp Glu Lys Val Phe Ser Ala Gly Thr
            20                  25                  30

Ser Ile Phe Arg Gly Ile Leu Glu Lys Val Lys Ala Pro Leu Met Tyr
            35                  40                  45

Gly Asp Arg Glu Val Trp Gly Met Ala Arg Ala Ser Glu Asp Phe Phe
            50                  55                  60

Phe Ile Leu Pro Val Thr Asp Asp Leu Thr Pro Val Leu Phe Tyr Asn
65                  70                  75                  80

Arg Leu Thr Asn Glu Pro Cys Phe Val Ser Asp Gln Gly Ile Thr Glu
            85                  90                  95

Tyr Phe Lys Phe Ala Gln Glu Gly Asp Tyr Ile Glu Val Glu Gly Ser
            100                 105                 110

Ser Val Phe Met Ala Asn Leu Leu Tyr Tyr Arg Phe Phe Pro Thr Arg
            115                 120                 125

Ile Thr Ser Tyr Asn Ala Pro Ile Glu Gly Val Val Ser Lys Thr Gly
            130                 135                 140

Asn Pro Ala Phe Thr Ile Pro Met Leu Pro Gly Val Ser Asp Cys Ile
145                 150                 155                 160

Glu Ile Ser Asn Asn Arg Lys Val Phe Leu Thr Asn Gln Leu Gly Val
            165                 170                 175

Val Asn Ile Thr Asp Gly Met Glu Pro Pro Ile Ile Ala Gly Val Ser
            180                 185                 190

Ala Ser Tyr Gly Ser Ser Val Arg Val Tyr Gly His Val Ser Gln Arg
            195                 200                 205

Trp Asp Ile Ile Gly His Cys Tyr Leu Asp Ile Tyr Pro Thr Asn Cys
            210                 215                 220

Tyr Pro Leu Ser Thr Lys Pro Val Ala Gly Asp Asp Glu Val Phe Val
225                 230                 235                 240

Lys Gln Gln Gly Arg Gln Ile Glu Ile Asp Ser Asn Ser Pro Ile Val
            245                 250                 255

Gln Val Val Val Tyr Asp Leu Glu Gly Lys Ser Val Phe Arg Lys Arg
            260                 265                 270

Met Thr Glu Asn Ala Tyr Thr Leu Ser Phe Arg Ala Pro Met Leu Gly
            275                 280                 285
```

```
Phe Met Thr Ile Met Ile Glu Thr Gln Asn Ser Ile Ile Asn Lys Lys
            290                 295                 300

Leu Asn Val Thr Gln Leu
305                 310

<210> SEQ ID NO 148
<211> LENGTH: 405
<212> TYPE: PRT
<213> ORGANISM: Porphyromonas gingivalis

<400> SEQUENCE: 148

Met Lys Lys Thr Thr Ile Ile Ser Leu Ile Val Phe Gly Ala Phe Phe
1               5                   10                  15

Ala Ala Val Gly Gln Thr Lys Asp Asn Ser Ser Tyr Lys Pro Phe Ser
            20                  25                  30

Lys Glu Asp Ile Ala Gly Gly Val Tyr Ser Leu Pro Thr Gln Asn Arg
        35                  40                  45

Ala Gln Lys Asp Asn Ala Glu Trp Leu Leu Thr Ala Thr Val Ser Thr
    50                  55                  60

Asn Gln Ser Ala Asp Thr His Phe Ile Phe Asp Glu Asn Asn Arg Tyr
65                  70                  75                  80

Ile Ala Arg Asp Ile Lys Ala Asn Gly Val Arg Lys Ser Thr Asp Ser
                85                  90                  95

Ile Tyr Tyr Asp Ala Asn Gly Arg Ile Ser His Val Asp Leu Tyr Ile
            100                 105                 110

Ser Phe Ser Gly Gly Glu Pro Ala Leu Asp Thr Arg Phe Lys Tyr Thr
        115                 120                 125

Tyr Asp Asp Glu Gly Lys Met Thr Val Arg Glu Val Phe Met Leu Val
    130                 135                 140

Met Asp Pro Asn Thr Pro Ile Ser Arg Leu Glu Tyr His Tyr Asp Ala
145                 150                 155                 160

Gln Gly Arg Leu Thr His Trp Ile Ser Phe Ala Phe Gly Ala Glu Ser
                165                 170                 175

Gln Lys Asn Thr Tyr His Tyr Asn Glu Lys Gly Leu Leu Val Ser Glu
            180                 185                 190

Val Leu Ser Asn Ala Met Gly Thr Thr Tyr Ser Asp Thr Gly Lys Thr
        195                 200                 205

Glu Tyr Ser Tyr Asp Asp Ala Asp Asn Met Val Lys Ala Glu Tyr Phe
    210                 215                 220

Val Val Gln Gln Gly Lys Ala Trp Gln Val Leu Lys Arg Glu Glu Tyr
225                 230                 235                 240

Thr Tyr Glu Asp Asn Ile Cys Ile Gln Tyr Leu Ala Ile Asn Gly Thr
                245                 250                 255

Asp Thr Lys Val Tyr Lys Arg Asp Ile Glu Ser Asp Lys Ser Ile Ser
            260                 265                 270

Ala Asn Val Ile Asp Ile Pro Ser Met Pro Gln Thr Trp Pro Asn
        275                 280                 285

Met Tyr Gly Phe Asn Ala Lys Arg Leu Lys Thr Tyr Ser Ser Tyr
    290                 295                 300

Glu Gly Asp Val Ala Thr Pro Ile Phe Asp Tyr Ile Tyr Thr Tyr Lys
305                 310                 315                 320

Ala Leu Thr Ser Met Ala Thr Pro Ser Thr Glu Ala Gln Val Ala Val
                325                 330                 335

Tyr Leu Asn Pro Ser Thr Asp Arg Leu Val Ile Leu Ala Asn Gly Ile
            340                 345                 350
```

```
Thr His Leu Ser Met Tyr Asp Leu Gln Gly Lys Leu Ile Arg Asp Cys
        355                 360                 365

Ala Leu Ser Gly Asp Lys Val Glu Met Gly Val Gly Ser Leu Thr Lys
    370                 375                 380

Gly Thr Tyr Leu Leu Lys Val Asn Thr Asp Gln Gly Ala Phe Val Arg
385                 390                 395                 400

Lys Val Val Ile Arg
            405
```

<210> SEQ ID NO 149
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 149
gcgccatatg ctggccgaac cggcc                                        25

<210> SEQ ID NO 150
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 150
gcgcctcgag tcaattcatt tccttataga g                                 31

<210> SEQ ID NO 151
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 151
cgcggtatac atgaaaagaa tgacgc                                       26

<210> SEQ ID NO 152
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 152
cgcgagatct gaaagacaac tgaatacc                                     28

<210> SEQ ID NO 153
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 153
gcgcgtatac atgaagaaat caagtgtag                                    29

<210> SEQ ID NO 154
<211> LENGTH: 30
<212> TYPE: DNA
<213> ORGANISM: Artificial Sequence
<220> FEATURE:
<223> OTHER INFORMATION: Synthetic oligonucleotide -continued

<400> SEQUENCE: 154
gcgcagatct cttcagcgta ccttgctgtg                                          30

<210> SEQ ID NO 155
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 155
cttctgtata cttacagcgg acatcataaa atc                                      33

<210> SEQ ID NO 156
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 156
ttccaggagg gtaccacgca actcttcttc gat                                      33

<210> SEQ ID NO 157
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 157
ttgcaacata tgatcagaac gatactttca                                          30

<210> SEQ ID NO 158
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 158
agcaatctcg agcggttcat gagccaaagc                                          30

<210> SEQ ID NO 159
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 159
taaacatatg tgcctcgaac ccataattgc tccg                                     34

<210> SEQ ID NO 160
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 160
cgtccgcgga agctttgatc ggccattgct act                                      33

<210> SEQ ID NO 161
<211> LENGTH: 28
<212> TYPE: DNA

<213> ORGANISM: Artificial Sequence
<220> FEATURE:
<223> OTHER INFORMATION: Synthetic oligonucleotide

<400> SEQUENCE: 161
cgcggtatac atggagttca agattgtg                                      28

<210> SEQ ID NO 162
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 162
cgcgagatct gttttctgaa agcttttc                                      28

<210> SEQ ID NO 163
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 163
cgcggtatac atggaaaact taaagaac                                      28

<210> SEQ ID NO 164
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 164
cgcgagatct gttttctgaa agcttttc                                      28

<210> SEQ ID NO 165
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 165
cgcggatatc atggataaag tgagctatgc                                    30

<210> SEQ ID NO 166
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 166
cgcgagatct tttgttgata ctcaataatt c                                  31

<210> SEQ ID NO 167
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 167
gcgcgtatac atgagagcaa acatttggca gatactttcc g                       41

```
<210> SEQ ID NO 168
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 168
gcgcagatct gcgcaagcgc agtatatcgc c                              31

<210> SEQ ID NO 169
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 169
gcgcgtatac atgaatagca gacatctgac aatcacaatc attgccgg             48

<210> SEQ ID NO 170
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 170
gcgcagatct gctgttctgt gagtgcagtt gtttaagtg                       39

<210> SEQ ID NO 171
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 171
gcgccatatg cggacaaaaa ctatcttttt tgcg                            34

<210> SEQ ID NO 172
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 172
gcgcctcgag gttgttgaat cgaatcgcta tttgagc                         37

<210> SEQ ID NO 173
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 173
gcgcggcgcc atgacggaca acaaacaacg taatatcg                        38

<210> SEQ ID NO 174
<211> LENGTH: 38
<212> TYPE: DNA
<213> ORGANISM: Artificial Sequence
<220> FEATURE:
<223> OTHER INFORMATION: Synthetic oligonucleotide
```

<400> SEQUENCE: 174
gcgcctcgag ttacttgcgt atgatcacgg acataccc                38

<210> SEQ ID NO 175
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 175
ccccggatcc gatgcgactg atcaaggc                28

<210> SEQ ID NO 176
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 176 cccccctcgag cggaacgggg tcatagcc                28

<210> SEQ ID NO 177
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 177
cgcggtatac atgaattacc tgtacatac                29

<210> SEQ ID NO 178
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 178
cgcgggatcc gttcgattgg tcgtcgatgg                30

<210> SEQ ID NO 179
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 179
cgcgcatatg gagattgctt tcctttcttc g                31

<210> SEQ ID NO 180
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 180
cgcgctcgag ttagttcgat tggtcgtcg                29

<210> SEQ ID NO 181
<211> LENGTH: 34
<212> TYPE: DNA

```
<213> ORGANISM: Artificial Sequence
<220> FEATURE:
<223> OTHER INFORMATION: Synthetic oligonucleotide

<400> SEQUENCE: 181
gcgcgatatc gctagcatga aaaagctatt tctc                                34

<210> SEQ ID NO 182
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 182
gcgcagatct ctcgagtttg ccatcggatt gcggattg                            38

<210> SEQ ID NO 183
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 183
cgctgaattc cagatttcgt tcggagggga accc                                34

<210> SEQ ID NO 184
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 184
ctatgcggcc gcctgcttca cgatcttttg gctca                               35

<210> SEQ ID NO 185
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 185
tgctggatcc caagagatct caggcatgaa tgca                                34

<210> SEQ ID NO 186
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 186
gagtgcggcc gctcggcctc tttatctcta ccttttc                             37

<210> SEQ ID NO 187
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 187
gcttgcggcc gcccttatga aagatttgca gat                                 33
```

```
<210> SEQ ID NO 188
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 188
ggtgctcgag tatactcaac aagcaccttc tgcac                                35

<210> SEQ ID NO 189
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 189
ggcgggatcc gctcaggagc aactgaatgt ggta                                 34

<210> SEQ ID NO 190
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 190
gagtgcggcc gctgtggaac aaattgcgca atccatc                              37

<210> SEQ ID NO 191
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 191
agcagaattc ggaaacgcac agagcttttg ggaa                                 34

<210> SEQ ID NO 192
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 192
gagtgcggcc gcttacctgc accttatgac tgaatac                              37

<210> SEQ ID NO 193
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 193
tgctgaattc cagacgatgg gaggagatga tgtc                                 34

<210> SEQ ID NO 194
<211> LENGTH: 37
<212> TYPE: DNA
<213> ORGANISM: Artificial Sequence
<220> FEATURE:
<223> OTHER INFORMATION: Synthetic oligonucleotide
```

-continued

```
<400> SEQUENCE: 194
gagtgcggcc gctttccacg atgagcttct ctacgaa                              37

<210> SEQ ID NO 195
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 195
ggccgagctc caagaggaag gtatttggaa tacc                                 34

<210> SEQ ID NO 196
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 196
gagtgcggcc gctttgtcct accacgatca ttttctt                              37

<210> SEQ ID NO 197
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 197
tgctgagctc caaacgcaaa tgcaagcaga ccga                                 34

<210> SEQ ID NO 198
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 198
gagtgcggcc gcttttgaga attttcattg tctcacg                              37

<210> SEQ ID NO 199
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 199
ggcgggatcc cagtttgttc cggctcccac caca                                 34

<210> SEQ ID NO 200
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 200
gagtgcggcc gctctgtttg atgagcttag tggtata                              37

<210> SEQ ID NO 201
<211> LENGTH: 34
<212> TYPE: DNA
```

```
<213> ORGANISM: Artificial Sequence
<220> FEATURE:
<223> OTHER INFORMATION: Synthetic oligonucleotide

<400> SEQUENCE: 201
agcagaattc caagaaagag tcgatgaaaa agta                              34

<210> SEQ ID NO 202
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 202
gagtgcggcc gcttagctgt gtaacattaa gtttttatt gat                     43

<210> SEQ ID NO 203
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 203
tgctgaattc aaggacaatt cttcttacaa acct                              34

<210> SEQ ID NO 204
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 204
gagtgcggcc gcttcgaatc acgactttc tcacaaa                            37

<210> SEQ ID NO 205
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 205
ggcagaattc cagtctttga gcacaatcaa agta                              34

<210> SEQ ID NO 206
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 206
gagtgcggcc gctgatagcc agcttgatgc tcttagc                           37

<210> SEQ ID NO 207
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 207
ggccgaattc cagatggata ttggtggaga cgat                              34
```

```
<210> SEQ ID NO 208
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 208
gagtgcggcc gctctctaca atgatttttt ccacgaa                              37

<210> SEQ ID NO 209
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 209
gaacggatcc aacgtgtctg ctcagtcacc ccga                                 34

<210> SEQ ID NO 210
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 210
gagtgcggcc gcttctgagc gatactttttg cacgtat                             37

<210> SEQ ID NO 211
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 211
gcgcctcgag attcatttcc ttatagag                                        28

<210> SEQ ID NO 212
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 212
cttcttgtcg actacagcgg acatcataaa atc                                  33

<210> SEQ ID NO 213
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 213
ttccacctcg agttaacgca actcttcttc gat                                  33

<210> SEQ ID NO 214
<211> LENGTH: 34
<212> TYPE: DNA
<213> ORGANISM: Artificial Sequence
<220> FEATURE:
<223> OTHER INFORMATION: Synthetic oligonucleotide
```

```
<400> SEQUENCE: 214
taaagaattc tgcctcgaac ccataattgc tccg                                    34

<210> SEQ ID NO 215
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 215
cgcgcatatg gataaagtga gctatgc                                            27

<210> SEQ ID NO 216
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 216
cgcgctcgag tttgttgata ctcaataatt c                                       31

<210> SEQ ID NO 217
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 217
gcccggcgcc atgcggacaa aaactatctt ttttgcg                                 37

<210> SEQ ID NO 218
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 218
gcccggcgcc ttagttgttg aatcgaatcg ctatttgagc                              40
```